US007902334B2

(12) United States Patent
Bintrim et al.

(10) Patent No.: US 7,902,334 B2
(45) Date of Patent: Mar. 8, 2011

(54) **PESTICIDALLY ACTIVE PROTEINS AND POLYNUCLEOTIDES OBTAINABLE FROM *PAENIBACILLUS* SPECIES**

(75) Inventors: Scott B. Bintrim, Westfield, IN (US); Scott A. Bevan, Indianapolis, IN (US); Baolong Zhu, San Diego, CA (US); Donald J. Merlo, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 302 days.

(21) Appl. No.: 11/775,663

(22) Filed: Jul. 10, 2007

(65) Prior Publication Data

US 2008/0019914 A1 Jan. 24, 2008

Related U.S. Application Data

(62) Division of application No. 10/609,113, filed on Jun. 27, 2003, now abandoned.

(60) Provisional application No. 60/392,633, filed on Jun. 28, 2002, provisional application No. 60/441,647, filed on Jan. 21, 2003.

(51) Int. Cl.
*C07K 14/00* (2006.01)

(52) U.S. Cl. ................................ 530/350; 506/7; 506/13

(58) Field of Classification Search ........................ None
See application file for complete search history.

(56) References Cited

U.S. PATENT DOCUMENTS

| | | | |
|---|---|---|---|
| 5,712,248 | A | 1/1998 | Kalman et al. |
| 6,043,415 | A | 3/2000 | Strizhov et al. |
| 6,048,838 | A | 4/2000 | Ensign et al. |
| 6,174,860 | B1 | 1/2001 | Kramer et al. |
| 6,277,823 | B1 | 8/2001 | Kramer et al. |
| 6,281,413 | B1 | 8/2001 | Kramer et al. |
| 6,528,484 | B1 | 3/2003 | Ensign et al. |
| 2002/0078478 | A1 | 6/2002 | ffrench-Constant |

FOREIGN PATENT DOCUMENTS

| | | | |
|---|---|---|---|
| WO | WO 94/21795 | A1 | 9/1994 |
| WO | WO 95/00647 | A1 | 1/1995 |
| WO | WO 97/17432 | A1 | 5/1997 |
| WO | WO 98/08388 | A1 | 3/1998 |
| WO | WO 98/08932 | A1 | 3/1998 |
| WO | WO 98/50427 | A1 | 11/1998 |
| WO | WO 99/03328 | A1 | 1/1999 |
| WO | WO 99/42589 | A2 | 8/1999 |
| WO | WO 99/54472 | A1 | 10/1999 |
| WO | WO 00/30453 | A2 | 6/2000 |
| WO | WO 00/42855 | A1 | 7/2000 |

OTHER PUBLICATIONS

Bowen et al., Science, 280:2129-2132 (1998).*

Crickmore et al. "Revision of the Nomenclature for the *Bacillus thuringiensis* Pesticidal Crystal Proteins", Microbiol. Mol. Bio. Review, Sep. 1998, pp. 807-813, vol. 62, No. 3.

Ffrench-Constant et al. "Novel insecticidal toxins from nematode-symbiotic bacteria", Cellular and Mol. Life Sciences, May 2000, pp. 828-833, vol. 57, No. 5 (abstract).

Ffrench-Constant et al. "A Genomic Sample Sequence of the Entomopathogenic Bacterium *Photorhabdus* . . . ", Appl. Environ. Microbiol., Aug. 2000, pp. 3310-3329, vol. 66, No. 8.

Forst et al. "Molecular Biology of the Symbiotic-Pathogenic Bacteria *Xenorhabdus* spp. and *Photohabdus* spp.", Microbiological Reviews, Mar. 1996, pp. 21-43, vol. 60, No. 1.

Hofte et al. "Insecticidal Crystal Proteins of *Bacillus thuringiensis*", Microbiological Reviews, Jun. 1989, pp. 242-255, vol. 53, No. 2.

Morgan et al., *Xenorhabdus nematophilus* genes, GENBANK Accession No. AJ308438, May 11, 2001.

Morgan et al. "Sequence Analysis of Insecticidal Genes from *Xenorhabdus nematophilus* PMFI296", Appl. Environ. Microbiol., May 2001, pp. 2062-2069, vol. 67, No. 5.

Pettersson et al. "Transfer of *Bacillus lentimorbus* and *Bacillus popilliae* to the genus *Paenibacillus* . . . ", Int. J. Syst. Bacteriol., 1999, pp. 531-540, vol. 49, No. 2 (abstract).

Shida et al. "Emended description of *Paenibacillus amylolyticus* and description of *Paenibacillus* . . . ", Int. J. Syst. Bacteriol., 1997, pp. 299-306, vol. 47, No. 2 (abstract).

Waterfield et al. "Oral Toxicity of *Photorhabdus luminescens* W14 Toxin Complexes in *Escherichia coli*", Appl. Environ. Microbiol., Nov. 2001, pp. 5017-5024, vol. 67, No. 11.

Widner et al. "Two Highly Related Insecticidal Crystal Proteins of *Bacillus thuringiensis* subsp. kurstaki Possess . . . ", J. Bacteriol., Feb. 1989, pp. 965-974, vol. 171, No. 2.

Zhang et al. "Cloning and Analysis of the First cry Gene from *Bacillus popilliae*", J. Bacteriol., Jul. 1997, pp. 4336-4341, vol. 179, No. 13.

Bowen, D. et al. "*Photorhabdus luminescens* insecticidal toxin complex proteins . . . ", GENBANK Accession No. AF046867, Jun. 30, 1998.

Bowen, D. et al., Insecticidal toxin complex protein TcaC (*Photorhabdus luminescens*), GENBANK Accession No. AAC38625, Jun. 30, 1998.

(Continued)

*Primary Examiner* — Jeffrey S. Lundgren

(74) *Attorney, Agent, or Firm* — Donald R. Stuart; Baker & Daniels LLP

(57) ABSTRACT

The subject invention provides unique biological alternatives for pest control. More specifically, the present invention relates to novel pesticidal proteins, novel sources of pesticidal proteins, polynucleotides that encode such toxins, and to methods of using these toxins to control insects and other plant pests. The subject invention relates to the surprising discovery that *Paenibacillus* species, and proteins therefrom, have toxicity to lepidopterans. There have been no known reports of a *Paenibacillus* species, strain, or protein having toxicity to lepidopterans. This is also the first known example of a *Paenibacillus* Cry protein that is toxic to lepidopterans. Furthermore, this is the first known report of a *Paenibacillus* having toxin complex (TC)-like proteins. The DAS1529 isolate disclosed here is also the first known example of a natural bacterium that produces both a Cry toxin and TC proteins. The subject invention also relates to new classes of Cry and TC proteins that are pesticidally active.

4 Claims, 15 Drawing Sheets

OTHER PUBLICATIONS

Campobasso, N. et al., Chain A, Thiaminase I from *Bacillus thiaminolyticus*, GENBANK Accession No. 2THI_A, Sep. 17, 1998.

Costello, C.A. et al., Thiaminase I precursor, GENBANK Accession No. AAC44156, Jul. 22, 1996.

Donovan, W.P. et al., *Bacillus thuringiensis* cryIIIB2 gene, complete cds, GENBANK Accession No. M89794, Apr. 26, 1993.

Herrnstadt, C. et al., *B. thuringiensis* cryC gene encoding delta-endotoxin, 5' end, GENBANK Accession No. M22472, Apr. 26, 1993.

Hurst, M.R. et al., SepB (*Serratia entomophila*), GENBANK Accession No. AAG09643, Nov. 5, 2003.

Hurst, M.R. et al., SepC (*Serratia entomophila*), GENBANK Accession No. AAG09644, Nov. 5, 2003.

Lambert, B. et al., *B. thuringiensis* cryIIID gene for coleopteran-active insecticidal crystal protein, GENBANK Accession No. X59797, Mar. 10, 1992.

Morgan et al., XptB1 protein (*Xenorhabdus nematophila*), GENBANK Accession No. CAC38402, May 11, 2001.

Morgan et al., XptC1 protein (*Xenorhabdus nematophila*), GENBANK Accession No. CAC38403, May 11, 2001.

Sick, A. et al., *Bacillus thuringiensis* cryIIIB gene for coleopteran-active delta-endotoxin (partial), GENBANK Accession No. X17123, Jun. 22, 1992.

Waterfield, N.R. et al., toxin complex protein (*Photorhabdus luminescens*), GENBANK Accession No. AAL18473, Oct. 25, 2001.

Waterfield, N.R. et al., TcdB1; toxin complex protein (*Photorhabdus luminescens*), GENBANK Accession No. AAL18487, Jul. 17, 2003.

Waterfield, N.R. et al., TccC2 (*Photorhabdus luminescens*), GENBANK Accession No. AAL18492, Jul. 17, 2003.

Waterfield, N.R. et al., TccC4 (*Photorhabdus luminescens*), GENBANK Accession No. AAO17196, Jul. 17, 2003.

Waterfield, N.R. et al., TcdB2 (*Photorhabdus luminescens*), GENBANK Accession No. AAO17202, Jul. 17, 2003.

Waterfield, N.R. et al., TccC3 (*Photorhabdus luminescens*), GENBANK Accession No. AAO17204, Jul. 17, 2003.

Waterfield, N.R. et al., TccC5 (*Photorhabdus luminescens*), GENBANK Accession No. AAO17210, Jul. 17, 2003.

Harrison, H. et al. "*Paenibacillus* Associated with Milky Disease in Central and South American Scarabs", J. Invertebr. Pathol., Oct. 2000, pp. 169-175, vol. 76, No. 3.

Patel, R. et al. "Detection of Two New cry Genes in *Paenibacillus papillae*", Abstracts of the General Meeting of the American Society for Microbiology, May 24, 2000, p. 476, vol. 100 (abstract).
Gardener, B. B. "Ecology of *Bacillus* and *Paenibacillus* spp. in Agricultural Systems", *Phytopathology*, 2004, pp. 1252-1258, vol. 94, No. 11.
Heyndrickx, M. et al. "Reclassification of *Paenibacillus* (formerly *Bacillus*) *pulvifaciens* (Nakamura 1984) Ash et al. 1994, a Later Subjective Synonym of *Paenibacillus* (formerly *Bacillus*) *larvae* (White 1906) Ash et al. 1994, as a Subspecies of *P. larvae*, with Emended Descriptions of *P. larvae* as *P. larvae* subsp. *Larvae* and *P. larvae* subsp. *Pulvifaciens*", Int. Journal of Systematic Bacteriology, Jan. 1996, pp. 270-279, vol. 46, No. 1.

* cited by examiner

*Photorhabdus*
*tca*
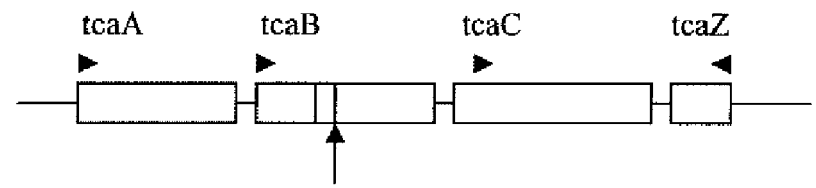
*tcb*
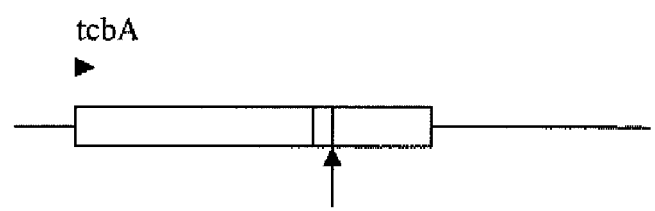
*tcc*
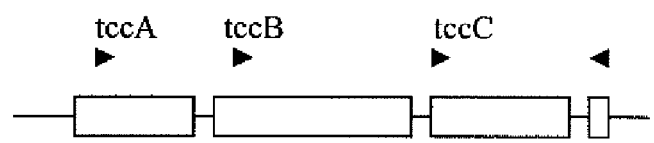
*tcd*
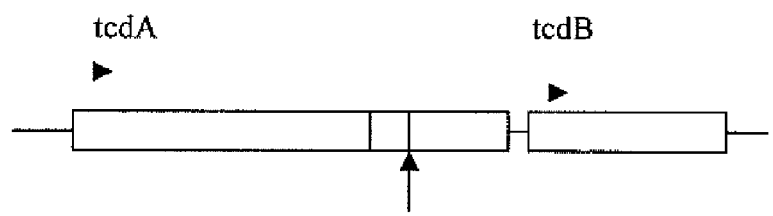
FIG. 1

Fig. 2

2THIA
or
AAC44156:     DITLKVAIYPYVPDPARFQA
              |||||||||||||||  ||||
SEQ ID NO:17: DITLKVAIYPYVPDPSRFQA

Fig. 3

Cry1529 (ORF7) Activity on TBW

| Cell Pellet Concentration | Score |
|---|---|
| 5X | ~1.9 |
| 2.5X | ~1.6 |
| 1.25X | ~1.9 |
| .63X | ~1.4 |
| .31X | ~1.4 |

Fig. 6

```
             SEQ ID NO:9(top) x SEQ ID NO:5(bottom)

1 MTKEGDKHMSTSTLLQSIKEARRDALVNHYIANQVPTALADKITDADSLY 50
     ||||:|:|||||||| ||| |||||||||||| ||  | |||||||||||
   1 MTKEGGKNMSTSTLLQLIKESRRDALVNHYIANNVPRELTDKITDADSLY 50

51 EYLLLDTKISELVKTSPIAEAISSVQLYMNRCVEGYEGKLTPESNTHFGP 100
     |||||||||||||||||||||||||||||||||||||||||||:| ||||
  51 EYLLLDTKISELVKTSPIAEAISSVQLYMNRCVEGYEGKLTPEGNSHFGP 100

101 GKFLYNWDTYNKRFSTWAGKERLKYYAGSYIEPSLRYNKTDPFLNLEQSI 150
     ||||:||||||||| ||||||||||||||||| |||||||||||||||:|
 101 GKFLNNWDTYNKRYSTWAGKERLKYYAGSYIDPSLRYNKTDPFLNLEQNI 150

151 SQGRITDDTVKNALQHYLTEYEVLADLDYISVNKGGDESVLLFVGRTKTV 200
     |||||||||||||||||||||||||||| |||||||| ||||| |||||:
 151 SQGRITDDTVKNALQHYLTEYEVLADLEYISVNKGADESVLFFVGRTKTM 200

201 PYEYYWRRLLLKRDNNNKLVPAVWSQWKKISANIGEAVDSYVVPRWHKNR 250
     ||||||||| :|||||||||||:||||||| ||||||||::||| :||:||
 201 PYEYYWRRLTLKKDNNNKLVPAIWSQWKKITANIGEAVNNYVVLHWHNNR 250

251 LHVQWCSIEKSENDAGEPIEKRYLNDWFMDSSGVWSSFRKIPVVEKSFEY 300
     ||||| | || ||:|||||||||||||||:|:|||||||| : |:|| |
 251 LHVQWGSTEKTQNDDGEPIEKRYLNDWFMDKSSVWSSFRKVSYIENSFTY 300

301 LDGSLDPRFVALVRNQILIDEPEIFRITVSAPNPIDANGRVEVHFEENYA 350
     | |  ::|| | |: | | |  ::: :  : 
 301 TEGIIDSRNITIAGNQLFCDDSNTFKATITA.LPFDQIRVYLEKIYGTGG 349

351 NRYNITIKYGTTSLAIPAGQVGHPNISINETLRVEFGTRPDWYYTFRYLG 400
     : ::   ::|:   :  :|:        :       ||      :
 350 SITVTGENKGYIIKVGEPREVSFSPNTLLDVFIGSNASPRDPYFKATFNR 399

401 NTIQNSYGSIVNNQFSPPSGSNIKGPIDLTLKNNIDLSALLDESLDALFD 450
     |||||||: || |||||||||||||||||||||||||||| ||||:|||
 400 EALQNSYGSIKINQYTPPSGSNIKGPIDLTLKNNIDLSALLEESLDVLFD 449

451 YTIQGDNQLGGLAAFNGPYGLYLWEIFFHVPFLMAVRFHTE--QRYELAERW 500
     |||||:|||||| |||||||||||||| ||||||||||||--||||||||
 450 YTIQGNNQLGGLEAFNGPYGLYLWEIFLIVPFLMAVRFHTE][QRYELAERW 499

501 FKFIFNSAGYRDDYGSLLTDDKGNVRYWNVIPLQEDTEWDDTLSLATTDP 550
     ||||||||||| ||:||||||||||||||:|||||||||||||||||||
 500 FKFIFNSAGYRDGYGNLLTDDKGNVRYWNVVPLQEDTEWDDTLSLATTDP 549

551 DEIAMADPMQYKLAIFIHTMDFLISRGDSLYRMLERDTLAEAKMYYIQAS 600
     |||||||||||||||||||| ||||||||||||||||| ||||||||||
 550 DEIAMADPMQYKLAIFIHTLDFLISRGDSLYRMLERDTLTEAKMYYIQAS 599

601 QLLGPRPDIRLNHSWPNPTLQSEADAVTAVPTRSDSPAAPILALRALLTG 650
     |||||||| || |||||:|||||||||||||||||||||||||||||| 
 600 QLLGPRPEIRINHSWPDPTLQSEADAVTAVPTRSDSPAAPILALRALLNA 649
```

Fig. 7A

```
651  ENGHFLPPYNDELFAFWDKIDLRLYNLRHNLSLDGQPLHLPLFAEPVNPR  700
     ||||||||||||| ||||||||||||||||||||||||||||| ||||||
650  ENGHFLPPYNDELLAFWDKIDLRLYNLRHNLSLDGQPLHLPLFTEPVNPR  699

701  ELQVQHGPGDGLGGSAGSAQSRQSVYRFPLVIDKARNAANSVIQFGNALE  750
     ||||||| ||||||||||| |||||||||||||||||||:|||||||||
700  ELQVQHGAGDGLGGSAGSVQSRQSVYRFPLVIDKARNAASSVIQFGNALE  749

751  NALTKQDSEAMTMLLQSQQQIVLQQTRDIQEKNLAALQASLEATMTAKAG  800
     ||||||||||||||||||||||||||||||||||| |||||||||||||
750  NALTKQDSEAMTMLLQSQQQIVLQQTRDIQEKNLASLQASLEATMTAKAG  799

801  AESRKTHFAGLADNWMSDNETASLALRTTAGIINTSSTVPIAITGGLDMA  850
     | ||||||||||||||:||||||||||||||||||||||||||||||||
800  AKSRKTHFAGLADNWMSHNETASLALRTTAGIINTSSTVPIAITGGLDMA  849

851  PNIFGFAVGGSRWGAASAAVAQGLQIAAGVMEQTANIIDISESYRRRED  900
     |||||||||||||||||||||||||||||||||||||||||||||||||
850  PNIFGFAVGGSRWGAASAAVAQGLQIAAGVMEQTANIIDISESYRRRED  899

901  WLLQRDVAENEAAQLDSQIAALREQMDMARKQLALAETEQAHAQAVYELQ  950
     ||||||||||||||||||||||||||||||||||||||||||||||||
900  WLLQRDVAENEAAQLDSQIAALREQMDMARKQLALAETEQAHAQAVYELL  949

951  STRFTNQALYNWMAGRLSSLYYQMYDAALPLCLMAKQALEKEIGSDKTVG  1000
     ||||||||||||||||||||||||||||||||||||||||||||:||||
950  STRFTNQALYNWMAGRLSSLYYQMYDAALPLCLMAKQALEKEIGNDKTVG  999

1001 VLSLPAWNDLYQGLLAGEALLLELQKLENLWLEEDKRGMEAVKTVSLDTL  1050
      ||||||||||||||||||||||||||||||||||||||||:|||||||
1000 IFTLPAWNDLYQGLLAGEALLLELQKLENLWLEEDKRGMEAVRTVSLDTL  1049

1051 LRKTNPNSGFADLVKEALDENGKTPDPVSGVGVQLQNNIFSATLDLSVLG  1100
     ||| :| ||||| ||   : :|||||||||:||||||||||||||| ||
1050 LRKEKPESGFADFVK..EVLDGKTPDPVSGVSVQLQNNIFSATLDLSTLG  1097

1101 LDRSYNQAEKSRRIKNMSVTLPALLGPYQDIEATLSLGGETVALSHGVDD  1150
     ||| |||||| :|||| |||||||||||||| |||||||||||||||||
1098 LDRFYNQAEKAHRIKNLSVTLPALLGPYQDIAATLSLGGETVALSHGVDD  1147

1151 SGLFITDLNDSRFLPFEGMDPLSGTLVLSIFHAGQDGDQRLLLESLNDVI  1200
     |||||||||||||||||||||||||||||| ||||||||||||||||||
1148 SGLFITDLNDSRFLPFEGMDPLSGTLVLSILHAGQDGDQRLLLESLNDVI  1197

1201 FHIRYVMK*  1209
     |||||||||
1198 FHIRYVMK*  1206
```

Fig. 7B

```
             501                                              550
tcaA2-1529  (500) AGTCGCTGATCCTCAATAATGACAATATGAACCGAGAGGTAT CTTCTCTG
tcaA1-1529  (485) AGTCGCTGATCCTCAATAATGACAATATGAACCGTGAGGTGT CTTCCCTG
  tcaA-W14  (485) AGGATCTGATATTAAGCGAAACGACGATGAATAAAGAGGTCA CTTCCCTT 551                                              600
tcaA2-1529  (550) GATATCCTTCTGGATGTGCT GCAGCCCGAAGGCTCTGACACGCTGACATC
tcaA1-1529  (535) GATATCCTGCTGGATGTGCT GCAGTCCGAAGGCTCCGGCACACTGACATC
  tcaA-W14  (535) GATATCTTGTTGGATGTGCT ACAAA---AAGGCGGTAAAGATATTACTGA
                    SB105
```

Fig. 11A

```
             1901                                             1950
tcaA2-1529  (1824) GATGCGCAGCACGGGTCTTTCCTTTGAGCAG TTGGATTGGCTGATTGCCA
tcaA1-1529  (1788) GGCGCGCAGCACGGGACTTTCCTTTGAGCAG TTGGATTGGCTGATTACCA
  tcaA-W14  (1809) ATCATCCCAGACCGGGCTATCATTTGAAGAA TTGGACTGGCTGATTGCCA
                                                                SB106
             1951                                             2000
tcaA2-1529  (1874) ATGCCAGCCGT GCCGTTATCGAACACGGTGGAGAGCTTTTTCTGGATAAG
tcaA1-1529  (1838) ATACCAGCCGT GCCGTAATCGAACATGGTGGAGAACTGATTCTGGATAAG
  tcaA-W14  (1859) ATGCCAGTCGT AGTGTGCCGGACCACCACGACAAAATTGTGCTGGATAAG
```

Fig. 11B

```
              1651                                              1700
tcaB2-1529 (1611) GGAGTGGGATGACACGTTGTCCCTGGCAACGACCGACCCGGACGAGATTG
  tcaB-W14 (1557) CGCATGGGATACCACACAGCCC---GCCACCACTGATCCAGATGTGATCG
tcaB1-1529 (1608) GGAGTGGGATGACACGTTGTCCCTGGCAACGACCGACCCGGACGAGATTG 1701                                              1750
tcaB2-1529 (1661) CGATGGCCGACCCGATGCAATACAAGCTGGCTATATTTATTCACACCATG
  tcaB-W14 (1604) CTATGGCGGACCCGATGCATTACAAGCTGGCGATATTCCTGCATACCCTT
tcaB1-1529 (1658) CGATGGCCGACCCGATGCAATACAAGCTGGCTATCTTTATTCACACCTTG
                  SB101
```

Fig. 12A

```
              2051                                              2100
tcaB2-1529 (1999) TGGGACAAAATCGATCTGCGTTTATACAATTTGCGCCACAATTTGAGTCT
  tcaB-W14 (1951) TGGGATAAACTTGAGTTACGCCTATACAACCTGCGCCACAATCTGAGTCT
tcaB1-1529 (1996) TGGGATAAAATCGACCTGCGTCTCTACAATTTACGCCACAATCTGAGCCT
                                                      SB102
              2101                                              2150
tcaB2-1529 (2049) GGACGGTCAGCCGCTTCATTTGCCGCTCTTTGCCGAACCGGTCAATCCGC
  tcaB-W14 (2001) GGATGGTCAACCGCTAAATCTGCCACTGTATGCCACGCCGGTAGACCCGA
tcaB1-1529 (2046) GGACGGTCAGCCGCTTCATTTGCCGCTCTTTACCGAACCGGTCAATCCTC
```

Fig. 12B

```
              2901                                              2950
tcaB2-1529 (2845) CTGCAAAGCACCCGCTTTACGAATCAAGCTTTGTATAACTGGATGGCTGG
  tcaB-W14 (2797) CTGCAAACCACTCGTTTTACCGGGCAGGCACTGTATAACTGGATGGCCGG
tcaB1-1529 (2842) CTGCTAAGCACCCGTTTTACGAATCAAGCTTTGTATAACTGGATGGCCGG
                                                      SB103
              2951                                              3000
tcaB2-1529 (2895) ACGTCTGTCGTCTCTATACTATCAAATGTATGACGCCGCATTGCCGCTCT
  tcaB-W14 (2847) TCGTCTCTCGCGCTCTATTACCAAATGTATGATTCCACTCTGCCAATCT
tcaB1-1529 (2892) ACGTCTGTCGTCTCTATACTATCAAATGTATGACGCCGCATTGCCGCTCT
```

Fig. 12C

```
                 2201                                                    2250
tcaC-1529  (2125) AGCTCGTTTTGGTAC CGAAGCTCCACCCAGTATTGGCTGGATGAGAAA CA
tcdB1-W14  (2149) CACACCTTGCATTAC CGTAGCTCTGTCCAGTTCTGGCTGGATGAAAAA GC
tcdB2-W14  (2128) CACACCTTGCGTTAC CGCAGTTCCTCCCAATTCTGGCTGGATGAAAAA GC
xptC1-Xwi  (2188) ACCACGCTGTATTAT CGCAGCTCTGCCCAGTTCTGGCTGGATGAGAAA TT
                                              SB215
```

Fig. 13A

```
                 4501                                                    4550
tcaC-1529  (4263) A TGGTTTACAGTAAACGAAGATGAAAATGATAC CATGGACTCATCATTAT
tcdB1-W14  (4380) G TGGTTTACCGTGAGTGAGGATGAGAATGATAC GGCCG-CTGATGCGCTG
tcdB2-W14  (4362) C TGGTTTACTGTCAATGAAGATGAAAATGACAC AGCCG-CTGAGGTGAAG
xptC1-Xwi  (4428) C TGGTTTGTGGTGAATGAAGATGAAAATGACAC TGCCG-GTGAAATGACA
                                      SB217
```

Fig. 13B

```
              1051                                                    1100
tccC-1529  (1027) TAT CGTTATGAATATGATCCGGTAGGCAAT ATCCTTTCTATTTACAATGA
tccC1-W14   (973) CTA CGCTATAAGTATGATCCGGTGGGGAAT GTTATCAGTATCCATAATGA
tccC2-W14   (940) TTA CGCTATCAATATGACCCGGTAGGCAAT GTGATCAATATCCGTAATGA
tccC3-W14   (961) CTG CGCTATGAATATGACCCGGTAGGCAAT GTCATCAGCATCCGTAATGA
tccC4-W14   (961) CTA CGCTATGAACATGATCCTGTAGGGAAT ATTATTAGTGTCCGTAATGA
tccC5-W14   (955) CTA CGCTATCAATATGACCCAGTAGGCAAT GTCATTAGTATCCGTAATGA
xptB1-Xwi   (973) CTG CGTTATGAATATGATCCTGTCGGAAAT GTGCTGAAATCAACTAATGA
                                   SB212
```

Fig. 14A

```
              1951                                                    2000
tccC-1529  (1903) TACAAGACCATC CGCTATTCAGGCAAAGAGCGGGATG CCACAGGCCTGTA
tccC1-W14  (1861) TACAAATTTATT CGTTACTCCGGTAAAGAGCGGGATG CCACTGGATTGTA
tccC2-W14  (1807) TATAAACGATT CGCTATTCCGGCAAAGAACGAGATG CCACCGGGTTGTA
tccC3-W14  (1849) TATAAACTATC CGTTATTCAGGCAAAGAGCGGGATG CCACCGGGCTATA
tccC4-W14  (1849) TACAAAATCCTC CGTTACTCAGGTAAAGAACGCGATG CTACCGGGCTCTA
tccC5-W14  (1822) TATAAAACCATT CGTTATTCTGGTAAAGAGCGGGATG TTACCGGGCTGTA
xptB1-Xwi  (1855) TACAAAACCGTG CGTTATTCTGGCAAAGAGCGGGATG CAACAGGGTTGTA
                                   SB213
```

Fig. 14B

SEQUENCE LISTING

<160> NUMBER OF SEQ ID NOS: 49

<210> SEQ ID NO 1
<211> LENGTH: 33521
<212> TYPE: DNA
<213> ORGANISM: Artificial Sequence
<220> FEATURE:
<223> OTHER INFORMATION: Nucleic acid sequence of the entire insert of SB12.

<400> SEQUENCE: 1

```
gatcacacgg ccggcgtatt ccggctcgga accgaagaat taacagaagc gcttcagcag     60
tccggttatc ggacagtctt tgatattgca tctgaaaatc ttgcggaatt tcagaaaagc    120
aatccggaga ttccctcttc cgacgcgaag gagattcatc aattagccgt ccagaggaca    180
gaaaacttat gcatgcttta taaggcctgg caactgcaca atgatccggt cgtccagagc    240
cttcccaaat tatccgcgga taccggcctg cgaggcatgc gtgccgcgtt ggagcggagt    300
cttggagggg gagccgattt tggagacttg ttcccggagc gatcgccaga gggctatgcg    360
gaagcctcct ctatacagtc gctttttttcg ccgggacgtt accttacggt gctgtataaa    420
attgcgcagg atctccacga cccaaaagac aaactgcata ttgacaaccg ccgtccagat    480
```

```
ttgaagtcgc tgatcctcaa taatgacaat atgaaccgtg aggtgtcttc cctggatatc       540
ctgctggatg tgctgcagtc cgaaggctcc ggcacactga catccctgaa ggatacctac       600
tatccgatga cccttcccta tgatgacgac cttgcgcaaa tcaatgccgt ggcggaggcg       660
cgctcatcca atttgctggg gatctgggat accctgctgg acacgcagcg gacttccatc       720
ctgcaggatt ccgccgctgt ccaccggata agcaagccgc ggcactcggc atacgtcaat       780
cagagagtct ccgatgatga accggtattg atcgcgggag aggaattcta cttggagacc       840
ggcggtgttg ccgacacgac cccgtctccg ccaacgaggg aagcgctttc cttgacgcca       900
aacagcttcc gtctgctggt caaccccgag ccgacagcag acgacatcgc caatcactac       960
aacgttaaga ctcaagatcc tgccgctctg ccgccgtctc taaatgtggt cgatgacttt      1020
tgcctgaaaa ccggtttgag ctttaatgag ttgctggact taacgatgca gaaggatgat      1080
gaatcgatcg gcagcgagta caaaagccgg tttgtaaaat ttggcggcga ggccaatgtt      1140
ccggtttcaa cctatggagc tgtatttctg acaggaacgg aagaaactcc gttgtgggta      1200
ggaaaaggag ctgtgataag ccctgcagcg gacgcctatg ttcgtaatgg gacatatgca      1260
aacacgaatt atggatcaga cactagtctt gttgtgaagc aggatgggtc tagtggatac      1320
agtagggaag catatatcag gtttgatttg acaggtcttt ccggagttgt ggaggaagct      1380
aaaatttctc taacaactag agcgaaacaa ttgtctagct taagacacca agctcatttg      1440
gtcagtgaca acagttggga tgaattgaaa atcacatgga ataacaaacc tgcaggagga      1500
gcgatcatcg caagctggga tgttcccgaa gttggtgaga atgtaaaggt tgatgtgacc      1560
cggcaagtaa atgatgcgct cgcaaacggt caagataaac tatcaattgt tattcgttct      1620
agtgcaaatt atggcagtct gggcgatgtc tcttatgcct ctagagaaca ccctgaaaaa      1680
gcctcacgac cttctatgga aatcaaggcg ataacgggtg ctggtttaaa ttttacggcg      1740
gataatgttg tagctctggc aggaaggggcg gaaaagcttg tccggctggc gcgcagcacg      1800
ggactttcct ttgagcagtt ggattggctg attaccaata ccagccgtgc cgtaatcgaa      1860
catggtggag aactgattct ggataagccg gtactggagt ctgtggccga attcacaagg      1920
ctccataagc gttatggcat cacagcggat atgttcgccg cgtttatcgg cgaagtcaat      1980
acgtatgctg aagcaggtaa agagagcttt tatcagacga ttttcagcac ggccgaccat      2040
tcggctgcct taccctttagg cgcaactttg caatttgagg tgagcaaaca ggatcgatat      2100
gaagcgattt gctgcggggc catggggggtg accgccgatg agttctctcg tatcggcaaa      2160
tactgctttg gcgacaacgc gcagcaagtt accgccaatg aaacaaccgt tgcgcagctt      2220
tatcgtttag gccgaattcc tcacatgctt ggattgcgtt ttaccgaggc ggagctgttg      2280
tggaaattga tggctggcgg cgaggatacc ttgctccgca cgattggcgc gaagcctcgc      2340
agtttacaag ccttagagat tattcgccgt actgaggtcc ttttggactg gatggatgct      2400
catcagcttg atgttgtctc cctgcaagcc atggttacca atcggtacag cggcacagcc      2460
acgccggagc tgtacaactt tttggcacag gtgcaccaat ccacaagcag tgccgcgaac      2520
gtgtccaaag cggatgctca ggatacccctg cccgcggaca agctgttccg ggccttggcg      2580
gtaggcttca acctgaaggc caacgtgatg gcgcaggtca ttgactggtt ggacaaaacc      2640 gacgagcgt ttacgctgcg ggctttctgg gacaagcttc aagcgtattt cagcgccgat      2700
catgaagaag aactgacggc cttggaagga gaagccgact tgctgcagtg gtgccaacag      2760
atcagccagt atgcgctcat tgtccgctgg tgcgggttaa gcgatcagga tctggcgctg      2820
ctgaccgggc atcccgggca gcttctgtcc ggacaacata cggtgccggt accctcgctg      2880
```

```
catctcctgc tggtgctgac ccgcctgaag gaatggcagc agcgcgtcca ggtttccagc    2940
gaggaggcca tgcgctattt tgcccaggcc gatgcgccaa ccgtcacacg cgatgctgcg    3000
gtcaagctgc ttgcccgtat ccatggctgg aatgaacagg ataccgcctc gatgaatgac    3060
tacctgctgg gagagaacga atatcctaag aactttgagc agatctttac tttggaaagc    3120
tgggtcaacc tgggccgtca actgaatgtt ggcagccgaa cgttgggaga gctggttgac    3180
atgtcagaag aggatgatac cgcggaaaac acggatttga ttatctcggt cgcccaaagc    3240
ctgatggctg cggtgcaggc ctgaaccaac atgaccaagg aaggtggtaa gaatatgtct    3300
acttcaaccc tgttgcaatt gattaaggaa tcccgccggg atgcgttggt caaccattat    3360
atcgccaaca atgtcccgag agagcttacg ataagatta cagacgcaga cagcctgtat     3420
gagtatttgc tgctggatac caagatcagt gaactcgtaa aaacatcgcc gatagctgag    3480
gccattagca gcgttcagtt atacatgaac cgatgcgtgg aaggctatga aggcaagctg    3540
actccggaag gcaacagcca tttcgggccg ggaaaattcc tgaataattg gataccctat    3600
aacaagcgtt attccacttg ggccggcaag gaacgtctga atattatgc aggcagttat     3660 attgacccgt ccttgcgcta taacaaaacg gatccgttcc tgaacctgga acagaatatc    3720
agccagggaa gaatcaccga tgacaccgta agaacgcgc tgcaacacta cctgactgaa     3780
tatgaagtgt tggcggattt ggaatatatc agcgtaaata aaggcgccga tgaaagtgta    3840
ttattcttcg taggccgcac caaaacaatg ccatacgaat attactggcg ccgattaacg    3900
ttgaaaaagg acaataacaa taaactggtg cctgccatct ggtctcaatg gaaaaaaata    3960
actgccaata tcggcgaagc agttaataat tatgtggtgc ttcactggca taataaccgc    4020
ttacatgtac aatggggttc tacagagaaa acacaaaatg atgacggaga acccattgag    4080
aaacgatatt tgaatgactg gttcatggat aagtccagtg tctggtcttc attccgaaag    4140
gtttcatata tagaaaatag ttttacttat actgagggca tcattgattc aagaaatatt    4200
actatagctg gaaatcaact gttctgtgat gattcaaata cttttaaggc aacaataacg    4260
gcacttccat ttgaccaaat acgtgtttac ttagaaaaga tttacggtac aggcggcagc    4320
atcacggtta ctgagaaaaa taaaggctat attattaagg tggggagcc aagagaagtc     4380 agtttctctc ctaatacgtt actagatgta ttcataggta gtaatgcaag ccctcgagac    4440
ccatatttca aagctacatt taatagagaa gctctccaaa attcatacgg ctcaattaaa    4500
ataaatcaat acaccctcc ttctggaagc aatatcaaag gtcctatcga ccttaccctg      4560
aaaaataaca tcgacctgtc ggcgttgttg gaagagagcc ttgacgtact gttcgactat    4620
accattcagg ggaataacca attgggcggc ttagaggcct taacgggcc ttacggactt     4680 tatttgtggg aaatcttcct ccatgttcca tttttaatgg cggttcgctt ccacaccgag    4740
cactgagaga tcccctcata atttccccaa agcgtaacca tgtgtgaata aattttgagc    4800
tagtagggtt gcagccacga gtaagtcttc ccttgttatt gtgtagccag aatgccgcaa    4860
aacttccatg cctaagcgaa ctgttgagag tacgtttcga tttctgactg tgttagcctg    4920
gaagtgcttg tcccaacctt gtttctgagc atgaacgccc gcaagccaac atgttagttg    4980
aagcatcagg gcgattagca gcatgatatc aaaacgctct gagctgctcg ttcggctatg    5040
gcgtaggcct agtccgtagg caggactttt caagtctcgg aaggtttctt caatctgcat    5100
tcgcttcgaa tagatattaa caagttgttt gggtgttcga atttcaacag gtaagttagt    5160
tgctagaatc catggctcct ttgccgacgc tgagtagatt ttaggtgacg ggtggtgaca    5220
atgagtccgt gtcgagcgct gatttttccg gcctttagag cgagatttat acaatagaat    5280
```

```
ttggcatgag attggattgc ttttagtcag cctcttatag cctaaagtct ttgagtgact    5340
agatgacata tcatgtaagt tgctgatagg tttccagttt tccgctccta ggtctgcata    5400
ttgtactttt cctcttactc gacttaacca gtaccaaccc agcttctcaa cggatttata    5460
ccatggcact ttaaagccag catcactgac aatgagcgt gtggtgttac tcggtagaat    5520
gctcgcaagg tcggctagaa attggtcatg agctttcttt gaacattgct ctgaaagcgg    5580
gaacgctttc tcataaagag taacagaacg accgtgtagt gcgactgaag ctcgcaatac    5640
cataagccgt ttttgctcac ggatatcaga ccagtcaaca agtacaatgg gcatcgtatt    5700
gcccgaacag ataaagctag catgccaacg gtatacagcg agtcgctctt tgtggaggtg    5760
acgattacct aacaatcggt cgattcgttt gatgttatgt tttgttctcg ctttggttgg    5820
caggttacgg ccaagttcgg taagagtgag agttttacag tcaagtaagg cgtggcaagc    5880
caacgttaag ctgttgagtc gttttaagtg taattcgggg cagaattggt aaagagagtc    5940
gtgtaaaata tcgagttcgc acattttgtt gtctgattat tgattttttgg cgaaaccatt    6000
tgatcatatg acaagatgtg tatctacctt aacttaatga ttttgataaa aatcattagg    6060
ggattcatca gcaccgagca gcggtatgag ttggcggaac gatggtttaa attcattttc    6120
aacagcgcag gttaccgtga tggctacggc aatctgctga cggatgacaa aggcaacgtg    6180
cgctactgga acgtcgtgcc tctgcaggag gatacggagt gggatgacac gttgtccctg    6240
gcaacgaccg acccggacga gattgcgatg gccgacccga tgcaatacaa gctggctatc    6300
tttattcaca ccttggactt cttgatcagc cgcggcgaca gcttgtaccg gatgctggag    6360
cgggatacct tgaccgaagc gaagatgtat tacattcagg ccagccaact gcttgggcct    6420
cgtcccgaga tccggatcaa tcacagctgg cctgatccga ccctgcaaag cgaagcggac    6480
gcggtaaccg ccgtgccgac gcgaagcgat tcgccggcag cgccaattct cgccttgcga    6540
gcgcttctga atgcggaaaa cgggcatttc ctgccgcctt ataatgatga actattagct    6600
ttctgggata aaatcgacct gcgtctctac aatttacgcc acaatctgag cctgacggt     6660
cagccgcttc atttgccgct ctttaccgaa ccggtcaatc ctcgtgagct gcaggttcag    6720
catggggcag gcgatggatt aggggaagc gccggttccg tccaaagccg tcaaagtgtc     6780
tatcgttttc ctctggtcat cgataaggcg cgcaatgccg cgagtagtgt atccaattc     6840
gggaatgccc tggaaaacgc gctgacaaag caggacagcg aggccatgac tatgctgttg    6900
caatcccagc agcagattgt cctgcagcaa acccgcgata ttcaggagaa gaacctggcc    6960
tcgctgcaag caagtctgga agcaacgatg acagccaaag cgggcgcgaa atcccgaaag    7020
acccattttg ccggcctggc ggataactgg atgtcgcata atgaaaccgc ctcacttgca    7080
ctgcgtacca ctgcgggaat tatcaataca agctcgaccg tgccaatcgc tatcactggc    7140
ggcttggata tggctccgaa catttttggt ttcgcagttg gaggttcccg ctggggagca    7200
gccagcgcg ctgtagccca aggattgcaa atcgccgccg gcgtaatgga acagacggcc      7260
aatatcatcg atatcagcga aagctaccgc cggcgccggg aggattggct gctgcagcgg    7320
gatgttgccg agaatgaagc ggcgcagttg gattcgcaga ttgcgccct gcgggaacag     7380
atggatatgg cgcgaaaaca acttgcgctg gcggagacgg aacaggcaca cgcgcaagcg    7440
gtctacgagc tgctaagcac ccgttttacg aatcaagctt tgtataactg gatggccgga    7500
cgtctgtcgt ctctatacta tcaaatgtat gacgccgcat tgccgctctg cttgatggcc    7560
aaacaggctt tagagaaaga aatcggcaat gataaaacgg ttggaatctt cacccctccg    7620
gcctggaatg atttgtatca gggattgcta gcgggcgagg cgctgctgct cgagcttcag    7680
```

```
aagctggaga atctgtggct ggaggaggac aagcgcggaa tggaagctgt aagaacggta    7740 tcttttagata cccttctccg caaagaaaag ccagaatccg gttttgcaga tttcgtcaag   7800
gaagttctgg acggaaagac gcctgaccct gtaagcggag ttagcgtaca gctgcaaaac   7860
aatattttca gtgcaaccct tgacctgtcc acccttggcc tggatcgctt ttacaaccaa   7920
gcggaaaagg cccacaggat caaaaacctg tcggttacct tacccgcgct attgggacct   7980
tatcaggata ttgcggcaac cttatcgcta ggtggcgaga ccgttgcgct ttcccatggc   8040
gtggatgaca gcggcttgtt tatcacggat ctcaacgaca gccgtttcct gcctttcgag   8100
ggtatggatc ctttatccgg cacactcgtt ctgtcgatac tccatgccgg gcaagacggt   8160
gaccagcgcc tcctgctgga aagcctgaac gacgtcatct tccacattcg atatgtcatg   8220
aaatagaaga caaactcccg cgaaatagtt caaccgcggg agttctttat tttccaccca   8280
aatcattgac ataaatatac tttaataata tgttggagga agaagaggag gttgttattg   8340
gtgagaataa agaaaatgtt tgaagtagcg atgatgttat cattggcgtg tttgtttttt   8400
gttacatcag ctgcttcagc aaaaacaact aatttaactt cttccccgaa acttatgaac   8460
tgctttgatg tagctggtaa cgtaacctac aaaaccgctc ctgatggttc aattacgaaa   8520
ataatcgaag tacaagatgt tagtaaattc agtgaacaaa ccaatctcag gttggctcca   8580
gattctaaag ttaccattta tattcctgac tccagtgaca ataaccagcc caattactcc   8640
aataataatt ccaatgacta tagtgaacaa aattacctca atactaaccc caacgttgaa   8700
ccatttgttg aacctttgt tgaacttata agtatattg cgaacgtaag tgatccatat    8760
gaagcgtgtg atcaaaatc gattagagat tctgattatg atcctcccgg cggaaaaatg    8820
ataataaaac aagggataca ggctacacac tcaaccacgg tttctatcga tgccaaaatc    8880
gtttcaactg ccttaaaata tgatgtaaca acgagttatt ccattgaaga ggagcaaaat    8940
attaaagtac cagacaataa agaggaagaa attattgctt atccaaagta tgatgtcaac    9000 accttttgaaa tatgggaagc tggtctaata tataataaaa agattggaga cggtacggct    9060
ttctatccta aaggagtatg ttttgttaca attattaatt aactttcaaa taagagaagc    9120
tgtttcttaa gaataaagaa gcagcttctt gcattttta ttatgatatt acactctatc    9180
ttctgtcaga tgctccctct caacttccat tcccaatccc ctcttcttaa aaggccataa    9240
aagttacact tatcatttcc gtcattgcta atctaccttg cagttaacct aaaatatacc    9300
ttccgggatt cctgaaggat gaaacatatt ttcacccatc agtgaaacta tctatgcttt    9360
tttgattgaa gcgagaggta tgcttgggtt gtaaatgaaa ggggggacct gttcatggaa    9420
aactacctaa aacggtaacg gatagcttct atggttttga tgtctgcagt cattttgtct    9480
tggggagtac tcatcattca gaacacaaga ggaggagttc atggtgtcaa caacagacaa    9540
cacggccggc gtattccggc tcggaaccga agaattaaca gaagcgctta agcagtccgg    9600
ttatcggacc gtctttgata ttgtatctga caatcttgcg gaatttcaga aaacaatcc    9660 ggagattccc tcttctgacg cgaaggagat tcatcaatta gccgtccaga ggacagaaaa    9720
cttatgcatg ctttataagg cctggcagct gcacaatgat ccggttgtcc agagccttcc    9780
caaattatcc gcggataccg gcctgcaagg catgcgtgcc gcgttggagc ggagtcttgg    9840
aggcggagcc gatttggag acttgttccc ggagcgatcg ccagggggct atgcggaagc    9900
ctcctctata cagtcgcttt tctcgccggg acgttacctg acggtgctgt ataaaattgc    9960
gcgggatctc cacgacccaa aagataaact gcatattgac aaccgccgtc cagatttgaa   10020
gtcgctgatc ctcaataatg acaatatgaa ccgagaggta tcttctctgg atatccttct   10080
```

```
ggatgtgctg cagcccgaag gctctgacac gctgacatcc ttgaaggata cctaccatcc   10140
gatgacccTt ccctatgatg acgaccTtgc gcaaatcaat gccgtggcgg aggcgcgttc   10200
atctaatttg ctggggattt gggatacccT gctggacacg cagcggacTt ccatcctgca   10260
gaattccgcc gctgcccgcc ggataagcaa ggcgcggcac tcggcatacg ccaatcagaa   10320
agcctccaat gatgagccgg tattcatcac gggagaggaa atctacctgg aaaccggagg   10380
taaacggcTt tttctggcgc ataaactcga gataggttca actattagcg ctaaaatcaa   10440
cattggaccg ccgcaagcgg ccgatatcgc gccggcaaag ttgcaactcg tatattacgg   10500
cagaggcgga agagggaact acttcctgcg cgtggcagac gatgtgtccc tcggtggaaa   10560
gctgctgacc aattgttatc tgaccagcga tgacggacag agcaacaata ttagcgggcc   10620
atactgccta atgatcaacc gaggcaccgg cagcatgcct agcgggactc accttccagt   10680
tcagattgaa agagtgaccg atacatccat ccgcattttt gtgccggatc acggctattt   10740
ggggctaggc gaaagccttg ccagcaactg gaatgaaccg ttggcgctga atctgggctt   10800
ggatgaagcg ttgacctTta ccttgagaaa gaaggagacg ggaaatgaca ccatttccat   10860
aatcgacatg ctgccgccgg tagcgaacac gactccgtct ccgccgacga gggaaacgct   10920
ttccttgacg ccaaacagct tccgtctgct ggtcaaccct gagccgacag cggaggacat   10980
cgccaagcac tacaacgtca cgacggtaac ccgggctcct gccgatctgg cctccgcctt   11040
aaatgttgtc gatgatttct gcttgaaaac cggTttgagc tttaacgaat tgctggattt   11100
aaccatgcag aaggattatc agtcaaaaag cagtgagtac aaaagccgat tgtaaaatt   11160 cggcggcggg gagaatgttc cggtatcaag ctatggcgca gcctttctga caggagcgga   11220
agatactcct ttgtgggtga acagtataa cagcgtgggg actgcaacaa gcacccctgt   11280
tttaaactTt acgccagata tgttgtggc tttggcagga agggcggaaa agcttgtccg   11340
gctgatgcgc agcacgggtc tttcctttga gcagttggat tggctgattg ccaatgccag   11400
ccgtgccgtt atcgaacacg gtggagagct ttttctggat aagccggtac tggaagctgt   11460
ggccgaattc acaaggctca ataagcgtta tggcgtcaca tcggatatgt cgccgcgtt   11520 tatcggcgaa gtcaatacgt atacagaagc gggcaaggac agcttttatc aggcgagtTt   11580
cagcacggcc gaccattcgg ctaccTtacc tttgggcgct tctttgcaac ttgaggtgag   11640
caagcaggat cgatatgaag cgatttgctg cggggctatg ggggtgaccg ccgatgagtt   11700
ctcccgtatc ggcaaatact gcTttgggga taaagcacag caaatcacgg ccaatgaaac   11760
aaccgttgcc cagctttatc gtttaggccg aattcctcat atgctaggct tgcgttttac   11820
cgaggcagag ctgttgtgga aattgatggc tgggggcgag gataccttgc tccgcacgat   11880
tggcgcgaac cctcgcagTt tagaagcgtt agagattatt cgccgacgg aggtccttTt   11940 ggactggatg gatgcccatc agctggatgt tgtctcccTg caagccatgg ttaccaatcg   12000
gtacagcgga acagccacgc cggagctgta aatttTtTtg gcacaggtgc atcaatccgc   12060
aagcagtgcc gcgaacgtgg ccagagcgga tggTcaggaT acgTtgcctg cggacaagct   12120
gctccgggca ttggcggcgg gcTtcaaact gaaagccaac gtgatggcgc gagtaatcga   12180
ctggatggac aaaaccaata aagcgtttac gctgcgggct ttctgggaca gcTtcaagc   12240 gtatttcagc gccgatcatg aagaagaact gaccgccctg gaaggagaag ccgcaatgct   12300
gcagtggtgc cagcagatca gccagtatgc gctcattgtc cgctggtgcg ggTtaagcga   12360
gcaggatctg gcgctgctga ccgggaatcc ggagcagcTt ctggacggac aacatacggt   12420
gcccgtaccc tcgctgcatc tcctgctggt gctgacccgc ctgaaggaat ggcagcagcg   12480
```

```
cgtccaggtt tccagcgagg aggctatgcg ctattttgcc caggccgatt cgccaaccgt   12540
cacgcgcgac gatgcggtta atctgcttgc ccgtatccat ggctggaatg aagcggatac   12600
cgtctcgatg aatgactacc tgctgggaga gaacgaatat cctaagaact ttgatcagat   12660
ctttgcactg gaaagctggg tcaacctggg ccgtcaactg aacgtgggca gcagaacgct   12720
gggagagctg gttgacatgg ctgaagagga taaaaccgcg gaaaacatgg atctgattac   12780
ttcggtggcc catagcctga tggctgcagc gaaagcctga accaacatga ccaaggaagg   12840
tgataagcat atgtctactt caaccctgtt gcaatcgatt aaagaagccc gccgggatgc   12900
gctggtcaac cattatattg ctaatcaggt tccgacagcg cttgcggaca agattacgga   12960
cgcggacagc ctgtatgagt acttgctgct ggataccaag atcagtgaac tcgtaaaaac   13020
atcgccgata gcggaggcca tcagcagcgt gcagttatac atgaaccgct gcgtcgaagg   13080
ctatgaaggc aagttgactc cggaaagtaa tactcatttt ggcccaggta aatttctata   13140
taactgggat acgtacaaca aacgtttttc cacctgggca ggaaaagaac gcttgaaata   13200
ttatgcaggc agctatattg agccgtcctt gcgctacaac aaaaccgatc cattcctgaa   13260
cctggaacag agcatcagcc agggaagaat tactgatgat accgtaaaga acgcgctgca   13320
acactacctg actgaatatg aagtgttggc ggatctggat tatatcagcg ttaataaagg   13380
cggcgacgaa agtgttttac tctttgttgg acgcaccaaa accgtaccgt atgaatacta   13440
ctggcgccgt ttgcttttaa aaagggacaa taataataag ctagtaccag cagtctggtc   13500
tcagtggaaa aaaatcagtg ccaatatcgg tgaagcggtt gatagttatg tggtgcctcg   13560
gtggcataaa aaccggctac atgtgcaatg gtgttctata gagaaaagtg aaaatgatgc   13620
cggtgaaccc attgagaaac gatatttgaa tgactggttc atggatagtt ccggagtctg   13680
gtcttcattt cgaaagattc cggttgtgga aaagagtttc gaatatttgg acggaagcct   13740
cgatccccga tttgtcgctc ttgttagaaa tcaaatatta attgatgagc agaaatatt   13800 cagaattaca gtatcagccc ctaatccgat agatgcaaat ggaagagtag aggtacattt   13860
tgaagaaaac tatgcaaaca gatataatat taccattaaa tatgggacaa cgagtcttgc   13920
tattcctgca gggcaggtag ggcatccaaa tatctctatt aatgaaacat aagggttga   13980 attcggcacc aggccggatt ggtattatac tttcagatat ttaggaaata caatccaaaa   14040
ctcatacggt tcaattgtca ataatcaatt ttcacctcca tcaggaagca atattaaagg   14100
tcctatcgac cttaccctga aaaataacat cgacctgtcg gccttgttgg atgagagcct   14160
tgacgcactg ttcgactata ccattcaggg cgataaccaa ttgggcggct agctgccttt   14220
taacgggcct tacggacttt acttgtggga atcttcttc catgttcctt ttttaatggc   14280
ggttcgcttc cacaccgagc agcggtatga gttggcggaa cgttggttta aattcatctt   14340
caacagcgca ggataccgtg atgattacgg cagtctgctg acggatgaca aaggcaacgt   14400
gcgttactgg aacgtgatac cgctgcaaga ggacacggag tgggatgaca cgttgtccct   14460
ggcaacgacc gacccggacg agattgcgat ggccgacccg atgcaataca agctggctat   14520
atttattcac accatggact tcctgatcag ccgcggcgat agcttgtacc ggatgctgga   14580
gcgggatacc ctggccgaag ccaagatgta ttacattcag gccagccaac tgcttgggcc   14640
ccgccccgac atccggctca atcacagttg gcctaatccg accttgcaaa gcgaagcgga   14700
cgcggtaacc gccgtgccga cgcgaagcga ttcgccggca gcgccaattt tggccttgcg   14760
agcgcttctg acaggcgaaa acggtcattt cctgccgcct tataatgatg aactgttcgc   14820
tttctgggac aaaatcgatc tgcgtttata caatttgcgc cacaatttga gtctggacgg   14880
```

```
tcagccgctt catttgccgc tctttgccga accggtcaat ccgcgtgaat tgcaggttca    14940
gcatggcccg ggcgatggct tgggggggaag cgcgggttcc gcccaaagcc gtcagagtgt    15000
ctatcgtttt cctctggtca tcgataaggc gcgcaatgcg ccaacagtg tcatccaatt    15060 cggcaatgcc ctggaaaacg cactgaccaa gcaagacagc gaagcaatga ccatgctgtt    15120
gcagtcccag cagcagattg tcctgcagca aacccgcgat attcaggaga gaacctggc    15180 cgcgctgcaa gcaagtctgg aagcaacgat gacagcgaaa gcggggcgg agtcccggaa    15240 gacccatttt gccggcttgg cggacaactg gatgtcggac aatgaaaccg cctcactcgc    15300
actgcgtacc accgcgggaa tcatcaatac cagctcaacc gtgccgatcg ccatcaccgg    15360
cggcttggat atggctccga acattttgg tttcgcagtt ggaggttccc gctggggagc    15420
agccagcgcg gctgtagccc aaggattgca atcgccgcc ggcgtaatgg aacagacggc    15480
caatattatc gatattagcg aaagctaccg ccggcgccgg gaggattggc tgctgcagcg    15540
ggatgttgcc gaaaatgaag cggcgcagtt ggattcgcag attgcggccc tgcgggaaca    15600
gatggatatg gcgcgcaagc aacttgcgct ggcggagacg gaacaggcgc acgcgcaagc    15660
ggtctacgag ctgcaaagca cccgctttac gaatcaagct ttgtataact ggatggctgg    15720
acgtctgtcg tctctatact atcaaatgta tgacgccgca ttgccgctct gcttgatggc    15780
gaagcaggct ttagagaaag aaatcggttc ggataaaacg gtcggagtct tgtccctccc    15840
ggcctggaat gatctatatc agggattatt ggcgggcgag gcgctgctgc tcgagcttca    15900
gaagctggag aatctgtggc tggaggaaga caagcgcgga atggaagccg taaaaacagt    15960
ctctctggat actcttctcc gcaaaacaaa tccgaactcc gggtttgcgg atctcgtcaa    16020
ggaggcactg gacgaaaacg gaaagacgcc tgacccggtg agcggagtcg gcgtacagct    16080
gcaaaacaat attttcagcg caaccttga cctctccgtt cttggcctgg atcgctctta    16140
caatcaggcg gaaaagtccc gcaggatcaa aatatgtcg gttaccttac ctgcgctatt    16200
ggggccttac caggatatag aggcaacctt atcgctaggc ggcgagaccg ttgcgctgtc    16260
ccatggcgtg gatgacagcg gcttgttcat cactgatctc aacgacagcc ggttcctgcc    16320
tttcgagggc atggatccgt tatccggcac actcgtcctg tcgatattcc atgccgggca    16380
agacggcgac cagcgcctcc tgctggaaag tctcaatgac gtcatcttcc acattcgata    16440
tgttatgaaa tagcttttaca gtcagatata ttccgggggct tgtattcaca agcccctcca    16500
aggaggaatt gggttatgcc acaatctagc aatgccgata tcaagctatt gtcgccatcg    16560
ctgccaaagg gcggcggttc catgaaggga atcgaagaaa acatcgcggc tcccggctcc    16620
gacggcatgg cacgttgtaa tgtgccgctg ccggtaacct ccggccgcta tattactcct    16680
gatataagcc tgtcctatgc gagcggccac ggcaacggcg cttatggaat gggctggacg    16740
atgggagtga tgagcattag ccggagaaca agccgaggga cccccagtta tacatccgaa    16800
gaccagttcc ttggtccgga tggggaggtg cttgttccgg aaagcaacga acaagggag    16860 atcattaccc gccacaccga tacggcccaa gggataccgt taggcgagac gtttacggtt    16920
acacgctatt ttccccggat cgagagcgct tttcatttgc tggaatactg ggaagcgcaa    16980
gcaggaagcg caacagcgtc gttttggctt attcactctg ccgatggagt gctgcactgt    17040
ctgggtaaaa ctgctcaggc gaggatagcc gcccctgacg attccgccaa gatcgcagaa    17100
tggctagtgg aggagtccgt ctccccttc ggagagcata tttattacca atacaaagaa    17160
gaagacaatc aaggcgtgaa tctgaggaa gacaatcatc aatatggggc gaaccgctat    17220
ctgaaatcga ttcgctatgg aaataaggtt gcctctcctt ctctctatgt ctggaagggg    17280
```

```
gaaattccgg cagacggcca atggctgtat tccgttatcc tggattatgg cgagaacgat   17340
acctcagcgg atgttcctcc cctatacacg ccccaagggg agtggctggt gcgcccggac   17400 cgttttccc gctatgacta cggatttgag gtccggactt ccgcttgtg ccgccaggtc     17460 ttgatgttcc acgtctttaa ggagcttggc ggggagccgg cgctggtgtg gcggatgcag   17520
ttggaatacg acgagaaccc ggcggcgtcc atgctgagcg cggtccggca attggcttat   17580
gaagcagatg gggccattcg aagcttgccg ccgctggaat tcgattatac tccatttggc   17640
atcgagacaa cggccgattg gcagccttt ctgcctgtgc ctgaatgggc ggatgaagaa    17700
cattatcagt tggtcgattt gtacggagaa ggcataccgg gcttattata tcagaacaat   17760
gaccactggc attatcgttc gcccgcccgg ggcgacacac cggacgggat cgcctataac   17820
agctggcggc cgcttcctca tatccccgtg aactcccgga acgggatgct gatgatctg    17880 aatggagacg ggtatctgga atggttgctt gcggaacccg gggttgcggg cgctatagc    17940 atgaacccgg ataagagctg gtccggtttt gtgccgctcc aggcactgcc aacggaattc   18000
ttccatccgc aggcacagct tgccaatgtt accggatcgg gtttaaccga cttggttatg   18060
atcggtccga gagcgtccg gttttatgcc ggagaagaag cgggcttcaa gcgcgcatgt    18120
gaagtgtggc agcaagtggg cattactttg cctgtggaac gcgtggataa aaaggaactg   18180
gtggcattca gcgatatgct gggatcgggt cagtctcatc tggtgcgcat ccggcatgat   18240
ggcgttacat gctggcctaa tctggggaac ggcgtgttcg gggcgccgtt ggcccttcac   18300
gggtttacgg catcggagcg ggaattcaat ccggaacgtg tatatcttgt ggaccttgat   18360
ggatccggcg cttccgatat catttatgct tctcgtgacg ctctactcat ttaccgaaat   18420 cttccggca atggctttgc tgatccggtg cgggttccgc tgcctgacgg cgtgcggttt    18480
gataatctgt gccggctgct gcctgccgat atccgcgggt taggtgtggc cagtctggtg   18540
ctgcatgtac cttacatggc cccccgcagt tggaaattag atttctttgc ggcgaagccg   18600
tatttattgc aaacggtcag caacaatctt ggagcttcca gctcgttttg gtaccgaagc   18660
tccacccagt attggctgga tgagaaacag gcggcctcat cggctgtctc cgctttgccc   18720
ttcccgataa acgtggtatc ggatatgcac acggtggacg aaatcagcgg ccgcaccagg   18780
actcagaagt atacttaccg ccatggcgtg tatgaccgga ccgaaaagga atttgccgga   18840
ttcggccgca ttgacacatg ggaagaggag cgggattccg aaggaaccct gagcgtcagc   18900
actccgcccg tgctgacgcg gacctggtat cataccgggc aaaagcagga tgaggagcgt   18960
gccgtgcagc aatattggca aggcgaccct gcggcttttc aggttaaacc cgtccggctt   19020
actcgattcg atgcggcagc ggcccaggat ctgccgctag attctaataa tgggcagcaa   19080
gaatactggc tgtaccgatc attacaaggg atgccgctgc ggactgagat ttttgcggga   19140
gatgttggcg ggtcgcctcc ttatcaggta gagagcttcc gttatcaagt gcgcttggtg   19200
cagagcatcg attcggaatg tgttgccttg cccatgcagt tggagcagct tacgtacaac   19260
tatgagcaaa tcgcctctga tccgcagtgt tcacagcaga tacagcaatg gttcgacgaa   19320
tacggcgtgg cggcacagag tgtaacaatc caatatccgc gccgggcaca gccggaggac   19380
aatccgtacc ctcgcacgct gccggatacc agctggagca gcagttatga ttcgcagcaa   19440
atgctgctgc ggttgaccag gcaaaggcaa aaagcgtacc accttgcaga tcctgaaggc   19500
tggcgcttga atattcccca tcagacacgc ctggatgcct tcatttattc tgctgacagc   19560
gtgcccgccg aaggaataag cgccgagctg ctggaggtgg acggcacgtt acgatcttcg   19620
gcgctggaac aggcttatgg cggccagtca gagatcatct atgcgggcgg gggcgaaccg   19680
```

```
gatttgcgag ccctggtcca ttacaccaga agcgcggttc ttgatgaaga ctgtttacaa    19740
gcctatgaag gcgtactgag cgatagccaa ttgaactcgc ttcttgcctc ttccggctat    19800
caacgaagcg caagaatatt gggttcgggc gatgaagtgg atattttgt cgcggaacaa     19860 ggatttaccc gttatgcgga tgaaccgaat tttttccgta ttctggggca acaatcctct    19920
ctcttgtccg gggaacaagt attaacatgg gatgataatt tctgtgcggt tacatccatc    19980
gaagacgcgc ttggcaatca aattcagatt gcatatgatt accgctttgt ggaggccatc    20040
cagattaccg atacgaataa taatgtgaat caggtcgccc tggatgctct cggccgggtc    20100
gtatacagcc ggacctgggg cacggaggaa gggataaaga ccggcttccg cccggaggtg    20160
gaattcgcga cgcccgagac aatggagcag gcgcttgccc tggcatctcc cttgccggtt    20220
gcatcctgct gtgtatatga tgcgcatagc tggatgggaa cgataactct tgcacaactg    20280
tcagagcttg ttccagatag tgaaaagcaa tggtcgttct tgatagacaa tcgcttgatt    20340
atgccggacg gcagaatcag atcccgcggt cgggatccat ggtcgcttca ccggctattg    20400
ccgcctgctg tgggcgaatt gctgagcgag gcggaccgta aaccgccgca tacggtaatt    20460
ttggcagcag atcgttaccc ggatgaccca tcccagcaaa ttcaggcgag catcgtgttt    20520
agcgatggct ttgggcgtac gatacaaact gctaaaagag aagatacccg atgggcgatt    20580
gcggaacggg tggactatga cggaaccgga gccgtaatcc gcagcttca gccttttat      20640 cttgacgact ggaattatgt gggcgaagag gctgtcagca gctctatgta cgcaacgatc    20700
tattattatg atgctctggc acgacaatta aggatggtca acgctaaagg atatgagagg    20760
agaactgctt tttacccatg gtttacagta aacgaagatg aaaatgatac catggactca    20820
tcattatttg cttcaccgcc tgcgcggtga gatggaggtt aaacctatga acacaacgtc    20880
catatatagg ggcacgccta cgatttcagt tgtggataac cggaacttgg agattcgcat    20940
tcttcagtat aaccgtatcg cggctgaaga tccggcagat gagtgtatcc tgcgaacac     21000 gtatacgccg ttaagctatc ttggcagcag catggatccc cgtttgttct cgcaatatca    21060
ggatgatcgc ggaacaccgc cgaatatacg aaccatggct tccctgagag gcgaagcgct    21120
gtgttcggaa agtgtggatg ccggccgcaa ggcggagctt tttgatatcg aggggcggcc    21180
cgtctggctt atcgatgcca acggcacaga gacgactctc gaatatgatg tcttaggcag    21240
gccaacagcc gtattcgagc aacaggaagg tacggactcc ccccagtgca gggagcggtt    21300
tatttatggt gagaaggagg cggatgccca ggccaacaat ttgcgcggac aactggttcg    21360
ccactacgat accgcgggcc ggatacagac cgacagcatc tccttggctg gactgccgtt    21420
gcgccaaagc cgtcaactgc tgaaaaattg ggatgaacct ggcgactgga gtatggatga    21480
ggaaagcgcg tgggcctcgt tgctggctgc cgaagcttat gatacgagct ggcggtatga    21540
cgcgcaggac agggtgctcg cccaaaccga cgccaaaggg aatctccagc aactgactta    21600
caatgacgcc ggccagccgc aggcggtcag cctcaagctg caaggccaag cggagcaacg    21660
gatttggaac cggatcgagt acaacgcggc gggtcaagtg gatctcgccg aagccgggaa    21720
tggaatcgta acggaatata cttacgagga aagcacgcag cggttaatcc gaaaaaaaga    21780
ttcccgcgga ctgtcctccg gggaaagaga agtgctgcag gattatcgtt atgaatatga    21840
tccggtagga aatatccttt ctatttacaa tgaagcggag ccggttcgtt atttccgcaa    21900
tcaggccgtt gctccgaaaa ggcaatatgc ctacgatgcc ttgtatcagc ttgtatctag    21960
ttcggggcgg gaatccgacg cgcttcggca gcagacgtcg cttcctccct tgatcacgcc    22020
tatccctctg gacgatagcc aatacgtcaa ttacgctgaa aaatacagct atgatcaggc    22080
```

```
gggcaattta atcaagctta gccataacgg ggcaagtcaa tatacaacga atgtgtatgt    22140
ggacaaaagc tcaaaccggg ggatttggcg gcaaggggaa gacatcccgg atatcgcggc    22200
ttcctttgac agagcaggca atcaacaagc tttattcccg gggagaccgt tggaatggga    22260
tacacgcaat caattaagcc gtgtccatat ggtcgtgcgc gaaggcggag acaacgactg    22320
ggaaggctat ctctatgaca gctcgggaat gcgtatcgta aaacgatcta cccgcaaaac    22380
acagacaacg acgcaaacgg atacgaccct ctatttgccg ggcctggagc tgcgaatccg    22440
ccagaccggg gaccgggtca cggaagcatt gcaggtcatt accgtggatg agggagcggg    22500
acaagtgagg gtgctgcact gggaggatgg aaccgagccg ggcggcatcg ccaatgatca    22560
gtaccggtac agcctgaacg atcatcttac ctcctcttta ttggaagttg acgggcaagg    22620
tcagatcatt agtaaggaag aattttatcc ctatggcggc acagccctgt ggacagcccg    22680
gtcagaggta gaggcaagct acaagaccat ccgctattca ggcaaagagc gggatgccac    22740
aggcctgtat tattacggac accgctacta tatgccatgg ttgggtcgct ggctgaatcc    22800
ggacccggcc ggaatggtag atggactaaa cctgtaccgt atggtcagga acaatcctat    22860
aggactgatg gatccgaatg ggaatgcgcc aatcaacgtg gcggattata gcttcgtgca    22920
tggtgattta gtttatggtc ttagtaagga aagaggaaga tatctaaagc tatttaatcc    22980
aaactttaat atggaaaaat cagactctcc tgctatggtt atagatcaat ataataataa    23040
tgttgcattg agtataacta accaatataa agtagaagaa ttgatgaaat ttcaaaaaga    23100
cccacaaaaa gccgcacgga aaataaaggt tccagaaggg aatcgtttat cgaggaacga    23160
aaattatcct ttgtggcacg attatattaa cattggagaa gctaaagctg catttaaggc    23220
ctctcatatt ttccaagaag tgaaggggaa ttatgggaaa gattattatc ataaattatt    23280
attagacaga atgatagaat cgccgttgct gtggaaacga ggcagcaaac tcgggctaga    23340
aatcgccgct accaatcaga gaacaaaaat acactttgtt cttgacaatt taaatatcga    23400
gcaggtggtt acgaaagagg gtagcggcgg tcagtcaatc acagcttcgg agctccgtta    23460
tatttatcga aatcgcgaaa gattgaacgg gcgtgtcatt ttctatagaa ataatgaaag    23520
gctagatcag gctccatggc aagaaaatcc ggacttatgg agcaaatatc aaccgggtct    23580
tagacaaagc agcagttcaa gagtcaaaga acgagggatt gggaactttt tccgccggtt    23640
ttcaatgaag agaaagtagc atgtaactaa aattgctccc cattggttgt gtaaactaat    23700
ggggagttgt gattcactcc tgttcaacgc cattcatgta gaattgtttt gggaggttaa    23760
accgattgga tgccggcccc aaggcggagc ttttgatac cgaggggctt cgagtgtggc    23820
ttatcgatat caacggcaca cagacgactc tcgaatatga tgtattaggc aggcctgcag    23880
ccgtattcga gcatcaggaa ggcaaggaat ttcctaagtg ccgggatcgg tttagaatga    23940
gtctgatgcc aagccaacaa tttgcgaggg cagttgatgc gccactacga tacaatcccg    24000
ttacattcct tgataataag gggcttaaaa tcgtaattac cctaagtctc gtcgaggttg    24060
ctatagaatt gtatcgtctt catggtggcg ttcttttgct tcataatagt acgtgctgct    24120
agaattgtgc aggacgtcgc acattgctga tgtaaatgta tgtcttttc ttggaatagt    24180 agatccgctc cttgttctga tgtgttcatt ctactagccc ttatttttc tggccaacta    24240 agtcctatat ataattataa aaaaagcata gatatcttca tctataggtg aggatatcta    24300
tgcttttcat tttttgatta gagatatact tgtagtgcaa ggaaaagtag ataggagggt    24360
gaatttaaca gaagttacaa actgttgttt acttaaaaaa ttaatatgga gggaaataaa    24420
tatgaactca aatgaaccaa atttatctga tgttgttaat tgtttaagtg accccaatag    24480
```

```
tgacttggag aagtctggcg gtggagtagc gctagatgtt ggaatgtcat tgatatccga   24540
acttcttggt acggttccag ttgctggatc aattcttcaa tttgtattcg ataaattgtg   24600 gtttatttttt ggcccttctg agtgggactc acttatggaa catgttgaag cattaattga   24660
tagtaaaata caagagcagg taaaagaag tgcacaagat gaactaaatg caattacaaa   24720
taacttatct acgtatttga aatttctaga tgcatgggaa aatgattcta ataatttaag   24780
agcgagagct gtagtgaaag accaatttgt aggccttgaa cagactcttg aaagaaaaat   24840
ggttagtgtt tttggaagta cgggtcatga agtgcatctt ttgccaattt tcgctcaagc   24900
agccaacctc cacctaattc tattaagaga tgctgagaaa tatggaaaga gatggggttg   24960
ggcagataga gaaattcaag tatattatga taaccagatt cgttatatcc atgaatatac   25020
ggaccattgt attaaatatt ataatcaagg attaagtaaa ctgaaaggtt ctacctatca   25080
agattgggat aagtataatc gttttagaag agaaatgacc ctaactgttc ttgatttgat   25140
ttcaattttc ccatcgtatg atactagaac ttacccaatt gatacaatag gtcaattgac   25200
aagggaagtt tattcggatt tacttattgc taacccgtct gggatgcaga ctttcactaa   25260
tgtagatttc gacaatattc ttattagaaa acctcattta atggatttct taagaactct   25320
tgagattttt accgatcgac ataacgcaag cagacacaac gtatattggg gcggacatcg   25380
agtgcattct tcttacacag gaggtaattt tgaaaatttt gaatctccct tatatggcag   25440
tgaagcaaat gtagaaccc gaacatggtt gagttttgga gaatctcaag tctataatat   25500
acgttcgaag cctgagtggg atagaggaag tactgcaatt agtggctcct atgaatttcg   25560
aggagtgaca ggatgttctt tttatcgaat gggaaatttt gctggcaccg tagccctaac   25620
ttaccgacag tttggtaacg aaggttctca aatcccattg cacaggctat gtcatgttac   25680
ttattttaga agatctcaag ctgtgggggc gacttcgaga cagacgttaa caagtggtcc   25740 gctatttttcc tggacacata gtagtgctac ggaaacgaat atcattcacc cgacaaaaat   25800
tacacaaata ccaatggtga aggctagttc ccttggatca ggtacttctg ttgtccaagg   25860
accaggcttt acaggagggg atgtacttcg aagaaatagc cccggtagca caggaacttt   25920
aagagttaac gtcaattcac cattatcaca gagatatcgt ataagaattc gttacgcttc   25980
tactacggat ttagatttt ttgtcattcg cggaaatacg acagttaata attttagatt   26040
tgggaacact atgcgtaaag gagaccctat aacctctcga tcatttagat ttgcggcttt   26100
tagtacacca tttacttttg ctagctcaca ggatgaactt agaataaatg tacaaaattt   26160
caataatggt gaagaagttt atatagatag aatcgaagtt attccagttt gatactacag   26220
atgtttatgt tgatacccta ggtaatacac ctactgagac gttgggaaga agtgtaaaaa   26280
actcatctca aaatcgaaag taaaagagcc cttcttaaaa tttttaagagg ggctcagctc   26340 attgttgcac agttactcca gggtctgtca aggattttgc ttaaattgat ttatatgaac   26400
ctaccccgag ggggagacga gcctcaaggc aaaatgctgg ccgatgcgtt ctggaaagaa   26460
tacggagaac tgcagcagca ttttcggaca gcaggcggaa atagcctgag agaagacgat   26520
gaggttgtcg acccaggtga tcaggatgtc ctggactccc cgattcttaa gatcgttcag   26580
aatgctgagc cagaacttcg tggactcgtt ttccccgatc cacatgctca gtacgacctt   26640
attgccgtcc aaatcgatgc cgtacacatt ctggagatga tcttcaatct cccgtgtact   26700
tacgtcctct tggcgtagag ggcgaatatc agtcctcgat gccggttacg ctcgtttgat   26760
tcttcttcac aacgatgggc tcgaacttga ttaggcggtc tcgggaacgg aaatcgcctg   26820
tacgccgtac tcacctggtg atcgtcttct tgctcttacc attgcggcta tttgccgtct   26880
```

```
gctggttctg cacatcatac ctctcataac ccagatgcgt gtcctccccc aacctttcta    26940
gtcctttcat tgttagtgga tttgattgag tttacacgaa gtatttacga ctcttggaac    27000
ccgggtgttt tttgcaagtg aaaaatgctg agttttgctg caaaaagtgc caggctccct    27060
tgccagccaa aacattactg cggaatgcgt tccattgcct gcttgaggcg gaaactctcg    27120
cctgtgaacg agagaatatg cgcgtggtgc acgagacggt cgaccaaggc tgaggtgagc    27180
ttagtatccc caaatatgga ggtccattgg ccaaactcca ggtactgggc tgtgggtttt    27240
gcgcttgcga agggcggcgt tccagtcgct ctggtcggca tagcgtttgg ccgttcgcca    27300
gtgaatgccc acctaccttg cgatttcgct cactgagcag ccttctgttt cgcgtaaaaa    27360
agttgttgag gcattttcag catccttccc gtctccttcg tcaagttctc ggcaaaccta    27420
acgataggag gattttaagg ggctgacaag tgcctttttt gcatctgact tcagcatttt    27480
tacgctgcaa ttctaggcat ttttagtatg caataaacac ccgggtctcc atctctgaca    27540
tgagcctgcc gggcactcat ataatataaa aagcatcaga gctgaatgag tcggctgctg    27600
atgcttattt attggaccga acgatatctc tgcaagtaca agtacgaatg gagcccggta    27660
ttgttgatac ccccgttttt ataaggatag actaagcagt tctttaatag actttaaatc    27720
tttcaggatg agtttatctg gtatccaaat gacaggaatt tgagttttat tgattttgta    27780
attggttata atgaaatcga atttgaccgt attgcttggt tcggtttgaa ggtttagaac    27840
gttacccaat tcattattta atttgtgata gatgaatttt ttccaattgg ttggtccgga    27900
taaaagcaat aaaaccttt tttttataatt tgacaggaga atagataaaa tatgaaacgt    27960
gatgtggtag ctctcatctt cagataatct attttcattt atttctttat tccatgcgac    28020
aataagaggg tgaatgatgt tgtagccctc tattaattca ttaggaatcg tcttaaatct    28080
accccaatag tattctaacg gtaaattgag attttaaat atatagatct tgtggaaaga    28140
aaaatggatg ttatgtctta tttcttctat tactttggca ttcatattta cttcacttga    28200
aatcatgtca attaaagcaa ggtgcttatc gtaaagttgt ttatatgatc cacgatagta    28260
attcttgatt ttactttttt cattatcatc ccctcggag atgaggaaaa aaaatagtgt    28320
aaaaaactta agttcatttt gctggaagct gaccttatag aaattttcaa tggcagagac    28380
aatggcatag gtgcaatcta acttttgaga gctaaatatg tagtccatat taaaactttt    28440
ggaaataaaa tgcttgtata tatttctatt tacagacaca ttgatgagta tggttaatag    28500
attataatcg atctccattt tatagaaacg aatatagttc tcaattttt gttgcaagtc    28560
taggtccggt ttaaagattt ctttatactt ttgcacgtga aaaaaagaa ccatatgaaa    28620
gtatctaata ttcagttcct ttccaattat ttggatcgtt gttctgaaat taaaatcaag    28680
gttaaaatgt ctaagtattt ttctgaaatt atttaatttt tcttcaatg ttaatttatc    28740
taagtacaat atttgagacc attttttccaa gctataatac ttctgattga atattcccat    28800
taaaatgatg taaagttcac tgtttattat ataagtagct ataatagtgg aaaggtgatc    28860
taaaggatct ttttttagaa cgtaaccttt ggaattaatg cttattatat cccaattatc    28920
tggaagatcc tgtttttaatt gagaaatgtc acttataatc gttctgcttg tacattgcag    28980
cttacgggct aaagaactgg aagacacgat accttcgctg tcaattaagg attctaatat    29040
ttggattttt cgaataattg aatgattttg aattaagtga gcggtgaatt catccattta    29100
gtctcccccct cgaaaagcga taactggtta aagtgcagat gtactatcct tgttcgaag     29160
ttgctagtaa tcaattctgc ggatctcttc aaagtgctcc aggtgctatg gatttacgaa    29220
tttcccctaa acatatcttt ctaatgtttg tcttcttaat gaaaatcttt attatttttc    29280
```

```
tccttttcac aatttaaatt tcaattagaa agtaacgtaa ttttggaatg aaaaacgata    29340
cataatttca ttaatagatg aaaatatgta tggtttttaa aatgtttgta aaggtcagct    29400
taatgcggtt aatagaaggt taagagattt tattgtgcaa ggggggacga agaaggatat    29460
aagatagaac atatccgaaa gggaggaggc taacgaaatt tgaaattatt tgttgggtag    29520
tgtttgcaaa actcgaatta tatggtaatc tatagatggt caattatttg caatgccaaa    29580
ggaaggtgag gctgtgagta ccgttgctgc gaagccacag aggttgggggg agctaataca    29640 gtactatcgg cagaagaagg aattgagtct gtcgaagctg caagaagcgg tcggcattga    29700
taaaggcagc ctgtcgagaa ttgaaaacag cgaggtcaaa cgccctgatt ttcgatccat    29760
cttgtcgatc gccgcggtat tggacattcc ccatgacgcc atcgtagaac agtacatcga    29820
gatcggacat aaatcggaag tcatatacac tattttacag aacgaattga caaccctcga    29880
gcatccatcg ctcataccga aaattgccgc aaagtttctt gaagcgccca atgaagacag    29940
tctggatgca gtagagaagt tgtaccgaac gataggctcc gtgaatcatc cttccactca    30000
gttatcttta tacaccctca tcgtagacta ctcacgcgcc catggaatca tgccttacat    30060
tgccaaagga ttatttcgga agtacatgat tgaacgaaat gatttcagca ggttgaagga    30120
aacgtatcag gttggaaaaa atgtgctgga ctatgctaat ttttttgagcg agaaagagcg    30180 gatacttcta tactatggct tgagtgttca cgcttatagt cttatgtttt atcatgatgc    30240
cataaaattc ggtaattatg ttgtggaaaa tggggaagaa gaaccgctag caaatgcaac    30300
tcataatgtt tgcaatgcct attaccattt ggggaattat gacgattgca atacctatct    30360
cgaaaagtat agtcatttcc catatccttt cgtcaaagag aatgttaaat taatgactgc    30420
ctttcttaac gggaagaaag ggaatattga gtccgccatt actcagttta ataactgttt    30480 agatacctg tcctcatata atttgattca tgccgtaact gaattaatgg aactatatct    30540
ccataaaaac gatcttgttg cagcagatca actccttatg tatgaagaac aaataattga    30600
gagcatcacc caaccacgaa ctacgccata taaaaggtca agattagcgc actactttcg    30660
catcaaagga caattgttaa ctcgtaaaca acatgaaaaa gacgctgttg atagtttctt    30720
gaaaagtaca ttagagtacg taaaaattgg tcgttttacg gaagcttttg aatcattgtc    30780
gtttgtgacg cattcaatga tacataatca gtcaatcatt aatagtgaaa taattaaaaa    30840
ggttgataat attttacaaa taattgctgc aaaataatta aggaggaata tggtgccatg    30900
agaaaacgta aacttctttt cattgcctct cttctagttt ttggagcaat cagcatggag    30960
catattgttt catacatcga tgccccgtgg ataactaact tctaatgaat ataacatctc    31020
ataacgctag tcatggcccc gccattcgtt ggtggggtaa catccttcga aagcccgatt    31080
cttttactgg caatgttgct gcaattgtaa ggggcctcac tcactccaag tgctgtctct    31140
gcagatcctc tttggtttat gccatcggtc tatagcagca gtaactcgat cgacagataa    31200
aaatttgaaa attctcttcg aaaggagatt gacgcattaa gacgccttta tgggcgtttt    31260
tttgtttttt atgtataaag ttgttgcata ataatccaga atcaagtcat atttaccaac    31320
ttcatctata atcaggtcaa ataatacagt ttatggatga ggtgtggaaa tgagccatca    31380
accggtatac aaaggtgact taatcccttt tacttatagc tatgagaaag ctggctgttt    31440
aattgaaatc attgagagca ctcgacagga gcttatagta gcggccacgg aaaaaaagtg    31500
tcttaccgac gaaactgttg taagattaag ccaaaagtta gatacatacc tattggaatt    31560
tcaaagaagg agctgcggct agaagaatag gatgtgataa tccggattat taggggaagg    31620
tgaggctgtg agtatcggtt ctgtgaagcc taaaagcttg ggggagttaa tcaagtatta    31680
```

```
tcgaaaaatg aatagcgaaa tcgcagatca gacattgaga ttgagcaaaa acctaaagtc    31740
attttctcaa tcttgcagaa cgaattggaa acactcgagc atccagcatt aatacccgaa    31800
atagccgcca aatttcttga cttatcaaat ggtatggagg gggtaaaaga gctttacaga    31860
gtaattgact cggtagaaga tacctccatt caattagctg tgtacaacct tattattgat    31920
tactctcgcg ctcatggaat gatgccctat attgctaagg gattataccg aaaatacatg    31980
atcgaacgaa atgatttcag caaattgaaa gaaacctatc aactaggtaa gtgtgtattg    32040
gactatatac agtttctggg cgacgaagaa cgaattgtat tttattattc aataggagtt    32100
cacgctgaca gcttaatgaa ctatgatgac tctgtaccct atatgaaata tgtggtggag    32160
aacgataact cagaaaatgg tgcctataga gcgaatgctt atcttagtct atgcaattct    32220
tcctataata ctggtgatta caaagcaagc caggaatatt tagatgagta cagtaagtac    32280 tcttttttcat atgtagccga taatgtgcat tttatgtcgg cttgtataga gggcaagatg    32340
gggaacgtgg atagttcgat ttcaaagtta cgttcttatt tacaaagttc atgggaagta    32400
tcccgttgaa aagggaacct aaatatattc aaacgccttg tggtgtctca gattgttgaa    32460
aaaccctgtc cttttctaaa ggtacagggg ttctcacatg aaaaggactc acgaaacgaa    32520
ccttccgatg aacccggcca cggttttttc gtacgtttcc cgatccatcc ggtatgcttc    32580
tccatgtccg gctttcggaa cgatgtatag ctctttctcg gcggggcaat tttcgtaaac    32640
tttatgcacc atctccgtcg gcacaaaagt atcgttggcc ccatgaatga agagagtcgg    32700
ggttttcgac ttttttcacct gctccagtgc ggaggcttct ccgaaaaagt accctgcccg    32760
tagcctggtc agcaggctgg tggtatccac gatcgggaat gccggaagat gatacatgcg    32820
ccgcagctgg aaggaaagct gatccttcac agaggtataa ccacagtctt cgacgatggc    32880
tttcacgttc ggcggcaaat tctcgccgct ggtcatcatc acggttgccc ctcccatcga    32940
cacgccgtgg agaacgattt tgaattcgt cccattcgtg tccaaaaccc gctgaatcca    33000
tttcaaataa tccttacgct cgggccagcc gaaaccgata taatgccctt cgctttcccc    33060
atgtccccga gcatcgggga gcaggatgtt gtagccccat ttctcgtggt acattctggc    33120
gtaaccgctc atttgcgttg cgttcccgga atatccgtgc gcgatgatga ccgttttgtc    33180
cgacggcttg gatgccggca aataatacgc cttcagatga atgccgtcat ccgagtccat    33240
ctcccagcgc tcaaagcttt ggttgttcca ccattccttg tccgccagcg tggtttgctt    33300
tgattcctcc acctcaggac tggttttcag gtcgggattg tcgctcaaaa agtctttcga    33360
agcgcgcgca atcgccactt gataaaagta aaagctcccg gcggtaagga taataatgac    33420
aaatacaatc aaggaaataa agcctgtcac cattttttc ttcaattctg ttctctccta    33480
gtaaactctc atgttagtta ttttaatata tcataatgat c                        33521
```

<210> SEQ ID NO 2
<211> LENGTH: 3264
<212> TYPE: DNA
<213> ORGANISM: Paenibacillus strain IDAS 1529

<400> SEQUENCE: 2

```
gatcacacgg ccggcgtatt ccggctcgga accgaagaat taacagaagc gcttcagcag     60
tccggttatc ggacagtctt tgatattgca tctgaaaatc ttgcggaatt tcagaaaagc    120
aatccggaga ttccctcttc cgacgcgaag gagattcatc aattagccgt ccagaggaca    180
gaaaacttat gcatgcttta taaggcctgg caactgcaca atgatccggt cgtccagagc    240
cttcccaaat tatccgcgga taccggcctg cgaggcatgc gtgccgcgtt ggagcggagt    300
```

-continued

```
cttggagggg gagccgattt tggagacttg ttcccggagc gatcgccaga gggctatgcg       360
gaagcctcct ctatacagtc gctttttcg ccgggacgtt accttacggt gctgtataaa        420
attgcgcagg atctccacga cccaaaagac aaactgcata ttgacaaccg ccgtccagat       480
ttgaagtcgc tgatcctcaa taatgacaat atgaaccgtg aggtgtcttc cctggatatc       540
ctgctggatg tgctgcagtc cgaaggctcc ggcacactga catccctgaa ggatacctac       600
tatccgatga cccttcccta tgatgacgac cttgcgcaaa tcaatgccgt ggcggaggcg       660
cgctcatcca atttgctggg gatctgggat accctgctgg acacgcagcg gacttccatc       720
ctgcaggatt ccgccgctgt ccaccggata agcaagccgc ggcactcggc atacgtcaat       780
cagagagtct ccgatgatga accggtattg atcgcgggag aggaattcta cttggagacc       840
ggcggtgttg ccgacacgac cccgtctccg ccaacgaggg aagcgctttc cttgacgcca       900
aacagcttcc gtctgctggt caaccccgag ccgacagcag acgacatcgc caatcactac       960
aacgttaaga ctcaagatcc tgccgctctg ccgccgtct taaatgtggt cgatgacttt       1020
tgcctgaaaa ccggtttgag ctttaatgag ttgctggact taacgatgca aaggatgat       1080 gaatcgatcg gcagcgagta caaaagccgg tttgtaaaat ttggcggcga ggccaatgtt       1140
ccggtttcaa cctatggagc tgtatttctg acaggaacgg aagaaactcc gttgtgggta       1200
ggaaaaggag ctgtgataag ccctgcagcg gacgcctatg ttcgtaatgg acatatgca        1260 aacacgaatt atggatcaga cactagtctt gttgtgaagc aggatgggtc tagtggatac       1320
agtagggaag catatatcag gtttgatttg acaggtcttt ccggagttgt ggaggaagct       1380
aaaatttctc taacaactag agcgaaacaa ttgtctagct taagacacca agctcatttg       1440
gtcagtgaca acagttggga tgaattgaaa atcacatgga ataacaaacc tgcaggagga       1500
gcgatcatcg caagctggga tgttcccgaa gttggtgaga atgtaaaggt tgatgtgacc       1560
cggcaagtaa atgatgcgct cgcaaacggt caagataaac tatcaattgt tattcgttct       1620
agtgcaaatt atggcagtct gggcgatgtc tcttatgcct ctagagaaca ccctgaaaaa       1680
gcctcacgac cttctatgga aatcaaggcg ataacgggtg ctggtttaaa ttttacggcg       1740
gataatgttg tagctctggc aggaagggcg gaaaagcttg tccggctggc gcgcagcacg       1800
ggactttcct ttgagcagtt ggattggctg attaccaata ccagccgtgc cgtaatcgaa       1860
catggtggag aactgattct ggataagccg gtactggagt ctgtggccga attcacaagg       1920
ctccataagc gttatggcat cacagcggat atgttcgccg cgtttatcgg cgaagtcaat       1980
acgtatgctg aagcaggtaa agagagcttt tatcagacga ttttcagcac ggccgaccat       2040
tcggctgcct tacctttagg cgcaactttg caatttgagg tgagcaaaca ggatcgatat       2100
gaagcgattt gctgcgggc catggggtg accgccgatg agttctctcg tatcggcaaa       2160
tactgctttg cgacaacgc gcagcaagtt accgccaatg aaacaaccgt tgcgcagctt       2220
tatcgtttag gccgaattcc tcacatgctt ggattgcgtt ttaccgaggc ggagctgttg       2280
tggaaattga tggctggcgg cgaggatacc ttgctccgca cgattggcgc gaagcctcgc       2340
agtttacaag ccttagagat tattcgccgt actgaggtcc ttttggactg gatggatgct       2400
catcagcttg atgttgtctc cctgcaagcc atggttacca atcggtacag cggcacagcc       2460
acgccggagc tgtacaactt tttggcacag gtgcaccaat ccacaagcag tgccgcgaac       2520
gtgtccaaag cggatgctca ggataccctg cccgcggaca agctgttccg ggccttggcg       2580
gtaggcttca acctgaaggc caacgtgatg gcgcaggtca ttgactggtt ggacaaaacc       2640
gacggagcgt ttacgctgcg ggctttctgg gacaagcttc aagcgtattt cagcgccgat       2700
```

```
catgaagaag aactgacggc cttggaagga gaagccgact tgctgcagtg gtgccaacag    2760
atcagccagt atgcgctcat tgtccgctgg tgcgggttaa gcgatcagga tctggcgctg    2820
ctgaccgggc atcccgggca gcttctgtcc ggacaacata cggtgccggt accctcgctg    2880
catctcctgc tggtgctgac ccgcctgaag gaatggcagc agcgcgtcca ggtttccagc    2940
gaggaggcca tgcgctattt tgcccaggcc gatgcgccaa ccgtcacacg cgatgctgcg    3000
gtcaagctgc ttgcccgtat ccatggctgg aatgaacagg ataccgcctc gatgaatgac    3060
tacctgctgg gagagaacga atatcctaag aactttgagc agatctttac tttggaaagc    3120
tgggtcaacc tggccgtca  actgaatgtt ggcagccgaa cgttgggaga gctggttgac    3180
atgtcagaag aggatgatac cgcggaaaac acggatttga ttatctcggt cgcccaaagc    3240
ctgatggctg cggtgcaggc ctga                                           3264
```

<210> SEQ ID NO 3
<211> LENGTH: 1087
<212> TYPE: PRT
<213> ORGANISM: Paenibacillus strain IDAS 1529

<400> SEQUENCE: 3

```
Asp His Thr Ala Gly Val Phe Arg Leu Gly Thr Glu Glu Leu Thr Glu
1               5                   10                  15

Ala Leu Gln Gln Ser Gly Tyr Arg Thr Val Phe Asp Ile Ala Ser Glu
            20                  25                  30

Asn Leu Ala Glu Phe Gln Lys Ser Asn Pro Glu Ile Pro Ser Ser Asp
        35                  40                  45

Ala Lys Glu Ile His Gln Leu Ala Val Gln Arg Thr Glu Asn Leu Cys
    50                  55                  60

Met Leu Tyr Lys Ala Trp Gln Leu His Asn Asp Pro Val Val Gln Ser
65                  70                  75                  80

Leu Pro Lys Leu Ser Ala Asp Thr Gly Leu Arg Gly Met Arg Ala Ala
                85                  90                  95

Leu Glu Arg Ser Leu Gly Gly Gly Ala Asp Phe Gly Asp Leu Phe Pro
            100                 105                 110

Glu Arg Ser Pro Glu Gly Tyr Ala Glu Ala Ser Ser Ile Gln Ser Leu
        115                 120                 125

Phe Ser Pro Gly Arg Tyr Leu Thr Val Leu Tyr Lys Ile Ala Gln Asp
    130                 135                 140

Leu His Asp Pro Lys Asp Lys Leu His Ile Asp Asn Arg Arg Pro Asp
145                 150                 155                 160

Leu Lys Ser Leu Ile Leu Asn Asn Asp Asn Met Asn Arg Glu Val Ser
                165                 170                 175

Ser Leu Asp Ile Leu Leu Asp Val Leu Gln Ser Glu Gly Ser Gly Thr
            180                 185                 190

Leu Thr Ser Leu Lys Asp Thr Tyr Tyr Pro Met Thr Leu Pro Tyr Asp
        195                 200                 205

Asp Asp Leu Ala Gln Ile Asn Ala Val Ala Glu Ala Arg Ser Ser Asn
    210                 215                 220

Leu Leu Gly Ile Trp Asp Thr Leu Leu Asp Thr Gln Arg Thr Ser Ile
225                 230                 235                 240

Leu Gln Asp Ser Ala Ala Val His Arg Ile Ser Lys Pro Arg His Ser
                245                 250                 255

Ala Tyr Val Asn Gln Arg Val Ser Asp Asp Glu Pro Val Leu Ile Ala
            260                 265                 270

Gly Glu Glu Phe Tyr Leu Glu Thr Gly Gly Val Ala Asp Thr Thr Pro
```

```
                275                 280                 285
Ser Pro Pro Thr Arg Glu Ala Leu Ser Leu Thr Pro Asn Ser Phe Arg
290                 295                 300
Leu Leu Val Asn Pro Glu Pro Thr Ala Asp Asp Ile Ala Asn His Tyr
305                 310                 315                 320
Asn Val Lys Thr Gln Asp Pro Ala Ala Leu Ala Ala Val Leu Asn Val
                325                 330                 335
Val Asp Asp Phe Cys Leu Lys Thr Gly Leu Ser Phe Asn Glu Leu Leu
            340                 345                 350
Asp Leu Thr Met Gln Lys Asp Asp Glu Ser Ile Gly Ser Glu Tyr Lys
            355                 360                 365
Ser Arg Phe Val Lys Phe Gly Gly Glu Ala Asn Val Pro Val Ser Thr
    370                 375                 380
Tyr Gly Ala Val Phe Leu Thr Gly Thr Glu Glu Thr Pro Leu Trp Val
385                 390                 395                 400
Gly Lys Gly Ala Val Ile Ser Pro Ala Ala Asp Ala Tyr Val Arg Asn
                405                 410                 415
Gly Thr Tyr Ala Asn Thr Asn Tyr Gly Ser Asp Thr Ser Leu Val Val
                420                 425                 430
Lys Gln Asp Gly Ser Ser Gly Tyr Ser Arg Glu Ala Tyr Ile Arg Phe
            435                 440                 445
Asp Leu Thr Gly Leu Ser Gly Val Val Glu Glu Ala Lys Ile Ser Leu
    450                 455                 460
Thr Thr Arg Ala Lys Gln Leu Ser Ser Leu Arg His Gln Ala His Leu
465                 470                 475                 480
Val Ser Asp Asn Ser Trp Asp Glu Leu Lys Ile Thr Trp Asn Asn Lys
                485                 490                 495
Pro Ala Gly Gly Ala Ile Ile Ala Ser Trp Asp Val Pro Glu Val Gly
            500                 505                 510
Glu Asn Val Lys Val Asp Val Thr Arg Gln Val Asn Asp Ala Leu Ala
            515                 520                 525
Asn Gly Gln Asp Lys Leu Ser Ile Val Ile Arg Ser Ser Ala Asn Tyr
    530                 535                 540
Gly Ser Leu Gly Asp Val Ser Tyr Ala Ser Arg Glu His Pro Glu Lys
545                 550                 555                 560
Ala Ser Arg Pro Ser Met Glu Ile Lys Ala Ile Thr Gly Ala Gly Leu
                565                 570                 575
Asn Phe Thr Ala Asp Asn Val Val Ala Leu Ala Gly Arg Ala Glu Lys
            580                 585                 590
Leu Val Arg Leu Ala Arg Ser Thr Gly Leu Ser Phe Glu Gln Leu Asp
            595                 600                 605
Trp Leu Ile Thr Asn Thr Ser Arg Ala Val Ile Glu His Gly Gly Glu
    610                 615                 620
Leu Ile Leu Asp Lys Pro Val Leu Glu Ser Val Ala Glu Phe Thr Arg
625                 630                 635                 640
Leu His Lys Arg Tyr Gly Ile Thr Ala Asp Met Phe Ala Ala Phe Ile
                645                 650                 655
Gly Glu Val Asn Thr Tyr Ala Glu Ala Gly Lys Glu Ser Phe Tyr Gln
                660                 665                 670
Thr Ile Phe Ser Thr Ala Asp His Ser Ala Ala Leu Pro Leu Gly Ala
            675                 680                 685
Thr Leu Gln Phe Glu Val Ser Lys Gln Asp Arg Tyr Glu Ala Ile Cys
    690                 695                 700
```

Cys Gly Ala Met Gly Val Thr Ala Asp Glu Phe Ser Arg Ile Gly Lys
705                 710                 715                 720

Tyr Cys Phe Gly Asp Asn Ala Gln Gln Val Thr Ala Asn Glu Thr Thr
            725                 730                 735

Val Ala Gln Leu Tyr Arg Leu Gly Arg Ile Pro His Met Leu Gly Leu
        740                 745                 750

Arg Phe Thr Glu Ala Glu Leu Leu Trp Lys Leu Met Ala Gly Gly Glu
    755                 760                 765

Asp Thr Leu Leu Arg Thr Ile Gly Ala Lys Pro Arg Ser Leu Gln Ala
770                 775                 780

Leu Glu Ile Ile Arg Arg Thr Glu Val Leu Leu Asp Trp Met Asp Ala
785                 790                 795                 800

His Gln Leu Asp Val Val Ser Leu Gln Ala Met Val Thr Asn Arg Tyr
                805                 810                 815

Ser Gly Thr Ala Thr Pro Glu Leu Tyr Asn Phe Leu Ala Gln Val His
            820                 825                 830

Gln Ser Thr Ser Ser Ala Ala Asn Val Ser Lys Ala Asp Ala Gln Asp
        835                 840                 845

Thr Leu Pro Ala Asp Lys Leu Phe Arg Ala Leu Ala Val Gly Phe Asn
850                 855                 860

Leu Lys Ala Asn Val Met Ala Gln Val Ile Asp Trp Leu Asp Lys Thr
865                 870                 875                 880

Asp Gly Ala Phe Thr Leu Arg Ala Phe Trp Asp Lys Leu Gln Ala Tyr
                885                 890                 895

Phe Ser Ala Asp His Glu Glu Leu Thr Ala Leu Glu Gly Glu Ala
            900                 905                 910

Asp Leu Leu Gln Trp Cys Gln Gln Ile Ser Gln Tyr Ala Leu Ile Val
        915                 920                 925

Arg Trp Cys Gly Leu Ser Asp Gln Asp Leu Ala Leu Leu Thr Gly His
930                 935                 940

Pro Gly Gln Leu Leu Ser Gly Gln His Thr Val Pro Val Pro Ser Leu
945                 950                 955                 960

His Leu Leu Leu Val Leu Thr Arg Leu Lys Glu Trp Gln Gln Arg Val
                965                 970                 975

Gln Val Ser Ser Glu Glu Ala Met Arg Tyr Phe Ala Gln Ala Asp Ala
            980                 985                 990

Pro Thr Val Thr Arg Asp Ala Ala Val Lys Leu Leu Ala Arg Ile His
        995                 1000                1005

Gly Trp Asn Glu Gln Asp Thr Ala Ser Met Asn Asp Tyr Leu Leu
        1010                1015                1020

Gly Glu Asn Glu Tyr Pro Lys Asn Phe Glu Gln Ile Phe Thr Leu
        1025                1030                1035

Glu Ser Trp Val Asn Leu Gly Arg Gln Leu Asn Val Gly Ser Arg
        1040                1045                1050

Thr Leu Gly Glu Leu Val Asp Met Ser Glu Glu Asp Asp Thr Ala
        1055                1060                1065

Glu Asn Thr Asp Leu Ile Ile Ser Val Ala Gln Ser Leu Met Ala
        1070                1075                1080

Ala Val Gln Ala
        1085

<210> SEQ ID NO 4
<211> LENGTH: 3618
<212> TYPE: DNA
<213> ORGANISM: Paenibacillus strain IDAS 1529

```
<400> SEQUENCE: 4
atgaccaagg aaggtggtaa gaatatgtct acttcaaccc tgttgcaatt gattaaggaa      60
tcccgccggg atgcgttggt caaccattat atcgccaaca atgtcccgag agagcttacg     120
gataagatta cagacgcaga cagcctgtat gagtatttgc tgctggatac caagatcagt     180
gaactcgtaa aaacatcgcc gatagctgag gccattagca gcgttcagtt atacatgaac     240
cgatgcgtgg aaggctatga aggcaagctg actccggaag gcaacagcca tttcgggccg     300
ggaaaattcc tgaataattg ggatacctat aacaagcgtt attccacttg ggccggcaag     360
gaacgtctga atattatgc aggcagttat attgacccgt ccttgcgcta taacaaaacg     420
gatccgttcc tgaacctgga acagaatatc agccagggaa gaatcaccga tgacaccgta     480
aagaacgcgc tgcaacacta cctgactgaa tatgaagtgt tggcggattt ggaatatatc     540 agcgtaaaata aaggcgccga tgaaagtgta ttattcttcg taggccgcac caaaacaatg     600
ccatacgaat attactggcg ccgattaacg ttgaaaaagg acaataacaa taaactggtg     660
cctgccatct ggtctcaatg gaaaaaaata actgccaata tcggcgaagc agttaataat     720
tatgtggtgc ttcactggca taataaccgc ttacatgtac aatggggttc tacagagaaa     780
acacaaaatg atgacggaga acccattgag aaacgatatt tgaatgactg gttcatggat     840
aagtccagtg tctggtcttc attccgaaag gtttcatata tagaaaatag ttttacttat     900
actgagggca tcattgattc aagaaatatt actatagctg gaaatcaact gttctgtgat     960
gattcaaata cttttaaggc aacaataacg gcacttccat ttgaccaaat acgtgtttac    1020
ttagaaaaga tttacggtac aggcggcagc atcacggtta ctggagaaaa taaaggctat    1080
attattaagg tgggggagcc aagagaagtc agtttctctc ctaatacgtt actagatgta    1140
ttcataggta gtaatgcaag ccctcgagac ccatatttca aagctacatt taatagagaa    1200
gctctccaaa attcatacgg ctcaattaaa ataaatcaat acaccctcc ttctggaagc    1260 aatatcaaag gtcctatcga ccttaccctg aaaaataaca tcgacctgtc ggcgttgttg    1320
gaagagagcc ttgacgtact gttcgactat accattcagg ggataaccaa attgggcggc    1380
ttagaggcct ttaacgggcc ttacggactt tatttgtggg aaatcttcct ccatgttcca    1440
tttttaatgg cggttcgctt ccacaccgag cagcggtatg agttggcgga acgatggttt    1500
aaattcattt tcaacagcgc aggttaccgt gatggctacg gcaatctgct gacgcgatgac    1560 aaaggcaacg tgcgctactg gaacgtcgtg cctctgcagg aggatacgga gtgggatgac    1620
acgttgtccc tggcaacgac cgacccggac gagattgcga tggccgaccc gatgcaatac    1680
aagctggcta tctttattca caccttggac ttcttgatca gccgcggcga cagcttgtac    1740
cggatgctgg agcgggatac cttgaccgaa gcgaagatgt attacattca ggccagccaa    1800
ctgcttgggc ctcgtcccga gatccggatc aatcacagct ggcctgatcc gaccctgcaa    1860
agcgaagcgg acgcggtaac cgccgtgccg acgcgaagcg attcgccggc agcgccaatt    1920
ctcgccttgc gagcgcttct gaatgcgaa acgggcatt tcctgccgcc ttataatgat    1980
gaactattag ctttctggga taaaatcgac ctgcgtctct acaatttacg ccacaatctg    2040
agcctggacg tcagccgct tcatttgccg ctctttaccg aaccggtcaa tcctcgtgag    2100
ctgcaggttc agcatgggc aggcgatgga ttaggggaa gcgccggttc cgtccaaagc    2160
cgtcaaagtg tctatcgttt tcctctggtc atcgataagg cgcgcaatgc cgcgagtagt    2220
gttatccaat cgggaatgc cctggaaaac gcgctgacaa agcaggacag cgaggccatg    2280
actatgctgt tgcaatccca gcagcagatt gtcctgcagc aaacccgcga tattcaggag    2340
```

-continued

```
aagaacctgg cctcgctgca agcaagtctg gaagcaacga tgacagccaa agcgggcgcg    2400
aaatcccgaa agacccatttt tgccggcctg gcggataact ggatgtcgca taatgaaacc   2460
gcctcacttg cactgcgtac cactgcggga attatcaata caagctcgac cgtgccaatc    2520
gctatcactg gcggcttgga tatggctccg aacattttg gtttcgcagt tggaggttcc    2580
cgctggggag cagccagcgc ggctgtagcc caaggattgc aaatcgccgc cggcgtaatg   2640
gaacagacgg ccaatatcat cgatatcagc gaaagctacc gccggcgccg ggaggattgg    2700
ctgctgcagc gggatgttgc cgagaatgaa gcggcgcagt tggattcgca gattgcggcc    2760
ctgcgggaac agatggatat ggcgcgaaaa caacttgcgc tggcggagac ggaacaggca    2820
cacgcgcaag cggtctacga gctgctaagc acccgttta cgaatcaagc tttgtataac     2880
tggatggccg gacgtctgtc gtctctatac tatcaaatgt atgacgccgc attgccgctc    2940
tgcttgatgg ccaaacaggc tttagagaaa gaaatcggca atgataaaac ggttggaatc    3000
ttcaccctcc cggcctggaa tgatttgtat caggattgc tagcgggcga ggcgctgctg     3060
ctcgagcttc agaagctgga gaatctgtgg ctggaggagg acaagcgcgg aatggaagct    3120
gtaagaacgg tatctttaga taccttctc cgcaaagaaa agccagaatc cggttttgca    3180
gatttcgtca aggaagttct ggacggaaag acgcctgacc ctgtaagcgg agttagcgta    3240
cagctgcaaa acaatatttt cagtgcaacc cttgacctgt ccaccttgg cctggatcgc    3300 ttttacaacc aagcggaaaa gcccacagg atcaaaaacc tgtcggttac cttacccgcg     3360
ctattgggac cttatcagga tattgcggca accttatcgc taggtggcga gaccgttgcg    3420 cttttcccatg gcgtggatga cagcggcttg tttatcacgg atctcaacga cagccgtttc   3480
ctgcctttcg agggtatgga tcctttatcc ggcacactcg ttctgtcgat actccatgcc    3540
gggcaagacg gtgaccagcg cctcctgctg gaaagcctga cgacgtcat cttccacatt    3600 cgatatgtca tgaaatag                                                  3618
```

<210> SEQ ID NO 5
<211> LENGTH: 1205
<212> TYPE: PRT
<213> ORGANISM: Paenibacillus strain IDAS 1529

<400> SEQUENCE: 5

```
Met Thr Lys Glu Gly Gly Lys Asn Met Ser Thr Ser Thr Leu Leu Gln
 1               5                  10                  15

Leu Ile Lys Glu Ser Arg Arg Asp Ala Leu Val Asn His Tyr Ile Ala
            20                  25                  30

Asn Asn Val Pro Arg Glu Leu Thr Asp Lys Ile Thr Asp Ala Asp Ser
        35                  40                  45

Leu Tyr Glu Tyr Leu Leu Leu Asp Thr Lys Ile Ser Glu Leu Val Lys
    50                  55                  60

Thr Ser Pro Ile Ala Glu Ala Ile Ser Ser Val Gln Leu Tyr Met Asn
65                  70                  75                  80

Arg Cys Val Glu Gly Tyr Glu Gly Lys Leu Thr Pro Glu Gly Asn Ser
                85                  90                  95

His Phe Gly Pro Gly Lys Phe Leu Asn Asn Trp Asp Thr Tyr Asn Lys
            100                 105                 110

Arg Tyr Ser Thr Trp Ala Gly Lys Glu Arg Leu Lys Tyr Tyr Ala Gly
        115                 120                 125

Ser Tyr Ile Asp Pro Ser Leu Arg Tyr Asn Lys Thr Asp Pro Phe Leu
    130                 135                 140
```

-continued

```
Asn Leu Glu Gln Asn Ile Ser Gln Gly Arg Ile Thr Asp Asp Thr Val
145                 150                 155                 160

Lys Asn Ala Leu Gln His Tyr Leu Thr Glu Tyr Glu Val Leu Ala Asp
            165                 170                 175

Leu Glu Tyr Ile Ser Val Asn Lys Gly Ala Asp Glu Ser Val Leu Phe
        180                 185                 190

Phe Val Gly Arg Thr Lys Thr Met Pro Tyr Glu Tyr Tyr Trp Arg Arg
    195                 200                 205

Leu Thr Leu Lys Lys Asp Asn Asn Lys Leu Val Pro Ala Ile Trp
210                 215                 220

Ser Gln Trp Lys Lys Ile Thr Ala Asn Ile Gly Glu Ala Val Asn Asn
225                 230                 235                 240

Tyr Val Val Leu His Trp His Asn Asn Arg Leu His Val Gln Trp Gly
            245                 250                 255

Ser Thr Glu Lys Thr Gln Asn Asp Asp Gly Glu Pro Ile Glu Lys Arg
        260                 265                 270

Tyr Leu Asn Asp Trp Phe Met Asp Lys Ser Ser Val Trp Ser Ser Phe
    275                 280                 285

Arg Lys Val Ser Tyr Ile Glu Asn Ser Phe Thr Tyr Thr Glu Gly Ile
290                 295                 300

Ile Asp Ser Arg Asn Ile Thr Ile Ala Gly Asn Gln Leu Phe Cys Asp
305                 310                 315                 320

Asp Ser Asn Thr Phe Lys Ala Thr Ile Thr Ala Leu Pro Phe Asp Gln
            325                 330                 335

Ile Arg Val Tyr Leu Glu Lys Ile Tyr Gly Thr Gly Gly Ser Ile Thr
        340                 345                 350

Val Thr Gly Glu Asn Lys Gly Tyr Ile Ile Lys Val Gly Glu Pro Arg
    355                 360                 365

Glu Val Ser Phe Ser Pro Asn Thr Leu Leu Asp Val Phe Ile Gly Ser
370                 375                 380

Asn Ala Ser Pro Arg Asp Pro Tyr Phe Lys Ala Thr Phe Asn Arg Glu
385                 390                 395                 400

Ala Leu Gln Asn Ser Tyr Gly Ser Ile Lys Ile Asn Gln Tyr Thr Pro
            405                 410                 415

Pro Ser Gly Ser Asn Ile Lys Gly Pro Ile Asp Leu Thr Leu Lys Asn
        420                 425                 430

Asn Ile Asp Leu Ser Ala Leu Leu Glu Glu Ser Leu Asp Val Leu Phe
    435                 440                 445

Asp Tyr Thr Ile Gln Gly Asn Asn Gln Leu Gly Gly Leu Glu Ala Phe
450                 455                 460

Asn Gly Pro Tyr Gly Leu Tyr Leu Trp Glu Ile Phe Leu His Val Pro
465                 470                 475                 480

Phe Leu Met Ala Val Arg Phe His Thr Glu Gln Arg Tyr Glu Leu Ala
            485                 490                 495

Glu Arg Trp Phe Lys Phe Ile Phe Asn Ser Ala Gly Tyr Arg Asp Gly
        500                 505                 510

Tyr Gly Asn Leu Leu Thr Asp Asp Lys Gly Asn Val Arg Tyr Trp Asn
    515                 520                 525

Val Val Pro Leu Gln Glu Asp Thr Glu Trp Asp Thr Leu Ser Leu
530                 535                 540

Ala Thr Thr Asp Pro Asp Glu Ile Ala Met Ala Asp Pro Met Gln Tyr
545                 550                 555                 560

Lys Leu Ala Ile Phe Ile His Thr Leu Asp Phe Leu Ile Ser Arg Gly
            565                 570                 575
```

```
Asp Ser Leu Tyr Arg Met Leu Glu Arg Asp Thr Leu Thr Glu Ala Lys
            580                 585                 590

Met Tyr Tyr Ile Gln Ala Ser Gln Leu Leu Gly Pro Arg Pro Glu Ile
        595                 600                 605

Arg Ile Asn His Ser Trp Pro Asp Pro Thr Leu Gln Ser Glu Ala Asp
610                 615                 620

Ala Val Thr Ala Val Pro Thr Arg Ser Asp Ser Pro Ala Ala Pro Ile
625                 630                 635                 640

Leu Ala Leu Arg Ala Leu Leu Asn Ala Glu Asn Gly His Phe Leu Pro
                645                 650                 655

Pro Tyr Asn Asp Glu Leu Leu Ala Phe Trp Asp Lys Ile Asp Leu Arg
            660                 665                 670

Leu Tyr Asn Leu Arg His Asn Leu Ser Leu Asp Gly Gln Pro Leu His
        675                 680                 685

Leu Pro Leu Phe Thr Glu Pro Val Asn Pro Arg Glu Leu Gln Val Gln
    690                 695                 700

His Gly Ala Gly Asp Gly Leu Gly Gly Ser Ala Gly Ser Val Gln Ser
705                 710                 715                 720

Arg Gln Ser Val Tyr Arg Phe Pro Leu Val Ile Asp Lys Ala Arg Asn
                725                 730                 735

Ala Ala Ser Ser Val Ile Gln Phe Gly Asn Ala Leu Glu Asn Ala Leu
            740                 745                 750

Thr Lys Gln Asp Ser Glu Ala Met Thr Met Leu Leu Gln Ser Gln Gln
        755                 760                 765

Gln Ile Val Leu Gln Thr Arg Asp Ile Gln Glu Lys Asn Leu Ala
    770                 775                 780

Ser Leu Gln Ala Ser Leu Glu Ala Thr Met Thr Ala Lys Ala Gly Ala
785                 790                 795                 800

Lys Ser Arg Lys Thr His Phe Ala Gly Leu Ala Asp Asn Trp Met Ser
                805                 810                 815

His Asn Glu Thr Ala Ser Leu Ala Leu Arg Thr Thr Ala Gly Ile Ile
            820                 825                 830

Asn Thr Ser Ser Thr Val Pro Ile Ala Ile Thr Gly Gly Leu Asp Met
        835                 840                 845

Ala Pro Asn Ile Phe Gly Phe Ala Val Gly Ser Arg Trp Gly Ala
    850                 855                 860

Ala Ser Ala Ala Val Ala Gln Gly Leu Gln Ile Ala Ala Gly Val Met
865                 870                 875                 880

Glu Gln Thr Ala Asn Ile Ile Asp Ile Ser Glu Ser Tyr Arg Arg Arg
                885                 890                 895

Arg Glu Asp Trp Leu Leu Gln Arg Asp Val Ala Glu Asn Glu Ala Ala
            900                 905                 910

Gln Leu Asp Ser Gln Ile Ala Ala Leu Arg Glu Gln Met Asp Met Ala
        915                 920                 925

Arg Lys Gln Leu Ala Leu Ala Glu Thr Glu Gln Ala His Ala Gln Ala
    930                 935                 940

Val Tyr Glu Leu Leu Ser Thr Arg Phe Thr Asn Gln Ala Leu Tyr Asn
945                 950                 955                 960

Trp Met Ala Gly Arg Leu Ser Ser Leu Tyr Tyr Gln Met Tyr Asp Ala
                965                 970                 975

Ala Leu Pro Leu Cys Leu Met Ala Lys Gln Ala Leu Glu Lys Glu Ile
            980                 985                 990

Gly Asn Asp Lys Thr Val Gly Ile Phe Thr Leu Pro Ala Trp Asn Asp
```

```
                 995                 1000                1005
Leu Tyr Gln Gly Leu Leu Ala Gly Glu Ala Leu Leu Glu Leu
    1010                1015                1020

Gln Lys Leu Glu Asn Leu Trp Leu Glu Glu Asp Lys Arg Gly Met
    1025                1030                1035

Glu Ala Val Arg Thr Val Ser Leu Asp Thr Leu Leu Arg Lys Glu
    1040                1045                1050

Lys Pro Glu Ser Gly Phe Ala Asp Phe Val Lys Glu Val Leu Asp
    1055                1060                1065

Gly Lys Thr Pro Asp Pro Val Ser Gly Val Ser Val Gln Leu Gln
    1070                1075                1080

Asn Asn Ile Phe Ser Ala Thr Leu Asp Leu Ser Thr Leu Gly Leu
    1085                1090                1095

Asp Arg Phe Tyr Asn Gln Ala Glu Lys Ala His Arg Ile Lys Asn
    1100                1105                1110

Leu Ser Val Thr Leu Pro Ala Leu Leu Gly Pro Tyr Gln Asp Ile
    1115                1120                1125

Ala Ala Thr Leu Ser Leu Gly Gly Glu Thr Val Ala Leu Ser His
    1130                1135                1140

Gly Val Asp Asp Ser Gly Leu Phe Ile Thr Asp Leu Asn Asp Ser
    1145                1150                1155

Arg Phe Leu Pro Phe Glu Gly Met Asp Pro Leu Ser Gly Thr Leu
    1160                1165                1170

Val Leu Ser Ile Leu His Ala Gly Gln Asp Gly Asp Gln Arg Leu
    1175                1180                1185

Leu Leu Glu Ser Leu Asn Asp Val Ile Phe His Ile Arg Tyr Val
    1190                1195                1200

Met Lys
    1205

<210> SEQ ID NO 6
<211> LENGTH: 3300
<212> TYPE: DNA
<213> ORGANISM: Paenibacillus strain IDAS 1529

<400> SEQUENCE: 6
atggtgtcaa caacagacaa cacggccggc gtattccggc tcggaaccga agaattaaca      60
gaagcgctta agcagtccgg ttatcggacc gtctttgata ttgtatctga caatcttgcg     120
gaatttcaga aaaacaatcc ggagattccc tcttctgacg cgaaggagat tcatcaatta     180
gccgtccaga ggacagaaaa cttatgcatg ctttataagg cctggcagct gcacaatgat     240
ccggttgtcc agagccttcc caaattatcc gcggataccg gctgcaaggc catgcgtgcc     300
gcgttggagc ggagtcttgg aggcggagcc gattttggag acttgttccc ggagcgatcg     360
ccagagggct atgcggaagc ctcctctata cagtcgcttt tctcgccggg acgttacctg     420
acggtgctgt ataaaattgc gcgggatctc cacgacccaa agataaact gcatattgac     480 aaccgccgtc cagatttgaa gtcgctgatc ctcaataatg acaatatgaa ccgagaggta     540
tcttctctgg atatccttct ggatgtgctg cagcccgaag ctctgacac gctgacatcc      600 ttgaaggata cctaccatcc gatgaccctt ccctatgatg acgaccttgc gcaaatcaat     660
gccgtggcgg aggcgcgttc atctaatttg ctggggattt gggataccct gctggacacg     720
cagcggactt ccatcctgca gaattccgcc gctgccccgcc ggataagcaa ggcgcggcac     780
tcggcatacg ccaatcagaa agcctccaat gatgagccgg tattcatcac gggagaggaa     840
```

```
atctacctgg aaaccggagg taaacggctt tttctggcgc ataaactcga gataggttca      900
actattagcg ctaaaatcaa cattggaccg ccgcaagcgg ccgatatcgc gccggcaaag      960
ttgcaactcg tatattacgg cagaggcggc agagggaact acttcctgcg cgtggcagac     1020
gatgtgtccc tcggtggaaa gctgctgacc aattgttatc tgaccagcga tgacggacag     1080
agcaacaata ttagcgggcc atactgccta atgatcaacc gaggcaccgg cagcatgcct     1140
agcgggactc accttccagt tcagattgaa agagtgaccg atacatccat ccgcattttt     1200
gtgccggatc acggctattt ggggctaggc gaaagccttg ccagcaactg gaatgaaccg     1260
ttggcgctga atctgggctt ggatgaagcg ttgacccttta ccttgagaaa gaaggagacg     1320
ggaaatgaca ccatttccat aatcgacatg ctgccgccgg tagcgaacac gactccgtct     1380
ccgccgacga gggaaacgct ttccttgacg ccaaacagct tccgtctgct ggtcaaccct     1440
gagccgacag cggaggacat cgccaagcac tacaacgtca cgacggtaac ccgggctcct     1500
gccgatctgg cctccgcctt aaatgttgtc gatgatttct gcttgaaaac cggtttgagc     1560
tttaacgaat tgctggattt aaccatgcag aaggattatc agtcaaaaag cagtgagtac     1620
aaaagccgat ttgtaaaatt cggcggcggg gagaatgttc cggtatcaag ctatggcgca     1680
gcctttctga caggagcgga agatactcct ttgtgggtga acagtataa cagcgtgggg     1740
actgcaacaa gcacccctgt tttaaacttt acgccagata atgttgtggc tttggcagga     1800
agggcggaaa agcttgtccg gctgatgcgc agcacgggtc tttccttttga gcagttggat     1860
tggctgattg ccaatgccag ccgtgccgtt atcgaacacg gtggagagct ttttctggat     1920
aagccggtac tggaagctgt ggccgaattc acaaggctca ataagcgtta tggcgtcaca     1980
tcggatatgt tcgccgcgtt tatcggcgaa gtcaatacgt atacagaagc gggcaaggac     2040
agcttttatc aggcgagttt cagcacgcc gaccattcgg ctaccttacc tttgggcgct     2100
tctttgcaac ttgaggtgag caagcaggat cgatatgaag cgatttgctg cggggctatg     2160
ggggtgaccg ccgatgagtt ctcccgtatc ggcaaatact gctttgggga taaagcacag     2220
caaatcacgg ccaatgaaac aaccgttgcc cagctttatc gtttaggccg aattcctcat     2280
atgctaggct tgcgttttac cgaggcagag ctgttgtgga aattgatggc tggggcgag     2340
gataccttgc tccgcacgat tggcgcgaac cctcgcagtt tagaagcgtt agagattatt     2400
cgccggacg aggtcctttt ggactggatg gatgcccatc agctggatgt tgtctccctg     2460
caagccatgg ttaccaatcg gtacagcggc acagccacgc cggagctgta caatttttg     2520
gcacaggtgc atcaatccgc aagcagtgcc gcgaacgtgg ccagagcgga tggtcaggat     2580
acgttgcctg cggacaagct gctccgggca ttggcggcgg gcttcaaact gaaagccaac     2640
gtgatgcgc gagtaatcga ctggatggac aaaaccaata aagcgtttac gctgcgggct     2700
ttctgggaca gcttcaagc gtatttcagc gccgatcatg aagaagaact gaccgccctg     2760
gaaggagaag ccgcaatgct gcagtggtgc cagcagatca gccagtatgc gctcattgtc     2820
cgctggtgcg ggttaagcga gcaggatctg gcgctgctga ccgggaatcc ggagcagctt     2880
ctggacggac aacatacggt gcccgtaccc tcgctgcatc tcctgctggt gctgacccgc     2940
ctgaaggaat ggcagcagcg cgtccaggtt tccagcgagg aggctatgcg ctattttgcc     3000
caggccgatt cgccaaccgt cacgcgcgac gatgcggtta atctgcttgc ccgtatccat     3060
ggctggaatg aagcggatac cgtctcgatg aatgactacc tgctgggaga gaacgaatat     3120
cctaagaact ttgatcagat cttttgcactg gaaagctggg tcaacctggg ccgtcaactg     3180
aacgtgggca gcagaacgct gggagagctg gttgacatgg ctgaagagga taaaaccgcg     3240
```

-continued

```
gaaaacatgg atctgattac ttcggtggcc catagcctga tggctgcagc gaaagcctga    3300
```

<210> SEQ ID NO 7
<211> LENGTH: 1099
<212> TYPE: PRT
<213> ORGANISM: Paenibacillus strain IDAS 1529

<400> SEQUENCE: 7

| | | | | | | | | | | | | | | |
|---|---|---|---|---|---|---|---|---|---|---|---|---|---|---|
| Met | Val | Ser | Thr | Thr | Asp | Asn | Thr | Ala | Gly | Val | Phe | Arg | Leu | Gly | Thr |
| 1 | | | | 5 | | | | | 10 | | | | | 15 | |
| Glu | Glu | Leu | Thr | Glu | Ala | Leu | Lys | Gln | Ser | Gly | Tyr | Arg | Thr | Val | Phe |
| | | | 20 | | | | | 25 | | | | | 30 | | |
| Asp | Ile | Val | Ser | Asp | Asn | Leu | Ala | Glu | Phe | Gln | Lys | Asn | Asn | Pro | Glu |
| | | 35 | | | | | 40 | | | | | 45 | | | |
| Ile | Pro | Ser | Ser | Asp | Ala | Lys | Glu | Ile | His | Gln | Leu | Ala | Val | Gln | Arg |
| | 50 | | | | | 55 | | | | | 60 | | | | |
| Thr | Glu | Asn | Leu | Cys | Met | Leu | Tyr | Lys | Ala | Trp | Gln | Leu | His | Asn | Asp |
| 65 | | | | | 70 | | | | | 75 | | | | | 80 |
| Pro | Val | Val | Gln | Ser | Leu | Pro | Lys | Leu | Ser | Ala | Asp | Thr | Gly | Leu | Gln |
| | | | | 85 | | | | | 90 | | | | | 95 | |
| Gly | Met | Arg | Ala | Ala | Leu | Glu | Arg | Ser | Leu | Gly | Gly | Ala | Asp | Phe |
| | | | 100 | | | | | 105 | | | | | 110 | | |
| Gly | Asp | Leu | Phe | Pro | Glu | Arg | Ser | Pro | Glu | Gly | Tyr | Ala | Glu | Ala | Ser |
| | | 115 | | | | | 120 | | | | | 125 | | | |
| Ser | Ile | Gln | Ser | Leu | Phe | Ser | Pro | Gly | Arg | Tyr | Leu | Thr | Val | Leu | Tyr |
| | 130 | | | | | 135 | | | | | 140 | | | | |
| Lys | Ile | Ala | Arg | Asp | Leu | His | Asp | Pro | Lys | Asp | Lys | Leu | His | Ile | Asp |
| 145 | | | | | 150 | | | | | 155 | | | | | 160 |
| Asn | Arg | Arg | Pro | Asp | Leu | Lys | Ser | Leu | Ile | Leu | Asn | Asn | Asp | Asn | Met |
| | | | | 165 | | | | | 170 | | | | | 175 | |
| Asn | Arg | Glu | Val | Ser | Ser | Leu | Asp | Ile | Leu | Leu | Asp | Val | Leu | Gln | Pro |
| | | | 180 | | | | | 185 | | | | | 190 | | |
| Glu | Gly | Ser | Asp | Thr | Leu | Thr | Ser | Leu | Lys | Asp | Thr | Tyr | His | Pro | Met |
| | | 195 | | | | | 200 | | | | | 205 | | | |
| Thr | Leu | Pro | Tyr | Asp | Asp | Asp | Leu | Ala | Gln | Ile | Asn | Ala | Val | Ala | Glu |
| | 210 | | | | | 215 | | | | | 220 | | | | |
| Ala | Arg | Ser | Ser | Asn | Leu | Leu | Gly | Ile | Trp | Asp | Thr | Leu | Leu | Asp | Thr |
| 225 | | | | | 230 | | | | | 235 | | | | | 240 |
| Gln | Arg | Thr | Ser | Ile | Leu | Gln | Asn | Ser | Ala | Ala | Ala | Arg | Arg | Ile | Ser |
| | | | | 245 | | | | | 250 | | | | | 255 | |
| Lys | Ala | Arg | His | Ser | Ala | Tyr | Ala | Asn | Gln | Lys | Ala | Ser | Asn | Asp | Glu |
| | | | 260 | | | | | 265 | | | | | 270 | | |
| Pro | Val | Phe | Ile | Thr | Gly | Glu | Glu | Ile | Tyr | Leu | Glu | Thr | Gly | Gly | Lys |
| | | 275 | | | | | 280 | | | | | 285 | | | |
| Arg | Leu | Phe | Leu | Ala | His | Lys | Leu | Glu | Ile | Gly | Ser | Thr | Ile | Ser | Ala |
| | 290 | | | | | 295 | | | | | 300 | | | | |
| Lys | Ile | Asn | Ile | Gly | Pro | Pro | Gln | Ala | Ala | Asp | Ile | Ala | Pro | Ala | Lys |
| 305 | | | | | 310 | | | | | 315 | | | | | 320 |
| Leu | Gln | Leu | Val | Tyr | Tyr | Gly | Arg | Gly | Gly | Arg | Gly | Asn | Tyr | Phe | Leu |
| | | | | 325 | | | | | 330 | | | | | 335 | |
| Arg | Val | Ala | Asp | Asp | Val | Ser | Leu | Gly | Gly | Lys | Leu | Leu | Thr | Asn | Cys |
| | | | 340 | | | | | 345 | | | | | 350 | | |
| Tyr | Leu | Thr | Ser | Asp | Asp | Gly | Gln | Ser | Asn | Asn | Ile | Ser | Gly | Pro | Tyr |
| | | 355 | | | | | 360 | | | | | 365 | | | |
| Cys | Leu | Met | Ile | Asn | Arg | Gly | Thr | Gly | Ser | Met | Pro | Ser | Gly | Thr | His |

-continued

```
                370                 375                 380
Leu Pro Val Gln Ile Glu Arg Val Thr Asp Thr Ser Ile Arg Ile Phe
385                 390                 395                 400

Val Pro Asp His Gly Tyr Leu Gly Leu Gly Glu Ser Leu Ala Ser Asn
            405                 410                 415

Trp Asn Glu Pro Leu Ala Leu Asn Leu Gly Leu Asp Glu Ala Leu Thr
            420                 425                 430

Phe Thr Leu Arg Lys Lys Glu Thr Gly Asn Asp Thr Ile Ser Ile Ile
            435                 440                 445

Asp Met Leu Pro Pro Val Ala Asn Thr Thr Pro Ser Pro Pro Thr Arg
450                 455                 460

Glu Thr Leu Ser Leu Thr Pro Asn Ser Phe Arg Leu Leu Val Asn Pro
465                 470                 475                 480

Glu Pro Thr Ala Glu Asp Ile Ala Lys His Tyr Asn Val Thr Thr Val
            485                 490                 495

Thr Arg Ala Pro Ala Asp Leu Ala Ser Ala Leu Asn Val Asp Asp
            500                 505                 510

Phe Cys Leu Lys Thr Gly Leu Ser Phe Asn Glu Leu Leu Asp Leu Thr
            515                 520                 525

Met Gln Lys Asp Tyr Gln Ser Lys Ser Ser Glu Tyr Lys Ser Arg Phe
            530                 535                 540

Val Lys Phe Gly Gly Glu Asn Val Pro Ser Ser Tyr Gly Ala
545                 550                 555                 560

Ala Phe Leu Thr Gly Ala Glu Asp Thr Pro Leu Trp Val Lys Gln Tyr
            565                 570                 575

Asn Ser Val Gly Thr Ala Thr Ser Thr Pro Val Leu Asn Phe Thr Pro
            580                 585                 590

Asp Asn Val Val Ala Leu Ala Gly Arg Ala Glu Lys Leu Val Arg Leu
            595                 600                 605

Met Arg Ser Thr Gly Leu Ser Phe Glu Gln Leu Asp Trp Leu Ile Ala
610                 615                 620

Asn Ala Ser Arg Ala Val Ile Glu His Gly Gly Glu Leu Phe Leu Asp
625                 630                 635                 640

Lys Pro Val Leu Glu Ala Val Ala Glu Phe Thr Arg Leu Asn Lys Arg
            645                 650                 655

Tyr Gly Val Thr Ser Asp Met Phe Ala Ala Phe Ile Gly Glu Val Asn
            660                 665                 670

Thr Tyr Thr Glu Ala Gly Lys Asp Ser Phe Tyr Gln Ala Ser Phe Ser
            675                 680                 685

Thr Ala Asp His Ser Ala Thr Leu Pro Leu Gly Ala Ser Leu Gln Leu
            690                 695                 700

Glu Val Ser Lys Gln Asp Arg Tyr Glu Ala Ile Cys Cys Gly Ala Met
705                 710                 715                 720

Gly Val Thr Ala Asp Glu Phe Ser Arg Ile Gly Lys Tyr Cys Phe Gly
            725                 730                 735

Asp Lys Ala Gln Gln Ile Thr Ala Asn Glu Thr Thr Val Ala Gln Leu
            740                 745                 750

Tyr Arg Leu Gly Arg Ile Pro His Met Leu Gly Leu Arg Phe Thr Glu
            755                 760                 765

Ala Glu Leu Leu Trp Lys Leu Met Ala Gly Gly Glu Asp Thr Leu Leu
            770                 775                 780

Arg Thr Ile Gly Ala Asn Pro Arg Ser Leu Glu Ala Leu Glu Ile Ile
785                 790                 795                 800
```

```
Arg Arg Thr Glu Val Leu Leu Asp Trp Met Asp Ala His Gln Leu Asp
            805                 810                 815

Val Val Ser Leu Gln Ala Met Val Thr Asn Arg Tyr Ser Gly Thr Ala
        820                 825                 830

Thr Pro Glu Leu Tyr Asn Phe Leu Ala Gln Val His Gln Ser Ala Ser
        835                 840                 845

Ser Ala Ala Asn Val Ala Arg Ala Asp Gly Gln Asp Thr Leu Pro Ala
        850                 855                 860

Asp Lys Leu Leu Arg Ala Leu Ala Ala Gly Phe Lys Leu Lys Ala Asn
865                 870                 875                 880

Val Met Ala Arg Val Ile Asp Trp Met Asp Lys Thr Asn Lys Ala Phe
                885                 890                 895

Thr Leu Arg Ala Phe Trp Asp Lys Leu Gln Ala Tyr Phe Ser Ala Asp
        900                 905                 910

His Glu Glu Glu Leu Thr Ala Leu Glu Gly Glu Ala Ala Met Leu Gln
        915                 920                 925

Trp Cys Gln Gln Ile Ser Gln Tyr Ala Leu Ile Val Arg Trp Cys Gly
    930                 935                 940

Leu Ser Glu Gln Asp Leu Ala Leu Leu Thr Gly Asn Pro Glu Gln Leu
945                 950                 955                 960

Leu Asp Gly Gln His Thr Val Pro Val Pro Ser Leu His Leu Leu
                965                 970                 975

Val Leu Thr Arg Leu Lys Glu Trp Gln Gln Arg Val Gln Val Ser Ser
            980                 985                 990

Glu Glu Ala Met Arg Tyr Phe Ala  Gln Ala Asp Ser Pro  Thr Val Thr
                995                 1000                1005

Arg Asp  Asp Ala Val Asn Leu  Leu Ala Arg Ile His  Gly Trp Asn
    1010                1015                1020

Glu Ala  Asp Thr Val Ser Met  Asn Asp Tyr Leu Leu  Gly Glu Asn
    1025                1030                1035

Glu Tyr  Pro Lys Asn Phe Asp  Gln Ile Phe Ala Leu  Glu Ser Trp
    1040                1045                1050

Val Asn  Leu Gly Arg Gln Leu  Asn Val Gly Ser Arg  Thr Leu Gly
    1055                1060                1065

Glu Leu  Val Asp Met Ala Glu  Asp Lys Thr Ala  Glu Asn Met
    1070                1075                1080

Asp Leu  Ile Thr Ser Val Ala  His Ser Leu Met Ala  Ala Ala Lys
    1085                1090                1095

Ala

<210> SEQ ID NO 8
<211> LENGTH: 3627
<212> TYPE: DNA
<213> ORGANISM: Paenibacillus strain IDAS 1529

<400> SEQUENCE: 8
atgaccaagg aaggtgataa gcatatgtct acttcaaccc tgttgcaatc gattaaagaa    60
gcccgccggg atgcgctggt caaccattat attgctaatc aggttccgac agcgcttgcg   120
gacaagatta cggacgcgga cagcctgtat gagtacttgc tgctggatac caagatcagt   180
gaactcgtaa aacatcgcc gatagcggag gccatcagca gcgtgcagtt atacatgaac   240
cgctgcgtcg aaggctatga aggcaagttg actccggaaa gtaatactca ttttggccca   300
ggtaaatttc tatataactg ggatacgtac aacaaacgtt tttccacctg gcaggaaaa   360 gaacgcttga atattatgc aggcagctat attgagccgt ccttgcgcta caacaaaacc   420
```

```
gatccattcc tgaacctgga acagagcatc agccagggaa gaattactga tgataccgta    480
aagaacgcgc tgcaacacta cctgactgaa tatgaagtgt tggcggatct ggattatatc    540
agcgttaata aaggcggcga cgaaagtgtt ttactctttg ttggacgcac caaaaccgta    600
ccgtatgaat actactggcg ccgtttgctt ttaaaaaggg acaataataa taagctagta    660
ccagcagtct ggtctcagtg gaaaaaaatc agtgccaata tcggtgaagc ggttgatagt    720
tatgtggtgc ctcggtggca taaaaaccgg ctacatgtgc aatggtgttc tatagagaaa    780
agtgaaaatg atgccggtga acccattgag aaacgatatt tgaatgactg gttcatggat    840
agttccggag tctggtcttc atttcgaaag attccggttg tggaaaagag tttcgaatat    900
ttggacggaa gcctcgatcc ccgatttgtc gctcttgtta gaaatcaaat attaattgat    960
gagccagaaa tattcagaat tacagtatca gccccctaatc cgatagatgc aaatggaaga   1020
gtagaggtac attttgaaga aaactatgca aacagatata atattaccat taaatatggg   1080
acaacgagtc ttgctattcc tgcagggcag gtagggcatc caaatatctc tattaatgaa   1140
acattaaggg ttgaattcgg caccaggccg gattggtatt atactttcag atatttagga   1200
aatacaatcc aaaactcata cggttcaatt gtcaataatc aattttcacc tccatcagga   1260
agcaatatta aaggtcctat cgaccttacc ctgaaaaata acatcgacct gtcggccttg   1320
ttggatgaga gccttgacgc actgttcgac tataccattc agggcgataa ccaattgggc   1380
ggcttagctg cctttaacgg gccttacgga ctttacttgt gggaaatctt cttccatgtt   1440 cctttttttaa tggcggttcg cttccacacc gagcagcggt atgagttggc ggaacgttgg   1500
tttaaattca tcttcaacag cgcaggatac cgtgatgatt acggcagtct gctgacggat   1560
gacaaaggca acgtgcgtta ctggaacgtg ataccgctgc aagaggacac ggagtgggat   1620
gacacgttgt ccctggcaac gaccgacccg gacgagattg cgatggccga cccgatgcaa   1680
tacaagctgg ctatatttat tcacaccatg gacttcctga tcagccgcgg cgatagcttg   1740
taccggatgc tggagcggga taccctggcc gaagccaaga tgtattacat tcaggccagc   1800
caactgcttg gccccgccc cgacatccgg ctcaatcaca gttggcctaa tccgaccttg   1860
caaagcgaag cggacgcggt aaccgccgtg ccgacgcgaa gcgattcgcc ggcagcgcca   1920
attttggcct tgcgagcgct tctgacaggc gaaaacggtc atttcctgcc gccttataat   1980
gatgaactgt tcgctttctg ggacaaaatc gatctgcgtt tatacaattt gcgccacaat   2040
ttgagtctgg acggtcagcc gcttcatttg ccgctctttg ccgaaccggt caatccgcgt   2100
gaattgcagg ttcagcatgg cccgggcgat ggcttggggg gaagcgcggg ttccgcccaa   2160
agccgtcaga gtgtctatcg ttttcctctg gtcatcgata aggcgcgcaa tgcggccaac   2220
agtgtcatcc aattcggcaa tgccctggaa aacgcactga ccaagcaaga cagcgaagca   2280
atgaccatgc tgttgcagtc ccagcagcag attgtcctgc agcaaacccg cgatattcag   2340
gagaagaacc tggccgcgct gcaagcaagt ctggaagcaa cgatgacagc gaaagcgggg   2400
gcggagtccc ggaagaccca ttttgccggc ttggcggaca actggatgtc ggacaatgaa   2460
accgcctcac tcgcactgcg taccaccgcg ggaatcatca taccagctc aaccgtgccg   2520 atcgccatca ccggcggctt ggatatggct ccgaacattt ttggtttcgc agttggaggt   2580
tcccgctggg gagcagccag cgcggctgta gcccaaggat tgcaaatcgc cgccggcgta   2640
atggaacaga cggccaatat tatcgatatt agcgaaagct accgccggcg ccgggaggat   2700
tggctgctgc agcgggatgt tgccgaaaat gaagcggcgc agttggattc gcagattgcg   2760
gccctgcggg aacagatgga tatggcgcgc aagcaacttg cgctggcgga gacggaacag   2820
```

```
gcgcacgcgc aagcggtcta cgagctgcaa agcacccgct ttacgaatca agctttgtat    2880
aactggatgg ctggacgtct gtcgtctcta tactatcaaa tgtatgacgc cgcattgccg    2940
ctctgcttga tggcgaagca ggctttagag aaagaaatcg gttcggataa acggtcgga     3000 gtcttgtccc tcccggcctg gaatgatcta tatcagggat tattggcggg cgaggcgctg    3060
ctgctcgagc ttcagaagct ggagaatctg tggctggagg aagacaagcg cggaatggaa    3120
gccgtaaaaa cagtctctct ggatactctt ctccgcaaaa caaatccgaa ctccgggttt    3180
gcggatctcg tcaaggaggc actggacgaa aacggaaaga cgcctgaccc ggtgagcgga    3240
gtcggcgtac agctgcaaaa caatattttc agcgcaaccc ttgacctctc cgttcttggc    3300
ctggatcgct cttacaatca ggcggaaaag tcccgcagga tcaaaaatat gtcggttacc    3360
ttacctgcgc tattggggcc ttaccaggat atagaggcaa ccttatcgct aggcggcgag    3420
accgttgcgc tgtcccatgg cgtggatgac agcggcttgt tcatcactga tctcaacgac    3480
agccggttcc tgcctttcga gggcatggat ccgttatccg gcacactcgt cctgtcgata    3540
ttccatgccg ggcaagacgg cgaccagcgc ctcctgctgg aaagtctcaa tgacgtcatc    3600
ttccacattc gatatgttat gaaatag                                        3627
```

<210> SEQ ID NO 9
<211> LENGTH: 1208
<212> TYPE: PRT
<213> ORGANISM: Paenibacillus strain IDAS 1529

<400> SEQUENCE: 9

```
Met Thr Lys Glu Gly Asp Lys His Met Ser Thr Ser Thr Leu Leu Gln
 1               5                  10                  15

Ser Ile Lys Glu Ala Arg Arg Asp Ala Leu Val Asn His Tyr Ile Ala
            20                  25                  30

Asn Gln Val Pro Thr Ala Leu Ala Asp Lys Ile Thr Asp Ala Asp Ser
        35                  40                  45

Leu Tyr Glu Tyr Leu Leu Leu Asp Thr Lys Ile Ser Glu Leu Val Lys
    50                  55                  60

Thr Ser Pro Ile Ala Glu Ala Ile Ser Ser Val Gln Leu Tyr Met Asn
65                  70                  75                  80

Arg Cys Val Glu Gly Tyr Glu Gly Lys Leu Thr Pro Glu Ser Asn Thr
                85                  90                  95

His Phe Gly Pro Gly Lys Phe Leu Tyr Asn Trp Asp Thr Tyr Asn Lys
            100                 105                 110

Arg Phe Ser Thr Trp Ala Gly Lys Glu Arg Leu Lys Tyr Tyr Ala Gly
        115                 120                 125

Ser Tyr Ile Glu Pro Ser Leu Arg Tyr Asn Lys Thr Asp Pro Phe Leu
    130                 135                 140

Asn Leu Glu Gln Ser Ile Ser Gln Gly Arg Ile Thr Asp Asp Thr Val
145                 150                 155                 160

Lys Asn Ala Leu Gln His Tyr Leu Thr Glu Tyr Glu Val Leu Ala Asp
                165                 170                 175

Leu Asp Tyr Ile Ser Val Asn Lys Gly Gly Asp Glu Ser Val Leu Leu
            180                 185                 190

Phe Val Gly Arg Thr Lys Thr Val Pro Tyr Glu Tyr Tyr Trp Arg Arg
        195                 200                 205

Leu Leu Leu Lys Arg Asp Asn Asn Lys Leu Val Pro Ala Val Trp
    210                 215                 220

Ser Gln Trp Lys Lys Ile Ser Ala Asn Ile Gly Glu Ala Val Asp Ser
```

```
            225                 230                 235                 240
        Tyr Val Val Pro Arg Trp His Lys Asn Arg Leu His Val Gln Trp Cys
                        245                 250                 255

Ser Ile Glu Lys Ser Glu Asn Asp Ala Gly Glu Pro Ile Glu Lys Arg
                        260                 265                 270

Tyr Leu Asn Asp Trp Phe Met Asp Ser Ser Gly Val Trp Ser Ser Phe
                        275                 280                 285

Arg Lys Ile Pro Val Val Glu Lys Ser Phe Glu Tyr Leu Asp Gly Ser
                        290                 295                 300

Leu Asp Pro Arg Phe Val Ala Leu Val Arg Asn Gln Ile Leu Ile Asp
        305                 310                 315                 320

Glu Pro Glu Ile Phe Arg Ile Thr Val Ser Ala Pro Asn Pro Ile Asp
                        325                 330                 335

Ala Asn Gly Arg Val Glu Val His Phe Glu Glu Asn Tyr Ala Asn Arg
                        340                 345                 350

Tyr Asn Ile Thr Ile Lys Tyr Gly Thr Thr Ser Leu Ala Ile Pro Ala
                        355                 360                 365

Gly Gln Val Gly His Pro Asn Ile Ser Ile Asn Glu Thr Leu Arg Val
                        370                 375                 380

Glu Phe Gly Thr Arg Pro Asp Trp Tyr Tyr Thr Phe Arg Tyr Leu Gly
        385                 390                 395                 400

Asn Thr Ile Gln Asn Ser Tyr Gly Ser Ile Val Asn Asn Gln Phe Ser
                        405                 410                 415

Pro Pro Ser Gly Ser Asn Ile Lys Gly Pro Ile Asp Leu Thr Leu Lys
                        420                 425                 430

Asn Asn Ile Asp Leu Ser Ala Leu Leu Asp Glu Ser Leu Asp Ala Leu
                        435                 440                 445

Phe Asp Tyr Thr Ile Gln Gly Asp Asn Gln Leu Gly Gly Leu Ala Ala
        450                 455                 460

Phe Asn Gly Pro Tyr Gly Leu Tyr Leu Trp Glu Ile Phe Phe His Val
        465                 470                 475                 480

Pro Phe Leu Met Ala Val Arg Phe His Thr Glu Gln Arg Tyr Glu Leu
                        485                 490                 495

Ala Glu Arg Trp Phe Lys Phe Ile Phe Asn Ser Ala Gly Tyr Arg Asp
                        500                 505                 510

Asp Tyr Gly Ser Leu Leu Thr Asp Asp Lys Gly Asn Val Arg Tyr Trp
                        515                 520                 525

Asn Val Ile Pro Leu Gln Glu Asp Thr Glu Trp Asp Asp Thr Leu Ser
                        530                 535                 540

Leu Ala Thr Thr Asp Pro Asp Glu Ile Ala Met Ala Asp Pro Met Gln
        545                 550                 555                 560

Tyr Lys Leu Ala Ile Phe Ile His Thr Met Asp Phe Leu Ile Ser Arg
                        565                 570                 575

Gly Asp Ser Leu Tyr Arg Met Leu Glu Arg Asp Thr Leu Ala Glu Ala
                        580                 585                 590

Lys Met Tyr Tyr Ile Gln Ala Ser Gln Leu Leu Gly Pro Arg Pro Asp
                        595                 600                 605

Ile Arg Leu Asn His Ser Trp Pro Asn Pro Thr Leu Gln Ser Glu Ala
                        610                 615                 620

Asp Ala Val Thr Ala Val Pro Thr Arg Ser Asp Ser Pro Ala Ala Pro
        625                 630                 635                 640

Ile Leu Ala Leu Arg Ala Leu Leu Thr Gly Glu Asn Gly His Phe Leu
                        645                 650                 655
```

-continued

Pro Pro Tyr Asn Asp Glu Leu Phe Ala Phe Trp Asp Lys Ile Asp Leu
        660                 665                 670

Arg Leu Tyr Asn Leu Arg His Asn Leu Ser Leu Asp Gly Gln Pro Leu
        675                 680                 685

His Leu Pro Leu Phe Ala Glu Pro Val Asn Pro Arg Glu Leu Gln Val
    690                 695                 700

Gln His Gly Pro Gly Asp Gly Leu Gly Gly Ser Ala Gly Ser Ala Gln
705                 710                 715                 720

Ser Arg Gln Ser Val Tyr Arg Phe Pro Leu Val Ile Asp Lys Ala Arg
            725                 730                 735

Asn Ala Ala Asn Ser Val Ile Gln Phe Gly Asn Ala Leu Glu Asn Ala
        740                 745                 750

Leu Thr Lys Gln Asp Ser Glu Ala Met Thr Met Leu Leu Gln Ser Gln
        755                 760                 765

Gln Gln Ile Val Leu Gln Thr Arg Asp Ile Gln Glu Lys Asn Leu
770                 775                 780

Ala Ala Leu Gln Ala Ser Leu Glu Ala Thr Met Thr Ala Lys Ala Gly
785                 790                 795                 800

Ala Glu Ser Arg Lys Thr His Phe Ala Gly Leu Ala Asp Asn Trp Met
                805                 810                 815

Ser Asp Asn Glu Thr Ala Ser Leu Ala Leu Arg Thr Thr Ala Gly Ile
        820                 825                 830

Ile Asn Thr Ser Ser Thr Val Pro Ile Ala Ile Thr Gly Gly Leu Asp
        835                 840                 845

Met Ala Pro Asn Ile Phe Gly Phe Ala Val Gly Gly Ser Arg Trp Gly
850                 855                 860

Ala Ala Ser Ala Ala Val Ala Gln Gly Leu Gln Ile Ala Ala Gly Val
865                 870                 875                 880

Met Glu Gln Thr Ala Asn Ile Ile Asp Ile Ser Glu Ser Tyr Arg Arg
                885                 890                 895

Arg Arg Glu Asp Trp Leu Leu Gln Arg Asp Val Ala Glu Asn Glu Ala
            900                 905                 910

Ala Gln Leu Asp Ser Gln Ile Ala Ala Leu Arg Glu Gln Met Asp Met
        915                 920                 925

Ala Arg Lys Gln Leu Ala Leu Ala Glu Thr Glu Gln Ala His Ala Gln
930                 935                 940

Ala Val Tyr Glu Leu Gln Ser Thr Arg Phe Thr Asn Gln Ala Leu Tyr
945                 950                 955                 960

Asn Trp Met Ala Gly Arg Leu Ser Ser Leu Tyr Gln Met Tyr Asp
                965                 970                 975

Ala Ala Leu Pro Leu Cys Leu Met Ala Lys Gln Ala Leu Glu Lys Glu
        980                 985                 990

Ile Gly Ser Asp Lys Thr Val Gly Val Leu Ser Leu Pro Ala Trp Asn
        995                 1000                1005

Asp Leu Tyr Gln Gly Leu Leu Ala Gly Glu Ala Leu Leu Leu Glu
    1010                1015                1020

Leu Gln Lys Leu Glu Asn Leu Trp Leu Glu Glu Asp Lys Arg Gly
    1025                1030                1035

Met Glu Ala Val Lys Thr Val Ser Leu Asp Thr Leu Leu Arg Lys
    1040                1045                1050

Thr Asn Pro Asn Ser Gly Phe Ala Asp Leu Val Lys Glu Ala Leu
    1055                1060                1065

Asp Glu Asn Gly Lys Thr Pro Asp Pro Val Ser Gly Val Gly Val
    1070                1075                1080

```
Gln Leu Gln Asn Asn Ile Phe Ser Ala Thr Leu Asp Leu Ser Val
    1085                1090                1095

Leu Gly Leu Asp Arg Ser Tyr Asn Gln Ala Glu Lys Ser Arg Arg
    1100                1105                1110

Ile Lys Asn Met Ser Val Thr Leu Pro Ala Leu Leu Gly Pro Tyr
    1115                1120                1125

Gln Asp Ile Glu Ala Thr Leu Ser Leu Gly Gly Glu Thr Val Ala
    1130                1135                1140

Leu Ser His Gly Val Asp Asp Ser Gly Leu Phe Ile Thr Asp Leu
    1145                1150                1155

Asn Asp Ser Arg Phe Leu Pro Phe Glu Gly Met Asp Pro Leu Ser
    1160                1165                1170

Gly Thr Leu Val Leu Ser Ile Phe His Ala Gly Gln Asp Gly Asp
    1175                1180                1185

Gln Arg Leu Leu Leu Glu Ser Leu Asn Asp Val Ile Phe His Ile
    1190                1195                1200

Arg Tyr Val Met Lys
    1205
```

<210> SEQ ID NO 10
<211> LENGTH: 4335
<212> TYPE: DNA
<213> ORGANISM: Paenibacillus strain IDAS 1529

<400> SEQUENCE: 10

```
atgccacaat ctagcaatgc cgatatcaag ctattgtcgc catcgctgcc aaagggcggc    60
ggttccatga agggaatcga agaaaacatc gcggctcccg gctccgacgg catggcacgt   120
tgtaatgtgc cgctgccggt aacctccggc cgctatatta ctcctgatat aagcctgtcc   180
tatgcgagcg gccacggcaa cggcgcttat ggaatgggct ggacgatggg agtgatgagc   240
attagccgga gaacaagccg agggaccccc agttatacat ccgaagacca gttccttggt   300
ccggatgggg aggtgcttgt tccggaaagc aacgaacaag gggagatcat tacccgccac   360
accgatacgg cccaagggat accgttaggc gagacgttta cggttacacg ctatttccc    420
cggatcgaga gcgcttttca tttgctggaa tactgggaag cgcaagcagg aagcgcaaca   480
gcgtcgtttt ggcttattca ctctgccgat ggagtgctgc actgtctggg taaaactgct   540
caggcgagga tagccgcccc tgacgattcc gccaagatcg cagaatggct agtggaggag   600
tccgtctccc ccttcggaga gcatatttat taccaataca agaagaagaa caatcaaggc   660
gtgaatctgg aggaagacaa tcatcaatat ggggcgaacc gctatctgaa atcgattcgc   720
tatggaaata aggttgcctc tccttctctc tatgtctgga aggggaaat tccggcagac   780
ggccaatggc tgtattccgt tatcctggat tatggcgaga acgataccct cagcggatgt t  840
cctccccctat acacgcccca aggggagtgg ctggtgcgcc cggaccgttt ttcccgctat   900
gactacggat tgaggtccg gacttgccgc ttgtgccgcc aggtcttgat gttccacgtc   960
tttaaggagc ttggcgggga ccggcgctg gtgtggcgga tgcagttgga atacgacgag  1020
aacccggcgg cgtccatgct gagcgcggtc cggcaattgg cttatgaagc agatggggcc  1080
attgaagct tgccgccgct ggaattcgat atactccat ttggcatcga acaacggcc  1140
gattggcagc ctttctgcc tgtgcctgaa tgggcggatg aagaacatta tcagttggtc  1200
gatttgtacg gagaaggcat accgggctta ttatatcaga acaatgacca ctggcattat  1260
cgttcgcccg cccggggcga cacaccggac gggatcgcct ataacagctg gcggccgctt  1320
```

```
cctcatatcc ccgtgaactc ccggaacggg atgctgatgg atctgaatgg agacgggtat    1380
ctggaatggt tgcttgcgga acccgggtt gcggggcgct atagcatgaa cccggataag    1440
agctggtccg gttttgtgcc gctccaggca ctgccaacgg aattcttcca tccgcaggca    1500
cagcttgcca atgttaccgg atcgggttta accgacttgg ttatgatcgg tccgaagagc    1560
gtccggtttt atgccggaga agaagcgggc ttcaagcgcg catgtgaagt gtggcagcaa    1620
gtgggcatta ctttgcctgt ggaacgcgtg gataaaaagg aactggtggc attcagcgat    1680
atgctgggat cgggtcagtc tcatctggtg cgcatccggc atgatggcgt tacatgctgg    1740
cctaatctgg ggaacggcgt gttcggggcg ccgttggccc ttcacgggtt tacggcatcg    1800
gagcgggaat tcaatccgga acgtgtatat cttgtggacc ttgatggatc cggcgcttcc    1860
gatatcattt atgcttctcg tgacgctcta ctcatttacc gaaatctttc cggcaatggc    1920
tttgctgatc cggtgcgggt tccgctgcct gacggcgtgc ggtttgataa tctgtgccgg    1980
ctgctgcctg ccgatatccg cgggttaggt gtggccagtc tggtgctgca tgtaccttac    2040
atggcccccc gcagttggaa attagatttc tttgcggcga agccgtattt attgcaaacg    2100
gtcagcaaca atcttggagc ttccagctcg ttttggtacc gaagctccac ccagtattgg    2160
ctggatgaga aacaggcggc ctcatcggct gtctccgctt tgcccttccc gataaacgtg    2220
gtatcggata tgcacacggt ggacgaaatc agcggccgca ccaggactca gaagtatact    2280
taccgccatg gcgtgtatga ccggaccgaa aaggaatttg ccggattcgg ccgcattgac    2340
acatgggaag aggagcggga ttccgaagga accctgagcg tcagcactcc gcccgtgctg    2400
acgcggacct ggtatcatac cgggcaaaag caggatgagg agcgtgccgt gcagcaatat    2460
tggcaaggcg accctgcggc ttttcaggtt aaacccgtcc ggcttactcg attcgatgcg    2520
gcagcggccc aggatctgcc gctagattct aataatgggc agcaagaata ctggctgtac    2580
cgatcattac aagggatgcc gctgcggact gagattttg cgggagatgt tggcgggtcg    2640
cctccttatc aggtagagag cttccgttat caagtgcgct ggtgcagag catcgattcg    2700 gaatgtgttg ccttgcccat gcagttggag cagcttacgt acaactatga gcaaatcgcc    2760
tctgatccgc agtgttcaca gcagatacag caatggttcg acgaatacgg cgtggcggca    2820
cagagtgtaa caatccaata tccgcgccgg gcacagccgg aggacaatcc gtaccctcgc    2880
acgctgccgg ataccagctg gagcagcagt tatgattcgc agcaaatgct gctgcggttg    2940
accaggcaaa ggcaaaaagc gtaccacctt gcagatcctg aaggctggcg cttgaatatt    3000
ccccatcaga cacgcctgga tgccttcatt tattctgctg acagcgtgcc cgccgaagga    3060
ataagcgccg agctgctgga ggtggacggc acgttacgat cttcggcgct ggaacaggct    3120 tatgcggcc agtcagagat catctatgcg ggcgggggcg aaccggattt gcgagccctg    3180
gtccattaca ccagaagcgc ggttcttgat gaagactgtt tacaagccta tgaaggcgta    3240
ctgagcgata gccaattgaa ctcgcttctt gcctcttccg gctatcaacg aagcgcaaga    3300
atattgggtt cgggcgatga agtggatatt tttgtcgcgg aacaaggatt tacccgttat    3360
gcggatgaac cgaatttttt ccgtattctg ggcaacaat cctctctctt gtccggggaa    3420
caagtattaa catgggatga taatttctgt gcggttacat ccatcgaaga cgcgcttggc    3480
aatcaaattc agattgcata tgattaccgc tttgtggagg ccatccagat taccgatacg    3540
aataataatg tgaatcaggt cgccctggat gctctcggcc gggtcgtata cagccggacc    3600
tggggcacgg aggaagggat aaagaccggc ttccgcccgg aggtgaatt cgcgacgccc    3660 gagacaatgg agcaggcgct tgccctggca tctcccttgc cggttgcatc ctgctgtgta    3720
```

-continued

```
tatgatgcgc atagctggat gggaacgata actcttgcac aactgtcaga gcttgttcca    3780
gatagtgaaa agcaatggtc gttcttgata gacaatcgct tgattatgcc ggacggcaga    3840
atcagatccc gcggtcggga tccatggtcg cttcaccggc tattgccgcc tgctgtgggc    3900
gaattgctga gcgaggcgga ccgtaaaccg ccgcatacgg taattttggc agcagatcgt    3960
tacccggatg acccatccca gcaaattcag gcgagcatcg tgtttagcga tggctttggg    4020
cgtacgatac aaaactgctaa aagagaagat acccgatggg cgattgcgga acgggtggac    4080
tatgacggaa ccggagccgt aatccgcagc tttcagcctt tttatcttga cgactggaat    4140
tatgtgggcg aagaggctgt cagcagctct atgtacgcaa cgatctatta ttatgatgct    4200
ctggcacgac aattaaggat ggtcaacgct aaaggatatg agaggagaac tgctttttac    4260
ccatggttta cagtaaacga agatgaaaat gataccatgg actcatcatt atttgcttca    4320
ccgcctgcgc ggtga                                                     4335
```

<210> SEQ ID NO 11
<211> LENGTH: 1444
<212> TYPE: PRT
<213> ORGANISM: Paenibacillus strain IDAS 1529

<400> SEQUENCE: 11

```
Met Pro Gln Ser Ser Asn Ala Asp Ile Lys Leu Leu Ser Pro Ser Leu
1               5                   10                  15

Pro Lys Gly Gly Gly Ser Met Lys Gly Ile Glu Glu Asn Ile Ala Ala
            20                  25                  30

Pro Gly Ser Asp Gly Met Ala Arg Cys Asn Val Pro Leu Pro Val Thr
        35                  40                  45

Ser Gly Arg Tyr Ile Thr Pro Asp Ile Ser Leu Ser Tyr Ala Ser Gly
    50                  55                  60

His Gly Asn Gly Ala Tyr Gly Met Gly Trp Thr Met Gly Val Met Ser
65                  70                  75                  80

Ile Ser Arg Arg Thr Ser Arg Gly Thr Pro Ser Tyr Thr Ser Glu Asp
                85                  90                  95

Gln Phe Leu Gly Pro Asp Gly Glu Val Leu Val Pro Glu Ser Asn Glu
            100                 105                 110

Gln Gly Glu Ile Ile Thr Arg His Thr Asp Thr Ala Gln Gly Ile Pro
        115                 120                 125

Leu Gly Glu Thr Phe Thr Val Thr Arg Tyr Phe Pro Arg Ile Glu Ser
    130                 135                 140

Ala Phe His Leu Leu Glu Tyr Trp Glu Ala Gln Ala Gly Ser Ala Thr
145                 150                 155                 160

Ala Ser Phe Trp Leu Ile His Ser Ala Asp Gly Val Leu His Cys Leu
                165                 170                 175

Gly Lys Thr Ala Gln Ala Arg Ile Ala Ala Pro Asp Asp Ser Ala Lys
            180                 185                 190

Ile Ala Glu Trp Leu Val Glu Ser Val Ser Pro Phe Gly Glu His
        195                 200                 205

Ile Tyr Tyr Gln Tyr Lys Glu Glu Asp Asn Gln Gly Val Asn Leu Glu
    210                 215                 220

Glu Asp Asn His Gln Tyr Gly Ala Asn Arg Tyr Leu Lys Ser Ile Arg
225                 230                 235                 240

Tyr Gly Asn Lys Val Ala Ser Pro Ser Leu Tyr Val Trp Lys Gly Glu
                245                 250                 255

Ile Pro Ala Asp Gly Gln Trp Leu Tyr Ser Val Ile Leu Asp Tyr Gly
            260                 265                 270
```

-continued

```
Glu Asn Asp Thr Ser Ala Asp Val Pro Pro Leu Tyr Thr Pro Gln Gly
            275                 280                 285
Glu Trp Leu Val Arg Pro Asp Arg Phe Ser Arg Tyr Asp Tyr Gly Phe
        290                 295                 300
Glu Val Arg Thr Cys Arg Leu Cys Arg Gln Val Leu Met Phe His Val
305                 310                 315                 320
Phe Lys Glu Leu Gly Gly Glu Pro Ala Leu Val Trp Arg Met Gln Leu
                325                 330                 335
Glu Tyr Asp Glu Asn Pro Ala Ala Ser Met Leu Ser Ala Val Arg Gln
            340                 345                 350
Leu Ala Tyr Glu Ala Asp Gly Ala Ile Arg Ser Leu Pro Pro Leu Glu
        355                 360                 365
Phe Asp Tyr Thr Pro Phe Gly Ile Glu Thr Thr Ala Asp Trp Gln Pro
370                 375                 380
Phe Leu Pro Val Pro Glu Trp Ala Asp Glu Glu His Tyr Gln Leu Val
385                 390                 395                 400
Asp Leu Tyr Gly Glu Gly Ile Pro Gly Leu Leu Tyr Gln Asn Asn Asp
                405                 410                 415
His Trp His Tyr Arg Ser Pro Ala Arg Gly Asp Thr Pro Asp Gly Ile
            420                 425                 430
Ala Tyr Asn Ser Trp Arg Pro Leu Pro His Ile Pro Val Asn Ser Arg
        435                 440                 445
Asn Gly Met Leu Met Asp Leu Asn Gly Asp Gly Tyr Leu Glu Trp Leu
        450                 455                 460
Leu Ala Glu Pro Gly Val Ala Gly Arg Tyr Ser Met Asn Pro Asp Lys
465                 470                 475                 480
Ser Trp Ser Gly Phe Val Pro Leu Gln Ala Leu Pro Thr Glu Phe Phe
                485                 490                 495
His Pro Gln Ala Gln Leu Ala Asn Val Thr Gly Ser Gly Leu Thr Asp
            500                 505                 510
Leu Val Met Ile Gly Pro Lys Ser Val Arg Phe Tyr Ala Gly Glu Glu
        515                 520                 525
Ala Gly Phe Lys Arg Ala Cys Glu Val Trp Gln Gln Val Gly Ile Thr
        530                 535                 540
Leu Pro Val Glu Arg Val Asp Lys Lys Glu Leu Val Ala Phe Ser Asp
545                 550                 555                 560
Met Leu Gly Ser Gly Gln Ser His Leu Val Arg Ile Arg His Asp Gly
                565                 570                 575
Val Thr Cys Trp Pro Asn Leu Gly Asn Gly Val Phe Gly Ala Pro Leu
            580                 585                 590
Ala Leu His Gly Phe Thr Ala Ser Glu Arg Glu Phe Asn Pro Glu Arg
        595                 600                 605
Val Tyr Leu Val Asp Leu Asp Gly Ser Gly Ala Ser Asp Ile Ile Tyr
        610                 615                 620
Ala Ser Arg Asp Ala Leu Leu Ile Tyr Arg Asn Leu Ser Gly Asn Gly
625                 630                 635                 640
Phe Ala Asp Pro Val Arg Val Pro Leu Pro Asp Gly Val Arg Phe Asp
                645                 650                 655
Asn Leu Cys Arg Leu Leu Pro Ala Asp Ile Arg Gly Leu Gly Val Ala
            660                 665                 670
Ser Leu Val Leu His Val Pro Tyr Met Ala Pro Arg Ser Trp Lys Leu
        675                 680                 685
Asp Phe Phe Ala Ala Lys Pro Tyr Leu Leu Gln Thr Val Ser Asn Asn
```

```
            690              695              700
Leu Gly Ala Ser Ser Phe Trp Tyr Arg Ser Thr Gln Tyr Trp
705              710              715              720

Leu Asp Glu Lys Gln Ala Ala Ser Ser Ala Val Ser Ala Leu Pro Phe
            725              730              735

Pro Ile Asn Val Val Ser Asp Met His Thr Val Asp Glu Ile Ser Gly
            740              745              750

Arg Thr Arg Thr Gln Lys Tyr Thr Tyr Arg His Gly Val Tyr Asp Arg
            755              760              765

Thr Glu Lys Glu Phe Ala Gly Phe Gly Arg Ile Asp Thr Trp Glu Glu
770              775              780

Glu Arg Asp Ser Glu Gly Thr Leu Ser Val Ser Thr Pro Pro Val Leu
785              790              795              800

Thr Arg Thr Trp Tyr His Thr Gly Gln Lys Gln Asp Glu Glu Arg Ala
            805              810              815

Val Gln Gln Tyr Trp Gln Gly Asp Pro Ala Ala Phe Gln Val Lys Pro
            820              825              830

Val Arg Leu Thr Arg Phe Asp Ala Ala Ala Gln Asp Leu Pro Leu
            835              840              845

Asp Ser Asn Asn Gly Gln Gln Glu Tyr Trp Leu Tyr Arg Ser Leu Gln
850              855              860

Gly Met Pro Leu Arg Thr Glu Ile Phe Ala Gly Asp Val Gly Gly Ser
865              870              875              880

Pro Pro Tyr Gln Val Glu Ser Phe Arg Tyr Gln Val Arg Leu Val Gln
            885              890              895

Ser Ile Asp Ser Glu Cys Val Ala Leu Pro Met Gln Leu Glu Gln Leu
            900              905              910

Thr Tyr Asn Tyr Glu Gln Ile Ala Ser Asp Pro Gln Cys Ser Gln Gln
            915              920              925

Ile Gln Gln Trp Phe Asp Glu Tyr Gly Val Ala Ala Gln Ser Val Thr
            930              935              940

Ile Gln Tyr Pro Arg Arg Ala Gln Pro Glu Asp Asn Pro Tyr Pro Arg
945              950              955              960

Thr Leu Pro Asp Thr Ser Trp Ser Ser Tyr Asp Ser Gln Met
            965              970              975

Leu Leu Arg Leu Thr Arg Gln Arg Gln Lys Ala Tyr His Leu Ala Asp
            980              985              990

Pro Glu Gly Trp Arg Leu Asn Ile Pro His Gln Thr Arg Leu Asp Ala
            995              1000             1005

Phe Ile Tyr Ser Ala Asp Ser Val Pro Ala Glu Gly Ile Ser Ala
            1010             1015             1020

Glu Leu Leu Glu Val Asp Gly Thr Leu Arg Ser Ala Leu Glu
            1025             1030             1035

Gln Ala Tyr Gly Gly Gln Ser Glu Ile Ile Tyr Ala Gly Gly Gly
            1040             1045             1050

Glu Pro Asp Leu Arg Ala Leu Val His Tyr Thr Arg Ser Ala Val
            1055             1060             1065

Leu Asp Glu Asp Cys Leu Gln Ala Tyr Glu Gly Val Leu Ser Asp
            1070             1075             1080

Ser Gln Leu Asn Ser Leu Leu Ala Ser Ser Gly Tyr Gln Arg Ser
            1085             1090             1095

Ala Arg Ile Leu Gly Ser Gly Asp Glu Val Asp Ile Phe Val Ala
            1100             1105             1110
```

| | | | | | | | | | | |
|---|---|---|---|---|---|---|---|---|---|---|
| Glu | Gln | Gly | Phe | Thr | Arg | Tyr | Ala | Asp | Glu | Pro | Asn | Phe | Phe | Arg |
| | 1115 | | | | 1120 | | | | 1125 | |

Ile Leu Gly Gln Gln Ser Ser Leu Leu Ser Gly Glu Gln Val Leu
    1130                1135                1140

Thr Trp Asp Asp Asn Phe Cys Ala Val Thr Ser Ile Glu Asp Ala
    1145                1150                1155

Leu Gly Asn Gln Ile Gln Ile Ala Tyr Asp Tyr Arg Phe Val Glu
    1160                1165                1170

Ala Ile Gln Ile Thr Asp Thr Asn Asn Asn Val Asn Gln Val Ala
    1175                1180                1185

Leu Asp Ala Leu Gly Arg Val Val Tyr Ser Arg Thr Trp Gly Thr
    1190                1195                1200

Glu Glu Gly Ile Lys Thr Gly Phe Arg Pro Glu Val Glu Phe Ala
    1205                1210                1215

Thr Pro Glu Thr Met Glu Gln Ala Leu Ala Leu Ala Ser Pro Leu
    1220                1225                1230

Pro Val Ala Ser Cys Cys Val Tyr Asp Ala His Ser Trp Met Gly
    1235                1240                1245

Thr Ile Thr Leu Ala Gln Leu Ser Glu Leu Val Pro Asp Ser Glu
    1250                1255                1260

Lys Gln Trp Ser Phe Leu Ile Asp Asn Arg Leu Ile Met Pro Asp
    1265                1270                1275

Gly Arg Ile Arg Ser Arg Gly Arg Asp Pro Trp Ser Leu His Arg
    1280                1285                1290

Leu Leu Pro Pro Ala Val Gly Glu Leu Leu Ser Glu Ala Asp Arg
    1295                1300                1305

Lys Pro Pro His Thr Val Ile Leu Ala Ala Asp Arg Tyr Pro Asp
    1310                1315                1320

Asp Pro Ser Gln Gln Ile Gln Ala Ser Ile Val Phe Ser Asp Gly
    1325                1330                1335

Phe Gly Arg Thr Ile Gln Thr Ala Lys Arg Glu Asp Thr Arg Trp
    1340                1345                1350

Ala Ile Ala Glu Arg Val Asp Tyr Asp Gly Thr Gly Ala Val Ile
    1355                1360                1365

Arg Ser Phe Gln Pro Phe Tyr Leu Asp Asp Trp Asn Tyr Val Gly
    1370                1375                1380

Glu Glu Ala Val Ser Ser Ser Met Tyr Ala Thr Ile Tyr Tyr Tyr
    1385                1390                1395

Asp Ala Leu Ala Arg Gln Leu Arg Met Val Asn Ala Lys Gly Tyr
    1400                1405                1410

Glu Arg Arg Thr Ala Phe Tyr Pro Trp Phe Thr Val Asn Glu Asp
    1415                1420                1425

Glu Asn Asp Thr Met Asp Ser Ser Leu Phe Ala Ser Pro Pro Ala
    1430                1435                1440

Arg

<210> SEQ ID NO 12
<211> LENGTH: 2793
<212> TYPE: DNA
<213> ORGANISM: Paenibacillus strain IDAS 1529

<400> SEQUENCE: 12
atgaacacaa cgtccatata tagggggcacg cctacgattt cagttgtgga taaccggaac    60
ttggagattc gcattcttca gtataaccgt atcgcggctg aagatccggc agatgagtgt   120

```
atcctgcgga acacgtatac gccgttaagc tatcttggca gcagcatgga tccccgtttg    180
ttctcgcaat atcaggatga tcgcggaaca ccgccgaata tacgaaccat ggcttccctg    240
agaggcgaag cgctgtgttc ggaaagtgtg gatgccggcc gcaaggcgga gcttttgat    300
atcgaggggc ggcccgtctg gcttatcgat gccaacggca cagagacgac tctcgaatat    360
gatgtcttag gcaggccaac agccgtattc gagcaacagg aaggtacgga ctcccccag    420
tgcagggagc ggtttattta tggtgagaag gaggcggatg cccaggccaa caatttgcgc    480
ggacaactgg ttcgccacta cgataccgcg ggccggatac agaccgacag catctccttg    540
gctggactgc cgttgcgcca aagccgtcaa ctgctgaaaa attgggatga acctggcgac    600
tggagtatgg atgaggaaag cgcctgggcc tcgttgctgg ctgccgaagc ttatgatacg    660
agctggcggt atgacgcgca ggacagggtg ctcgcccaaa ccgacgccaa agggaatctc    720
cagcaactga cttacaatga cgccggccag ccgcaggcgg tcagcctcaa gctgcaaggc    780
caagcggagc aacggatttg gaaccggatc gagtacaacg cggcgggtca agtggatctc    840
gccgaagccg ggaatggaat cgtaacggaa tatacttacg aggaaagcac gcagcggtta    900
atccgaaaaa aagattcccg cggactgtcc tccggggaaa gagaagtgct gcaggattat    960
cgttatgaat atgatccggt aggcaatatc ctttctattt acaatgaagc ggagccggtt   1020
cgttatttcc gcaatcaggc cgttgctccg aaaaggcaat atgcctacga tgccttgtat   1080
cagcttgtat ctagttcggg gcgggaatcc gacgcgcttc ggcagcagac gtcgcttcct   1140
cccttgatca cgcctatccc tctggacgat agccaatacg tcaattacgc tgaaaaatac   1200
agctatgatc aggcgggcaa tttaatcaag cttagccata acggggcaag tcaatataca   1260
acgaatgtgt atgtggacaa aagctcaaac cggggggattt ggcggcaagg ggaagacatc   1320
ccggatatcg cggcttcctt tgacagagca ggcaatcaac aagctttatt cccggggaga   1380
ccgttggaat gggatacacg caatcaatta agccgtgtcc atatggtcgt gcgcgaaggc   1440
ggagacaacg actgggaagg ctatctctat gacagctcgg gaatgcgtat cgtaaaacga   1500
tctacccgca aaacacagac aacgacgcaa acgatacga ccctctattt gccgggcctg   1560
gagctgcgaa tccgccagac cggggaccgg gtcacgaag cattgcaggt cattaccgtg   1620
gatgagggag cgggacaagt gagggtgctg cactgggagg atggaaccga gccgggcggc   1680
atcgccaatg atcagtaccg gtacagcctg aacgatcatc ttacctcctc tttattggaa   1740
gttgacgggc aaggtcagat cattagtaag gaagaatttt atccctatgg cggcacagcc   1800
ctgtggacag cccggtcaga ggtagaggca agctacaaga ccatccgcta ttcaggcaaa   1860
gagcgggatg ccacaggcct gtattattac ggacaccgct actatatgcc atggttgggt   1920
cgctggctga atccggaccc ggccggaatg gtagatggac taaacctgta ccgtatggtc   1980
aggaacaatc ctataggact gatggatccg aatgggaatg cgccaatcaa cgtggcggat   2040
tatagcttcg tgcatggtga tttagtttat ggtcttagta aggaaagagg aagatatcta   2100
aagctatttta atccaaactt taatatggaa aaatcagact ctcctgctat ggttatagat   2160
caatataata ataatgttgc attgagtata actaaccaat ataaagtaga agaattgatg   2220
aaatttcaaa aagacccaca aaaagccgca cggaaaataa aggttccaga agggaatcgt   2280
ttatcgagga acgaaaatta tccttttgtgg cacgattata ttaacattgg agaagctaaa   2340
gctgcatttta aggcctctca tattttccaa gaagtgaagg ggaattatgg gaaagattat   2400
tatcataaat tattattaga cagaatgata gaatcgccgt tgctgtggaa acgaggcagc   2460
aaactcgggc tagaaatcgc cgctaccaat cagagaacaa aaatacactt tgttcttgac   2520
```

```
aatttaaaata tcgagcaggt ggttacgaaa gagggtagcg gcggtcagtc aatcacagct    2580
tcggagctcc gttatattta tcgaaatcgc gaaagattga acgggcgtgt catttttctat    2640 agaaataatg aaaggctaga tcaggctcca tggcaagaaa atccggactt atggagcaaa    2700
tatcaaccgg gtcttagaca aagcagcagt tcaagagtca agaacgagg gattgggaac    2760 tttttccgcc ggttttcaat gaagagaaag tag                                 2793
```

<210> SEQ ID NO 13
<211> LENGTH: 930
<212> TYPE: PRT
<213> ORGANISM: Paenibacillus strain IDAS 1529

<400> SEQUENCE: 13

```
Met Asn Thr Thr Ser Ile Tyr Arg Gly Thr Pro Thr Ile Ser Val Val
1               5                   10                  15

Asp Asn Arg Asn Leu Glu Ile Arg Ile Leu Gln Tyr Asn Arg Ile Ala
            20                  25                  30

Ala Glu Asp Pro Ala Asp Glu Cys Ile Leu Arg Asn Thr Tyr Thr Pro
        35                  40                  45

Leu Ser Tyr Leu Gly Ser Ser Met Asp Pro Arg Leu Phe Ser Gln Tyr
    50                  55                  60

Gln Asp Asp Arg Gly Thr Pro Pro Asn Ile Arg Thr Met Ala Ser Leu
65                  70                  75                  80

Arg Gly Glu Ala Leu Cys Ser Glu Ser Val Asp Ala Gly Arg Lys Ala
                85                  90                  95

Glu Leu Phe Asp Ile Glu Gly Arg Pro Val Trp Leu Ile Asp Ala Asn
            100                 105                 110

Gly Thr Glu Thr Thr Leu Glu Tyr Asp Val Leu Gly Arg Pro Thr Ala
        115                 120                 125

Val Phe Glu Gln Gln Glu Gly Thr Asp Ser Pro Gln Cys Arg Glu Arg
    130                 135                 140

Phe Ile Tyr Gly Glu Lys Glu Ala Asp Ala Gln Ala Asn Asn Leu Arg
145                 150                 155                 160

Gly Gln Leu Val Arg His Tyr Asp Thr Ala Gly Arg Ile Gln Thr Asp
                165                 170                 175

Ser Ile Ser Leu Ala Gly Leu Pro Leu Arg Gln Ser Arg Gln Leu Leu
            180                 185                 190

Lys Asn Trp Asp Glu Pro Gly Asp Trp Ser Met Asp Glu Glu Ser Ala
        195                 200                 205

Trp Ala Ser Leu Leu Ala Ala Glu Ala Tyr Asp Thr Ser Trp Arg Tyr
    210                 215                 220

Asp Ala Gln Asp Arg Val Leu Ala Gln Thr Asp Ala Lys Gly Asn Leu
225                 230                 235                 240

Gln Gln Leu Thr Tyr Asn Asp Ala Gly Gln Pro Gln Ala Val Ser Leu
                245                 250                 255

Lys Leu Gln Gly Gln Ala Glu Gln Arg Ile Trp Asn Arg Ile Glu Tyr
            260                 265                 270

Asn Ala Ala Gly Gln Val Asp Leu Ala Glu Ala Gly Asn Gly Ile Val
        275                 280                 285

Thr Glu Tyr Thr Tyr Glu Glu Ser Thr Gln Arg Leu Ile Arg Lys Lys
    290                 295                 300

Asp Ser Arg Gly Leu Ser Ser Gly Glu Arg Glu Val Leu Gln Asp Tyr
305                 310                 315                 320

Arg Tyr Glu Tyr Asp Pro Val Gly Asn Ile Leu Ser Ile Tyr Asn Glu
                325                 330                 335
```

```
Ala Glu Pro Val Arg Tyr Phe Arg Asn Gln Ala Val Ala Pro Lys Arg
            340                 345                 350

Gln Tyr Ala Tyr Asp Ala Leu Tyr Gln Leu Val Ser Ser Ser Gly Arg
        355                 360                 365

Glu Ser Asp Ala Leu Arg Gln Gln Thr Ser Leu Pro Pro Leu Ile Thr
    370                 375                 380

Pro Ile Pro Leu Asp Asp Ser Gln Tyr Val Asn Tyr Ala Glu Lys Tyr
385                 390                 395                 400

Ser Tyr Asp Gln Ala Gly Asn Leu Ile Lys Leu Ser His Asn Gly Ala
                405                 410                 415

Ser Gln Tyr Thr Thr Asn Val Tyr Val Asp Lys Ser Ser Asn Arg Gly
            420                 425                 430

Ile Trp Arg Gln Gly Glu Asp Ile Pro Asp Ile Ala Ala Ser Phe Asp
        435                 440                 445

Arg Ala Gly Asn Gln Gln Ala Leu Phe Pro Gly Arg Pro Leu Glu Trp
    450                 455                 460

Asp Thr Arg Asn Gln Leu Ser Arg Val His Met Val Val Arg Glu Gly
465                 470                 475                 480

Gly Asp Asn Asp Trp Glu Gly Tyr Leu Tyr Asp Ser Ser Gly Met Arg
                485                 490                 495

Ile Val Lys Arg Ser Thr Arg Lys Thr Gln Thr Thr Thr Gln Thr Asp
            500                 505                 510

Thr Thr Leu Tyr Leu Pro Gly Leu Glu Leu Arg Ile Arg Gln Thr Gly
        515                 520                 525

Asp Arg Val Thr Glu Ala Leu Gln Val Ile Thr Val Asp Glu Gly Ala
    530                 535                 540

Gly Gln Val Arg Val Leu His Trp Glu Asp Gly Thr Glu Pro Gly Gly
545                 550                 555                 560

Ile Ala Asn Asp Gln Tyr Arg Tyr Ser Leu Asn Asp His Leu Thr Ser
                565                 570                 575

Ser Leu Leu Glu Val Asp Gly Gln Gly Gln Ile Ile Ser Lys Glu Glu
            580                 585                 590

Phe Tyr Pro Tyr Gly Gly Thr Ala Leu Trp Thr Ala Arg Ser Glu Val
        595                 600                 605

Glu Ala Ser Tyr Lys Thr Ile Arg Tyr Ser Gly Lys Glu Arg Asp Ala
    610                 615                 620

Thr Gly Leu Tyr Tyr Gly His Arg Tyr Tyr Met Pro Trp Leu Gly
625                 630                 635                 640

Arg Trp Leu Asn Pro Asp Pro Ala Gly Met Val Asp Gly Leu Asn Leu
                645                 650                 655

Tyr Arg Met Val Arg Asn Asn Pro Ile Gly Leu Met Asp Pro Asn Gly
            660                 665                 670

Asn Ala Pro Ile Asn Val Ala Asp Tyr Ser Phe Val His Gly Asp Leu
        675                 680                 685

Val Tyr Gly Leu Ser Lys Glu Arg Gly Arg Tyr Leu Lys Leu Phe Asn
    690                 695                 700

Pro Asn Phe Asn Met Glu Lys Ser Asp Ser Pro Ala Met Val Ile Asp
705                 710                 715                 720

Gln Tyr Asn Asn Asn Val Ala Leu Ser Ile Thr Asn Gln Tyr Lys Val
                725                 730                 735

Glu Glu Leu Met Lys Phe Gln Lys Asp Pro Gln Lys Ala Ala Arg Lys
            740                 745                 750

Ile Lys Val Pro Glu Gly Asn Arg Leu Ser Arg Asn Glu Asn Tyr Pro
```

```
                755             760             765
Leu Trp His Asp Tyr Ile Asn Ile Gly Glu Ala Lys Ala Ala Phe Lys
    770                 775                 780

Ala Ser His Ile Phe Gln Glu Val Lys Gly Asn Tyr Gly Lys Asp Tyr
785                 790                 795                 800

Tyr His Lys Leu Leu Leu Asp Arg Met Ile Glu Ser Pro Leu Leu Trp
            805                 810                 815

Lys Arg Gly Ser Lys Leu Gly Leu Glu Ile Ala Ala Thr Asn Gln Arg
            820                 825                 830

Thr Lys Ile His Phe Val Leu Asp Asn Leu Asn Ile Glu Gln Val Val
            835                 840                 845

Thr Lys Glu Gly Ser Gly Gln Ser Ile Thr Ala Ser Glu Leu Arg
850                 855                 860

Tyr Ile Tyr Arg Asn Arg Glu Arg Leu Asn Gly Arg Val Ile Phe Tyr
865                 870                 875                 880

Arg Asn Asn Glu Arg Leu Asp Gln Ala Pro Trp Gln Glu Asn Pro Asp
                885                 890                 895

Leu Trp Ser Lys Tyr Gln Pro Gly Leu Arg Gln Ser Ser Ser Ser Arg
            900                 905                 910

Val Lys Glu Arg Gly Ile Gly Asn Phe Phe Arg Arg Phe Ser Met Lys
        915                 920                 925

Arg Lys
    930

<210> SEQ ID NO 14
<211> LENGTH: 1791
<212> TYPE: DNA
<213> ORGANISM: Artificial Sequence
<220> FEATURE:
<223> OTHER INFORMATION: Nucleic acid sequence of ORF7, which encodes a
      cry-like protein.

<400> SEQUENCE: 14
atgaactcaa atgaaccaaa tttatctgat gttgttaatt gtttaagtga ccccaatagt      60
gacttggaga agtctggcgg tggagtagcg ctagatgttg gaatgtcatt gatatccgaa     120
cttcttggta cggttccagt tgctggatca attcttcaat ttgtattcga taaattgtgg     180 tttattttg gcccttctga gtgggactca cttatggaac atgttgaagc attaattgat      240
agtaaaatac aagagcaggt aaaaagaagt gcacaagatg aactaaatgc aattacaaat     300
aacttatcta cgtatttgaa atttctagat gcatgggaaa atgattctaa taatttaaga    360
gcgagagctg tagtgaaaga ccaatttgta ggccttgaac agactcttga agaaaaatg    420 gttagtgttt ttggaagtac gggtcatgaa gtgcatcttt tgccaatttt cgctcaagca     480
gccaacctcc acctaattct attaagagat gctgagaaat atggaaagag atggggttgg    540
gcagatagag aaattcaagt atattatgat aaccagattc gttatatcca tgaatatacg    600
gaccattgta ttaaatatta taatcaagga ttaagtaaac tgaaaggttc tacctatcaa     660
gattgggata gtataatcg ttttagaaga gaaatgaccc taactgttct tgatttgatt     720
tcaattttcc catcgtatga tactagaact tacccaattg atacaatagg tcaattgaca     780
agggaagttt attcggattt acttattgct aacccgtctg ggatgcagac tttcactaat     840
gtagatttcg acaatattct tattagaaaa cctcatttaa tggatttctt aagaactctt     900
gagattttta ccgatcgaca taacgcaagc agacacaacg tatattgggg cggacatcga     960
gtgcattctt cttacacagg aggtaatttt gaaaattttg aatctccctt atatggcagt    1020
```

-continued

```
gaagcaaatg tagaaccccg aacatggttg agttttggag aatctcaagt ctataatata    1080
cgttcgaagc ctgagtggga tagaggaagt actgcaatta gtggctccta tgaatttcga    1140
ggagtgacag gatgttcttt ttatcgaatg ggaaattttg ctggcaccgt agccctaact    1200
taccgacagt ttggtaacga aggttctcaa atcccattgc acaggctatg tcatgttact    1260
tattttagaa gatctcaagc tgtggggcg acttcgagac agacgttaac aagtggtccg     1320
ctattttcct ggacacatag tagtgctacg gaaacgaata tcattcaccc gacaaaaatt    1380
acacaaatac caatggtgaa ggctagttcc cttggatcag gtacttctgt tgtccaagga    1440
ccaggcttta caggagggga tgtacttcga gaaatagcc ccggtagcac aggaacttta     1500
agagttaacg tcaattcacc attatcacag agatatcgta taagaattcg ttacgcttct    1560
actacggatt tagattttt tgtcattcgc ggaaatacga cagttaataa ttttagattt     1620
gggaacacta tgcgtaaagg agaccctata acctctcgat catttagatt tgcggctttt    1680
agtacaccat ttacttttgc tagctcacag gatgaactta gaataaatgt acaaaatttc    1740
aataatggtg aagaagttta tatagataga atcgaagtta ttccagtttg a             1791
```

<210> SEQ ID NO 15
<211> LENGTH: 596
<212> TYPE: PRT
<213> ORGANISM: Artificial Sequence
<220> FEATURE:
<223> OTHER INFORMATION: Amino acid sequence encoded by ORF7.

<400> SEQUENCE: 15

```
Met Asn Ser Asn Glu Pro Asn Leu Ser Asp Val Val Asn Cys Leu Ser
1               5                   10                  15

Asp Pro Asn Ser Asp Leu Glu Lys Ser Gly Gly Gly Val Ala Leu Asp
                20                  25                  30

Val Gly Met Ser Leu Ile Ser Glu Leu Leu Gly Thr Val Pro Val Ala
            35                  40                  45

Gly Ser Ile Leu Gln Phe Val Phe Asp Lys Leu Trp Phe Ile Phe Gly
        50                  55                  60

Pro Ser Glu Trp Asp Ser Leu Met Glu His Val Glu Ala Leu Ile Asp
65                  70                  75                  80

Ser Lys Ile Gln Glu Gln Val Lys Arg Ser Ala Gln Asp Glu Leu Asn
                85                  90                  95

Ala Ile Thr Asn Asn Leu Ser Thr Tyr Leu Lys Phe Leu Asp Ala Trp
            100                 105                 110

Glu Asn Asp Ser Asn Asn Leu Arg Ala Arg Ala Val Val Lys Asp Gln
        115                 120                 125

Phe Val Gly Leu Glu Gln Thr Leu Glu Arg Lys Met Val Ser Val Phe
    130                 135                 140

Gly Ser Thr Gly His Glu Val His Leu Leu Pro Ile Phe Ala Gln Ala
145                 150                 155                 160

Ala Asn Leu His Leu Ile Leu Leu Arg Asp Ala Glu Lys Tyr Gly Lys
                165                 170                 175

Arg Trp Gly Trp Ala Asp Arg Glu Ile Gln Val Tyr Tyr Asp Asn Gln
            180                 185                 190

Ile Arg Tyr Ile His Glu Tyr Thr Asp His Cys Ile Lys Tyr Tyr Asn
        195                 200                 205

Gln Gly Leu Ser Lys Leu Lys Gly Ser Thr Tyr Gln Asp Trp Asp Lys
    210                 215                 220

Tyr Asn Arg Phe Arg Arg Glu Met Thr Leu Thr Val Leu Asp Leu Ile
225                 230                 235                 240
```

```
Ser Ile Phe Pro Ser Tyr Asp Thr Arg Thr Tyr Pro Ile Asp Thr Ile
            245                 250                 255

Gly Gln Leu Thr Arg Glu Val Tyr Ser Asp Leu Leu Ile Ala Asn Pro
            260                 265                 270

Ser Gly Met Gln Thr Phe Thr Asn Val Asp Phe Asp Asn Ile Leu Ile
            275                 280                 285

Arg Lys Pro His Leu Met Asp Phe Leu Arg Thr Leu Glu Ile Phe Thr
290                 295                 300

Asp Arg His Asn Ala Ser Arg His Asn Val Tyr Trp Gly Gly His Arg
305                 310                 315                 320

Val His Ser Ser Tyr Thr Gly Gly Asn Phe Glu Asn Phe Glu Ser Pro
            325                 330                 335

Leu Tyr Gly Ser Glu Ala Asn Val Glu Pro Arg Thr Trp Leu Ser Phe
            340                 345                 350

Gly Glu Ser Gln Val Tyr Asn Ile Arg Ser Lys Pro Glu Trp Asp Arg
            355                 360                 365

Gly Ser Thr Ala Ile Ser Gly Ser Tyr Glu Phe Arg Gly Val Thr Gly
            370                 375                 380

Cys Ser Phe Tyr Arg Met Gly Asn Phe Ala Gly Thr Val Ala Leu Thr
385                 390                 395                 400

Tyr Arg Gln Phe Gly Asn Glu Gly Ser Gln Ile Pro Leu His Arg Leu
            405                 410                 415

Cys His Val Thr Tyr Phe Arg Arg Ser Gln Ala Val Gly Ala Thr Ser
            420                 425                 430

Arg Gln Thr Leu Thr Ser Gly Pro Leu Phe Ser Trp Thr His Ser Ser
            435                 440                 445

Ala Thr Glu Thr Asn Ile Ile His Pro Thr Lys Ile Thr Gln Ile Pro
            450                 455                 460

Met Val Lys Ala Ser Ser Leu Gly Ser Gly Thr Ser Val Val Gln Gly
465                 470                 475                 480

Pro Gly Phe Thr Gly Gly Asp Val Leu Arg Arg Asn Ser Pro Gly Ser
            485                 490                 495

Thr Gly Thr Leu Arg Val Asn Val Asn Ser Pro Leu Ser Gln Arg Tyr
            500                 505                 510

Arg Ile Arg Ile Arg Tyr Ala Ser Thr Thr Asp Leu Asp Phe Phe Val
            515                 520                 525

Ile Arg Gly Asn Thr Thr Val Asn Asn Phe Arg Phe Gly Asn Thr Met
530                 535                 540

Arg Lys Gly Asp Pro Ile Thr Ser Arg Ser Phe Arg Phe Ala Ala Phe
545                 550                 555                 560

Ser Thr Pro Phe Thr Phe Ala Ser Ser Gln Asp Glu Leu Arg Ile Asn
            565                 570                 575

Val Gln Asn Phe Asn Asn Gly Glu Glu Val Tyr Ile Asp Arg Ile Glu
            580                 585                 590

Val Ile Pro Val
        595

<210> SEQ ID NO 16
<211> LENGTH: 1547
<212> TYPE: DNA
<213> ORGANISM: Artificial Sequence
<220> FEATURE:
<223> OTHER INFORMATION: Nucleic acid sequence of the 16S rDNA of
      IDAS1529.

<400> SEQUENCE: 16
```

```
tggagagttt gatcctggct caggacgaac gctggcggcg tgcctaatac atgcaagtcg     60
agcggakcaa cggtttcctt cgggaaaccr ttagcttagc ggcggacggg tgagtaatac    120
gtaggtaacc tgcccttaag accgggataa ctcacggaaa cgtgggctaa taccggatag    180
gcgatttcct cgcatgaggg aatcgggaaa ggcggagcaa tctgccactt atggatggac    240
ctacggcgca ttagctagtt ggtggggtaa cggctcacca aggcgacgat gcgtagccga    300
cctgagaggg tgatcggcca cactgggact gagacacggc ccagactcct acgggaggca    360
gcagtaggga atcttccgca atggacgcaa gtctgacgga gcaacgccgc gtgagtgatg    420
aaggttttcg gatcgtaaag ctctgttgcc agggaagaac gctatggaga gtaactgttc    480
cataggtgac ggtacctgag aagaaagccc cggctaacta cgtgccagca gccgcggtaa    540
tacgtagggg gcaagcgttg tccggaatta ttgggcgtaa agcgcgcgca ggcggtcatg    600
taagtctggt gtttaaaccc ggggctcaac tccgggtcgc atcggaaact gtgtgacttg    660
agtgcagaag aggaaagtgg aattccacgt gtagcggtga aatgcgtaga gatgtggagg    720
aacaccagtg gcgaaggcga ctttctgggc tgtaactgac gctgaggcgc gaaagcgtgg    780
ggagcaaaca ggattagata ccctggtagt ccacgccgta aacgatgaat gctaggtgtt    840
aggggtttcg atacccttgg tgccgaagtt aacacattaa gcattccgcc tggggagtac    900
ggtcgcaaga ctgaaactca aaggaattga cggggacccg cacaagcagt ggagtatgtg    960
gtttaattcg aagcaacgcg aagaacctta ccaggtcttg acatccctct gaccgtccta   1020
gagatagggc ttcccttcgg ggcagaggag acaggtggtg catggttgtc gtcagctcgt   1080
gtcgtgagat gttgggttaa gtcccgcaac gagcgcaacc cttaacttta gttgccagca   1140
ttaagttggg cactctagag tgactgccgg tgacaaaccg gaggaaggtg gggatgacgt   1200
caaatcatca tgccccttat gacctgggct acacacgtac tacaatggct ggtacaacgg   1260
gaagcgaagc cgcgaggtgg agcgaatcct aaaaagccag tctcagttcg gattgcaggc   1320
tgcaactcgc ctgcatgaag tcggaattgc tagtaatcgc ggatcagcat gccgcggtga   1380
atacgttccc gggtcttgta cacaccgccc gtcacaccac gagagtttac aacacccgaa   1440
gtcggtgggg taaccgcaag gagccagccg ccgaaggtgg ggtagatgat tggggtgaag   1500
tcgtaacaag gtagccgtat cggaaggtgc ggytggatca cctcctt                 1547
```

<210> SEQ ID NO 17
<211> LENGTH: 20
<212> TYPE: PRT
<213> ORGANISM: Artificial Sequence
<220> FEATURE:
<223> OTHER INFORMATION: N-terminal amino acid sequence for the purified toxin from the broth fraction from IDAS1529.

<400> SEQUENCE: 17

```
Asp Ile Thr Leu Lys Val Ala Ile Tyr Pro Tyr Val Pro Asp Pro Ser
1               5                   10                  15

Arg Phe Gln Ala
            20
```

<210> SEQ ID NO 18
<211> LENGTH: 379
<212> TYPE: PRT
<213> ORGANISM: Artificial Sequence
<220> FEATURE:
<223> OTHER INFORMATION: Amino acid sequence of thiaminase I from Bacillus thiaminolyticus.

<400> SEQUENCE: 18

```
Ala His Ser Asp Ala Ser Ser Asp Ile Thr Leu Lys Val Ala Ile Tyr
  1               5                   10                  15

Pro Tyr Val Pro Asp Pro Ala Arg Phe Gln Ala Ala Val Leu Asp Gln
             20                  25                  30

Trp Gln Arg Gln Glu Pro Gly Val Lys Leu Glu Phe Thr Asp Trp Asp
         35                  40                  45

Ser Tyr Ser Ala Asp Pro Pro Asp Asp Leu Asp Val Phe Val Leu Asp
     50                  55                  60

Ser Ile Phe Leu Ser His Phe Val Asp Ala Gly Tyr Leu Leu Pro Phe
 65                  70                  75                  80

Gly Ser Gln Asp Ile Asp Gln Ala Glu Asp Val Leu Pro Phe Ala Leu
                 85                  90                  95

Gln Gly Ala Lys Arg Asn Gly Glu Val Tyr Gly Leu Pro Gln Ile Leu
                100                 105                 110

Cys Thr Asn Leu Leu Phe Tyr Arg Lys Gly Asp Leu Lys Ile Gly Gln
            115                 120                 125

Val Asp Asn Ile Tyr Glu Leu Tyr Lys Lys Ile Gly Thr Ser His Ser
130                 135                 140

Glu Gln Ile Pro Pro Pro Gln Asn Lys Gly Leu Leu Ile Asn Met Ala
145                 150                 155                 160

Gly Gly Thr Thr Lys Ala Ser Met Tyr Leu Glu Ala Leu Ile Asp Val
                165                 170                 175

Thr Gly Gln Tyr Thr Glu Tyr Asp Leu Leu Pro Pro Leu Asp Pro Leu
                180                 185                 190

Asn Asp Lys Val Ile Arg Gly Leu Arg Leu Leu Ile Asn Met Ala Gly
            195                 200                 205

Glu Lys Pro Ser Gln Tyr Val Pro Glu Asp Gly Asp Ala Tyr Val Arg
210                 215                 220

Ala Ser Trp Phe Ala Gln Gly Ser Gly Arg Ala Phe Ile Gly Tyr Ser
225                 230                 235                 240

Glu Ser Met Met Arg Met Gly Asp Tyr Ala Glu Gln Val Arg Phe Lys
                245                 250                 255

Pro Ile Ser Ser Ser Ala Gly Gln Asp Ile Pro Leu Phe Tyr Ser Asp
                260                 265                 270

Val Val Ser Val Asn Ser Lys Thr Ala His Pro Glu Leu Ala Lys Lys
            275                 280                 285

Leu Ala Asn Val Met Ala Ser Ala Asp Thr Val Glu Gln Ala Leu Arg
290                 295                 300

Pro Gln Ala Asp Gly Gln Tyr Pro Gln Tyr Leu Leu Pro Ala Arg His
305                 310                 315                 320

Gln Val Tyr Glu Ala Leu Met Gln Asp Tyr Pro Ile Tyr Ser Glu Leu
                325                 330                 335

Ala Gln Ile Val Asn Lys Pro Ser Asn Arg Val Phe Arg Leu Gly Pro
            340                 345                 350

Glu Val Arg Thr Trp Leu Lys Asp Ala Lys Gln Val Leu Pro Glu Ala
                355                 360                 365

Leu Gly Leu Thr Asp Val Ser Ser Leu Ala Ser
370                 375
```

<210> SEQ ID NO 19
<211> LENGTH: 953
<212> TYPE: PRT
<213> ORGANISM: Paenibacillus strain IDAS 1529

<400> SEQUENCE: 19

```
Met Lys Met Ile Pro Trp Thr His His Tyr Leu Leu His Arg Leu Arg
1               5                   10                  15

Gly Glu Met Glu Val Lys Pro Met Asn Thr Thr Ser Ile Tyr Arg Gly
            20                  25                  30

Thr Pro Thr Ile Ser Val Val Asp Asn Arg Asn Leu Glu Ile Arg Ile
                35                  40                  45

Leu Gln Tyr Asn Arg Ile Ala Ala Glu Asp Pro Ala Asp Glu Cys Ile
    50                  55                  60

Leu Arg Asn Thr Tyr Thr Pro Leu Ser Tyr Leu Gly Ser Ser Met Asp
65                  70                  75                  80

Pro Arg Leu Phe Ser Gln Tyr Gln Asp Asp Arg Gly Thr Pro Pro Asn
                85                  90                  95

Ile Arg Thr Met Ala Ser Leu Arg Gly Glu Ala Leu Cys Ser Glu Ser
                100                 105                 110

Val Asp Ala Gly Arg Lys Ala Glu Leu Phe Asp Ile Glu Gly Arg Pro
            115                 120                 125

Val Trp Leu Ile Asp Ala Asn Gly Thr Glu Thr Thr Leu Glu Tyr Asp
        130                 135                 140

Val Leu Gly Arg Pro Thr Ala Val Phe Glu Gln Gln Glu Gly Thr Asp
145                 150                 155                 160

Ser Pro Gln Cys Arg Glu Arg Phe Ile Tyr Gly Glu Lys Glu Ala Asp
                165                 170                 175

Ala Gln Ala Asn Asn Leu Arg Gly Gln Leu Val Arg His Tyr Asp Thr
            180                 185                 190

Ala Gly Arg Ile Gln Thr Asp Ser Ile Ser Leu Ala Gly Leu Pro Leu
        195                 200                 205

Arg Gln Ser Arg Gln Leu Leu Lys Asn Trp Asp Glu Pro Gly Asp Trp
    210                 215                 220

Ser Met Asp Glu Glu Ser Ala Trp Ala Ser Leu Leu Ala Ala Glu Ala
225                 230                 235                 240

Tyr Asp Thr Ser Trp Arg Tyr Asp Ala Gln Asp Arg Val Leu Ala Gln
                245                 250                 255

Thr Asp Ala Lys Gly Asn Leu Gln Gln Leu Thr Tyr Asn Asp Ala Gly
            260                 265                 270

Gln Pro Gln Ala Val Ser Leu Lys Leu Gln Gly Gln Ala Glu Gln Arg
        275                 280                 285

Ile Trp Asn Arg Ile Glu Tyr Asn Ala Ala Gly Gln Val Asp Leu Ala
    290                 295                 300

Glu Ala Gly Asn Gly Ile Val Thr Glu Tyr Thr Tyr Glu Glu Ser Thr
305                 310                 315                 320

Gln Arg Leu Ile Arg Lys Lys Asp Ser Arg Gly Leu Ser Ser Gly Glu
                325                 330                 335

Arg Glu Val Leu Gln Asp Tyr Arg Tyr Glu Tyr Asp Pro Val Gly Asn
            340                 345                 350

Ile Leu Ser Ile Tyr Asn Glu Ala Glu Pro Val Arg Tyr Phe Arg Asn
        355                 360                 365

Gln Ala Val Ala Pro Lys Arg Gln Tyr Ala Tyr Asp Ala Leu Tyr Gln
    370                 375                 380

Leu Val Ser Ser Ser Gly Arg Glu Ser Asp Ala Leu Arg Gln Gln Thr
385                 390                 395                 400

Ser Leu Pro Pro Leu Ile Thr Pro Ile Pro Leu Asp Asp Ser Gln Tyr
                405                 410                 415

Val Asn Tyr Ala Glu Lys Tyr Ser Tyr Asp Gln Ala Gly Asn Leu Ile
```

-continued

```
                420                 425                 430
Lys Leu Ser His Asn Gly Ala Ser Gln Tyr Thr Thr Asn Val Tyr Val
            435                 440                 445

Asp Lys Ser Ser Asn Arg Gly Ile Trp Arg Gln Gly Glu Asp Ile Pro
        450                 455                 460

Asp Ile Ala Ala Ser Phe Asp Arg Ala Gly Asn Gln Gln Ala Leu Phe
465                 470                 475                 480

Pro Gly Arg Pro Leu Glu Trp Asp Thr Arg Asn Gln Leu Ser Arg Val
                485                 490                 495

His Met Val Val Arg Glu Gly Gly Asp Asn Asp Trp Glu Gly Tyr Leu
            500                 505                 510

Tyr Asp Ser Ser Gly Met Arg Ile Val Lys Arg Ser Thr Arg Lys Thr
        515                 520                 525

Gln Thr Thr Thr Gln Thr Asp Thr Thr Leu Tyr Leu Pro Gly Leu Glu
    530                 535                 540

Leu Arg Ile Arg Gln Thr Gly Asp Arg Val Thr Glu Ala Leu Gln Val
545                 550                 555                 560

Ile Thr Val Asp Glu Gly Ala Gly Gln Val Arg Val Leu His Trp Glu
                565                 570                 575

Asp Gly Thr Glu Pro Gly Gly Ile Ala Asn Asp Gln Tyr Arg Tyr Ser
            580                 585                 590

Leu Asn Asp His Leu Thr Ser Ser Leu Leu Glu Val Asp Gly Gln Gly
        595                 600                 605

Gln Ile Ile Ser Lys Glu Glu Phe Tyr Pro Tyr Gly Gly Thr Ala Leu
    610                 615                 620

Trp Thr Ala Arg Ser Glu Val Glu Ala Ser Tyr Lys Thr Ile Arg Tyr
625                 630                 635                 640

Ser Gly Lys Glu Arg Asp Ala Thr Gly Leu Tyr Tyr Gly His Arg
                645                 650                 655

Tyr Tyr Met Pro Trp Leu Gly Arg Trp Leu Asn Pro Asp Pro Ala Gly
            660                 665                 670

Met Val Asp Gly Leu Asn Leu Tyr Arg Met Val Arg Asn Asn Pro Ile
        675                 680                 685

Gly Leu Met Asp Pro Asn Gly Asn Ala Pro Ile Asn Val Ala Asp Tyr
    690                 695                 700

Ser Phe Val His Gly Asp Leu Val Tyr Gly Leu Ser Lys Glu Arg Gly
705                 710                 715                 720

Arg Tyr Leu Lys Leu Phe Asn Pro Asn Phe Asn Met Glu Lys Ser Asp
                725                 730                 735

Ser Pro Ala Met Val Ile Asp Gln Tyr Asn Asn Asn Val Ala Leu Ser
            740                 745                 750

Ile Thr Asn Gln Tyr Lys Val Glu Glu Leu Met Lys Phe Gln Lys Asp
        755                 760                 765

Pro Gln Lys Ala Ala Arg Lys Ile Lys Val Pro Glu Gly Asn Arg Leu
    770                 775                 780

Ser Arg Asn Glu Asn Tyr Pro Leu Trp His Asp Tyr Ile Asn Ile Gly
785                 790                 795                 800

Glu Ala Lys Ala Ala Phe Lys Ala Ser His Ile Phe Gln Glu Val Lys
                805                 810                 815

Gly Asn Tyr Gly Lys Asp Tyr Tyr His Lys Leu Leu Leu Asp Arg Met
            820                 825                 830

Ile Glu Ser Pro Leu Leu Trp Lys Arg Gly Ser Lys Leu Gly Leu Glu
        835                 840                 845
```

```
Ile Ala Ala Thr Asn Gln Arg Thr Lys Ile His Phe Val Leu Asp Asn
        850                 855                 860

Leu Asn Ile Glu Gln Val Val Thr Lys Glu Gly Ser Gly Gly Gln Ser
865                 870                 875                 880

Ile Thr Ala Ser Glu Leu Arg Tyr Ile Tyr Arg Asn Arg Glu Arg Leu
                885                 890                 895

Asn Gly Arg Val Ile Phe Tyr Arg Asn Asn Glu Arg Leu Asp Gln Ala
                900                 905                 910

Pro Trp Gln Glu Asn Pro Asp Leu Trp Ser Lys Tyr Gln Pro Gly Leu
            915                 920                 925

Arg Gln Ser Ser Ser Arg Val Lys Glu Arg Gly Ile Gly Asn Phe
        930                 935                 940

Phe Arg Arg Phe Ser Met Lys Arg Lys
945                 950

<210> SEQ ID NO 20
<211> LENGTH: 4482
<212> TYPE: DNA
<213> ORGANISM: Xenorhabdus strain Xwi

<400> SEQUENCE: 20
atgcagggtt caacaccttt gaaacttgaa ataccgtcat tgccctctgg gggcggatca      60
ctaaaaggaa tgggagaagc actcaatgcc gtcggagcgg aaggggagc gtcattttca     120 ctgcccttgc cgatctctgt cgggcgtggt ctggtgccgg tgctatcact gaattacagc     180
agtactgccg gcaatgggtc attcgggatg ggtggcaat gtggggttgg ttttatcagc     240
ctgcgtaccg ccaagggcgt tccgcactat acgggacaag atgagtatct cgggccggat     300
ggggaagtgt tgagtattgt gccggacagc caagggcaac cagagcaacg caccgcaacc     360
tcactgttgg gacggttct gacacagccg catactgtta cccgctatca gtcccgcgtg     420
gcagaaaaaa tcgttcgttt agaacactgg cagccacagc agagacgtga ggaagagacg     480
tctttttggg tactttttac tgcggatggt ttagtgcacc tattcggtaa gcatcaccat     540
gcacgtattg ctgacccgca ggatgaaacc agaattgccc gctggctgat ggaggaaacc     600
gtcacgcata ccgggaaca tatttactat cactatcggg cagaagacga tcttgactgt     660
gatgagcatg aacttgctca gcattcaggt gttacggccc agcgttatct ggcaaaagtc     720
agctatggca atactcagcc ggaaaccgct tttttcgcgg taaaatcagg tattcctgct     780
gataatgact ggctgtttca tctggtattt gattacggtg agcgctcatc ttcgctgaac     840
tctgtacccg aattcaatgt gtcagaaaac aatgtgtctg aaaacaatgt gcctgaaaaa     900
tggcgttgtc gtccggacag tttctcccgc tatgaatatg gtttgaaat tcgaacccgt     960 cgcttgtgtc gccaagttct gatgtttcat cagctgaaag cgctggcagg ggaaaaggtt    1020
gcagaagaaa caccggcgct ggtttcccgt cttattctgg attatgacct gaacaacaag    1080
gtttccttgc tgcaaacggc ccgcagactg gcccatgaaa cggacggtac gccagtgatg    1140
atgtccccgc tggaaatgga ttatcaacgt gttaatcatg gcgtgaatct gaactggcag    1200
tccatgccgc agttagaaaa aatgaacacg ttgcagccat accaattggt tgatttatat    1260
ggagaaggaa tttccggcgt acttattcag gatactcaga aagcctggtg gtaccgtgct    1320
ccggtacggg atatcactgc cgaaggaacg aatgcggtta cctatgagga ggccaaacca    1380
ctgccacata ttccggcaca acaggaaagc gcgatgttgt tggacatcaa tggtgacggg    1440
cgtctggatt gggtgattac ggcatcaggg ttacggggct accacaccat gtcaccggaa    1500
ggtgaatgga cacccttat tccattatcc gctgtgccaa tggaatattt ccatccgcag    1560
```

```
gcaaaactgg ctgatattga tggggctggg ctgcctgact tagcgcttat cgggccaaat    1620
agtgtacgtg tctggtcaaa taatcgggca ggatgggatc gcgctcagga tgtgattcat    1680
ttgtcagata tgccactgcc ggttcccggc agaaatgagc gtcatcttgt cgcattcagt    1740
gatatgacag gctccgggca atcacatctg gtggaagtaa cggcagatag cgtgcgctac    1800
tggccgaacc tggggcatgg aaaatttggt gagcctctga tgatgacagg cttccagatt    1860
agcggggaaa cgtttaaccc cgacagactg tatatggtag acatagatgg ctcaggcacc    1920
accgatttta tttatgcccg caatacttac cttgaactct atgccaatga aagcggcaat    1980
cattttgctg aacctcagcg tattgatctg ccggatgggg tacgttttga tgatacttgt    2040
cggttacaaa tagcggatac acaaggatta gggactgcca gcattatttt gacgatcccc    2100
catatgaagg tgcagcactg gcgattggat atgaccatat tcaagccttg gctgctgaat    2160
gccgtcaata caatatggg aacagaaacc acgctgtatt atcgcagctc tgcccagttc    2220
tggctggatg agaaattaca ggcttctgaa tccgggatga cggtggtcag ctacttaccg    2280
ttcccggtgc atgtgttgtg gcgcacggaa gtgctggatg aaatttccgg taaccgattg    2340
accagccatt atcattactc acatggtgcc tgggatggtc tggaacggga gtttcgtggt    2400
tttgggcggg tgacacaaac tgatattgat tcacgggcga gtgcgacaca ggggacacat    2460
gctgaaccac cggcaccttc gcgcacggtt aattggtacg gcactggcgt acgggaagtc    2520
gatattcttc tgcccacgga atattggcag ggggatcaac aggcatttcc ccatttacc    2580 ccacgcttta cccgttatga cgaaaaatcc ggtggtgata tgacggtcac gccgagcgaa    2640
caggaagaat actggttaca tcgagcctta aaaggacaac gtttacgcag tgagctgtat    2700
ggggatgatg attctatact ggccggtacg ccttattcag tggatgaatc ccgcaccccaa    2760 gtacgtttgt taccggtgat ggtatcggac gtgcctgcgg tactggtttc ggtggccgaa    2820
tcccgccaat accgatatga acgggttgct accgatccac agtgcagcca aaagatcgtc    2880
cttaaatctg atgcgttagg atttccgcag gacaatcttg agattgccta ttcgagacgt    2940
ccacagcctg agttctcgcc ttatccggat accctgcccg aaacacttt caccagcagt    3000 ttcgacgaac agcagatgtt ccttcgtctg acacgccagc gttcttctta tcatcatctg    3060
aatcatgatg ataatacgtg gatcacaggg cttatggata cctcacgcag tgacgcacgt    3120
atttatcaag ccgataaagt gccggacggt ggattttccc ttgaatggtt ttctgccaca    3180
ggtgcaggag cattgttgtt gcctgatgcc gcagccgatt atctgggaca tcagcgtgta    3240 gcataccg gtccagaaga acaacccgct attcctccgc tggtggcata cattgaaacc    3300
gcagagtttg atgaacgatc gttggcggct tttgaggagg tgatggatga gcaggagctg    3360
acaaaacagc tgaatgatgc gggctggaat acggcaaaag tgccgttcag tgaaaagaca    3420
gatttccatg tctgggtggg acaaaaggaa tttacagaat atgccggtgc agacggattc    3480
tatcggccat tggtgcaacg ggaaaccaag cttacaggta aaacgacagt cacgtgggat    3540
agccattact gtgttatcac cgcaacagag gatgcggctg gcctgcgtat gcaagcgcat    3600
tacgattatc gatttatggt tgcggataac accacagatg tcaatgataa ctatcacacc    3660
gtgacgtttg atgcactggg gagggtaacc agcttccgtt tctggggac tgaaaacggt    3720 gaaaaacaag gatatacccc tgcggaaaat gaaactgtcc cctttattgt ccccacaacg    3780
gtggatgatg ctctggcatt gaaacccggt atacctgttg cagggctgat ggtttatgcc    3840
cctctgagct ggatggttca ggccagcttt tctaatgatg gggagcttta tggagagctg    3900
aaaccggctg ggatcatcac tgaagatggt tatctcctgt cgcttgcttt tcgccgctgg    3960
```

-continued

| | |
|---|---|
| caacaaaata acccctgccgc tgccatgcca aagcaagtca attcacagaa cccacccat | 4020 |
| gtactgagtg tgatcaccga ccgctatgat gccgatccgg aacaacaatt acgtcaaacg | 4080 |
| tttacgttta gtgatggttt tgggcgaacc ttacaaacag ccgtacgcca tgaaagtggt | 4140 |
| gaagcctggg tacgtgatga gtatggagcc attgtggctg aaaatcatgg cgcgcctgaa | 4200 |
| acggcgatga cagatttccg ttgggcagtt tccggacgta cagaatatga cggaaaaggc | 4260 |
| caagccctgc gtaagtatca accgtatttc ctgaatagtt ggcagtacgt cagtgatgac | 4320 |
| agtgcccggc aggatatata tgccgatacc cattactatg atccgttggg gcgtgaatat | 4380 |
| caggttatca cggccaaagg cgggtttcgt cgatccttat tcactccctg gtttgtggtg | 4440 |
| aatgaagatg aaaatgacac tgccggtgaa atgacagcat aa | 4482 |

<210> SEQ ID NO 21
<211> LENGTH: 3051
<212> TYPE: DNA
<213> ORGANISM: Xenorhabdus strain Xwi

<400> SEQUENCE: 21

| | |
|---|---|
| atgaagaatt tcgttcacag caatacgcca tccgtcaccg tactggacaa ccgtggtcag | 60 |
| acagtacgcg aaatagcctg gtatcggcac cccgatacac ctcaggtaac cgatgaacgc | 120 |
| atcaccggtt atcaatatga tgctcaagga tctctgactc agagtattga tccgcgattt | 180 |
| tatgaacgcc agcagacagc gagtgacaag aacgccatta cacccaatct tattctcttg | 240 |
| tcatcactca gtaagaaggc attgcgtacg caaagtgtgg atgccggaac ccgtgtcgcc | 300 |
| ctgcatgatg ttgccgggcg tcccgttttta gctgtcagcg ccaatggcgt tagccgaacg | 360 |
| tttcagtatg aaagtgataa ccttccggga cgattgctaa cgattaccga gcaggtaaaa | 420 |
| ggagagaacg cctgtatcac ggagcgattg atctggtcag gaaatacgcc ggcagaaaaa | 480 |
| ggcaataatc tggccggcca gtgcgtggtc cattatgatc ccaccggaat gaatcaaacc | 540 |
| aacagcatat cgttaaccag catacccttg tccatcacac agcaattact gaaagatgac | 600 |
| agcgaagccg attggcacgg tatggatgaa tctggctgga aaaacgcgct ggcgccggaa | 660 |
| agcttcactt ctgtcagcac aacggatgct accggcacgg tattaacgag tacagatgct | 720 |
| gccggaaaca gcaacgtat cgcctatgat gtggccggtc tgcttcaagg cagttggttg | 780 |
| gcgctgaagg ggaaacaaga acaagttatc gtgaaatccc tgacctattc ggctgccagc | 840 |
| cagaagctac gggaggaaca tggtaacggg atagtgacta catataccta tgaacccgag | 900 |
| acgcaacgag ttattggcat aaaaacagaa cgtccttccg gtcatgccgc tggggagaaa | 960 |
| attttacaaa acctgcgtta tgaatatgat cctgtcggaa atgtgctgaa atcaactaat | 1020 |
| gatgctgaaa ttacccgctt ttggcgcaac cagaaaattg taccggaaaa tacttacacc | 1080 |
| tatgacagcc tgtaccagct ggtttccgtc actgggcgtg aaatggcgaa tattggccga | 1140 |
| caaaaaaacc agttacccat ccccgctctg attgataaca atacttatac gaattactct | 1200 |
| cgcacttacg actatgatcg tgggggaaat ctgaccagaa ttcgccataa ttcaccgatc | 1260 |
| accggtaata actatacaac gaacatgacc gtttcagatc acagcaaccg ggctgtactg | 1320 |
| gaagagctgg cgcaagatcc cactcaggtg gatatgttgt tcacccccgg cgggcatcag | 1380 |
| acccggcttg ttcccggtca ggatcttttc tggacacccc gtgacgaatt gcaacaagtg | 1440 |
| atattggtca atagggaaaa tacgacgcct gatcaggaat tctaccgtta tgatgcagac | 1500 |
| agtcagcgtg tcattaagac tcatattcag aagacaggta acagtgagca aatacagcga | 1560 |
| acattatatt tgccagagct ggaatggcgc acgacatata gcggcaatac attaaaagag | 1620 |

```
tttttgcagg tcatcactgt cggtgaatcg ggtcaggcac aagtgcgggt gctgcattgg   1680
gaaacaggca aaccggcgga tatcagcaat gatcagctgc gctacagtta tggcaacctg   1740
attggcagta gcgggctgga attggacagt gacgggcaga tcattagtca ggaagaatat   1800 taccectatg ggggaaccgc cgtgtgggca gcccgaagtc agtcagaagc tgattacaaa   1860
accgtgcgtt attctggcaa agagcggat gcaacagggt tgtattacta cggttatcgt    1920
tattatcaat cgtggacagg gcgatggttg agtgtagatc ctgccggtga ggtcgatggt   1980
ctcaatttgt tccgaatgtg caggaataac cccatcgttt tttctgattc tgatggtcgt   2040
ttccccggtc agggtgtcct tgcctggata gggaaaaaag cgtatcgaaa ggcagtcaac   2100
atcacgacag aacacctgct tgaacaaggc gcttcctttg atacgttctt gaaattaaac   2160
cgaggattgc gaacgtttgt tttgggtgtg ggggtagcaa gtctgggggt gaaggcggcc   2220
acgattgcag gagcgtcgcc ttgggggatt gtcgggggctg ccattggtgg ttttgtctcc   2280
ggggcggtga tggggttttt cgcgaacaac atctcagaaa aaattgggga agttttaagt   2340
tatctgacgc gtaaacgttc tgttcctgtt caggttggcg cttttgttgt cacatcgctt   2400
gtgacgtctg cactatttaa cagctcttcg acaggtaccg ccatttccgc agcaacagcg   2460
gtcaccgttg gaggattaat ggctttagcc ggagagcata acacgggcat ggctatcagt   2520
attgccacac ccgccggaca aggtacgctg gatacgctca ggcccggtaa tgtcagcgcg   2580
ccagagcggt taggggcact atcaggcgca attattggcg gcatattact tggccgccat   2640
cagggaagtt ctgagctggg tgaacgggca gcgattggtg ctatgtatgg tgctcgatgg   2700
ggaaggatca ttggtaatct atgggatggc ccttatcggt ttatcggcag gttactgctc   2760
agaagaggca ttagctctgc catttcccac gctgtcagtt ccaggagctg gtttggccga   2820
atgataggag aaagtgtcgg gagaaatatt tctgaagtat tattaccttta tagccgtaca   2880 cccggtgaat gggttggtgc agccattggc gggacagccg cggccgctca tcatgccgtt   2940 ggagggggaag ttgccaatgc cgctagccgg gttacctgga gcggctttaa gcgggctttt   3000
aataacttct tctttaacgc ctctgcacgt cataatgaat ccgaagcata a             3051
```

```
<210> SEQ ID NO 22
<211> LENGTH: 32
<212> TYPE: DNA
<213> ORGANISM: Artificial Sequence
<220> FEATURE:
<223> OTHER INFORMATION: Primer SB101

<400> SEQUENCE: 22
gckatggcsg acccgatgca wtacaagctg gc                                  32

<210> SEQ ID NO 23
<211> LENGTH: 32
<212> TYPE: DNA
<213> ORGANISM: Artificial Sequence
<220> FEATURE:
<223> OTHER INFORMATION: Primer SB102

<400> SEQUENCE: 23
agcggytgac crtccagrct carattgtgg cg                                  32

<210> SEQ ID NO 24
<211> LENGTH: 28
<212> TYPE: DNA
<213> ORGANISM: Artificial Sequence
<220> FEATURE:
<223> OTHER INFORMATION: Primer SB103
```

```
<400> SEQUENCE: 24
tgtataactg gatggcyggw cgtctstc                                          28

<210> SEQ ID NO 25
<211> LENGTH: 26
<212> TYPE: DNA
<213> ORGANISM: Artificial Sequence
<220> FEATURE:
<223> OTHER INFORMATION: Primer SB104

<400> SEQUENCE: 25
tcraaaggca graamcggct gtcgtt                                            26

<210> SEQ ID NO 26
<211> LENGTH: 28
<212> TYPE: DNA
<213> ORGANISM: Artificial Sequence
<220> FEATURE:
<223> OTHER INFORMATION: Primer SB105

<400> SEQUENCE: 26
cttcyctkga tatcytkytg gatgtgct                                          28

<210> SEQ ID NO 27
<211> LENGTH: 30
<212> TYPE: DNA
<213> ORGANISM: Artificial Sequence
<220> FEATURE:
<223> OTHER INFORMATION: Primer SB106

<400> SEQUENCE: 27
acgrctggya ttggyaatca gccartccaa                                        30

<210> SEQ ID NO 28
<211> LENGTH: 27
<212> TYPE: DNA
<213> ORGANISM: Artificial Sequence
<220> FEATURE:
<223> OTHER INFORMATION: Primer SB212
<220> FEATURE:
<221> NAME/KEY: misc_feature
<222> LOCATION: (7)..(7)
<223> OTHER INFORMATION: n = i (inosine)

<400> SEQUENCE: 28
cgytatnaat atgayccckgt vggyaat                                          27

<210> SEQ ID NO 29
<211> LENGTH: 25
<212> TYPE: DNA
<213> ORGANISM: Artificial Sequence
<220> FEATURE:
<223> OTHER INFORMATION: Primer SB213
<220> FEATURE:
<221> NAME/KEY: misc_feature
<222> LOCATION: (17)..(17)
<223> OTHER INFORMATION: n = i (inosine)

<400> SEQUENCE: 29
catcbcgytc tttrccngar tarcg                                             25

<210> SEQ ID NO 30
<211> LENGTH: 33
<212> TYPE: DNA
<213> ORGANISM: Artificial Sequence
<220> FEATURE:
<223> OTHER INFORMATION: Primer SB215
```

```
<220> FEATURE:
<221> NAME/KEY: misc_feature
<222> LOCATION: (10)..(10)
<223> OTHER INFORMATION: n = i (inosine)

<400> SEQUENCE: 30
cghagctcyn cccagtwytg gctggatgar aaa                                    33

<210> SEQ ID NO 31
<211> LENGTH: 32
<212> TYPE: DNA
<213> ORGANISM: Artificial Sequence
<220> FEATURE:
<223> OTHER INFORMATION: Primer SB217
<220> FEATURE:
<221> NAME/KEY: misc_feature
<222> LOCATION: (24)..(24)
<223> OTHER INFORMATION: n = i (inosine)

<400> SEQUENCE: 31
gtrtcatttt catcttcrtt bacnryaaac ca                                     32

<210> SEQ ID NO 32
<211> LENGTH: 1293
<212> TYPE: DNA
<213> ORGANISM: Paenibacillus apairus strain DB482

<400> SEQUENCE: 32
gcagcccgaa ggctccggca cgctggcatc cttgaaggat acctaccatc cgatgaccct        60
tccctatgat gacgaccttg cgcaaatcaa tgccgtggcg gaggcgcact catctaattt       120
gctggggatt tgggataccc tgctggacac gcagcggact tccatcctgc agaattccgc       180
cgctgcctgc cggataagca aggcgcggca atcggcatcc ccggatcaga gagcctccga       240
tgatgagccg gtattgatta caggagaaga attctacctg gagacgggcg gcaaacggct       300
ttttctggcg cataaactcg agataggctc cacgataagc gccaaaatca acattggacc       360
gccgcaagcg gccgatatcg cgccagcaaa gttgcaactc gtttattacg gcagaggcgg       420
cagaggggac tacttccttc gtgtggcaga cgatgtgtcc ctcggtggaa aattgctgaa       480
caattgttat ctgaccagcg acgacggaca gagcaacaat attaacggac cattctgcct       540
aatgattaat cgaggcaccg gcagcatgcc cagcgggact cacctgccag ttcagattga       600
cagagtgaca gatacatccc tacgcatttt tgtgccgcaa cacggttact tgggactagg       660
agaaagcctt gccagcaact ggaatgaacc gttggcgctg aatctggact tggatcaagc       720
gttgaccttt accctaagaa agaatgagtc cggacaagat accatttcca taatcgatat       780
gatgccgcct gttgccgaca cgaccccgtc ccgccgacg agggaaacgc tttccttgac       840
gccaaacagc ttccgtctgc tggttaaccc cgagccgaca gaagaagaca tcgccaagca       900
ctacaacgtt aagactgcca taaccccgagc tcctgccgat ctggccgccg ccttaaatgt       960
tgtcgatgat ttctgcatga agaccggctt gagctttgat gaattgctga acttaacgat      1020
gcagaaggat tatcagtcaa aaagcagtga gtacaaaagc cgatttgtaa aatttggcgg      1080
cggggagcat gttccggttt caacctatgg agctgtgttt ttgacaggta cggaagaaac      1140
tccgttgtgg gcaaaacagt ataacagcgc aggcgctgca acagacaccc ctgttttgaa      1200
ctttacggcg gataatgttg cagctttggc aggaagagcg gaaaagcttg tgcggctggc      1260
gcgaagcacg ggtctttcct ttgagcagtt gga                                  1293

<210> SEQ ID NO 33
<211> LENGTH: 430
```

<212> TYPE: PRT
<213> ORGANISM: Paenibacillus apairius strain DB482

<400> SEQUENCE: 33

```
Gln Pro Glu Gly Ser Gly Thr Leu Ala Ser Leu Lys Asp Thr Tyr His
1               5                   10                  15

Pro Met Thr Leu Pro Tyr Asp Asp Asp Leu Ala Gln Ile Asn Ala Val
            20                  25                  30

Ala Glu Ala His Ser Ser Asn Leu Leu Gly Ile Trp Asp Thr Leu Leu
        35                  40                  45

Asp Thr Gln Arg Thr Ser Ile Leu Gln Asn Ser Ala Ala Ala Cys Arg
    50                  55                  60

Ile Ser Lys Ala Arg Gln Ser Ala Ser Pro Asp Gln Arg Ala Ser Asp
65                  70                  75                  80

Asp Glu Pro Val Leu Ile Thr Gly Glu Glu Phe Tyr Leu Glu Thr Gly
                85                  90                  95

Gly Lys Arg Leu Phe Leu Ala His Lys Leu Glu Ile Gly Ser Thr Ile
            100                 105                 110

Ser Ala Lys Ile Asn Ile Gly Pro Pro Gln Ala Ala Asp Ile Ala Pro
        115                 120                 125

Ala Lys Leu Gln Leu Val Tyr Tyr Gly Arg Gly Gly Arg Gly Asp Tyr
    130                 135                 140

Phe Leu Arg Val Ala Asp Asp Val Ser Leu Gly Gly Lys Leu Leu Asn
145                 150                 155                 160

Asn Cys Tyr Leu Thr Ser Asp Asp Gly Gln Ser Asn Asn Ile Asn Gly
                165                 170                 175

Pro Phe Cys Leu Met Ile Asn Arg Gly Thr Gly Ser Met Pro Ser Gly
            180                 185                 190

Thr His Leu Pro Val Gln Ile Asp Arg Val Thr Asp Thr Ser Leu Arg
        195                 200                 205

Ile Phe Val Pro Gln His Gly Tyr Leu Gly Leu Gly Glu Ser Leu Ala
    210                 215                 220

Ser Asn Trp Asn Glu Pro Leu Ala Leu Asn Leu Asp Leu Asp Gln Ala
225                 230                 235                 240

Leu Thr Phe Thr Leu Arg Lys Asn Glu Ser Gly Gln Asp Thr Ile Ser
                245                 250                 255

Ile Ile Asp Met Met Pro Pro Val Ala Asp Thr Thr Pro Ser Pro Pro
            260                 265                 270

Thr Arg Glu Thr Leu Ser Leu Thr Pro Asn Ser Phe Arg Leu Leu Val
        275                 280                 285

Asn Pro Glu Pro Thr Glu Glu Asp Ile Ala Lys His Tyr Asn Val Lys
    290                 295                 300

Thr Ala Ile Thr Arg Ala Pro Ala Asp Leu Ala Ala Ala Leu Asn Val
305                 310                 315                 320

Val Asp Asp Phe Cys Met Lys Thr Gly Leu Ser Phe Asp Glu Leu Leu
                325                 330                 335

Asn Leu Thr Met Gln Lys Asp Tyr Gln Ser Lys Ser Ser Glu Tyr Lys
            340                 345                 350

Ser Arg Phe Val Lys Phe Gly Gly Gly Glu His Val Pro Val Ser Thr
        355                 360                 365

Tyr Gly Ala Val Phe Leu Thr Gly Thr Glu Glu Thr Pro Leu Trp Ala
    370                 375                 380

Lys Gln Tyr Asn Ser Ala Gly Ala Ala Thr Asp Thr Pro Val Leu Asn
385                 390                 395                 400
```

```
Phe Thr Ala Asp Asn Val Ala Ala Leu Ala Gly Arg Ala Glu Lys Leu
                405                 410                 415
Val Arg Leu Ala Arg Ser Thr Gly Leu Ser Phe Glu Gln Leu
        420                 425                 430
```

<210> SEQ ID NO 34
<211> LENGTH: 340
<212> TYPE: DNA
<213> ORGANISM: Paenibacillus apairius strain DB482

<400> SEQUENCE: 34

```
tatatttatt cacaccttgg acttcctgat caaccgcggc gacagcttgt accggctgct    60
ggagcgggat actctgaccg aagccaagat gtattacatc caggccagcc aactgcttgg   120
tccccgcccc gatatccgga tcaatcacag ttggcctaat ccgaccctgc aaagcgaagc   180
ggacgcggtg accgccgtac cgacgcgaag cgattcgcgg gcaacgccaa tcctcgcctt   240
gcgagcgctt ctgaaagcgg aaaacgggca tttcctgccg ccttataatg atgaactgtt   300
agctttctgg gataaaatcg atctgcgttt atacaattta                         340
```

<210> SEQ ID NO 35
<211> LENGTH: 565
<212> TYPE: DNA
<213> ORGANISM: Paenibacillus apairius strain DB482

<400> SEQUENCE: 35

```
gtctctatac tatcaaatgt atgacgccgc attgccgctc tgcttgatgg ccaaacaggc    60
tttagagaaa gaaatcggca ctgataaaac gggtggagtt ttcaccctcc cggcctggaa   120
tgatctgtat cagggattac tggcggggga ggcgctgctg ctcgagcttc agaagctgga   180
gaatctgtgg ctggaggaag acaagcgcgg aatggaagcc gtaaaaacgg tatctttaga   240
taccttctc cgcaaagaaa cgccagagtc tagcttcgta gagctagtca aggaagttct   300
ggacggaaag acgcctgacc tgtaggcgg agtcggcgta cagctgcaaa acaatatttt   360
cagcgcaacc cttgacctgt ccgttcttgg cttgatcgc tcttacaacc aagcggaaaa   420
gacccgcagg atcaaaaatc tgtcggttac cttacccgcg cttttgggac ttaccagga   480
tatagaagca accttatcgc taggcggcga gaccgttgcg cttcccatg cgtggatga   540
cagcggcttg ttcatcacgg atctt                                        565
```

<210> SEQ ID NO 36
<211> LENGTH: 113
<212> TYPE: PRT
<213> ORGANISM: Paenibacillus apairius strain DB482

<400> SEQUENCE: 36

```
Ile Phe Ile His Thr Leu Asp Phe Leu Ile Asn Arg Gly Asp Ser Leu
1               5                   10                  15
Tyr Arg Leu Leu Glu Arg Asp Thr Leu Thr Glu Ala Lys Met Tyr Tyr
            20                  25                  30
Ile Gln Ala Ser Gln Leu Leu Gly Pro Arg Pro Asp Ile Arg Ile Asn
        35                  40                  45
His Ser Trp Pro Asn Pro Thr Leu Gln Ser Glu Ala Asp Ala Val Thr
    50                  55                  60
Ala Val Pro Thr Arg Ser Asp Ser Arg Ala Thr Pro Ile Leu Ala Leu
65                  70                  75                  80
Arg Ala Leu Leu Lys Ala Glu Asn Gly His Phe Leu Pro Pro Tyr Asn
                85                  90                  95
```

```
Asp Glu Leu Leu Ala Phe Trp Asp Lys Ile Asp Leu Arg Leu Tyr Asn
            100                 105                 110
Leu
```

<210> SEQ ID NO 37
<211> LENGTH: 188
<212> TYPE: PRT
<213> ORGANISM: Paenibacillus apairius strain DB482

<400> SEQUENCE: 37

```
Ser Leu Tyr Tyr Gln Met Tyr Asp Ala Ala Leu Pro Leu Cys Leu Met
1               5                   10                  15

Ala Lys Gln Ala Leu Glu Lys Glu Ile Gly Thr Asp Lys Thr Gly Gly
            20                  25                  30

Val Phe Thr Leu Pro Ala Trp Asn Asp Leu Tyr Gln Gly Leu Leu Ala
        35                  40                  45

Gly Glu Ala Leu Leu Leu Glu Leu Gln Lys Leu Glu Asn Leu Trp Leu
    50                  55                  60

Glu Glu Asp Lys Arg Gly Met Glu Ala Val Lys Thr Val Ser Leu Asp
65                  70                  75                  80

Thr Leu Leu Arg Lys Glu Thr Pro Glu Ser Ser Phe Val Glu Leu Val
                85                  90                  95

Lys Glu Val Leu Asp Gly Lys Thr Pro Asp Pro Val Gly Gly Val Gly
            100                 105                 110

Val Gln Leu Gln Asn Asn Ile Phe Ser Ala Thr Leu Asp Leu Ser Val
        115                 120                 125

Leu Gly Leu Asp Arg Ser Tyr Asn Gln Ala Glu Lys Thr Arg Arg Ile
    130                 135                 140

Lys Asn Leu Ser Val Thr Leu Pro Ala Leu Leu Gly Pro Tyr Gln Asp
145                 150                 155                 160

Ile Glu Ala Thr Leu Ser Leu Gly Gly Glu Thr Val Ala Leu Ser His
                165                 170                 175

Gly Val Asp Asp Ser Gly Leu Phe Ile Thr Asp Leu
            180                 185
```

<210> SEQ ID NO 38
<211> LENGTH: 2091
<212> TYPE: DNA
<213> ORGANISM: Paenibacillus apairius strain DB482

<400> SEQUENCE: 38

```
caggcaacct catcggctgt ctgtggtgtg ccattcccga tcaacgtggt atcggacata      60
cacacggtgg acgaaatcag cggcagcgcc aggattcaga agtatactta ccgcaatggc     120
gtgtatgacc ggaccgataa ggaatttgcc gggttcggcc acattgacac atgggaagag     180
gagcgggatt ccgagggaac ccttagcatc agcactcccc ccgtgctgac acggacctgg     240
tatcataccg ggcaaaagca ggatgaggag cgtgccgtgc agcaatattg gcaaggcgac     300
cctgccgctt ttcaggttaa acccgtccgg cttactcgat tcgatgcggc aacggcccag     360
gatgtcccgc tagactctcc caataggcgg gaagagtatt ggctgtatcg ctcgttgcga     420
gggatgccgc tgcgtaatga aattttgct ggagatgttg tggggttgcc tccttatcag     480
gtggagagct acgttatca agtgcgcttg atgcagagca ccgattcgga atgtgttaca     540
ttgcccatgc agttggagca gcttacgtac aactatgagc aaatcgcctc tgatccgcag     600
tgttcacagc agatacagca atggttcgac gaatacggcg tggcggcaca gagtataacg     660
atccaatatc cgcgccgggc acagccggag gacaatccgt accctcacac gctgccggat     720
```

```
accagctgga gcagcagtta tgattcgcag caaatgctgc tgcggttaac aaggcaaagg      780
caaaaagcgt accaccttgc agaccctgaa ggctggcgct tgaatatccc ccatcagaca      840
cgcctggatt ctttcatcta ttctgctgac agcgtgcctg ccgaaggaat aagcgcagag      900
ctgctggggg gtgacggcac gttacgatct ccggcgctgg aacaggctta tggcggccag      960
tcagagatca tctatgcggg cggggggaa ccggattcgc gagctctggt ccattacacc      1020
agaagcgcga ttctcgatga agcctgtttg caagcctatg aaggcgtact gagcgatagc      1080
caattgaact cgcttcttgc atcttccggc tatcaacgaa gcgcaagaat attgggttcc      1140
ggcgatgaag cggatatttt tgttgcgaa caaggattta cccgttatgc ggatgaacag      1200 aatttttttcc gtattctggg acaacaatcc tctctcttga ccggggaaca agtattaaca      1260
tgggatgata atttctgtgc ggtaacatcc atagaagacg cgcttggcaa tcaaattcag      1320
attgcatatg attaccgctt tgtggaggct atccagatta ccgatgcgaa taacaatgtg      1380
aatcaggtct ccctggatgc ctcggccgg gtcgtataca gccggacctg ggcacagag       1440 gaagggatag agacgggctt ccgcccggag gcggaattct cgccgcccga caatggag       1500 caggcgcttg ccctggcgtc tcccttgccg gttgcatcct gctgtgtta tgatgcgcat      1560 agctggatgg gaacgataac tcttgggcag ctgtcagcgc ttgttccaga tagtgaaaag      1620
caatggtcgt tcttgatagc caatcgcttg attatgccgg acggcaggat aagagcccgc      1680
ggccgggccc catggtggct tcaacggcta ttgccgcctg ccgtggccaa gctgctgagc      1740
gaggcggacc gtaagccgcc gcatacggta gttttggcag cagatcgcta cccggatgac      1800
ccatcccagc aaattcaggc cagcgtcgtg tttagcgatg gctttgggcg tacgatacaa      1860
accgctaaaa gagcagatac ccgatgggcg attacggaac ggattgacta tgacgaaacc      1920
ggagccgtaa tccgaagctt tcagcctttt tatattgatg actggaatta tgtgggcaaa      1980
gaggctgtca gcggctctat gtatgcaacg atctattact atgatgctct ggcacgccaa      2040
ctaaggatgg tcaacgccaa aggatatgag aggagaactg cttttttaccc a              2091
```

<210> SEQ ID NO 39
<211> LENGTH: 697
<212> TYPE: PRT
<213> ORGANISM: Paenibacillus apairius strain DB482

<400> SEQUENCE: 39

```
Gln Ala Thr Ser Ser Ala Val Cys Gly Val Pro Phe Pro Ile Asn Val
1               5                   10                  15

Val Ser Asp Ile His Thr Val Asp Glu Ile Ser Gly Ser Ala Arg Ile
            20                  25                  30

Gln Lys Tyr Thr Tyr Arg Asn Gly Val Tyr Asp Arg Thr Asp Lys Glu
        35                  40                  45

Phe Ala Gly Phe Gly His Ile Asp Thr Trp Glu Glu Arg Asp Ser
    50                  55                  60

Glu Gly Thr Leu Ser Ile Ser Thr Pro Pro Val Leu Thr Arg Thr Trp
65                  70                  75                  80

Tyr His Thr Gly Gln Lys Gln Asp Glu Glu Arg Ala Val Gln Gln Tyr
                85                  90                  95

Trp Gln Gly Asp Pro Ala Ala Phe Gln Val Lys Pro Val Arg Leu Thr
            100                 105                 110

Arg Phe Asp Ala Ala Thr Ala Gln Asp Val Pro Leu Asp Ser Pro Asn
        115                 120                 125

Arg Arg Glu Glu Tyr Trp Leu Tyr Arg Ser Leu Arg Gly Met Pro Leu
```

```
                130                 135                 140
Arg Asn Glu Ile Phe Ala Gly Asp Val Val Gly Leu Pro Pro Tyr Gln
145                 150                 155                 160

Val Glu Ser Leu Arg Tyr Gln Val Arg Leu Met Gln Ser Thr Asp Ser
                165                 170                 175

Glu Cys Val Thr Leu Pro Met Gln Leu Glu Gln Leu Thr Tyr Asn Tyr
                180                 185                 190

Glu Gln Ile Ala Ser Asp Pro Gln Cys Ser Gln Ile Gln Gln Trp
            195                 200                 205

Phe Asp Glu Tyr Gly Val Ala Ala Gln Ser Ile Thr Ile Gln Tyr Pro
210                 215                 220

Arg Arg Ala Gln Pro Glu Asp Asn Pro Tyr Pro His Thr Leu Pro Asp
225                 230                 235                 240

Thr Ser Trp Ser Ser Ser Tyr Asp Ser Gln Gln Met Leu Leu Arg Leu
                245                 250                 255

Thr Arg Gln Arg Gln Lys Ala Tyr His Leu Ala Asp Pro Glu Gly Trp
                260                 265                 270

Arg Leu Asn Ile Pro His Gln Thr Arg Leu Asp Ser Phe Ile Tyr Ser
                275                 280                 285

Ala Asp Ser Val Pro Ala Glu Gly Ile Ser Ala Glu Leu Leu Gly Gly
290                 295                 300

Asp Gly Thr Leu Arg Ser Pro Ala Leu Glu Gln Ala Tyr Gly Gly Gln
305                 310                 315                 320

Ser Glu Ile Ile Tyr Ala Gly Gly Glu Pro Asp Ser Arg Ala Leu
                325                 330                 335

Val His Tyr Thr Arg Ser Ala Ile Leu Asp Glu Ala Cys Leu Gln Ala
                340                 345                 350

Tyr Glu Gly Val Leu Ser Asp Ser Gln Leu Asn Ser Leu Leu Ala Ser
                355                 360                 365

Ser Gly Tyr Gln Arg Ser Ala Arg Ile Leu Gly Ser Gly Asp Glu Ala
                370                 375                 380

Asp Ile Phe Val Ala Glu Gln Gly Phe Thr Arg Tyr Ala Asp Glu Gln
385                 390                 395                 400

Asn Phe Phe Arg Ile Leu Gly Gln Gln Ser Ser Leu Leu Thr Gly Glu
                405                 410                 415

Gln Val Leu Thr Trp Asp Asp Asn Phe Cys Ala Val Thr Ser Ile Glu
                420                 425                 430

Asp Ala Leu Gly Asn Gln Ile Gln Ile Ala Tyr Asp Tyr Arg Phe Val
                435                 440                 445

Glu Ala Ile Gln Ile Thr Asp Ala Asn Asn Val Asn Gln Val Ser
450                 455                 460

Leu Asp Ala Leu Gly Arg Val Val Tyr Ser Arg Thr Trp Gly Thr Glu
465                 470                 475                 480

Glu Gly Ile Glu Thr Gly Phe Arg Pro Glu Ala Glu Phe Ser Pro Pro
                485                 490                 495

Glu Thr Met Glu Gln Ala Leu Ala Leu Ala Ser Pro Leu Pro Val Ala
                500                 505                 510

Ser Cys Cys Val Tyr Asp Ala His Ser Trp Met Gly Thr Ile Thr Leu
                515                 520                 525

Gly Gln Leu Ser Ala Leu Val Pro Asp Ser Glu Lys Gln Trp Ser Phe
                530                 535                 540

Leu Ile Ala Asn Arg Leu Ile Met Pro Asp Gly Arg Ile Arg Ala Arg
545                 550                 555                 560
```

```
Gly Arg Ala Pro Trp Trp Leu Gln Arg Leu Leu Pro Pro Ala Val Ala
            565                 570                 575

Lys Leu Leu Ser Glu Ala Asp Arg Lys Pro Pro His Thr Val Val Leu
        580                 585                 590

Ala Ala Asp Arg Tyr Pro Asp Asp Pro Ser Gln Gln Ile Gln Ala Ser
    595                 600                 605

Val Val Phe Ser Asp Gly Phe Gly Arg Thr Ile Gln Thr Ala Lys Arg
610                 615                 620

Ala Asp Thr Arg Trp Ala Ile Thr Glu Arg Ile Asp Tyr Asp Glu Thr
625                 630                 635                 640

Gly Ala Val Ile Arg Ser Phe Gln Pro Phe Tyr Ile Asp Asp Trp Asn
            645                 650                 655

Tyr Val Gly Lys Glu Ala Val Ser Gly Ser Met Tyr Ala Thr Ile Tyr
        660                 665                 670

Tyr Tyr Asp Ala Leu Ala Arg Gln Leu Arg Met Val Asn Ala Lys Gly
    675                 680                 685

Tyr Glu Arg Arg Thr Ala Phe Tyr Pro
690                 695
```

<210> SEQ ID NO 40
<211> LENGTH: 858
<212> TYPE: DNA
<213> ORGANISM: Paenibacillus apairius strain DB482

<400> SEQUENCE: 40

```
atcctgtcta tctgcaatga agcggagccg gtccgttatt tccgcaatca ggccgtcgct      60
ccgaaaaggc agtatgctta cgatgccctg tatcagcttg tatccagctc ggggcgggaa     120
tccgacgcgc ttcgtcagca gacgtcgctt cctcccttga tcacgcctat tcctctcgac     180
gatagccaat acgtcaatta tgctgagaga tacagctatg atcgggcggg caatctaatc     240
aagcttagcc atcatggggc aagtcaatat acaacgaatg tgcatgtgga caaaagttca     300
aaccggggga tttggcggca aggggaagac atcccggata tcgcggcttc ctttgacaga     360
gcaggcaatc aacaagattt attcccgggg agacggttgg aatgggatac acgcaatcag     420
ttatgccgtg tccatatggt cgtgcgcgaa ggcggcgata acgactggga gggctatctc     480
tatgacagct caggaatgcg catcgtaaaa cattctaccc gcaagacaca gacgacaacg     540
caaacggata cgacgatcta tttgccgggc ctggagcttc gcatccgcca aaccggggac     600
agggtcacgg aagcattgca ggtcattacc gtggatgagg gagcgggaca gtgagggtg     660
ctgcactggg aggatggaac cgagccgggc ggcatagcca atgatcagta tcggtacagc     720
ctaaacgatc atcttggctc ctctttattg gaagttgacg ggcaaagtca gatcattagc     780
aaggaagaat ttatcccta tggcggcaca gcattgtgga cagcccggtc agaggtggag     840
gcaagctaca agaccacg                                                   858
```

<210> SEQ ID NO 41
<211> LENGTH: 286
<212> TYPE: PRT
<213> ORGANISM: Paenibacillus apairius strain DB482

<400> SEQUENCE: 41

```
Ile Leu Ser Ile Cys Asn Glu Ala Glu Pro Val Arg Tyr Phe Arg Asn
1               5                   10                  15

Gln Ala Val Ala Pro Lys Arg Gln Tyr Ala Tyr Asp Ala Leu Tyr Gln
            20                  25                  30

Leu Val Ser Ser Ser Gly Arg Glu Ser Asp Ala Leu Arg Gln Gln Thr
```

```
                35                  40                  45
Ser Leu Pro Pro Leu Ile Thr Pro Ile Pro Leu Asp Asp Ser Gln Tyr
 50                  55                  60

Val Asn Tyr Ala Glu Arg Tyr Ser Tyr Asp Arg Ala Gly Asn Leu Ile
 65                  70                  75                  80

Lys Leu Ser His His Gly Ala Ser Gln Tyr Thr Thr Asn Val His Val
                 85                  90                  95

Asp Lys Ser Ser Asn Arg Gly Ile Trp Arg Gln Gly Glu Asp Ile Pro
            100                 105                 110

Asp Ile Ala Ala Ser Phe Asp Arg Ala Gly Asn Gln Gln Asp Leu Phe
        115                 120                 125

Pro Gly Arg Arg Leu Glu Trp Asp Thr Arg Asn Gln Leu Cys Arg Val
    130                 135                 140

His Met Val Val Arg Glu Gly Gly Asp Asn Asp Trp Glu Gly Tyr Leu
145                 150                 155                 160

Tyr Asp Ser Ser Gly Met Arg Ile Val Lys His Ser Thr Arg Lys Thr
                165                 170                 175

Gln Thr Thr Thr Gln Thr Asp Thr Thr Ile Tyr Leu Pro Gly Leu Glu
            180                 185                 190

Leu Arg Ile Arg Gln Thr Gly Asp Arg Val Thr Glu Ala Leu Gln Val
        195                 200                 205

Ile Thr Val Asp Glu Gly Ala Gly Gln Val Arg Val Leu His Trp Glu
    210                 215                 220

Asp Gly Thr Glu Pro Gly Gly Ile Ala Asn Asp Gln Tyr Arg Tyr Ser
225                 230                 235                 240

Leu Asn Asp His Leu Gly Ser Ser Leu Leu Glu Val Asp Gly Gln Ser
                245                 250                 255

Gln Ile Ile Ser Lys Glu Glu Phe Tyr Pro Tyr Gly Gly Thr Ala Leu
            260                 265                 270

Trp Thr Ala Arg Ser Glu Val Glu Ala Ser Tyr Lys Thr Thr
        275                 280                 285

<210> SEQ ID NO 42
<211> LENGTH: 4434
<212> TYPE: DNA
<213> ORGANISM: Photorhabdus strain W14

<400> SEQUENCE: 42
atgatgcaga attcacaaac attcagtgtt accgagctgt cattacccaa aggcggcggc        60
gctattaccg gtatgggtga agcattaaca ccagccgggc cggatggtat ggccgcctta       120
tccctgccat acccatttc cgccgggcgt ggttacgcac cctcgctcac tctgaattac        180
aacagtggaa ccggtaacag cccatttggt ctcggttggg actgcggcgt catggcaatt       240
cgtcgtcgca ccagtaccgg cgtaccgaat tacgatgaaa ccgatacttt tctgggccg        300 gaaggtgaag tgttggtcgt agcattaaat gaggcaggtc aagctgatat ccgcagtgaa       360
tcctcattgc agggcatcaa tttgggtgcg accttcaccg ttacctgtta tcgctcccgc       420
ctagaaagcc actttaaccg gttggaatac tggcaacccc aaacaaccgg cgcaaccgat       480
ttctggctga tatacagccc cgacggacag gtccatttac tgggcaaaaa tcctcaggca       540
cgtatcagca atccactcaa tgttaaccaa acagcgcaat ggctgttgga gcctcgata        600 tcatcccaca cgcgaacagat ttattatcaa tatcgcgctg aagatgaagc aggttgtgaa       660
accgacgagc tagcagccca ccccagcgca accgttcagc gctacctgca aacagtacat       720
tacgggaacc tgaccgccag cgacgttttt cctacactaa acggagatga cccacttaaa       780
```

```
tctggctgga tgttctgttt agtatttgac tacggtgagc gcaaaaacag cttatctgaa    840
atgccgctgt ttaaagccac aggcaattgg ctttgccgaa aagaccgttt ttcccgttat    900
gagtacggtt ttgaattgcg tactcgccgc ttatgccgcc aaatactgat gtttcaccgt    960
ctacaaaccc tatctggtca ggcaaagggg gatgatgaac ctgcgctagt gtcgcgtctg   1020
atactggatt atgacgaaaa cgcgatggtc agtacgctcg tttctgtccg ccgggtaggc   1080
catgaggaca caacacggt taccgcgctg ccaccactgg aactggccta tcagccttt    1140
gagccagaac aaaccgcact ctggcaatca atggatgtac tggcaaattt caacaccatt   1200
cagcgctggc aactgcttga cctgaaagga gaaggcgtgc ccggcattct ctatcaggat   1260
agaaatggct ggtggtatcg atctgcccaa cgtcaggccg gggaagagat gaatgcggtc   1320
acctggggga aaatgcaact ccttcccatc acaccagctg tgcaggataa cgcctcactg   1380
atggatatta cggtgacgg gcaactggac tgggtgatta ccgggccggg gctaaggggc   1440
tatcacagcc aacaccccgga tggcagttgg acgcgtttta cgccattaca tgccctgccg   1500
atagaatatt ctcatcctcg cgctcaactt gccgatttaa tgggagccgg gctgtccgat   1560
ttagtgctaa ttggtcccaa aagtgtgcgc ttatatgtca ataaccgtga tggttttacc   1620
gaagggcggg atgtggtgca atccggtgat atcaccctgc cgctaccggg cgccgatgcc   1680
cgtaagttag tggcatttag tgacgtactg ggttcaggcc aagcacatct ggttgaagtt   1740
agtgcaactc aagtcacctg ctggccgaat ctggggcatg ccgttttgg tcagccaatc   1800
gtattgccgg gattcagcca atctgccgcc agttttaatc ctgatcgagt tcatctggcc   1860
gatttggatg ggagcggccc tgccgatttg atttatgttc atgctgaccg tctggatatt   1920
ttcagcaatg aaagtggcaa cggttttgca aaaccattca cactctcttt tcctgacggc   1980
ctgcgttttg atgatacctg ccagttgcaa gtagccgatg tacaagggtt aggcgttgtc   2040
agcctgatcc taagcgtacc gcatatgcg ccacatcatt ggcgctgcga tctgaccaac   2100
gcgaaaccgt ggttactcag tgaaacgaac aacaatatgg gggccaatca caccttgcat   2160
taccgtagct ctgtccagtt ctggctggat gaaaaagctg cggcattggc taccggacaa   2220
acaccggtct gttacctgcc cttcccggtc catacccttt ggcaaacaga aaccgaggat   2280
gaaatcagcg gcaataagtt agtgaccacg ttacgttatg ctcacggcgc ttgggatgga   2340
cgtgaacggg aatttcgtgg ctttggttat gttgagcaga cagacagcca tcaactcgct   2400
caaggcaatg cgccggaacg tacaccaccg gcactcacca aaagctggta tgccaccgga   2460
ttacctgcgg tagataatgc gttatccgcc gggtattggc gtggcgataa gcaagctttc   2520
gccggtttta cgccacgttt tactctctgg aaagagggca aagatgttcc actgacaccg   2580
gaagatgacc ataatctata ctggttaaac cgggcgctaa aaggtcagcc actgcgtagt   2640
gaactctacg gctggatgg cagcgcacag caacagatcc cctatacagt gactgaatcc   2700
cgtccacagg tgcgccaatt acaagatggc gccaccgttt ccccggtgct ctgggcctca   2760
gtcgtggaaa gccgtagtta tcactacgaa cgtattatca gtgatcccca gtgcaatcag   2820
gatatcacgt tgtccagtga cctattcggg caaccactga acaggtttc cgtacaatat   2880
ccccgccgca acaaaccaac aaccaatccg tatcccgata ccctaccgga tacgctgttt   2940
gccagcagtt atgacgatca acaacagcta ttgcgattaa cctgccgaca atccagttgg   3000
caccatctta ttggtaatga gctaagagtg ttgggattac cggatggcac acgcagtgat   3060
gcctttactt acgatgccaa acaggtacct gtcgatggct taaatctgga aaccctgtgt   3120
gctgaaaata gcctgattgc cgatgataaa cctcgcgaat acctcaatca gcaacgaacg   3180
```

```
ttctataccg acgggaaaaa ccaaacaccg ctgaaaacac cgacacgaca agcgttaatc    3240
gcctttaccg aaacggcggt attaacggaa tctctgttat ccgcgtttga tggcggtatt    3300
acgccagacg aattaccggg aatactgaca caggccggat accaacaaga gccttatctg    3360
tttccacgca ccggcgaaaa caaagtttgg gtagcgcgtc aaggctatac cgattacggg    3420
acggaagcac aattttggcg tcctgtcgca caacgtaaca gcctgttaac cgggaaaatg    3480
acgttaaaat gggatactca ctattgtgtc atcacccaaa cccaagatgc tgccggcctc    3540
accgtctcag ccaattatga ctggcgtttt ctcacaccaa cgcaactgac tgacatcaac    3600
gataatgtgc atctcatcac cttggatgct ctgggacgcc tgtcacgca acgtttctgg    3660 gggatcgaaa gcggtgtggc aacaggttac tcttcatcag aagaaaaacc attctctcca    3720
ccaaacgata tcgataccgc tattaatcta accggaccac tccctgtcgc acagtgtctg    3780
gtctatgcac cggacagttg gatgccacta ttcagtcaag aaaccttcaa cacattaacg    3840
caggaagagc aggagacgct gcgtgattca cgtattatca cggaagattg gcgtatttgc    3900
gcactgactc gccgccgttg gctacaaagt caaaagatca gtacaccatt agttaaactg    3960
ttaaccaaca gcattggttt acctccccat aaccttacgc tgaccacaga ccgttatgac    4020
cgcgactctg agcagcaaat tcgccaacaa gtcgcattta gtgatggttt tggccgtctg    4080
ctacaagcgt ctgtacgaca tgaggcaggc gaagcctggc aacgtaacca agacggttct    4140
ctggtgacaa aagtggagaa taccaaaacg cgttgggcgg tcacgggacg caccgaatat    4200
gataataaag gcaaacgat acgcacttat cagccctatt tcctcaacga ctggcgatat    4260
gtcagtgatg acagcgccag aaaagaagcc tatgcggata ctcatattta tgatccaatt    4320
gggcgagaaa tccgggttat tactgcaaaa ggctggctgc gccaaagcca atatttcccg    4380
tggtttaccg tgagtgagga tgagaatgat acggccgctg atgcgctggt gtaa          4434

<210> SEQ ID NO 43
<211> LENGTH: 4425
<212> TYPE: DNA
<213> ORGANISM: Photorhabdus strain W14

<400> SEQUENCE: 43
atgcaaaatt cacaagattt tagtattacg gaactgtcac tgcccaaagg ggggggcgct      60
atcacgggaa tgggtgaagc attaaccccc actggaccgg atggtatggc cgcgctatct     120
ctaccattgc ctatttctgc cgggcgcggt tatgctcccg cattcactct gaattacaac     180
agcggcgccg gtaacagtcc atttggtctg ggttgggatt gcaacgttat gactatccgc     240
cgccgcaccc attttggcgt cccccattat gacgaaaccg ataccttttt ggggccagaa     300
ggcgaagtgc tggtggtagc ggatcaacct cgcgacgaat ccacattaca gggtatcaat     360
ttaggcgcca cctttaccgt taccggctac cgttcccgtc tggaaagcca ttcagccga     420 ttggaatatt ggcaacccaa aacaacaggt aaaacagatt tttggttgat atatagccca     480
gatgggcagg tgcatctact gggtaaatca ccgcaagcgc ggatcagcaa cccatcccaa     540
acgacacaaa cagcacaatg gctgctggaa gcctctgtat catcacgtgg cgaacaaatt     600
tattatcaat atcgcgccga agatgacaca ggttgcgaag cagatgaaat tacgcaccat     660
ttacaggcta cagcgcaacg ttatttacac atcgtgtatt acggcaaccg tacagccagc     720
gaaacattac ccggtctgga tggcagcgcc ccatcacaag cagactggtt gttctatctg     780
gtatttgatt acgcgaacg cagtaacaac ctgaaaacgc caccagcatt ttcgactaca     840
ggtagctggc tttgccgtca ggaccgtttt tcccgttatg aatatggctt tgagattcgt     900
```

```
acccgccgct tatgccgtca ggtattgatg taccatcacc tgcaagcact ggatagtaag    960
ataacagaac acaacggacc aacgctggtt tcacgcctga tactcaatta cgacgaaagc   1020
gcgatagcca gcacgctagt attcgttcgc cgagtgggac acgagcaaga tggtaatgtc   1080
gtcaccctgc cgccattaga attggcatat caggattttt caccgcgaca tcacgctcac   1140
tggcaaccaa tggatgtact ggcaaacttc aatgccattc agcgctggca gctagtcgat   1200
ctaaaaggcg aaggattacc cggcctgtta tatcaggata aaggcgcttg gtggtaccgc   1260
tccgcacagc gtctgggcga aattggctca gatgccgtca cttgggaaaa gatgcaacct   1320
ttatcggtta ttccttcttt gcaaagtaat gcctcgttgg tggatatcaa tggagacggc   1380
caacttgact gggttatcac cggacccgga ttacggggat atcatagtca acgcccggat   1440
ggcagttgga cacgttttac cccactcaac gctctgccgg tggaatacac ccatccacgc   1500
gcgcaactcg cagatttaat gggagccggg ctatccgatt tggtgctgat cggccctaag   1560
agcgtgcgtt tatatgccaa tacccgcgac ggctttgcca aaggaaaaga tgtggtgcaa   1620
tccggtgata tcacactgcc ggtgccgggc gccgatccac gtaagttggt ggcgtttagt   1680
gatgtattgg gttcaggtca agcccatctg gttgaagtaa gcgcgactaa agtcacctgc   1740
tggcctaatc tggggcgcgg acgttttggt caacccatta ccttaccggg attcagccag   1800
ccagcaaccg agtttaaccc ggctcaagtt tatctggccg atctggatgg cagcggtcca   1860
acggatctga tttatgttca tacaaaccgt ctggatatct tcctgaacaa agtggcaat   1920 ggctttgctg aaccagtgac attacgcttc ccggaaggtc tgcgttttga tcatacctgt   1980
cagttacaaa tggccgatgt acaaggatta ggcgtcgcca gcctgatact gagcgtgccg   2040
catatgtctc cccatcactg gcgctgcgat ctgaccaaca tgaagccgtg gttactcaat   2100
gaaatgaaca acaatatggg ggtccatcac accttgcgtt accgcagttc ctcccaattc   2160
tggctggatg aaaaagccgc ggcgctgact accggacaaa caccggtttg ctatctcccc   2220
ttcccgatcc acaccctatg gcaaacggaa acagaagatg aaatcagcgg caacaaatta   2280
gtcacaacac ttcgttatgc tcgtggcgca tgggacggac gcgagcggga atttcgcgga   2340
tttggttatg tagagcagac agacagccat caactggctc aaggcaacgc gccagaacgt   2400
acgccaccgg cgctgaccaa aaactggtat gccaccggac tgccggtgat agataacgca   2460
ttatcaaccg agtattggcg tgatgatcag gcttttgccg gtttctcacc gcgctttacg   2520
acttggcaag ataacaaaga tgtcccgtta acaccggaag atgataacag tcgttactgg   2580
ttcaaccgcg cgttgaaagg tcaactgcta cgtagtgaac tgtacggatt ggacgatagt   2640
acaaataaac acgttcccta tactgtcact gaatttcgtt cacaggtacg tcgattacag   2700
cataccgaca gccgataccc tgtactttgg tcatctgtag ttgaaagccg caactatcac   2760
tacgaacgta tcgccagcga cccgcaatgc agtcaaaata ttacgctatc cagtgatcga   2820
tttggtcagc cgctaaaaca gctttcggta cagtacccgc gccgccagca gccagcaatc   2880
aatctgtatc ctgatacatt gcctgataag ttgttagcca acagctatga tgaccaacaa   2940
cgccaattac ggctcaccta tcaacaatcc agttggcatc acctgaccaa caataccgtt   3000
cgagtattgg gattaccgga tagtacccgc agtgatatct ttacttatgg cgctgaaaat   3060
gtgcctgctg gtggtttaaa tctggaactt ctgagtgata aaaatagcct gatcgcggac   3120
gataaaccac gtgaatacct cggtcagcaa aaaccgctt ataccgatgg acaaaataca   3180
acgccgttgc aaacaccaac acggcaagcc ctgattgcct ttaccgaaac aacggtattc   3240
aaccagtcca cattatcagc gtttaacgga agcatcccgt ccgataaatt atcaacgacg   3300
```

-continued

```
ctggagcaag ctggatatca gcaaacaaat tatctattcc ctcgcactgg agaagataaa      3360
gtttgggtag cccatcacgg ctataccgat tatggtacag cggcacagtt ctggcgcccg      3420
caaaaacaga gcaacaccca actcaccggt aaaatcaccc tcatctggga tgcaaactat      3480
tgcgttgtgg tacaaacccg ggatgctgct ggactgacaa cctcagccaa atatgactgg      3540
cgttttctga ccccggtgca actcaccgat atcaatgaca atcagcacct tatcacactg      3600
gatgcattgg gccgaccaat cacattgcgc ttttggggaa ctgaaaacgg caagatgaca      3660
ggttattcct caccggaaaa agcatcattt tctccaccat ccgatgttaa tgccgctatt      3720
gagttaaaaa aaccgctccc tgtagcacag tgtcaggtct acgcaccaga aagctggatg      3780
ccagtattaa gtcagaaaac cttcaatcga ctggcagaac aagattggca aaagttatat      3840
aacgcccgaa tcatcaccga agatggacgt atctgcacac tggcttatcg ccgctgggta      3900
caaagccaaa aggcaatccc tcaactcatt agcctgttaa caacggaccc cgtttaccct      3960
cctcacagcc tgacattgac gacggatcgt tatgatcacg atcctgagca acagatccgt      4020
caacaggtgg tattcagtga tggctttggc cgcttgctgc aagccgctgc ccgacatgag      4080
gcaggcatgc cccggcaacg caatgaagac ggctctttga ttataaatgt ccagcatact      4140
gagaaccgtt gggcagtgac tggacgaacg gaatatgaca ataaggggca accgatacgt      4200
acctatcagc cctatttcct caatgactgg cgatacgtca gcaatgatag tgcccggcag      4260 gaaaagaag cttatgcaga tacccatgtc tatgatccca taggtcgaga aatcaaggtt      4320
atcaccgcaa aaggttggtt ccgtcgaacc ttgttcactc cctggtttac tgtcaatgaa      4380
gatgaaaatg acacagccgc tgaggtgaag aaggtaaaga tgtaa                     4425
```

<210> SEQ ID NO 44
<211> LENGTH: 3132
<212> TYPE: DNA
<213> ORGANISM: Photorhabdus strain W14

<400> SEQUENCE: 44

```
atgagcccgt ctgagactac tctttatact caaaccccaa cagtcagcgt gttagataat       60
cgcggtctgt ccattcgtga tattggtttt caccgtattg taatcggggg ggatactgac      120
acccgcgtca cccgtcacca gtatgatgcc cgtggacacc tgaactacag tattgaccca      180
cgcttgtatg atgcaaagca ggctgataac tcagtaaagc ctaattttgt ctggcagcat      240
gatctggccg tcatgccct gcggacagag agtgtcgatg ctggtcgtac tgttgcattg      300
aatgatattg aaggtcgttc ggtaatgaca atgaatgcga ccggtgttcg tcagacccgt      360
cgctatgaag caacacctt gcccggtcgc ttgttatctg tgagcgagca agttttcaac      420
caagagagtg ctaaagtgac agagcgcttt atctgggctg gaatacaac ctcggagaaa      480 gagtataacc tctccggtct gtgtatacga cactacgaca cagcgggagt gacccggttg      540
atgagtcagt cactggcggg cgccatgcta tcccaatctc accaattgct ggcggaaggg      600
caggaggcta actggagcgg tgacgacgaa actgtctggc agggaatgct ggcaagtgag      660
gtctatacga cacaaagtac cactaatgcc atcggggctt tactgaccca aaccgatgcg      720
aaaggcaata ttcagcgtct ggcttatgac attgccggtc agttaaaagg gagttggttg      780
acggtgaaag ccagagtga acaggtgatt gttaagtccc tgagctggtc agccgcaggt      840
cataaattgc gtgaagagca cggtaacggc gtggttacgg agtacagtta tgagccggaa      900
actcaacgtc tgataggtat caccacccgg cgtgccgaag ggagtcaatc aggagccaga      960
gtattgcagg atctacgcta taagtatgat ccggtgggga atgttatcag tatccataat     1020
```

```
gatgccgaag ctacccgctt ttggcgtaat cagaaagtgg agccggagaa tcgctatgtt    1080
tatgattctc tgtatcagct tatgagtgcg acagggcgtg aaatggctaa tatcggtcag    1140
caaagcaacc aacttccctc acccgttata cctgttccta ctgacgacag cacttatacc    1200
aattaccttc gtacctatac ttatgaccgt ggcggtaatt tggttcaaat ccgacacagt    1260
tcacccgcga ctcaaaatag ttacaccaca gatatcaccg tttcaagccg cagtaaccgg    1320
gcggtattga gtacattaac gacagatcca acccgagtgg atgcgctatt tgattccggc    1380
ggtcatcaga agatgttaat accggggcaa aatctggatt ggaatattcg ggtgaattg     1440 caacgagtca caccggtgag ccgtgaaaat agcagtgaca gtgaatggta tcgctatagc    1500
agtgatggca tgcggctgct aaaagtgagt gaacagcaga cgggcaacag tactcaagta    1560
caacgggtga cttatctgcc gggattagag ctacggacaa ctgggggttgc agataaaaca   1620 accgaagatt tgcaggtgat tacggtaggt gaagcgggtc gcgcacaggt aagggtattg    1680
cactgggaaa gtggtaagcc gacagatatt gacaacaatc aggtgcgcta cagctacgat    1740
aatctgcttg gctccagcca gcttgaactg gatagcgaag gcagattct cagtcaggaa     1800 gagtattatc cgtatggcgg tacggcgata tgggcggcga aaatcagac agaagccagc     1860 tacaaattta ttcgttactc cggtaaagag cgggatgcca ctggattgta ttattacggc    1920
taccgttatt atcaaccttg ggtgggtcga tggttgagtg ctgatccggc gggaaccgtg    1980
gatgggctga atttgtaccg aatggtgagg aataacccca tcacattgac tgaccatgac    2040
ggattagcac cgtctccaaa tagaaatcga aatacatttt ggtttgcttc atttttgttt    2100
cgtaaacctg atgagggaat gtccgcgtca atgagacggg gacaaaaaat tggcagagcc    2160
attgccggcg ggattgcgat tggcggtctt gcggctacca ttgccgctac ggctggcgcg    2220
gctatccccg tcattctggg ggttgcggcc gtaggcgcgg ggattggcgc gttgatggga    2280
tataacgtcg gtagcctgct ggaaaaaggc ggggcattac ttgctcgact cgtacagggg    2340
aaatcgacgt tagtacagtc ggcggctggc gcggctgccg gagcgagttc agccgcggct    2400
tatggcgcac gggcacaagg tgtcggtgtt gcatcagccg ccggggcggt aacaggggct    2460
gtgggatcat ggataaataa tgctgatcgg gggattggcg gcgctattgg ggccgggagt    2520
gcggtaggca ccattgatac tatgttaggg actgcctcta ccettaccca tgaagtcggg    2580 gcagcggcgg gtggggcggc gggtgggatg atcaccggta cgcaagggag tactcgggca    2640
ggtatccatg ccggtattgg cacctattat ggctcctgga ttggttttgg tttagatgtc    2700
gctagtaacc ccgccggaca tttagcgaat tacgcagtgg gttatgccgc tggtttgggt    2760
gctgaaatgg ctgtcaacag aataatgggt ggtggatttt tgagtaggct cttaggccgg    2820
gttgtcagcc catatgccgc cggtttagcc agacaattag tacatttcag tgtcgccaga    2880
cctgtctttg agccgatatt tagtgttctc ggcgggcttg tcgtggtat tggaactggc      2940 ctgcacagag tgatgggaag agagagttgg atttccagag cgttaagtgc tgccggtagt    3000
ggtatagatc atgtcgctgg catgattggt aatcagatca gaggcagggt cttgaccaca    3060
accgggatcg ctaatgcgat agactatggc accagtgctg tgggagccgc acgacgagtt    3120
ttttctttgt aa                                                         3132
```

<210> SEQ ID NO 45
<211> LENGTH: 2748
<212> TYPE: DNA
<213> ORGANISM: Photorhabdus strain W14

<400> SEQUENCE: 45

```
atgagcagtt acaattctgc aattgaccaa agacccct cgattaaggt attagataac    60
aggaaattaa atgtacgtac tttagaatat ctacgcactc aagctgacga aaacagtgat   120
gaattaatta cgttctatga gttcaatatt ccgggatttc aggtaaaaag caccgatcct   180
cgtaaaaata aaaccagag cggcccaaat ttcattcgtg tctttaatct tgccggtcaa   240
gttttacgtg aagaaagtgt tgatgccggt cggactatta ccctcaatga tattgaaagt   300
cgcccggtgt tgatcatcaa tgcaaccggt gtccgccaaa accatcgtta tgaagataac   360
acccttcccg gtcgtctgct cgctatcacc gaacaagtac aggcaggaga gaaaacgacc   420
gaacgtctta tctgggccgg caatacgccg caagaaaaag attacaacct cgccggtcag   480
tgtgtccgcc attacgatac cgcgggactt actcaactca atagccttc tctggctggc   540
gtcgtgctat cacaatctca gcaactactc gtcgatgata aaaatgctga ctggacaggt   600
gaagaccaaa gcctctggca gcaaaaactg agcagtgatg tctataccac ccaaaataaa   660
gccgatgcca ccggggcttt attgacccag accgatgcca aaggcaacat ccagcgtctg   720
gcctacgacg tagccgggca gctaaaaggc tgttggttga cactcaaagg tcaggccgag   780
caagtgatta tcaaatcgct gacctactcc gccgccggac aaaaattacg cgaagagcac   840
ggtaacgggg ttatcactga atacagctat gaaccagaaa cccaacggct tatcggtatt   900
gccacccgcc gtccgtcaga cgccaaagtg ttgcaagact tacgctatca atatgacccg   960
gtaggcaatg tgatcaatat ccgtaatgat gcggaagcca cccgcttttg gcgcaatcag  1020
aaagtggtcc ggagaatag ctatacctac gactccctgt atcagcttat cagtgccacc  1080
gggcgggaaa tggctaatat aggtcagcaa ataaccaac tgccctcccc tgcgctacct  1140
tctgacaaca atacctacac taactatact cgcagctaca gctatgatca cagtggtaat  1200
ctgacgcaaa ttcggcacag ctcgccagct acccagaaca actacaccgt ggctatcacc  1260
ctctcaaacc gcagcaatcg gggtgttctc agtacgctaa ccaccgatcc aaatcaagtg  1320
gatacgttgt ttgatgccgg tggtcaccaa accagtttat tacccggaca gacacttatc  1380
tggacaccac gaggagagtt aaagcaggtt aataatggcc cgggaaatga gtggtaccgc  1440
tacgacagca acggcatgag acaactgaaa gtgagtgaac agccaaccca gaatactacg  1500
cagcaacaac gggtaatcta tttgccggga ctggagctac gcacaaccca gagcaacgcc  1560
acaacaacgg aagagttaca cgttatcaca ctcggtgaag ccggtcgcgc acaggtacgg  1620
gtgttgcact gggagagcgg taagccagaa gatgtcaaca ataatcaact acgttacagc  1680
tacgataatc tgatcggctc cagccagctt gaactggaca accaaggaca aattatcagc  1740
gaggaagagt attatccatt tggcgggaca gcgctgtggg cagcaaacag ccaaacagaa  1800
gccagctata aaacgattcg ctattccggc aaagaacgag atgccaccgg gttgtattat  1860
tacggttatc gttattacca accgtgggcg ggcagatggt taagcgcgga cccggcagga  1920
accattgatg ggctgaatct ataccgaatg gtaagaaata tcctgtgag tttacaagat  1980
gaaaatggat tagcgccaga aaagggaaa tataccaaag aggtaaattt ctttgatgaa  2040
ttaaaattca aattggcagc caaaagttca catgttgtca aatggaacga gaagagagc  2100
agttatacaa aaaataaatc attgaaagtg gttcgtgtcg gtgattccga tccgtcgggt  2160
tatttgctaa gccacgaaga gttactaaaa ggtatagaaa aagtcaaat catatatagc  2220
cgacttgaag aaaacagctc cctttcagaa aaatcaaaaa cgaatctttc tttaggatct  2280
gaaatatccg gttatatggc aagaaccata caagatacga tatcagaata tgccgaagag  2340
cataaatata gaagtaatca ccctgattt tattcagaaa ccgatttctt tgcgttaatg  2400
```

```
gataaaagtg aaaaaaatga ttattccggt gaaagaaaaa tttatgcggc aatggaggtt    2460
aaggtttatc atgatttaaa aaataaacaa tcagaattac atgtcaacta tgcattggcc    2520
catccctata cgcaattgag taatgaagaa agagcgctgt tgcaagaaac agaacccgct    2580
attgcaatag atagagaata taatttcaaa ggtgttggca aattcctgac aatgaaagca    2640
attaaaaaat cattgaaagg acataaaatt aataggatat caacagaggc tattaatatt    2700
cgctctgcgg ctatcgctga gaatttagga atgcggagaa cttcataa                 2748

<210> SEQ ID NO 46
<211> LENGTH: 2883
<212> TYPE: DNA
<213> ORGANISM: Photorhabdus strain W14

<400> SEQUENCE: 46
atgaaaaaca ttgatcccaa actttatcaa aaaccccta ctgtcagcgt ttacgataac      60
cgtggtctga taatccgtaa catcgatttt catcgtacta ccgcaaatgg tgatcccgat    120
acccgtatta cccgccatca atacgatatt cacggacacc taaatcaaag catcgatccg    180
cgcctatatg aagccaagca aaccaacaat acgatcaaac ccaattttct ttggcagtat    240
gatttgaccg gtaatcccct atgtacagag agcattgatg caggtcgcac tgtcaccttg    300
aatgatattg aaggccgtcc gctactaacg gtgactgcaa caggggttat acaaactcga    360
caatatgaaa cttcttccct gcccggtcgt ctgttatctg ttgccgaaca aacacccgag    420
gaaaaaacat cccgtatcac cgaacgcctg atttgggctg caataccga agcagagaaa     480 gaccataacc ttgccggcca gtgcgtgcgt cactatgaca cggcgggagt tacccggtta    540
gagagtttat cactgaccgg tactgtttta tctcaatcca gccaactatt gatcgacact    600
caagaggcaa actggacagg tgataacgaa accgtctggc aaaacatgct ggctgatgac    660
atctacacaa ccctgagcac cttcgatgcc accggtgctt tactgactca gaccgatgcg    720
aaagggaaca ttcagagact ggcttatgat gtggccgggc agctaaacgg gagctggcta    780
acactcaaag gccagacgga acaagtgatt atcaaatccc tgacctactc cgccgccgga    840
caaaaattac gtgaggaaca cggcaatgat gttatcaccg aatacagtta tgaaccggaa    900
acccaacggc tgatcggtat caaaacccgc cgtccgtcag acactaaagt gctacaagac    960
ctgcgctatg aatatgaccc ggtaggcaat gtcatcagca tccgtaatga cgcggaagcc   1020
acccgctttt ggcacaatca gaaagtgatg ccggaaaaca cttataccta cgattccctg   1080
tatcagctta tcagcgccac cgggcgcgaa atggcgaata taggtcaaca aagtcaccaa   1140
tttccctcac ccgctctacc ttctgataac aacacctata ccaactatac ccgtacttat   1200
acttatgacc gtggcggcaa tctgaccaaa atccagcaca gttcaccggc gacgcaaaac   1260
aactacacca ccaatatcac ggtttcaaat cgcagcaacc gcgcagtact cagcacattg   1320
accgaagatc cggcgcaagt agatgctttg tttgatgcag gcggacatca gaacaccttg   1380
atatcaggac aaaacctgaa ctggaatact cgtggtgaac tgcaacaagt aacactggtt   1440
aaacgggaca agggcgccaa tgatgatcgg gaatggtatc gttatagcgg tgacggaaga   1500
aggatgttaa aaatcaatga acagcaggcc agcaacaacg ctcaaacaca acgtgtgact   1560
tatttgccga acttagaact tcgtctaaca caaaacagca cggccacaac cgaagatttg   1620
caagttatca ccgtaggcga agcgggccgg cacaggtac gagtattaca ttgggagagc   1680
ggtaaaccgg aagatatcga caataatcag ttgcgttata gttacgataa tcttatcggt   1740
tccagtcaac ttgaattaga tagcgaagga caaattatca gtgaagaaga atattatccc   1800
```

```
tatggtggaa cagcattatg ggccgccagg aatcagacag aagccagtta taaaactatc    1860
cgttattcag gcaaagagcg ggatgccacc gggctatatt actacggcta tcggtattac    1920
caaccgtgga taggacggtg gttaagctcc gatccggcag gaacaatcga tgggctgaat    1980
ttatatcgga tggtgaggaa taatccagtt accctccttg atcctgatgg attaatgcca    2040
acaattgcag aacgcatagc agcactaaaa aaaataaag taacagactc agcgccttcg    2100
ccagcaaatg ccacaaacgt agcgataaac atccgcccgc ctgtagcacc aaaacctagc    2160
ttaccgaaag catcaacgag tagccaacca accacacacc ctatcggagc tgcaaacata    2220
aaaccaacga cgtctgggtc atctattgtt gctccattga gtccagtagg aaataaatct    2280
acttctgaaa tctctctgcc agaaagcgct caaagcagtt cttcaagcac tacctcgaca    2340
aatctacaga aaaaatcatt tactttatat agagcagata acagatcctt tgaagaaatg    2400
caaagtaaat tccctgaagg atttaaagcc tggactcctc tagacactaa gatggcaagg    2460
caatttgcta gtatctttat tggtcagaaa gatacatcta atttacctaa agaaacagtc    2520
aagaacataa gcacatgggg agcaaagcca aaactaaaag atctctcaaa ttacataaaa    2580
tataccaagg acaaatctac agtatgggtt tctactgcaa ttaatactga agcaggtgga    2640
caaagctcag gggctccact ccataaaatt gatatggatc tctacgagtt tgccattgat    2700
ggacaaaaac taaatccact accggagggt agaactaaaa acatggtacc ttcccttta    2760 ctcgacaccc cacaaataga gacatcatcc atcattgcac ttaatcatgg accggtaaat    2820
gatgcagaaa tttcatttct gacaacaatt ccgcttaaaa atgtaaaacc tcataagaga    2880
taa                                                                  2883

<210> SEQ ID NO 47
<211> LENGTH: 2850
<212> TYPE: DNA
<213> ORGANISM: Photorhabdus strain W14

<400> SEQUENCE: 47
atgaaaaaca ttgacccaaa actttatcaa catacgccca ccgttaacgt ctacgataac      60
cgtggcctga ccattcgtaa catcgacttt caccgtgacg tcgcgggagg cgatacagat     120
actcgtatta cccgccacca atatgatacc cgaggacact tgagccaaag cattgatcca     180
cggctgtatg acgccaaaca aaccaataac tcgacaaacc ccaacttcct ctggcaatac     240
aatctcaccg cgacactttt gcggacagaa agtgtcgatg ccggccgtac cgtagccctc     300
aatgatattg aaggccgtca agtgttgatt gtaaccgcaa ccggcgccat tcagacccga     360
caatatgaag ccaataccct gcccggtcgt ctattatccg taagtgaaca agccccggga     420
gaacagactc cccgcgttac tgagcatttt atttgggctg gtaatacaca ggcggagaaa     480
gatcataatc ttgccggcca gtatgtgcgc cactacgaca cagcaggagt gacgcaactg     540
gaaagcctgt cattgacaga aaacatctta tctcaatccc gtcagttatt agccgacggt     600
caggaagcag actggacagg taacgatgaa accctctggc agaccaaact caatagcgaa     660
acttacacga cacaaagcac ctttgatgct accggcgctt tgctgaccca aaccgatgca     720
aaaggcaaca tgcaacgtct ggcttacaac gtggcaggac aattacaagg tagctggctg     780
acattgaaaa accaaagtga gcaagtcatt gtcaaatccc tgacctattc cgccgcaggc     840
cagaaattgc gtgaagaaca cggtaatggc gttatcactg aatacagcta tgaaccggaa     900
actctacgat tgatccggta cacactactcgc cgtcaatcag atagcaaggt gttacaagat     960
ctacgctatg aacatgatcc tgtagggaat attattagtg tccgtaatga tgcagaagcc    1020
```

```
acccgcttct ggcgcaatca gaaaatagtc cctgaaaata cctacaccta cgattccctg    1080
tatcagctta tcagtgcaac aggacgtgag atggctaaca tcggccagca aagcaaccaa    1140
cttccttcgc caatcatccc tcttcctact gatgaaaact catataccaa ctatactcgc    1200
agctataatt acgatcgcgg cggcaatttg gttcaaatcc ggcacagttc cccgccgcc    1260 caaaataact acaccacaga tatcaccgtt tcgaatcgca gtaaccgggc agtgctgagt    1320
tcgctaacct cagacccaac acaggtggag gcactgtttg atgccggcgg acatcaaaca    1380
aaattgttac cggggcaaga gctgagttgg aatacacgag gtgaactaaa acaggtaacg    1440
ccagtcagtc gcgagagcgc cagcgatcgg gaatggtatc gttacggcaa cgacggcatg    1500
cgacggttaa aagtcagtga gcaacagact ggcaacagca cgcagcagca acgagtaact    1560
tatcttcccg atctggagct acgtacaaca caaaatggga ctactacatc agaagacctg    1620
catgctatta ccgtgggagc agcaggccac gcacaagtgc gagttctaca ctgggaaact    1680
acgccaccag ccggtatcaa taacaatcag cttcgctata gctatgataa tttgattggt    1740
tccagtcaac ttgaactgga taacgcagga caaattatca gtcaggaaga gtattatcca    1800
tttggcggca cagcattatg ggcagcaaga accaaatag aagccagcta caaaatcctc    1860
cgttactcag gtaaagaacg cgatgctacc gggctctatt attacggcta ccgctattat    1920
cagccgtggg ttggtaggtg gttaagcgcc gatccggctg gaacaatcga tggactgaat    1980
ctataccgga tggtgagaaa taatccgtca acactggttg atatttctgg gcttgcacct    2040
acgaaataca atattcccgg atttgacttt gatgtagaaa tagatgagca aaaaagatct    2100
aaattaaaac caacgttgat aagaatcaaa gatgaatttt tacattatgg tcctgtagat    2160
aagctgttag aagaaaaaaa acccggcctc aatgtaccag aggagctatt tgatagaggt    2220
ccatccgaga atggagtgtc aacattaact ttcaaaaaag acctaccgat aagttgtatt    2280
agcaacacag aatataccct tgatatctta tacaacaaac atgagactaa accattccct    2340
tacgaaaacg aagcaacagt tggcgcagat ctgggagtaa taatgtccgt ggagtttgga    2400
aataaatcaa taggtaatgc ctctgacgaa gatttaaaag aagaacatct cccattagga    2460
aaatccacaa tggataaaac agacctgcca gatttaaaac aagggctaat gatcgcggag    2520
aagataaaaa gtgaaaaggg ggcatatcct tttcattttg gtgctgcaat agctgttgta    2580
tatggtgagg ataaaaaagt agccgcttca attctgacag atttatctga acctaaaaga    2640
gacgaaggcg agtatttgca aagtacgaga aaggtaagcg caatgtttat cacaaacgtc    2700
aatgaatttc gcggccatga ttacccaaaa agtaaatata gtatcggatt agttacagct    2760
gaaaaacgtc agccagtaat aagcaaaaaa cgtgcaaacc cggaagaggc cccttcatca    2820
tccagaaata aaaaattgca tgtacattaa                                     2850
```

<210> SEQ ID NO 48
<211> LENGTH: 2817
<212> TYPE: DNA
<213> ORGANISM: Photorhabdus strain W14

<400> SEQUENCE: 48

```
atggaaaaca ttgacccaaa actttatcac catacgccta ccgtcagtgt tcacgataac      60
cgtggactag ctatccgtaa tattagtttt caccgcacta ccgcagaagc aaataccgat     120
acccgtatta cccgccatca atataatgcc ggcggatatt tgaaccaaag cattgatcct     180
cgcctgtatg acgccaaaca gactaacaac gctgtacaac cgaattttat ctggcgacat     240
aatttgaccg gcaatatcct gcgaacagag agcgtcgatg ccggtcggac gattaccctc     300
```

```
aacgatattg aaggccgccc ggtgttgacc atcaatgcag ccggtgtccg gcaaaaccat       360
cgctacgaag ataacaccct gcccggtcgc ctgctcgcta tcagcgaaca aggacaggca       420
gaagagaaaa cgaccgagcg ccttatctgg gccggcaata cgccgcaaga aaaagaccac       480
aaccttgccg gtcagtgcgt ccgccattac gataccgcag gactcactca actcaacagc       540
cttgccctga ccggcgccgt tctatcacaa tctcaacaac tgcttaccga taaccaggat       600
gccgactgga caggtgaaga ccagagcctc tggcaacaaa aactgagtag tgatgtctat       660
atcacccaaa gtaacactga tgccaccggg gctttactga cccagaccga tgccaaaggc       720
aacattcagc ggctggccta tgatgtggcc gggcagctaa aagggagttg gttaacactc       780
aaaggtcagg cggaacaggt gattatcaaa tcgctaacct actccgccgc cgggcaaaaa       840
ttacgtgaag agcacggtaa cgggattgtc actgaataca gctacgaacc ggaaacccaa       900
cggcttatcg gcattaccac tcgccgtcca tcagacgcca aggtgttgca agacctacgc       960
tatcaatatg acccagtagg caatgtcatt agtatccgta atgatgcgga agccactcgc      1020
ttttggcgca atcagaaagt agccccggag aatagctata cctacgattc cctgtatcag      1080
cttatcagcg ccaccgggcg cgagatggcc aatatcggtc agcaaagcaa ccaacttccc      1140
tctccggcgc taccttctga taacaatacc tacaccaact atactcgcac ttatacttat      1200
gaccgtggcg gcaatttgac gaaaattcag catagttcac cagccgcgca aaataactac      1260
acgacggata taacggtttc aaatcgcagc aaccgcgcgg tactcagcac attgaccgca      1320
gatccaactc aagtcgatgc cttatttgat gcgggaggcc atcaaaccag cttgttatcc      1380
ggccaagttc taacttggac accgcgaggc gaattgaaac aagccaacaa tagcgcagga      1440
aatgagtggt atcgctacga tagcaacggc atacgccagc taaagtgaa tgaacaacaa       1500 actcagaata tcccgcaaca caaagggta acttatctac cggggctgga atacgtaca        1560 acccagaaca cgccacaac aacagaagag ttacacgtta tcacactcgg taaagccggc       1620
cgcgcgcaag tccgagtatt gcattgggag agcggtaaac cagaagatat taataacaat      1680
cagcttcgtt acagctacga taatcttatt ggctccagcc aacttcaatt agatagcgac      1740
ggacaaatta tcagtgaaga agaatattat ccatttggtg gtacagcgct gtgggcggca      1800
aggaatcaaa ccgaagccag ctataaaacc attcgttatt ctggtaaaga gcggatgtt       1860 accgggctgt attattatgg ctaccgttat taccaaccgt gggcgggcag atggttaagt      1920
gcagacccgg caggaaccat tgatggactg aatttatatc gcatggtgag aaataacccg      1980
gtgacgcaat ttgatgttca gggattatca ccggccaaca gaacagaaga agcgataata      2040
aaacagggtt cctttacggg aatggaagaa gctgttttata aaaaatggc taaacctcaa      2100 actttcaaac gccaaagagc tatcgctgcc caaacagagc aagaagccca tgaatcattg      2160
accaacaacc ctagtgtaga tattagccca attaaaaaact acaccacaga tagctcacaa     2220
attaatgccg cgataaggga aaatcgtatt acgccagcag tggaaagttt agacgccaca      2280
ttatcttccc tacaagatag acaaatgagg gtaacttatc gggtgatgac ctatgtagat      2340
aattccacgc catcgccttg gcactcgcca caggaaggaa atagtattaa tgttggtgat      2400
atcgtttcgg ataacgctta tttatcaaca tcggcccatc gtggttttct gaattttgtt      2460
cacaaaaaag aaaccagtga aactcgatac gtcaagatgg cattttttaac gaatgcgggt     2520 gtcaatgtct cagcagcatc tatgtataat aatgctggcg aggagcaagt atttaaaatg      2580
gatttaaacg attcaagaaa aagccttgct gaaaaattaa aactaagagt cagtggacca      2640
caatcgggac aagcggaaat attactacct agggaaacac agttcgaagt tgtttcaatg      2700
```

```
aaacatcaag gcagagatac ctatgtatta ttgcaagata ttaaccaatc cgcagccact   2760
catagaaatg tacgtaacac ttacaccggt aatttcaaat catccagtgc aaattaa      2817
```

<210> SEQ ID NO 49
<211> LENGTH: 2538
<212> TYPE: PRT
<213> ORGANISM: Xenorhabdus nematophilus

<400> SEQUENCE: 49

Met Tyr Ser Thr Ala Val Leu Leu Asn Lys Ile Ser Pro Thr Arg Asp
1               5                   10                  15

Gly Gln Thr Met Thr Leu Ala Asp Leu Gln Tyr Leu Ser Phe Ser Glu
                20                  25                  30

Leu Arg Lys Ile Phe Asp Asp Gln Leu Ser Trp Gly Glu Ala Arg His
            35                  40                  45

Leu Tyr His Glu Thr Ile Glu Gln Lys Lys Asn Asn Arg Leu Leu Glu
        50                  55                  60

Ala Arg Ile Phe Thr Arg Ala Asn Pro Gln Leu Ser Gly Ala Ile Arg
65                  70                  75                  80

Leu Gly Ile Glu Arg Asp Ser Val Ser Arg Ser Tyr Asp Glu Met Phe
                85                  90                  95

Gly Ala Arg Ser Ser Ser Phe Val Lys Pro Gly Ser Val Ala Ser Met
            100                 105                 110

Phe Ser Pro Ala Gly Tyr Leu Thr Glu Leu Tyr Arg Glu Ala Lys Asp
        115                 120                 125

Leu His Phe Ser Ser Ser Ala Tyr His Leu Asp Asn Arg Arg Pro Asp
    130                 135                 140

Leu Ala Asp Leu Thr Leu Ser Gln Ser Asn Met Asp Thr Glu Ile Ser
145                 150                 155                 160

Thr Leu Thr Leu Ser Asn Glu Leu Leu Leu Glu His Ile Thr Arg Lys
                165                 170                 175

Thr Gly Gly Asp Ser Asp Ala Leu Met Glu Ser Leu Ser Thr Tyr Arg
            180                 185                 190

Gln Ala Ile Asp Thr Pro Tyr His Gln Pro Tyr Glu Thr Ile Arg Gln
        195                 200                 205

Val Ile Met Thr His Asp Ser Thr Leu Ser Ala Leu Ser Arg Asn Pro
    210                 215                 220

Glu Val Met Gly Gln Ala Glu Gly Ala Ser Leu Leu Ala Ile Leu Ala
225                 230                 235                 240

Asn Ile Ser Pro Glu Leu Tyr Asn Ile Leu Thr Glu Ile Thr Glu
                245                 250                 255

Lys Asn Ala Asp Ala Leu Phe Ala Gln Asn Phe Ser Glu Asn Ile Thr
            260                 265                 270

Pro Glu Asn Phe Ala Ser Gln Ser Trp Ile Ala Lys Tyr Tyr Gly Leu
        275                 280                 285

Glu Leu Ser Glu Val Gln Lys Tyr Leu Gly Met Leu Gln Asn Gly Tyr
    290                 295                 300

Ser Asp Ser Thr Ser Ala Tyr Val Asp Asn Ile Ser Thr Gly Leu Val
305                 310                 315                 320

Val Asn Asn Glu Ser Lys Leu Glu Ala Tyr Lys Ile Thr Arg Val Lys
                325                 330                 335

Thr Asp Asp Tyr Asp Lys Asn Ile Asn Tyr Phe Asp Leu Met Tyr Glu
            340                 345                 350

Gly Asn Asn Gln Phe Phe Ile Arg Ala Asn Phe Lys Val Ser Arg Glu

```
            355                 360                 365
Phe Gly Ala Thr Leu Arg Lys Asn Ala Gly Pro Ser Gly Ile Val Gly
370                 375                 380

Ser Leu Ser Gly Pro Leu Ile Ala Asn Thr Asn Phe Lys Ser Asn Tyr
385                 390                 395                 400

Leu Ser Asn Ile Ser Asp Ser Glu Tyr Lys Asn Gly Val Lys Ile Tyr
                405                 410                 415

Ala Tyr Arg Tyr Thr Ser Ser Thr Ser Ala Thr Asn Gln Gly Gly Gly
            420                 425                 430

Ile Phe Thr Phe Glu Ser Tyr Pro Leu Thr Ile Phe Ala Leu Lys Leu
            435                 440                 445

Asn Lys Ala Ile Arg Leu Cys Leu Thr Ser Gly Leu Ser Pro Asn Glu
450                 455                 460

Leu Gln Thr Ile Val Arg Ser Asp Asn Ala Gln Gly Ile Ile Asn Asp
465                 470                 475                 480

Ser Val Leu Thr Lys Val Phe Tyr Thr Leu Phe Tyr Ser His Arg Tyr
                485                 490                 495

Ala Leu Ser Phe Asp Asp Ala Gln Val Leu Asn Gly Ser Val Ile Asn
                500                 505                 510

Gln Tyr Ala Asp Asp Ser Val Ser His Phe Asn Arg Leu Phe Asn
            515                 520                 525

Thr Pro Pro Leu Lys Gly Lys Ile Phe Glu Ala Asp Gly Asn Thr Val
530                 535                 540

Ser Ile Asp Pro Asp Glu Glu Gln Ser Thr Phe Ala Arg Ser Ala Leu
545                 550                 555                 560

Met Arg Gly Leu Gly Val Asn Ser Gly Glu Leu Tyr Gln Leu Gly Lys
                565                 570                 575

Leu Ala Gly Val Leu Asp Ala Gln Asn Thr Ile Thr Leu Ser Val Phe
                580                 585                 590

Val Ile Ser Ser Leu Tyr Arg Leu Thr Leu Leu Ala Arg Val His Gln
            595                 600                 605

Leu Thr Val Asn Glu Leu Cys Met Leu Tyr Gly Leu Ser Pro Phe Asn
610                 615                 620

Gly Lys Thr Thr Ala Ser Leu Ser Ser Gly Glu Leu Pro Arg Leu Val
625                 630                 635                 640

Ile Trp Leu Tyr Gln Val Thr Gln Trp Leu Thr Glu Ala Glu Ile Thr
                645                 650                 655

Thr Glu Ala Ile Trp Leu Leu Cys Thr Pro Glu Phe Ser Gly Asn Ile
                660                 665                 670

Ser Pro Glu Ile Ser Asn Leu Leu Asn Asn Leu Arg Pro Ser Ile Ser
            675                 680                 685

Glu Asp Met Ala Gln Ser His Asn Arg Glu Leu Gln Ala Glu Ile Leu
690                 695                 700

Ala Pro Phe Ile Ala Ala Thr Leu His Leu Ala Ser Pro Asp Met Ala
705                 710                 715                 720

Arg Tyr Ile Leu Leu Trp Thr Asp Asn Leu Arg Pro Gly Gly Leu Asp
                725                 730                 735

Ile Ala Gly Phe Met Thr Leu Val Leu Lys Glu Ser Leu Asn Ala Asn
                740                 745                 750

Glu Thr Thr Gln Leu Val Gln Phe Cys His Val Met Ala Gln Leu Ser
            755                 760                 765

Leu Ser Val Gln Thr Leu Arg Leu Ser Glu Ala Glu Leu Ser Val Leu
770                 775                 780
```

```
Val Ile Ser Gly Phe Ala Val Leu Gly Ala Lys Asn Gln Pro Ala Gly
785                 790                 795                 800

Gln His Asn Ile Asp Thr Leu Phe Ser Leu Tyr Arg Phe His Gln Trp
            805                 810                 815

Ile Asn Gly Leu Gly Asn Pro Gly Ser Asp Thr Leu Asp Met Leu Arg
                820                 825                 830

Gln Gln Thr Leu Thr Ala Asp Arg Leu Ala Ser Val Met Gly Leu Asp
            835                 840                 845

Ile Ser Met Val Thr Gln Ala Met Val Ser Ala Gly Val Asn Gln Leu
        850                 855                 860

Gln Cys Trp Gln Asp Ile Asn Thr Val Leu Gln Trp Ile Asp Val Ala
865                 870                 875                 880

Ser Ala Leu His Thr Met Pro Ser Val Ile Arg Thr Leu Val Asn Ile
                885                 890                 895

Arg Tyr Val Thr Ala Leu Asn Lys Ala Glu Ser Asn Leu Pro Ser Trp
            900                 905                 910

Asp Glu Trp Gln Thr Leu Ala Glu Asn Met Glu Ala Gly Leu Ser Thr
                915                 920                 925

Gln Gln Ala Gln Thr Leu Ala Asp Tyr Thr Ala Glu Arg Leu Ser Ser
930                 935                 940

Val Leu Cys Asn Trp Phe Leu Ala Asn Ile Gln Pro Glu Gly Val Ser
945                 950                 955                 960

Leu His Ser Arg Asp Asp Leu Tyr Ser Tyr Phe Leu Ile Asp Asn Gln
                965                 970                 975

Val Ser Ser Ala Ile Lys Thr Thr Arg Leu Ala Glu Ala Ile Ala Gly
            980                 985                 990

Ile Gln Leu Tyr Ile Asn Arg Ala  Leu Asn Arg Ile Glu  Pro Asn Ala
        995                 1000                1005

Arg Ala  Asp Val Ser Thr Arg  Gln Phe Phe Thr Asp  Trp Thr Val
    1010                1015                1020

Asn Asn  Arg Tyr Ser Thr Trp  Gly Gly Val Ser Arg  Leu Val Tyr
    1025                1030                1035

Tyr Pro  Glu Asn Tyr Ile Asp  Pro Thr Gln Arg Ile  Gly Gln Thr
    1040                1045                1050

Arg Met  Met Asp Glu Leu Leu  Glu Asn Ile Ser Gln  Ser Lys Leu
    1055                1060                1065

Ser Arg  Asp Thr Val Glu Asp  Ala Phe Lys Thr Tyr  Leu Thr Arg
    1070                1075                1080

Phe Glu  Thr Val Ala Asp Leu  Lys Val Val Ser Ala  Tyr His Asp
    1085                1090                1095

Asn Val  Asn Ser Asn Thr Gly  Leu Thr Trp Phe Val  Gly Gln Thr
    1100                1105                1110

Arg Glu  Asn Leu Pro Glu Tyr  Tyr Trp Arg Asn Val  Asp Ile Ser
    1115                1120                1125

Arg Met  Gln Ala Gly Glu Leu  Ala Ala Asn Ala Trp  Lys Glu Trp
    1130                1135                1140

Thr Lys  Ile Asp Thr Ala Val  Asn Pro Tyr Lys Asp  Ala Ile Arg
    1145                1150                1155

Pro Val  Ile Phe Arg Glu Arg  Leu His Leu Ile Trp  Val Glu Lys
    1160                1165                1170

Glu Glu  Val Ala Lys Asn Gly  Thr Asp Pro Val Glu  Thr Tyr Asp
    1175                1180                1185

Arg Phe  Thr Leu Lys Leu Ala  Phe Leu Arg His Asp  Gly Ser Trp
    1190                1195                1200
```

-continued

Ser Ala Pro Trp Ser Tyr Asp Ile Thr Thr Gln Val Glu Ala Val
    1205                1210                1215

Thr Asp Lys Lys Pro Asp Thr Glu Arg Leu Ala Leu Ala Ala Ser
    1220                1225                1230

Gly Phe Gln Gly Glu Asp Thr Leu Leu Val Phe Val Tyr Lys Thr
    1235                1240                1245

Gly Lys Ser Tyr Ser Asp Phe Gly Gly Ser Asn Lys Asn Val Ala
    1250                1255                1260

Gly Met Thr Ile Tyr Gly Asp Gly Ser Phe Lys Lys Met Glu Asn
    1265                1270                1275

Thr Ala Leu Ser Arg Tyr Ser Gln Leu Lys Asn Thr Phe Asp Ile
    1280                1285                1290

Ile His Thr Gln Gly Asn Asp Leu Val Arg Lys Ala Ser Tyr Arg
    1295                1300                1305

Phe Ala Gln Asp Phe Glu Val Pro Ala Ser Leu Asn Met Gly Ser
    1310                1315                1320

Ala Ile Gly Asp Asp Ser Leu Thr Val Met Glu Asn Gly Asn Ile
    1325                1330                1335

Pro Gln Ile Thr Ser Lys Tyr Ser Ser Asp Asn Leu Ala Ile Thr
    1340                1345                1350

Leu His Asn Ala Ala Phe Thr Val Arg Tyr Asp Gly Ser Gly Asn
    1355                1360                1365

Val Ile Arg Asn Lys Gln Ile Ser Ala Met Lys Leu Thr Gly Val
    1370                1375                1380

Asp Gly Lys Ser Gln Tyr Gly Asn Ala Phe Ile Ile Ala Asn Thr
    1385                1390                1395

Val Lys His Tyr Gly Gly Tyr Ser Asp Leu Gly Gly Pro Ile Thr
    1400                1405                1410

Val Tyr Asn Lys Thr Lys Asn Tyr Ile Ala Ser Val Gln Gly His
    1415                1420                1425

Leu Met Asn Ala Asp Tyr Thr Arg Arg Leu Ile Leu Thr Pro Val
    1430                1435                1440

Glu Asn Asn Tyr Tyr Ala Arg Leu Phe Glu Phe Pro Phe Ser Pro
    1445                1450                1455

Asn Thr Ile Leu Asn Thr Val Phe Thr Val Gly Ser Asn Lys Thr
    1460                1465                1470

Ser Asp Phe Lys Lys Cys Ser Tyr Ala Val Asp Gly Asn Asn Ser
    1475                1480                1485

Gln Gly Phe Gln Ile Phe Ser Ser Tyr Gln Ser Ser Gly Trp Leu
    1490                1495                1500

Asp Ile Asp Thr Gly Ile Asn Asn Thr Asp Ile Lys Ile Thr Val
    1505                1510                1515

Met Ala Gly Ser Lys Thr His Thr Phe Thr Ala Ser Asp His Ile
    1520                1525                1530

Ala Ser Leu Pro Ala Asn Ser Phe Asp Ala Met Pro Tyr Thr Phe
    1535                1540                1545

Lys Pro Leu Glu Ile Asp Ala Ser Ser Leu Ala Phe Thr Asn Asn
    1550                1555                1560

Ile Ala Pro Leu Asp Ile Val Phe Glu Thr Lys Ala Lys Asp Gly
    1565                1570                1575

Arg Val Leu Gly Lys Ile Lys Gln Thr Leu Ser Val Lys Arg Val
    1580                1585                1590

Asn Tyr Asn Pro Glu Asp Ile Leu Phe Leu Arg Glu Thr His Ser

-continued

```
            1595                1600                1605

Gly Ala Gln Tyr Met Gln Leu Gly Val Tyr Arg Ile Arg Leu Asn
        1610                1615                1620

Thr Leu Leu Ala Ser Gln Leu Val Ser Arg Ala Asn Thr Gly Ile
        1625                1630                1635

Asp Thr Ile Leu Thr Met Glu Thr Gln Arg Leu Pro Glu Pro Pro
        1640                1645                1650

Leu Gly Glu Gly Phe Phe Ala Asn Phe Val Leu Pro Lys Tyr Asp
        1655                1660                1665

Pro Ala Glu His Gly Asp Glu Arg Trp Phe Lys Ile His Ile Gly
        1670                1675                1680

Asn Val Gly Gly Asn Thr Gly Arg Gln Pro Tyr Tyr Ser Gly Met
        1685                1690                1695

Leu Ser Asp Thr Ser Glu Thr Ser Met Thr Leu Phe Val Pro Tyr
        1700                1705                1710

Ala Glu Gly Tyr Tyr Met His Glu Gly Val Arg Leu Gly Val Gly
        1715                1720                1725

Tyr Gln Lys Ile Thr Tyr Asp Asn Thr Trp Glu Ser Ala Phe Phe
        1730                1735                1740

Tyr Phe Asp Glu Thr Lys Gln Gln Phe Val Leu Ile Asn Asp Ala
        1745                1750                1755

Asp His Asp Ser Gly Met Thr Gln Gln Gly Ile Val Lys Asn Ile
        1760                1765                1770

Lys Lys Tyr Lys Gly Phe Leu Asn Val Ser Ile Ala Thr Gly Tyr
        1775                1780                1785

Ser Ala Pro Met Asp Phe Asn Ser Ala Ser Ala Leu Tyr Tyr Trp
        1790                1795                1800

Glu Leu Phe Tyr Tyr Thr Pro Met Met Cys Phe Gln Arg Leu Leu
        1805                1810                1815

Gln Glu Lys Gln Phe Asp Glu Ala Thr Gln Trp Ile Asn Tyr Val
        1820                1825                1830

Tyr Asn Pro Ala Gly Tyr Ile Val Asn Gly Glu Ile Ala Pro Trp
        1835                1840                1845

Ile Trp Asn Cys Arg Pro Leu Glu Glu Thr Thr Ser Trp Asn Ala
        1850                1855                1860

Asn Pro Leu Asp Ala Ile Asp Pro Asp Ala Val Ala Gln Asn Asp
        1865                1870                1875

Pro Met His Tyr Lys Ile Ala Thr Phe Met Arg Leu Leu Asp Gln
        1880                1885                1890

Leu Ile Leu Arg Gly Asp Met Ala Tyr Arg Glu Leu Thr Arg Asp
        1895                1900                1905

Ala Leu Asn Glu Ala Lys Met Trp Tyr Val Arg Thr Leu Glu Leu
        1910                1915                1920

Leu Gly Asp Glu Pro Glu Asp Tyr Gly Ser Gln Gln Trp Ala Ala
        1925                1930                1935

Pro Ser Leu Ser Gly Ala Ala Ser Gln Thr Val Gln Ala Ala Tyr
        1940                1945                1950

Gln Gln Asp Leu Thr Met Leu Gly Arg Gly Gly Val Ser Lys Asn
        1955                1960                1965

Leu Arg Thr Ala Asn Ser Leu Val Gly Leu Phe Leu Pro Glu Tyr
        1970                1975                1980

Asn Pro Ala Leu Thr Asp Tyr Trp Gln Thr Leu Arg Leu Arg Leu
        1985                1990                1995
```

-continued

```
Phe Asn Leu Arg His Asn Leu Ser Ile Asp Gly Gln Pro Leu Ser
     2000                2005                2010

Leu Ala Ile Tyr Ala Glu Pro Thr Asp Pro Lys Ala Leu Leu Thr
     2015                2020                2025

Ser Met Val Gln Ala Ser Gln Gly Gly Ser Ala Val Leu Pro Gly
     2030                2035                2040

Thr Leu Ser Leu Tyr Arg Phe Pro Val Met Leu Glu Arg Thr Arg
     2045                2050                2055

Asn Leu Val Ala Gln Leu Thr Gln Phe Gly Thr Ser Leu Leu Ser
     2060                2065                2070

Met Ala Glu His Asp Asp Ala Asp Glu Leu Thr Thr Leu Leu Leu
     2075                2080                2085

Gln Gln Gly Met Glu Leu Ala Thr Gln Ser Ile Arg Ile Gln Gln
     2090                2095                2100

Arg Thr Val Asp Glu Val Asp Ala Asp Ile Ala Val Leu Ala Glu
     2105                2110                2115

Ser Arg Arg Ser Ala Gln Asn Arg Leu Glu Lys Tyr Gln Gln Leu
     2120                2125                2130

Tyr Asp Glu Asp Ile Asn His Gly Glu Gln Arg Ala Met Ser Leu
     2135                2140                2145

Leu Asp Ala Ala Ala Gly Gln Ser Leu Ala Gly Gln Val Leu Ser
     2150                2155                2160

Ile Ala Glu Gly Val Ala Asp Leu Val Pro Asn Val Phe Gly Leu
     2165                2170                2175

Ala Cys Gly Gly Ser Arg Trp Gly Ala Ala Leu Arg Ala Ser Ala
     2180                2185                2190

Ser Val Met Ser Leu Ser Ala Thr Ala Ser Gln Tyr Ser Ala Asp
     2195                2200                2205

Lys Ile Ser Arg Ser Glu Ala Tyr Arg Arg Arg Gln Glu Trp
     2210                2215                2220

Glu Ile Gln Arg Asp Asn Ala Asp Gly Glu Val Lys Gln Met Asp
     2225                2230                2235

Ala Gln Leu Glu Ser Leu Lys Ile Arg Arg Glu Ala Ala Gln Met
     2240                2245                2250

Gln Val Glu Tyr Gln Glu Thr Gln Gln Ala His Thr Gln Ala Gln
     2255                2260                2265

Leu Glu Leu Leu Gln Arg Lys Phe Thr Asn Lys Ala Leu Tyr Ser
     2270                2275                2280

Trp Met Arg Gly Lys Leu Ser Ala Ile Tyr Tyr Gln Phe Phe Asp
     2285                2290                2295

Leu Thr Gln Ser Phe Cys Leu Met Ala Gln Glu Ala Leu Arg Arg
     2300                2305                2310

Glu Leu Thr Asp Asn Gly Val Thr Phe Ile Arg Gly Gly Ala Trp
     2315                2320                2325

Asn Gly Thr Thr Ala Gly Leu Met Ala Gly Glu Thr Leu Leu Leu
     2330                2335                2340

Asn Leu Ala Glu Met Glu Lys Val Trp Leu Glu Arg Asp Glu Arg
     2345                2350                2355

Ala Leu Glu Val Thr Arg Thr Val Ser Leu Ala Gln Phe Tyr Gln
     2360                2365                2370

Ala Leu Ser Ser Asp Asn Phe Asn Leu Thr Glu Lys Leu Thr Gln
     2375                2380                2385

Phe Leu Arg Glu Gly Lys Gly Asn Val Gly Ala Ser Gly Asn Glu
     2390                2395                2400
```

-continued

```
Leu Lys Leu Ser Asn Arg Gln Ile Glu Ala Ser Val Arg Leu Ser
    2405            2410                2415

Asp Leu Lys Ile Phe Ser Asp Tyr Pro Glu Ser Leu Gly Asn Thr
    2420            2425                2430

Arg Gln Leu Lys Gln Val Ser Val Thr Leu Pro Ala Leu Val Gly
    2435            2440                2445

Pro Tyr Glu Asp Ile Arg Ala Val Leu Asn Tyr Gly Gly Ser Ile
    2450            2455                2460

Val Met Pro Arg Gly Cys Ser Ala Ile Ala Leu Ser His Gly Val
    2465            2470                2475

Asn Asp Ser Gly Gln Phe Met Leu Asp Phe Asn Asp Ser Arg Tyr
    2480            2485                2490

Leu Pro Phe Glu Gly Ile Ser Val Asn Asp Ser Gly Ser Leu Thr
    2495            2500                2505

Leu Ser Phe Pro Asp Ala Thr Asp Arg Gln Lys Ala Leu Leu Glu
    2510            2515                2520

Ser Leu Ser Asp Ile Ile Leu His Ile Arg Tyr Thr Ile Arg Ser
    2525            2530                2535
```

PESTICIDALLY ACTIVE PROTEINS AND POLYNUCLEOTIDES OBTAINABLE FROM *PAENIBACILLUS* SPECIES

CROSS-REFERENCE TO RELATED APPLICATIONS

This application is a divisional of U.S. Ser. No. 10/609,113, filed Jun. 27, 2003 now abandoned, which claims the benefit of provisional application Ser. No. 60/392,633, filed Jun. 28, 2002, and to provisional application Ser. No. 60/441,647, filed Jan. 21, 2003.

The Sequence Listing for this application is provided in duplicate and labeled "seq-list-Copy-1" and "seq-list-Copy-2." Copy 1 and Copy 2 each contain the same information, was created on Jul. 10, 2007, and is 234 KB. The entire content of each document is incorporated herein by reference in its entirety.

BACKGROUND OF THE INVENTION

Insects and other pests cost farmers billions of dollars annually in crop losses and in the expense of keeping these pests under control. The losses caused by insect pests in agricultural production environments include decreases in crop yield, reduced crop quality, and increased harvesting costs. Insect pests are also a burden to vegetable and fruit growers, to producers of ornamental flowers, and to home gardeners and homeowners.

Cultivation methods, such as crop rotation and the application of high levels of nitrogen fertilizers, have partially addressed problems caused by agricultural pests. However, economic demands on the utilization of farmland restrict the use of crop rotation. In addition, overwintering traits of some insects are disrupting crop rotations in some areas.

Thus, synthetic chemical insecticides are relied upon most heavily to achieve a sufficient level of control. However, the use of synthetic chemical insecticides can have several drawbacks. For example, the use of some of these chemicals can adversely affect many beneficial insects. Target insects have also developed resistance to some chemical pesticides. This has been partially alleviated by various resistance management strategies, but there is an increasing need for alternative pest control agents. Furthermore, very high populations of larvae, heavy rains, and improper calibration of insecticide application equipment can result in poor control. The improper use of insecticides raises environmental concerns such as contamination of soil and of both surface and underground water supplies. Residues can also remain on treated fruits, vegetables, and on other treated plants. Working with some insecticides can also pose hazards to the persons applying them. Therefore, synthetic chemical pesticides are being increasingly scrutinized for their potential toxic environmental consequences. Stringent new restrictions on the use of pesticides and the elimination of some effective pesticides from the market place could limit economical and effective options for controlling damaging and costly pests.

Because of the problems associated with the use of synthetic chemical pesticides, there exists a clear need to limit the use of these agents and a need to identify alternative control agents. The replacement of synthetic chemical pesticides, or combination of these agents with biological pesticides, could reduce the levels of toxic chemicals in the environment.

Some biological pesticidal agents that are now being used with some success are derived from the soil microbe *Bacillus thuringiensis* (B.t.). The soil microbe *Bacillus thuringiensis* (B.t.) is a Gram-positive, spore-forming bacterium. Most strains of B.t. do not exhibit pesticidal activity. Some B.t. strains produce, and can be characterized by, parasporal crystalline protein inclusions. These inclusions often appear microscopically as distinctively shaped crystals. Some B.t. proteins are highly toxic to pests, such as insects, and are specific in their toxic activity. Certain insecticidal B.t. proteins are associated with the inclusions. These "δ-endotoxins" are different from exotoxins, which have a non-specific host range. Other species of *Bacillus* also produce pesticidal proteins.

Certain *Bacillus* toxin genes have been isolated and sequenced, and recombinant DNA-based products have been produced and approved for use. In addition, with the use of genetic engineering techniques, various approaches for delivering these toxins to agricultural environments are being perfected. These include the use of plants genetically engineered with toxin genes for insect resistance and the use of stabilized intact microbial cells as toxin delivery vehicles. Thus, isolated *Bacillus* toxin genes are becoming commercially valuable.

Commercial use of B.t. pesticides was initially restricted to targeting a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

More recently, new subspecies of B.t. have been identified, and genes responsible for active δ-endotoxin proteins have been isolated. Höfte and Whiteley classified B.t. crystal protein genes into four major classes (Höfte, H., H. R. Whiteley [1989] *Microbiological Reviews* 52(2):242-255). The classes were CryI (*Lepidoptera*-specific), CryII (Lepidoptera- and Diptera-specific), CryIII (Coleoptera-specific), and CryIV (Diptera-specific). The discovery of strains specifically toxic to other pests has been reported. For example, CryV and CryVI were proposed to designate a class of toxin genes that are nematode-specific.

The Lepidopteran-specific CryI crystal proteins, in their natural state, are approximately 130- to 140-kDa proteins, which accumulate in bipyramidal crystalline inclusions during the sporulation of *B. thuringiensis*. These proteins are protoxins which solubilize in the alkaline environment of the insect midgut and are proteolytically converted by crystal-associated or larval-midgut proteases into a toxic core fragment of 60 to 70 kDa. This activation can also be carried out in vitro with a variety of proteases. The toxic domain is localized in the N-terminal half of the protoxin. This was demonstrated for CryIA(b) and CryIC proteins through N-terminal amino acid sequencing of the trypsin-activated toxin. Höfte et al. 1989. Cleavage occurs on the C-terminal end of a conserved region called "Block 5," thus forming the C-terminus of the core toxin. A short, N-terminal protoxin segment can also be processed off. The N-terminal cleavage site is also highly conserved for CryIA and CryID proteins, suggesting that for these proteins, the N terminus of the toxic fragment is localized at the same position. CryIB, however, is different from the other CryI proteins in this region. It was not known whether this protein is also processed at the N terminus. Höfte et al. 1989.

Deletion analysis of several cryI genes further confirmed that the 3' half of the protoxin is not required for toxic activity. One of the shortest reported toxic fragments was localized between codons 29 and 607 for CryIAb. Further removal of four codons from the 3' end or eight codons from the 5' end completely abolished the toxic activity of the gene product. Similar observations were made for the cryIA(a) and cryIA(c) genes. Höfte et al. 1989.

The cryII genes encode 65-kDa proteins which form cuboidal inclusions in strains of several subspecies. These crystal proteins were previously designated "P2" proteins, as opposed to the 130-kDa P1 crystal proteins present in the same strains. Höfte et al. 1989.

A cryIIA gene was cloned from *B. thuringiensis* subsp. *kurstaki* HD-263 and expressed in *Bacillus megaterium*. Cells producing the CryIIA protein were toxic for the lepidopteran species *Heliothis virescens* and *Lymantria dispar* as well as for larvae of the dipteran *Aedes aegypti*. Widner and Whitely (1989, *J. Bacteriol.* 171:965-974) cloned two related genes (cryIIA and cryIIB) from *B. thuringiensis* subsp. *kurstaki* HD-1. Both genes encode proteins of 633 amino acids with a predicted molecular mass of 71 kDa (slightly larger than the apparent molecular mass determined for the P2 proteins produced in *B. thuringiensis*). Although the CryIIA and CryIIB proteins are highly homologous (87% amino acid identity), they differ in their insecticidal spectra. CryIIA is active against both a lepidopteran (*Manduca sexta*) and a dipteran (*Aedes aegypti*) species, whereas cryIIB is toxic only to the lepidopteran insect. Höfte et al. 1989. The CryII toxins, as a group, tend to be relatively more conserved at the sequence level (>80% identical) than other groups. In contrast, there are many CryI toxins, for example, including some that are less than 60% identical.

The 1989 nomenclature and classification scheme of Höfte and Whiteley for crystal proteins was based on both the deduced amino acid sequence and the host range of the toxin. That system was adapted to cover 14 different types of toxin genes which were divided into five major classes. The 1989 nomenclature scheme became unworkable as more and more genes were discovered that encoded proteins with varying spectrums of pesticidal activity. Thus, a revised nomenclature scheme was adopted, which is based solely on amino acid identity (Crickmore et al., 1998, *Microbiology and Molecular Biology Reviews* 62:807-813). The mnemonic "cry" has been retained for all of the toxin genes except cytA and cytB, which remain a separate class. Roman numerals have been exchanged for Arabic numerals in the primary rank, and the parentheses in the tertiary rank have been removed. Many of the original names have been retained, with the noted exceptions, although a number have been reclassified. There are now at least 37 primary classes of Cry proteins, and two primary classes of cyt toxins. Other types of toxins, such as those of WO 98/18932 and WO 97/40162, have also been discovered from *B. thuringiensis*.

There are some obstacles to the successful agricultural use of *Bacillus* (and other biological) pesticidal proteins. Certain insects can be refractory to the effects of *Bacillus* toxins. Insects such as boll weevils, black cutworm, and *Helicoverpa zea*, as well as adult insects of most species, heretofore have demonstrated no significant sensitivity to many B.t. δ-endotoxins.

Another potential obstacle is the development of resistance to B.t. toxins by insects. B.t. protein toxins were initially formulated as sprayable insect control agents. A more recent application of B.t. technology has been to isolate and transform plants with genes that encode these toxins. Transgenic plants subsequently produce the toxins, thereby providing insect control. See U.S. Pat. Nos. 5,380,831; 5,567,600; and 5,567,862 to Mycogen Corporation. Transgenic B.t. plants are quite efficacious, and usage is predicted to be high in some crops and areas. This has caused some concern that resistance management issues may arise more quickly than with traditional sprayable applications. While a number of insects have been selected for resistance to B.t. toxins in the laboratory, only the diamondback moth (*Plutella xylostella*) has demonstrated resistance in a field setting (Ferre, J. and Van Rie, J., *Annu. Rev. Entomol.* 47:501-533, 2002).

Resistance management strategies in B.t. transgene plant technology have become of great interest (for example, as in a natural bacterium, multiple diverse toxins can be exposed on the same plant, thereby greatly reducing the chance that an insect that might be resistant to one toxin would survive to spread the resistance). Several strategies have been suggested for preserving the ability to effectively use *B. thuringiensis* toxins. These strategies include high dose with refuge, and alternation with, or co-deployment of, different toxins (McGaughey et al. (1998), "B.t. Resistance Management," *Nature Biotechnol* 16:144-146).

Thus, there remains a great need for developing additional genes that can be expressed in plants in order to effectively control various insects. In addition to continually trying to discover new B.t. toxins, it would be quite desirable to discover other bacterial sources (distinct from B.t.) that produce toxins that could be used in transgenic plant strategies, or that could be combined with B.t.s to produce insect-controlling transgenic plants.

The recent efforts to clone insecticidal toxin genes from the *Photorhabdus/Xenorhabdus* group of bacteria present potential alternatives to toxins derived from *B. thuringiensis*. It has been known in the art that bacteria of the genus *Xenorhabdus* are symbiotically associated with the *Steinernema* nematode. Unfortunately, as reported in a number of articles, the bacteria only had pesticidal activity when injected into insect larvae and did not exhibit biological activity when delivered orally.

It has been difficult to effectively exploit the insecticidal properties of the nematode or its bacterial symbiont. Thus, it would be quite desirable to discover proteinaceous agents from *Xenorhabdus* bacteria that have oral activity so that the products produced therefrom could be formulated as a sprayable insecticide, or the bacterial genes encoding said proteinaceous agents could be isolated and used in the production of transgenic plants. WO 95/00647 relates to the use of *Xenorhabdus* protein toxin to control insects, but it does not recognize orally active toxins. WO 98/08388 relates to orally administered pesticidal agents from *Xenorhabdus*. U.S. Pat. No. 6,048,838 relates to protein toxins/toxin complexes, having oral activity, obtainable from *Xenorhabdus* species and strains.

*Photorhabdus* and *Xenorhabdus* spp. are Gram-negative bacteria that entomopathogenically and symbiotically associate with soil nematodes. These bacteria are found in the gut of entomopathogenic nematodes that invade and kill insects. When the nematode invades an insect host, the bacteria are released into the insect haemocoel (the open circulatory system), and both the bacteria and the nematode undergo multiple rounds of replication; the insect host typically dies. These bacteria can be cultured away from their nematode hosts. For a more detailed discussion of these bacteria, see Forst and Nealson, 60 *Microbiol. Rev.* 1 (1996), pp. 21-43.

The genus *Xenorhabdus* is taxonomically defined as a member of the Family Enterobacteriaceae, although it has certain traits atypical of this family. For example, strains of this genus are typically nitrate reduction negative and catalase negative. *Xenorhabdus* has only recently been subdivided to create a second genus, *Photorhabdus*, which is comprised of the single species *Photorhabdus luminescens* (previously *Xenorhabdus luminescens*) (Boemare et al., 1993 *Int. J. Syst. Bacteriol.* 43, 249-255). This differentiation is based on several distinguishing characteristics easily identifiable by the skilled artisan. These differences include the following: DNA-DNA characterization studies; phenotypic presence (*Photorhabdus*) or absence (*Xenorhabdus*) of catalase activity; presence (*Photorhabdus*) or absence (*Xenorhabdus*) of bioluminescence; the Family of the nematode host in that *Xenorhabdus* is found in Steinernematidae and *Photorhabdus* is found in Heterorhabditidae); as well as comparative, cellular fatty-acid analyses (Janse et al. 1990, *Lett. Appl. Microbiol.* 10, 131-135; Suzuki et al. 1990, *J. Gen. Appl. Microbiol.*, 36, 393-401). In addition, recent molecular studies focused on sequence (Rainey et al. 1995, *Int. J. Syst. Bacteriol.*, 45, 379-381) and restriction analysis (Brunel et al., 1997, *App. Environ. Micro.*, 63, 574-580) of 16S rRNA genes also support the separation of these two genera.

The expected traits for *Xenorhabdus* are the following: Gram stain negative rods, white to yellow/brown colony pigmentation, presence of inclusion bodies, absence of catalase, inability to reduce nitrate, absence of bioluminescence, ability to uptake dye from medium, positive gelatin hydrolysis, growth on Enterobacteriaceae selective media, growth temperature below 37° C., survival under anaerobic conditions, and motility.

Currently, the bacterial genus *Xenorhabdus* is comprised of four recognized species, *Xenorhabdus nematophilus*, *Xenorhabdus poinarii*, *Xenorhabdus bovienii* and *Xenorhabdus beddingii* (Brunel et al., 1997, *App. Environ. Micro.*, 63, 574-580). A variety of related strains have been described in the literature (e.g., Akhurst and Boemare 1988 *J. Gen. Microbiol.*, 134, 1835-1845; Boemare et al. 1993 *Int. J. Syst. Bacteriol.* 43, pp. 249-255; Putz et al. 1990, *Appl. Environ. Microbiol.*, 56, 181-186, Brunel et al., 1997, *App. Environ. Micro.*, 63, 574-580, Rainey et al. 1995, *Int. J. Syst. Bacteriol.*, 45, 379-381).

*Xenorhabdus* and *Photorhabdus* bacteria secrete a wide variety of substances into the culture medium; these secretions include lipases, proteases, antibiotics and lipopolysaccharides. Purification of different protease fractions has clearly demonstrated that they are not involved in the oral toxic activity of *P. luminescens* culture medium (which has been subsequently determined to reside with the Tc proteins only). Several of these substances have previously been implicated in insect toxicity but until recently no insecticidal genes had been cloned. However, protease purification and separation will also facilitate an examination of their putative role in, for example, inhibiting antibacterial proteins such as cecropin. R. H. ffrench-Constant and Bowen, *Current Opinions in Microbiology*, 1999, 12:284-288. See R. H. ffrench-Constant et al. 66 *AEM* No. 8, pp. 3310-3329 (August 2000), for a review of various factors involved in *Photorhabdus* virulence of insects.

There has been substantial progress in the cloning of genes encoding insecticidal toxins from both *Photorhabdus luminescens* and *Xenorhabdus nematophilus*. Toxin-complex encoding genes from *P. luminescens* were examined first. See, e.g., WO 98/08932. "Parallel" genes were more recently cloned from *X. nematophilus*. Morgan et al., *Applied and Environmental Microbiology* 2001, 67:2062-69.

Four different toxin complexes (TCs)—Tca, Tcb, Tcc and Tcd—have been identified in *Photorhabdus* spp. Each of these toxin complexes resolves as either a single or dimeric species on a native agarose gel but resolution on a denaturing gel reveals that each complex consists of a range of species between 25-280 kDa. The ORFs that encode the TCs from *Photorhabdus*, together with protease cleavage sites (vertical arrows), are illustrated in FIG. 1. See also R. H. ffrench-Constant and Bowen, 57 *Cell. Mol. Life Sci.* 828-833 (2000).

Genomic libraries of *P. luminescens* were screened with DNA probes and with monoclonal and/or polyclonal antibodies raised against the toxins. Four tc loci were cloned: tca, tcb, tcc and tcd. The tca locus is a putative operon of three open reading frames (ORFs), tcaA, tcaB, and tcaC transcribed from the same DNA strand, with a smaller terminal ORF (tcaZ) transcribed in the opposite direction. The tcc locus also is comprised of three ORFs putatively transcribed in the same direction (tccA, tccB, and tccC). The tcb locus is a single large ORF (tcbA), and the tcd locus is composed of two ORFs (tcdA and tcdB); tcbA and tcdA, each about 7.5 kb, encode large insect toxins. TcdB has some homology to TcaC. Many of these gene products were determined to be cleaved by proteases. For example, both TcbA and TcdA are cleaved into three fragments termed i, ii and iii (e.g. TcbAi, TcbAii and TcbAiii). Products of the tca and tcc ORFs are also cleaved. See FIG. 1. See also R. H. ffrench-Constant and D. J. Bowen, *Current Opinions in Microbiology*, 1999, 12:284-288.

Bioassays of the Tca toxin complexes revealed them to be highly toxic to first instar tomato hornworms (*Manduca sexta*) when given orally ($LD_{50}$ of 875 ng per square centimeter of artificial diet). R. H. ffrench-Constant and Bowen 1999. Feeding was inhibited at Tca doses as low as 40 ng/cm². Given the high predicted molecular weight of Tca, on a molar basis, *P. luminescens* toxins are highly active and relatively few molecules appear to be necessary to exert a toxic effect. R. H. ffrench-Constant and Bowen, *Current Opinions in Microbiology*, 1999, 12:284-288.

None of the four loci showed overall similarity to any sequences of known function in GenBank. Regions of sequence similarity raised some suggestion that these proteins (TcaC and TccA) may overcome insect immunity by attacking insect hemocytes. R. H. ffrench-Constant and Bowen, *Current Opinions in Microbiology*, 1999, 12:284-288.

TcaB, TcbA, and TcdA all show amino acid conservation (50% identity), compared with each other, immediately around their predicted protease cleavage sites. This conservation between three different TC proteins suggests that they may all be processed by the same or similar proteases. TcbA and TcdA also share ~50% identity overall, as well as a similar predicted pattern of both carboxy- and amino-terminal cleavage. It was postulated that these proteins might thus be homologs of one another. Furthermore, the similar, large size of TcbA and TcdA, and also the fact that both toxins appear to act on the gut of the insect, may suggest similar modes of action. R. H. ffrench-Constant and Bowen, *Current Opinions in Microbiology*, 1999, 12:284-288.

Deletion/knock-out studies suggest that products of the tca and tcd loci account for the majority of oral toxicity to lepidopterans. Deletion of either of the tca or tcd genes greatly reduced oral activity against *Manduca sexta*. That is, products of the tca and tcd loci are oral lepidopteran toxins on their own; their combined effect contributed most of the secreted oral activity. R. H. ffrench-Constant and D. J. Bowen, 57 *Cell. Mol. Life. Sci.* 831 (2000). Interestingly, deletion of either of the tcb or tcc loci alone also reduces mortality, suggesting that there may be complex interactions among the different gene products. Thus, products of the tca locus may enhance the toxicity of tcd products. Alternatively, tcd products may modulate the toxicity of tca products and possibly other complexes. Noting that the above relates to oral activity against a single insect species, tcb or tcc loci may produce toxins that are more active against other groups of insects (or active via injection directly into the insect haemocoel—the normal route of delivery when secreted by the bacteria in vivo). R. H. ffrench-Constant and Bowen, *Current Opinions in Microbiology*, 1999, 12:284-288.

WO 01/11029 discloses nucleotide sequences that encode TcdA and TcbA and have base compositions that have been altered from that of the native genes to make them more similar to plant genes. Also disclosed are transgenic plants that express Toxin A and Toxin B.

Of the separate toxins isolated from *Photorhabdus luminescens* (W-14), those designated Toxin A and Toxin B have been the subject of focused investigation for their activity against target insect species of interest (e.g., corn rootworm). Toxin A is comprised of two different subunits. The native gene tcdA encodes protoxin TcdA. As determined by mass spectrometry, TcdA is processed by one or more proteases to provide Toxin A. More specifically, TcdA is an approximately 282.9 kDa protein (2516 aa) that is processed to provide TcdAi (the first 88 amino acids), TcdAii (the next 1849 aa; an approximately 208.2 kDa protein encoded by nucleotides 265-5811 of tcdA), and TcdAiii, an approximately 63.5 kDa (579 aa) protein (encoded by nucleotides 5812-7551 of tcdA). TcdAii and TcdAiii appear to assemble into a dimer (perhaps aided by TcdAi), and the dimers assemble into a tetramer of four dimers. Toxin B is similarly derived from TcbA.

While the exact molecular interactions of the TC proteins with each other, and their mechanism(s) of action, are not currently understood, it is known, for example, that the Tca toxin complex of *Photorhabdus* is toxic to *Manduca sexta*. In addition, some TC proteins are known to have "stand alone" insecticidal activity, while other TC proteins are known to potentiate or enhance the activity of the stand-alone toxins. It is known that the TcdA protein is active, alone, against *Manduca sexta*, but that TcdB and TccC, together, can be used to enhance the activity of TcdA. Waterfield, N. et al., *Appl. Environ. Microbiol.* 2001, 67:5017-5024. TcbA (there is only one Tcb protein) is another stand-alone toxin from *Photorhabdus*. The activity of this toxin (TcbA) can also be enhanced by TcdB together with TccC-like proteins.

U.S. Patent Application 20020078478 provides nucleotide sequences for two potentiator genes, tcdB2 and tccC2, from the tcd genomic region of *Photorhabdus luminescens* W-14. It is shown therein that coexpression of tcdB and tccC1 with tcdA results in enhanced levels of oral insect toxicity compared to that obtained when tcdA is expressed alone. Coexpression of tcdB and tccC1 with tcdA or tcbA provide enhanced oral insect activity.

As indicated in the chart below, TccA has some level of homology with the N terminus of TcdA, and TccB has some level of homology with the C terminus of TcdA. TccA and TccB are much less active on certain test insects than is TcdA. TccA and TccB from *Photorhabdus* strain W-14 are called "Toxin D." "Toxin A" (TcdA), "Toxin B" (TcbA), and "Toxin C" (TcaA and TcaB) are also indicated below. Furthermore, TcaA has some level of homology with TccA and likewise with the N terminus of TcdA. Still further, TcaB has some level of homology with TccB and likewise with the N terminus of TcdA. TccA and TcaA are of a similar size, as are TccB and TcaB. TcdB has a significant level of similarity (both in sequence and size) to TcaC.

| *Photorhabdus* | *Photorhabdus* strain W14 nomenclature | Some homology to: |
|---|---|---|
| TcaA | Toxin C | TccA |
| TcaB | | TccB |
| TcaC | | TcdB |

-continued

| *Photorhabdus* | *Photorhabdus* strain W14 nomenclature | Some homology to: |
|---|---|---|
| TcbA | Toxin B | |
| TccA | Toxin D | TcdA N terminus |
| TccB | | TcdA C terminus |
| TccC | | |
| TcdA | Toxin A | TccA + TccB |
| TcdB | | TcaC |

The insect midgut epithelium contains both columnar (structural) and goblet (secretory) cells. Ingestion of tca products by *M. sexta* leads to apical swelling and blebbing of large cytoplasmic vesicles by the columnar cells, leading to the eventual extrusion of cell nuclei in vesicles into the gut lumen. Goblet cells are also apparently affected in the same fashion. Products of tca act on the insect midgut following either oral delivery or injection. R. H. ffrench-Constant and D. J. Bowen, *Current Opinions in Microbiology,* 1999, 12:284-288. Purified tca products have shown oral toxicity against *Manduca sexta* ($LD_{50}$ of 875 ng/$cm^2$). R. H. ffrench-Constant and D. J. Bowen, 57 *Cell. Mol. Life Sci.* 828-833 (2000).

WO 99/42589 and U.S. Pat. No. 6,281,413 disclose TC-like ORFs from *Photorhabdus luminescens*. WO 00/30453 and WO 00/42855 disclose TC-like proteins from *Xenorhabdus*. WO 99/03328 and WO 99/54472 (and U.S. Pat. Nos. 6,174,860 and 6,277,823) relate to other toxins from *Xenorhabdus* and *Photorhabdus.*

Relatively recent cloning efforts in *Xenorhabdus nematophilus* also appear to have identified novel insecticidal toxin genes with homology to the *P. luminescens* tc loci. See, e.g., WO 98/08388 and Morgan et al., *Applied and Environmental Microbiology* 2001, 67:2062-69. In R. H. ffrench-Constant and D. J. Bowen, *Current Opinions in Microbiology,* 1999, 12:284-288, cosmid clones were screened directly for oral toxicity to another lepidopteran, *Pieris brassicae*. One orally toxic cosmid clone was sequenced. Analysis of the sequence in that cosmid suggested that there are five different ORF's with similarity to *Photorhabdus* tc genes; orf2 and orf5 both have some level of sequence relatedness to both tcbA and tcdA, whereas orf1 is similar to tccB, orf3 is similar to tccC and orf4 is similar to tcaC. Importantly, a number of these predicted ORFs also share the putative cleavage site documented in *P. luminescens*, suggesting that active toxins may also be protealytically processed.

There are five typical *Xenorhabdus* TC proteins: XptA1, XptA2, XptB1, XptC1, and XptD1. XptA1 is a "stand-alone" toxin. XptA2 is another TC protein from *Xenorhabdus* that has stand-alone toxin activity. See GENBANK Accession No. AJ308438 for sequences from *Xenorhabdus nematophilus*. XptB1 and XptC1 are the *Xenorhabdus* potentiators that can enhance the activity of either (or both) of the XptA toxins. XptD1 has some level of homology with TccB. XptC1 has some level of similarity to TcaC. The XptA2 protein of *Xenorhabdus* has some degree of similarity to the TcdA protein. XptB1 has some level of similarity to TccC.

The finding of somewhat similar, toxin-encoding loci in these two different bacteria is interesting in terms of the possible origins of these virulence genes. The *X. nematophilus* cosmid also appears to contain transposase-like sequences whose presence may suggest that these loci can be transferred horizontally between different strains or species of bacteria. A range of such transfer events may also explain the apparently different genomic organization of the tc operons in the two different bacteria. Further, only a subset of *X. nematophilus* and *P. luminescens* strains appear toxic to *M. sexta*, suggesting either that different strains lack the tc genes or that they carry a different tc gene compliment. Detailed analysis of both a strain and toxin phylogeny within, and between, these bacterial species should help clarify the likely origin of the toxin genes and how they are maintained in different bacterial populations. R. H. ffrench-Constant and Bowen, *Current Opinions in Microbiology,* 1999, 12:284-288.

TC proteins and genes have more recently been described from other insect-associated bacteria such as *Serratia entomophila*, an insect pathogen. Waterfield et al., *TRENDS in Microbiology*, Vol. 9, No. 4, April 2001.

In summary, toxin complex proteins from *P. luminescens* and *X. nematophilus* appear to have little homology to previously identified bacterial toxins and should provide useful alternatives to toxins derived from *B. thuringiensis*. Although they have similar toxic effects on the insect midgut to other orally active toxins, their precise mode of action remains obscure. Future work could clarify their mechanism of action.

Although some *Xenorhabdus* TC proteins were found to "correspond" (have a similar function and some level of sequence homology) to some of the *Photorhabdus* TC proteins, a given *Photorhabdus* protein shares only about 40% sequence identity with the "corresponding" *Xenorhabdus* protein. This is illustrated below for four "stand-alone" toxins:

| | Identity to P.l. W-14 TcbA | Identity to P.l. W-14 TcdA |
|---|---|---|
| Xwi XptA1 | 44% | 46% |
| Xwi XptA2 | 41% | 41% |

(For a more complete review, see, e.g., Morgan et al., "Sequence Analysis of Insecticidal Genes from *Xenorhabdus nematophiles* PMFI296," Vol. 67, *Applied and Environmental Microbiology*, May 2001, pp. 2062-2069.)

Bacteria of the genus *Paenibacillus* are distinguishable from other bacteria by distinctive rRNA and phenotypic characteristics (C. Ash et al. (1993), "Molecular identification of rRNA group 3 bacilli (Ash, Farrow, Wallbanks and Collins) using a PCR probe test: Proposal for the creation of a new genus *Paenibacillus,*" *Antonie Van Leeuwenhoek* 64:253-260). Comparative 16S rRNA sequence analysis demonstrated that the genus *Bacillus* consisted of at least five phyletic lines. Ribosomal RNA group 3 bacilli (of Ash, Farrow, Wallbanks, and Collins (1991), comprising *Bacillus polymyxa* and close relatives), is phylogenetically so removed from *Bacillus subtilis* (the type species of the genus and other aerobic, endospore-forming bacilli) that they were reclassified as a new genus, *Paenibacillus.*

Some species in this genus were known to be pathogenic to honeybees (*Paenibacillus Larvae*) and scarab beetle grubs (*P. popilliae* and *P. lentimorbus*). Some other *Paenibacillus* species that have been found to be associated with honeybees, but they are non-pathogens. At least 18 additional species are known in this genus, including *P. thiaminolyticus*; they have no known insect association (Shida et al., 1997; Pettersson et al., 1999). Scarabs (coleopterans) are serious pests of turf nurseries, and food crops throughout North America, and are of quarantine concern. See U.S. Department of Agriculture, Agricultural Research Service website.

*P. larvae, P. popilliae*, and *P. lentimorbus* are considered obligate insect pathogens involved with milky disease of scarab beetles (D. P. Stahly et al. (1992), "The genus *Bacillus*: insect pathogens," p. 1697-1745, In A. Balows et al., ed., *The Procaryotes,* $2^{nd}$ Ed., Vol. 2, Springer-Verlag, New York, N.Y.). These three *Paenibacillus* species are characteristically slow-growing, fastidious organisms that cause disease by an invasive process in which the bacteria cross the midgut and proliferate to high numbers in the hemolymph and other tissues. For all three species, some general indications of protein involvement in insect pathogenicity have been proposed; however, no specific role for a specific protein has been demonstrated. Stahly et al. concluded for *P. larvae* that a question of the involvement of a toxin is an open one, and that the precise cause of death in milky disease (of beetles) is not understood.

A beetle (coleopteran) toxin, Cry18, has been identified in strains of *P. popilliae* and *P. lentimorbus*. Cry18 has about 40% identity to Cry2 proteins (Zhang et al., 1997; Harrison et al., 2000). While Zhang et al. (1997) speculate that Cry18 attacks the midgut to facilitate entry of vegetative cells to the hemocoel, Harrison et al. note that there is no direct evidence for this role and further state that "the role, if any, of the paraspore protein in milky disease is unknown." J. Zhang et al. (1997), "Cloning and Analysis of the First cry Gene from *Bacillus popilliae," J. Bacteriol.* 179:4336-4341; H. Harrison et al. (2000), "*Paenibacillus* Associated with Milky Disease in Central and South American Scarabs," *J. Invertebr. Pathol.* 76(3):169-175.

Stahly et al., Zhang et al., and Harrison et al. all point to the contrast in evidence for the role of crystal proteins of *B. thuringiensis* in intoxication of insects (where the high frequency of insect symptoms can be explained by the properties of the specific crystal proteins), versus the case of *Paenibacillus* and milky disease (where there is no such tie to the effects of a specific toxin).

Thus, while some species of *Paenibacillus* were known to be pathogenic to certain coleopterans and some associated with honeybees, no strain of *Paenibacillus* was heretofore known to be toxic to lepidopterans. Likewise, TC proteins and lepidopteran-toxic Cry proteins have never been reported in *Paenibacillus.*

BRIEF SUMMARY OF THE INVENTION

This is the first known disclosure of *Paenibacillus* protein toxins having activity against lepidopteran pests. Some species of *Paenibacillus* were known to be insecticidal, but they had activity against grubs/beetles/coleopterans. There have been no known reports of a *Paenibacillus* species or strain having toxicity to lepidopterans. Thus, the subject invention relates generally to *Paenibacillus* species that have activity against lepidopterans, and to screening *Paenibacillus* spp., proteins therefrom, and libraries of clones therefrom for activity against lepidopterans.

More specifically, the subject invention initially stemmed from a discovery of a novel strain of *Paenibacillus* referred to herein as DAS1529. This was a surprising discovery for a variety of reasons. This strain produces a unique, lepidopteran-toxic Cry protein. This strain, as well as DB482, produce unique, toxin complex (TC)-like proteins (having some similarity to *Xenorhabdus/Photorhabdus* TCs). *Paenibacillus* isolate DB482 and toxins obtainable therefrom are highly preferred, and all are within the scope of the subject invention.

This is the first known report of *Paenibacillus* having TC-like proteins. Thus, the subject invention relates to methods of screening *Paenibacillus* spp. for TC-like genes and proteins. *Paenibacillus* TC proteins of the subject invention are shown herein to be useful to enhance or potentiate the activity of a "stand-alone" *Xenorhabdus* toxin protein, for example. TC-like genes identified herein were not heretofore known to exist in the genus *Paenibacillus*. This discovery broadens the scope of organisms (bacterial genera) in which TC-like genes have been found. Thus, the subject invention generally relates to TC-like proteins obtainable from *Paenibacillus* species, to methods of screening *Paenibacillus* species for such proteins, and the like. One example is *Paenibacillus apairius*, which was also found to produce TC-like proteins.

While the subject TC-like proteins have some sequence relatedness to, and characteristics in common with, TC proteins of *Xenorhabdus* and *Photorhabdus*, the sequences of the subject TC-like proteins are very different from previously known TC proteins. Thus, the subject application provides new classes of TC-like proteins and genes that encode these proteins, which are obtainable from bacteria in the genera *Paenibacillus*, *Photorhabdus*, *Xenorhabdus*, and the like.

Another surprising feature of the DAS1529 strain is that it produces a unique, B.t.-like Cry protein that is toxic to lepidopterans. The subject Cry toxin is compressed/short and appears to lack a typical protoxin portion in its wild-type state. Thus, the subject invention generally relates to screening *Paenibacillus* isolates for lepidopteran-toxic Cry proteins. The subject invention also relates to methods of screening *Paenibacillus* spp. and *B. thuringiensis*, for example, for this new class of Cry genes and proteins.

The DAS1529 strain is the first known example of a natural bacterium that produces both a Cry-like toxin and TC-like proteins. Further surprising is that this is the first known example of a cry toxin gene being closely associated with (in genetic proximity to) TC protein genes. These pioneering observations have broad implications and thus enable one skilled in the art to screen appropriate species of bacteria for these types of unique operons and for these types of further components of known operons. Such techniques are within the scope of the subject invention.

A further aspect of the subject invention stems from the surprising discovery that the DAS1529 strain also produces a soluble insect toxin that was found to be very similar to a thiaminase. It was surprising that the *Paenibacillus* thiaminase protein was found to have insecticidal activity. While this type of protein was known, it was in no way expected in the art that this enzyme would have exhibited toxin-like activity against insects/insect-like pests. Thus, the subject invention also relates to methods of screening *Paenibacillus* and others for insecticidal thiaminase genes and proteins, and to the use of these genes and proteins for controlling insects and like pests.

Other objects, advantages, and features of the subject invention will be apparent to one skilled in the art having the benefit of the subject disclosure.

BRIEF DESCRIPTION OF THE FIGURES

FIG. 1 shows the TC operons from *Photorhabdus*.

Figure 2:
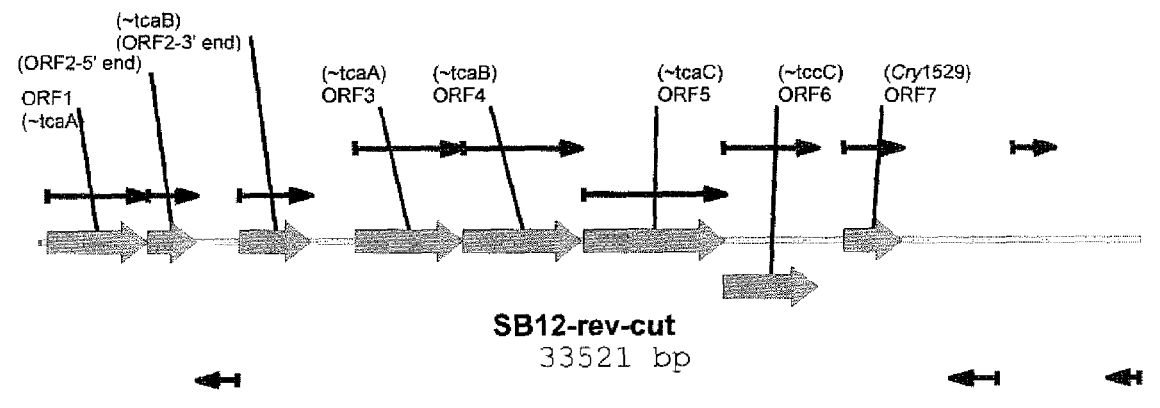

FIG. 2 shows a diagram of the DNA from DAS1529 inserted into the "SB12" clone that exhibited pesticidal activity, with open reading frames identified with block and line arrows.

FIG. 3 shows partial sequence alignments for SEQ ID NO:17 and thiaminase I from *Bacillus thiaminolyticus* (Campobasso et al., 1998) or AAC44156.

FIG. 6 shows Cry1529 (ORF 7) against tobacco bud worm (TBW).

FIG. 7 shows a comparison/alignment of SEQ ID NO:9 to SEQ ID NO:5 (tcaB$_2$ to tcaB$_1$); the brackets show the ORF2 junction.

FIGS. 11A and 11B show sequence alignments for tcaA primer design.

FIGS. 12A-C show sequence alignments for tcaB primer design.

FIGS. 13A and 13B show sequence alignments for tcaC primer design.

FIGS. 14A and 14B show sequence alignments for tccC primer design.

BRIEF DESCRIPTION OF THE SEQUENCES

Figure 4:
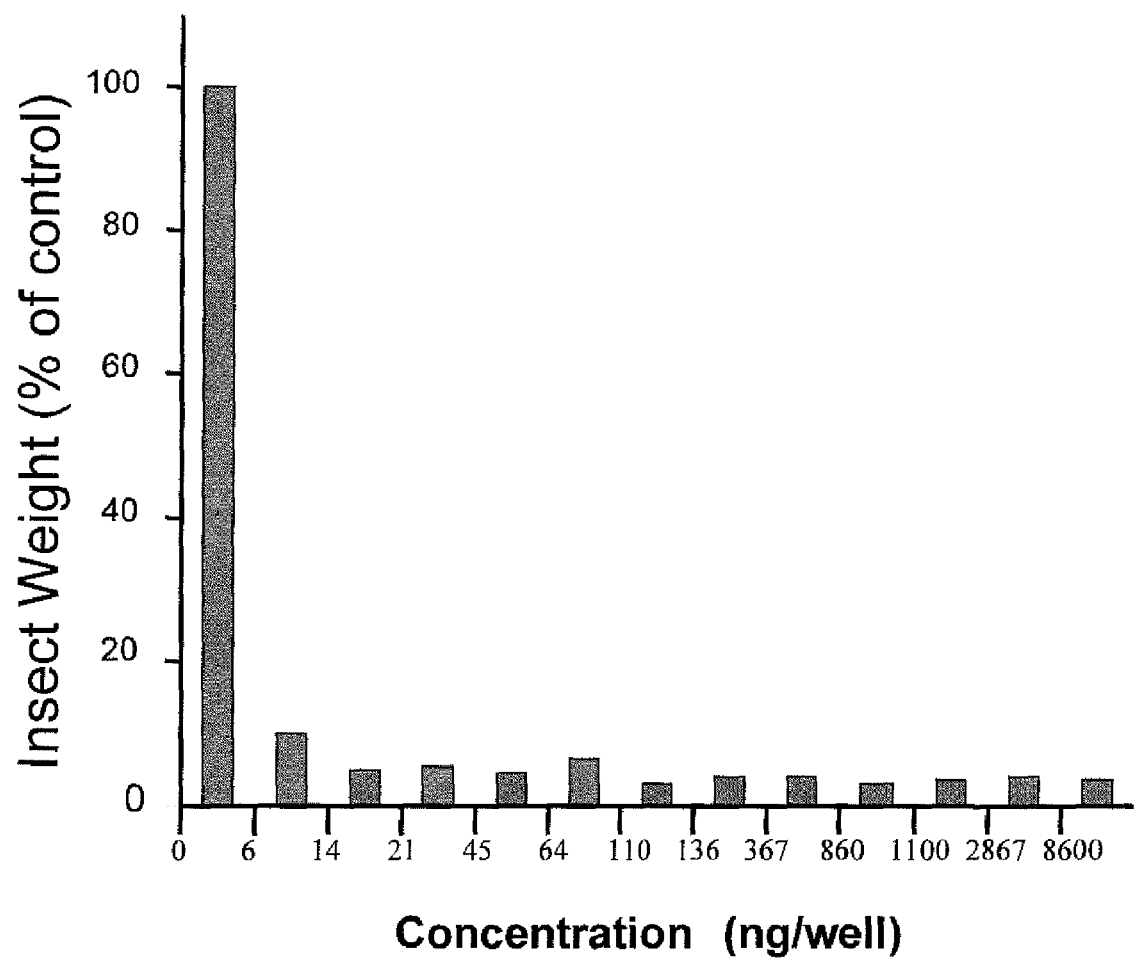
FIG. 4 shows test results of purified thiaminase from DAS1529 on CEW.

SEQ ID NO:1 is the nucleic acid sequence of the entire insert of SB12.

SEQ ID NO:2 is the nucleic acid sequence of ORF1, which encodes a tcaA-like protein (gene tcaA1, source organism *Paenibacillus* strain IDAS 1529, gene designation tcaA1-1529).

SEQ ID NO:3 is the amino acid sequence encoded by ORF1.

SEQ ID NO:4 is the nucleic acid sequence of ORF2, with an IS element removed, which encodes a tcaB-like protein (gene tcaB1, source organism *Paenibacillus* strain IDAS 1529, gene designation tcaB1-1529).

SEQ ID NO:5 is the amino acid sequence encoded by ORF2.

SEQ ID NO:6 is the nucleic acid sequence of ORF3, which encodes a tcaA-like protein (gene tcaA2, source organism *Paenibacillus* strain IDAS 1529, gene designation tcaA2-1529).

SEQ ID NO:7 is the amino acid sequence encoded by ORF3.

SEQ ID NO:8 is the nucleic acid sequence of ORF4, which encodes a tcaB-like protein (gene tcaB2, source organism *Paenibacillus* strain IDAS 1529, gene designation tcaB2-1529).

SEQ ID NO:9 is the amino acid sequence encoded by ORF4.

SEQ ID NO:10 is the nucleic acid sequence of ORF5, which encodes a tcaC-like protein (gene tcaC, source organism *Paenibacillus* strain IDAS 1529, gene designation tcaC-1529).

SEQ ID NO:11 is the amino acid sequence encoded by ORF5.

SEQ ID NO:12 is the nucleic acid sequence of ORF6, which encodes a tccC-like protein.

SEQ ID NO:13 is the amino acid sequence encoded by ORF6.

SEQ ID NO:14 is the nucleic acid sequence of ORF7, which encodes a Cry-like protein.

SEQ ID NO:15 is the amino acid sequence encoded by ORF7.

SEQ ID NO:16 is the partial nucleic acid sequence of the 16S rDNA of DAS1529 used for taxonomic placement.

SEQ ID NO:17 is the N-terminal amino acid sequence for the purified toxin from the broth fraction from DAS1529.

SEQ ID NO:18 is the amino acid sequence of thiaminase I from *Bacillus thiaminolyticus* (Campobasso et al., *J. Biochem.* 37(45):15981-15989 (1998)).

SEQ ID NO:19 is an alternate amino acid sequence encoded by ORF6 protein (gene tccC, source organism *Paenibacillus* strain IDAS 1529, gene designation tccC-1529).

SEQ ID NO:20 is gene xptC1, source organism *Xenorhabdus* strain Xwi, gene designation xptC1-Xwi.

SEQ ID NO:21 is gene xptB1, source organism *Xenorhabdus* strain Xwi, gene designation xptB1-Xwi.

SEQ ID NO:22 is primer SB101.

SEQ ID NO:23 is primer SB102.

SEQ ID NO:24 is primer SB103.

SEQ ID NO:25 is primer SB104.

SEQ ID NO:26 is primer SB105.

SEQ ID NO:27 is primer SB106.

SEQ ID NO:28 is primer SB212.

SEQ ID NO:29 is primer SB213.

SEQ ID NO:30 is primer SB215.

SEQ ID NO:31 is primer SB217.

SEQ ID NO:32 is a nucleotide sequence from a tcaA-like gene from *Paenibacillus apairius* strain DB482.

SEQ ID NO:33 is an amino acid sequence from a TcaA-like protein from *Paenibacillus apairius* strain DB482.

SEQ ID NO:34 is a nucleotide sequence from a tcaB-like gene from *Paenibacillus apairius* strain DB482.

SEQ ID NO:35 is a nucleotide sequence from a tcaB-like gene from *Paenibacillus apairius* strain DB482.

SEQ ID NO:36 is an amino acid sequence from a TcaB-like protein from *Paenibacillus apairius* strain DB482.

SEQ ID NO:37 is an amino acid sequence from a TcaB-like protein from *Paenibacillus apairius* strain DB482.

SEQ ID NO:38 is a nucleotide sequence from a tcaC-like gene from *Paenibacillus apairius* strain DB482.

SEQ ID NO:39 is an amino acid sequence from a TcaC-like protein from *Paenibacillus apairius* strain DB482.

SEQ ID NO:40 is a nucleotide sequence from a tccC-like gene from *Paenibacillus apairius* strain DB482.

SEQ ID NO:41 is an amino acid sequence from a TccC-like protein from *Paenibacillus apairius* strain DB482.

SEQ ID NO:42 is gene tcdB1, source organism *Photorhabdus* strain W14, gene designation tcdB1-W14.

SEQ ID NO:43 is gene tcdB2, source organism *Photorhabdus* strain W14, gene designation tcdB2-W14.

SEQ ID NO:44 is gene tccC1, source organism *Photorhabdus* strain W14, gene designation tccC1-W14.

SEQ ID NO:45 is gene tccC2, source organism *Photorhabdus* strain W14, gene designation tccC2-W14.

SEQ ID NO:46 is gene tccC3, source organism *Photorhabdus* strain W14, gene designation tccC3-W14.

SEQ ID NO:47 is gene tccC4, source organism *Photorhabdus* strain W14, gene designation tccC4-W14.

SEQ ID NO:48 is gene tccC5, source organism *Photorhabdus* strain W14, gene designation tccC5-W14.

SEQ ID NO:49 is the amino acid sequence of the XptA2 TC protein from *Xenorhabdus nematophilus* Xwi.

DETAILED DESCRIPTION OF THE INVENTION

The subject invention provides unique biological alternatives for pest control. More specifically, the subject invention provides new sources of proteins that have toxin activity against insects, preferably lepidopterans, and other similar pests. The invention also relates to new sources of novel polynucleotides that can be used to encode such toxins, and to methods of making and methods of using the toxins and corresponding nucleic acid sequences to control insects and other like plant pests. The present invention addresses the need for novel insect control agents. The present invention relates to novel pesticidal proteins that are obtainable from *Paenibacillus*, and other, bacteria.

The subject invention initially stemmed from a discovery of a novel strain of *Paenibacillus*. This strain is referred to herein as DAS1529. To demonstrate the broad implications of this discovery, the discovery of another *Paenibacillus* strain is also exemplified. These strains have been deposited with the Agricultural Research Service Patent Culture Collection (NRRL) at 1815 North University Street Peoria, Ill. 61604 U.S.A. The deposited strains and the corresponding deposit dates and deposit numbers are as follows:

| Deposited Strain | Deposit Date | Deposit Number |
|---|---|---|
| DAS1529 | Jun. 19, 2002 | NRRL B-30599 |
| DB482 | Jun. 17, 2003 | NRRL B-30670 |

These cultures have been deposited for the purposes of this patent application and were deposited under conditions that assure that access to the cultures is available during the pendency of this patent application to one determined by the Commissioner of Patents and Trademarks to be entitled thereto under 37 CFR 1.14 and 35 U.S.C. 122. These deposits will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits were made in accordance with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposits will be irrevocably removed upon the granting of a patent disclosing them.

The discovery of the subject DAS1529 strain was surprising for a variety of reasons. This strain produces a unique, lepidopteran-toxic Cry protein. This strain, as well as DB482, also produce unique, toxin complex (TC)-like proteins (having some similarity to *Xenorhabdus/Photorhabdus* TCs). *Paenibacillus* isolate DB482 and toxins obtainable therefrom are highly preferred, and all are within the scope of the subject invention.

This is the first known disclosure of a *Paenibacillus* protein toxin having activity against a lepidopteran pest. The DAS1529 strain was found to have toxin activity against lepidopteran pests. This was a surprising discovery. Some species of *Paenibacillus* were known to have insecticidal activity against grubs/beetles/coleopterans. There have been no known reports of a *Paenibacillus* species or strain having toxicity to lepidopterans. Thus, the subject invention relates generally to *Paenibacillus* species that have activity against lepidopterans, and to screening *Paenibacillus* cultures, proteins therefrom, and libraries of clones therefrom, for activity against lepidopterans, and/or for genes that encode "lep toxins," and more particularly, for lepidopteran-toxic Cry proteins.

This is also the first known report of *Paenibacillus* having TC-like proteins. Thus, the subject invention relates to methods of screening *Paenibacillus* spp. for TC-like genes and proteins. It was very surprising to find that the DAS1529 and DB482 strains have TC-like operons and produce TC proteins (having some level of similarity to TC proteins of *Xenorhabdus* and *Photorhabdus*). TC proteins and genes identified herein were not heretofore known to exist in the genus *Paenibacillus*. This discovery broadens the scope of organisms (bacterial genera) in which TC protein genes have been found. Thus, the subject invention generally relates to TC proteins obtainable from *Paenibacillus* species, to methods of screening *Paenibacillus* species for such proteins, and the like. An example of a *Paenibacillus* species found using the methods of the subject invention is *Paenibacillus apairius* strain DB482. This *P. apairius* strain also produces unique TC-like proteins.

While the subject TC proteins have some characteristics in common with TC proteins of *Xenorhabdus* and *Photorhabdus*, the subject TC proteins are unique and different from previously known TC proteins. Thus, the subject application provides new classes of TC-like proteins and genes that encode these proteins obtainable from bacteria in the genera *Paenibacillus*, *Photorhabdus*, *Xenorhabdus*, *Serratia*, and the like.

The subject invention also relates to lepidopteran-toxic Cry proteins that are obtainable from *Paenibacillus* species. Thus, the subject invention relates to methods of screening *Paenibacillus* species for cry genes and Cry proteins that have toxin activity against a lepidopteran pest.

The DAS1529 Cry toxin is a very unique, B.t.-like Cry protein toxin. One other strain of *Paenibacillus*, a strain with activity against grubs, was known to produce a coleopteran-toxic Cry protein. That was a Cry18 protein, which was most related to Cry2 proteins (but only about 40% identity). The Cry protein exemplified herein shows only a low level of sequence identity and similarity to previously known Cry proteins. With that noted, of all the known B.t. Cry proteins, the subject Cry protein shares the most similarity to Cry1 proteins. One surprising aspect of the subject Cry protein is that it is very short, i.e., even shorter than the Cry1Fa core toxin. The subject Cry protein has an identifiable Block 5 region at or near its C terminus. This toxin in its wild-type state has no protoxin portion, which is typically found on Cry1 toxins. The subject Cry toxin is surprisingly compressed. Thus, the subject invention generally relates to a new class of Cry proteins. This disclosure is also significant to the search for additional cry genes from *Bacillus thuringiensis* (B.t.). As would be clear to one skilled in the art having the benefit of the subject disclosure, other bacteria, such as B.t. and other *Bacillus* spp. (including *sphaericus*) could be screened for similar toxins and toxin genes. These methods of screening are within the scope of the subject invention.

The DAS1529 strain is the first known example of a natural bacterium that produces both a Cry-like toxin and TC-like proteins. Further surprising is that is the first known example of a cry toxin gene being closely associated with (in genetic proximity to) TC protein genes. These pioneering observations thus enable one skilled in the art to screen appropriate species of bacteria for these types of unique operons and for these types of further components of known operons. Such techniques are within the scope of the subject invention. The DAS1529 strain is an interesting example of a wild type strain having a TC-like operon with multiple TC protein genes of the same general type (i.e., in this case, two tcaA-like and two tcaB-like genes). This could have implications for further gene discovery.

A further aspect of the subject invention stems from the surprising discovery that the *Paenibacillus* thiaminase protein has insecticidal activity. While this protein was known, it was in no way expected in the art that this enzyme would have exhibited toxin-like activity against insects/insect-like pests.

*Paenibacillus* TC Proteins

More specifically regarding the exemplified TC proteins, the following TC proteins from strain DAS1529 have been fully characterized herein: two TcaA-like proteins ($TcaA_1$ and $TcaA_2$), two TcaB-like proteins ($TcaB_1$ and $TcaB_2$), a TcaC protein, and a TccC-like protein. The $TcaA_1$ and $TcaA_2$ proteins are highly similar to each other at the sequence level, and the $tcaB_1$ and $tcaB_2$ proteins are highly similar to each other at the sequence level. TC-like proteins obtainable from *Paenibacillus apairius* are also exemplified herein, and are within the scope of the subject invention.

The TC proteins of the subject invention can be used like other TC proteins. This would be readily apparent to one skilled in the art having the benefit of the subject disclosure when viewed in light of what was known in the art. See, e.g., the Background section, above, which discusses R. H. ffrench-Constant and Bowen (2000) and U.S. Pat. No. 6,048,838. For example, it was known that the Tca toxin complex of *Photorhabdus* is highly toxic to *Manduca sexta*.

While the exact molecular interactions of the TC proteins with each other, and their mechanism(s) of action, are not currently understood, some TC proteins were known to have "stand alone" insecticidal activity, and other TC proteins were known to enhance the activity of the stand-alone toxins produced by the same given organism. For example, it was known that the TcdA protein was active against *Manduca sexta*. TcaC and TccC, together, can be used to enhance the activity of TcdA. TcdB can be used (in place of TcaC) with TccC as a potentiator. TcbA is another *Photorhabdus* TC protein with stand-alone toxin activity. TcaC (or TcdB) together with TccC can also be used to enhance/potentiate the toxin activity of TcbA.

*Photorhabdus* TC proteins and "corresponding" TC proteins/genes from *Paenibacillus* are summarized below.

| *Photorhabdus* | *Photorhabdus* strain W14 nomenclature | *Photorhabdus* Self homology | *Paenibacillus* 1529 |
|---|---|---|---|
| TcaA | Toxin C | TccA | ORF3 (& 1) |
| TcaB | | TccB | ORF4 (& 2) |
| TcaC | | TcdB | ORF5 |
| Tcb | Toxin B | | |
| TccA | Toxin D | TcdA N terminus | |
| TccB | | TcdA C terminus | |
| TccC | | | ORF6 |
| TcdA | Toxin A | TccA + TccB | |
| TcdB | | TcaC | |

As indicated above, TccA has some level of homology with the N terminus of TcdA, and TccB has some level of homology with the C terminus of TcdA. Furthermore, TcdA is about 280 kDa, and TccA together with TccB are of about the same size, if combined, as TcdA. Furthermore, TcaA has some level of homology with TccA and likewise with the N terminus of TcdA. Still further, TcaB has some level of homology with TccB and likewise with the N terminus of TcdA. TccA and TcaA are of a similar size, as are TccB and TcaB.

Although some *Xenorhabdus* TC proteins were found to "correspond" to some of the *Photorhabdus* TC proteins, the "corresponding" proteins share only about 40% (approximately) sequence identity with each other. The subject TC proteins from *Paenibacillus* have about that same degree of sequence relatedness (~40% identity) with prior TC proteins.

As described in more detail below, one or more toxins of the subject invention can be used in combination with each other and/or with other toxins (i.e., the *Photorhabdus* Tca complex was known to be active against *Manduca sexta*; various "combinations" of *Photorhabdus* TC proteins, for example, can be used together to enhance the activity of other, stand-alone *Photorhabdus* toxins; the use of *Photorhabdus* toxins "with" B.t. toxins, for example, has been proposed for resistance management.) Furthermore, *Paenibacillus* TC proteins of the subject invention are shown herein to be useful to enhance or potentiate the activity of a "stand-alone" *Xenorhabdus* toxin protein, for example. Provisional application No. 60/441,723 (Timothy D. Hey et al.), entitled "Mixing and Matching TC Proteins for Pest Control," relates to the surprising discovery that a TC protein derived from an organism of one genus such as *Photorhabdus* can be used interchangeably with a "corresponding" TC protein derived from an organism of another genus. Further surprising data along these lines is presented below which further illustrate the utility of the *Paenibacillus* TC proteins of the subject invention. One reason that these results might be surprising is that there is only ~40% sequence identity between "corresponding" *Xenorhabdus*, *Photorhabdus*, and the subject *Paenibacillus* TC proteins.

Proteins and toxins. The present invention provides easily administered, functional proteins. The present invention also provides a method for delivering insecticidal toxins that are functionally active and effective against many orders of insects, preferably lepidopteran insects. By "functional activity" (or "active against") it is meant herein that the protein toxins function as orally active insect control agents (alone or in combination with other proteins), that the proteins have a toxic effect (alone or in combination with other proteins), or are able to disrupt or deter insect growth and/or feeding which may or may not cause death of the insect. When an insect comes into contact with an effective amount of a "toxin" of the subject invention delivered via transgenic plant expression, formulated protein compositions), sprayable protein composition(s), a bait matrix or other delivery system, the results are typically death of the insect, inhibition of the growth and/or proliferation of the insect, and/or prevention of the insects from feeding upon the source (preferably a transgenic plant) that makes the toxins available to the insects. Functional proteins of the subject invention can also enhance or improve the activity of other toxin proteins. Thus, terms such as "toxic," "toxicity," "toxin activity," and "pesticidally active" as used herein are meant to convey that the subject "toxins" have "functional activity" as defined herein.

Complete lethality to feeding insects is preferred, but is not required to achieve functional activity. If an insect avoids the toxin or ceases feeding, that avoidance will be useful in some applications, even if the effects are sublethal or lethality is delayed or indirect. For example, if insect resistant transgenic plants are desired, the reluctance of insects to feed on the plants is as useful as lethal toxicity to the insects because the ultimate objective is avoiding insect-induced plant damage.

There are many other ways in which toxins can be incorporated into an insects diet. For example, it is possible to adulterate the larval food source with the toxic protein by spraying the food with a protein solution, as disclosed herein. Alternatively, the purified protein could be genetically engineered into an otherwise harmless bacterium, which could then be grown in culture, and either applied to the food source or allowed to reside in the soil in an area in which insect eradication was desirable. Also, the protein could be genetically engineered directly into an insect food source. For instance, the major food source for many insect larvae is plant material. Therefore the genes encoding toxins can be transferred to plant material so that said plant material expresses the toxin of interest.

Transfer of the functional activity to plant or bacterial systems typically requires nucleic acid sequences, encoding the amino acid sequences for the toxins, integrated into a protein expression vector appropriate to the host in which the vector will reside. One way to obtain a nucleic acid sequence encoding a protein with functional activity is to isolate the native genetic material from the bacterial species which produce the toxins, using information deduced from the toxin's amino acid sequence, as disclosed herein. The native sequences can be optimized for expression in plants, for example, as discussed in more detail below. Optimized polynucleotide can also be designed based on the protein sequence.

The subject invention provides new classes of toxins having advantageous pesticidal activities. One way to characterize these classes of toxins and the polynucleotides that encode them is by defining a polynucleotide by its ability to hybridize, under a range of specified conditions, with an exemplified nucleotide sequence (the complement thereof and/or a probe or probes derived from either strand) and/or by their ability to be amplified by PCR using primers derived from the exemplified sequences.

There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other toxins. These antibodies can then be used to specifically identify equivalent toxins with the characteristic activity by immunoprecipitation, enzyme linked immunosorbent assay (ELISA), or western blotting. Antibodies to the toxins disclosed herein, or to equivalent toxins, or to fragments of these toxins, can be readily prepared using standard procedures. Monoclonal, polyclonal, specific, and/or cross-reactive antibodies can be made and used according to the subject invention. Such antibodies can be included in test kits for detecting the presence of proteins (and antigenic fragments thereof) of the subject invention.

One skilled in the art would readily recognize that toxins (and genes) of the subject invention can be obtained from a variety of sources. A toxin "from" or "obtainable from" the subject DAS 1529 isolate and/or the *P. apairius* isolate means that the toxin (or a similar toxin) can be obtained from this isolate or some other source, such as another bacterial strain or a transgenic plant. For example, one skilled in the art will readily recognize that, given the disclosure of a bacterial gene and toxin, a plant can be engineered to produce the toxin. Antibody preparations, nucleic acid probes (DNA and RNA), and the like may be prepared using the polynucleotide and/or amino acid sequences disclosed herein and used to screen and recover other toxin genes from other (natural) sources. Toxins of the subject invention can be obtained from a variety of sources/source microorganisms.

Polynucleotides and probes. The subject invention further provides nucleotide sequences that encode the toxins of the subject invention. The subject invention further provides methods of identifying and characterizing genes that encode pesticidal toxins. In one embodiment, the subject invention provides unique nucleotide sequences that are useful as hybridization probes and/or primers for PCR techniques. The primers produce characteristic gene fragments that can be used in the identification, characterization, and/or isolation of specific toxin genes. The nucleotide sequences of the subject invention encode toxins that are distinct from previously described toxins.

The polynucleotides of the subject invention can be used to form complete "genes" to encode proteins or peptides in a desired host cell. For example, as the skilled artisan would readily recognize, the subject polynucleotides can be appropriately placed under the control of a promoter in a host of interest, as is readily known in the art.

As the skilled artisan knows, DNA typically exists in a double-stranded form. In this arrangement, one strand is complementary to the other strand and vice versa. As DNA is replicated in a plant (for example), additional complementary strands of DNA are produced. The "coding strand" is often used in the art to refer to the strand that binds with the anti-sense strand. The mRNA is transcribed from the "anti-sense" strand of DNA. The "sense" or "coding" strand has a series of codons (a codon is three nucleotides that can be read as a three-residue unit to specify a particular amino acid) that can be read as an open reading frame (ORF) to form a protein or peptide of interest. In order to express a protein in vivo, a strand of DNA is typically transcribed into a complementary strand of mRNA which is used as the template for the protein. Thus, the subject invention includes the use of the exemplified polynucleotides shown in the attached sequence listing and/or equivalents including the complementary strands. RNA and PNA (peptide nucleic acids) that are functionally equivalent to the exemplified DNA are included in the subject invention.

In one embodiment of the subject invention, bacterial isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the toxin-encoding gene(s).

Further aspects of the subject invention include genes and isolates identified using the methods and nucleotide sequences disclosed herein. The genes thus identified encode toxins active against pests.

Toxins and genes of the subject invention can be identified and obtained by using oligonucleotide probes, for example. These probes are detectable nucleotide sequences which may be detectable by virtue of an appropriate label or may be made inherently fluorescent as described in International Application No. WO 93116094. The probes (and the polynucleotides of the subject invention) may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes). Thus, where a synthetic, degenerate oligonucleotide is referred to herein, and "n" is used generically, "n" can be G, A, T, C, or inosine. Ambiguity codes as used herein are in accordance with standard IUPAC naming conventions as of the filing of the subject application (for example, R means A or G, Y means C or T, etc.).

As is well known in the art, if a probe molecule hybridizes with a nucleic acid sample, it can be reasonably assumed that the probe and sample have substantial homology/similarity/identity. Preferably, hybridization of the polynucleotide is first conducted followed by washes under conditions of low, moderate, or high stringency by techniques well-known in the art, as described in, for example, Keller, G. H., M. M. Manak (1987) *DNA Probes*, Stockton Press, New York, N.Y., pp. 169-170. For example, as stated therein, low stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1× SSC/0.1% SDS for 30 minutes each at 55° C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water to 1 liter, followed by adjusting pH to 7.0 with 10 N NaOH. 10% SDS can be prepared by dissolving 10 g of SDS in 50 ml of autoclaved water, diluting to 100 ml, and aliquotting.

Detection of the probe provides a means for determining in a known manner whether hybridization has been maintained. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Probes for use according to the subject invention can be derived from a variety of sources, such as any gene mentioned or suggested herein. For example, all or part of any of the following types of genes (coding and/or noncoding or complementary strands thereof) can be used according to the subject invention: tcaA, tcaB, tcaC, tcbA, tccA, tccB, tccC, tcdA, tcdB, xptA1, xptD1, xptB1, xptC1, xptA2, sepA, sepB, and sepC. Unless specifically indicated otherwise, reference to a "tccC" gene, for example, includes all specific alleles (such as tccC1 and tccC2) of this type of gene. The same is true for all the other genes (e.g., tcdB2, tccC3, and the alleles mentioned in Table 17).

Hybridization characteristics of a molecule can be used to define polynucleotides of the subject invention. Thus the subject invention includes polynucleotides (and/or their complements, preferably their full complements) that hybridize with a polynucleotide (or an oligonucleotide or primer) exemplified or suggested herein.

As used herein "stringent" conditions for hybridization refers to conditions which achieve the same, or about the same, degree of specificity of hybridization as the conditions employed by the current applicants. Specifically, hybridization of immobilized DNA on Southern blots with $^{32}$P-labeled gene-specific probes was performed by standard methods (see, e.g., Maniatis, T., E. F. Fritsch, J. Sambrook [1982] *Molecular Cloning: A Laboratory Manual*, Cold Spring Harbor Laboratory, Cold Spring Harbor, N.Y.). In general, hybridization and subsequent washes were carried out under conditions that allowed for detection of target sequences. For double-stranded DNA gene probes, hybridization was carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos

[1983] *Methods of Enzymology*, R. Wu, L. Grossman and K. Moldave [eds.] Academic Press, New York 100:266-285):

$$Tm=81.5° C.+16.6 \text{ Log } [Na+]+0.41(\% G+C)-0.61(\% \text{ formamide})-600/\text{length of duplex in base pairs.}$$

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10-20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula:

$$Tm (° C.)=2(\text{number } T/A \text{ base pairs})+4(\text{number } G/C \text{ base pairs})$$

(Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683-693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

| Low: | 1 or 2× SSPE, room temperature |
| Low: | 1 or 2× SSPE, 42° C. |
| Moderate: | 0.2× or 1× SSPE, 65° C. |
| High: | 0.1× SSPE, 65° C. |

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

PCR technology. Polymerase Chain Reaction (PCR) is a repetitive, enzymatic, primed synthesis of a nucleic acid sequence. This procedure is well-known and commonly used by those skilled in this art (see Mullis, U.S. Pat. Nos. 4,683, 195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230: 1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. The extension product of each primer can serve as a template for the other primer, so each cycle essentially doubles the amount of DNA fragment produced in the previous cycle. This results in the exponential accumulation of the specific target fragment, up to several million-fold in a few hours. By using a thermostable DNA polymerase such as Taq polymerase, isolated from the thermophilic bacterium *Thermus aquaticus*, the amplification process can be completely automated. Other enzymes which can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions, and deletions can be produced in a given primer by methods known to an ordinarily skilled artisan.

Modification of genes and toxins. The genes and toxins useful according to the subject invention include not only the specifically exemplified full-length sequences, but also portions, segments and/or fragments (including internal and/or terminal deletions compared to the full-length molecules) of these sequences, variants, mutants, chimerics, and fusions thereof. For example, toxins of the subject invention may be used in the form of chimeric toxins produced by combining portions of two or more toxins/proteins.

Proteins of the subject invention can have substituted amino acids so long as they retain the characteristic pesticidal/functional activity of the proteins specifically exemplified herein. "Variant" genes have nucleotide sequences that encode the same toxins or equivalent toxins having pesticidal activity equivalent to an exemplified protein. The terms "variant proteins" and "equivalent toxins" refer to toxins having the same or essentially the same biological/functional activity against the target pests and equivalent sequences as the exemplified toxins. As used herein, reference to an "equivalent" sequence refers to sequences having amino acid substitutions, deletions, additions, or insertions which improve or do not adversely affect pesticidal activity. Fragments retaining pesticidal activity are also included in this definition. Fragments and other equivalents that retain the same or similar function, or "toxin activity," of a corresponding fragment of an exemplified toxin are within the scope of the subject invention. Changes, such as amino acid substitutions or additions, can be made for a variety of purposes, such as increasing (or decreasing) protease stability of the protein (without materially/substantially decreasing the functional activity of the toxin).

Equivalent toxins and/or genes encoding these equivalent toxins can be obtained/derived from wild-type or recombinant bacteria and/or from other wild-type or recombinant organisms using the teachings provided herein. Other *Bacillus, Paenibacillus, Photorhabdus*, and *Xenorhabdus* species, for example, can be used as source isolates.

Variations of genes may be readily constructed using standard techniques for making point mutations, for example. In addition, U.S. Pat. No. 5,605,793, for example, describes methods for generating additional molecular diversity by using DNA reassembly after random fragmentation. Variant genes can be used to produce variant proteins; recombinant hosts can be used to produce the variant proteins. Using these "gene shuffling" techniques, equivalent genes and proteins can be constructed that comprise any 5, 10, or 20 contiguous residues (amino acid or nucleotide) of any sequence exemplified herein. As one skilled in the art knows, the gene shuffling techniques can be adjusted to obtain equivalents having, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 or more contiguous residues (amino acid or nucleotide), corresponding to a segment (of the same size) in any of the exemplified sequences (or the complements (full complements) thereof). Similarly sized segments, especially those for conserved regions, can also be used as probes and/or primers.

Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

It is within the scope of the invention as disclosed herein that toxins may be truncated and still retain functional activity. By "truncated toxin" is meant that a portion of a toxin protein may be cleaved and yet still exhibit activity after cleavage. Cleavage can be achieved by proteases inside or outside of the insect gut. Furthermore, effectively cleaved proteins can be produced using molecular biology techniques wherein the DNA bases encoding said toxin are removed either through digestion with restriction endonucleases or other techniques available to the skilled artisan. After truncation, said proteins can be expressed in heterologous systems such as *E. coli*, baculoviruses, plant-based viral systems, yeast and the like and then placed in insect assays as disclosed herein to determine activity. It is well-known in the art that truncated toxins can be successfully produced so that they retain functional activity while having less than the entire, full-length sequence. It is well known in the art that B.t. toxins can be used in a truncated (core toxin) form. See, e.g., Adang et al., *Gene* 36:289-300 (1985), "Characterized full-length and truncated plasmid clones of the crystal protein of *Bacillus thuringiensis* subsp *kurstaki* HD-73 and their toxicity to *Manduca sexta*." There are other examples of truncated proteins that retain insecticidal activity, including the insect juvenile hormone esterase (U.S. Pat. No. 5,674,485 to the Regents of the University of California). As used herein, the term "toxin" is also meant to include functionally active truncations. On the other hand, a protoxin portion (typically the C-terminal half of a typical B.t. Cry toxin) can be added to form an active, full-length protein. See, e.g., U.S. Pat. No. 6,218,188.

Certain toxins of the subject invention have been specifically exemplified herein. As these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid similarity (and/or homology) with an exemplified toxin. The amino acid identity will typically be greater than 60%, preferably greater than 75%, more preferably greater than 80%, even more preferably greater than 90%, and can be greater than 95%. Preferred polynucleotides and proteins of the subject invention can also be defined in terms of more particular identity and/or similarity ranges. For example, the identity and/or similarity can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two nucleic acids is determined using the algorithm of Karlin and Altschul (1990), *Proc. Natl. Acad. Sci. USA* 87:2264-2268, modified as in Karlin and Altschul (1993), *Proc. Natl. Acad. Sci. USA* 90:5873-5877. Such an algorithm is incorporated into the NBLAST and XBLAST programs of Altschul et al. (1990), *J. Mol. Biol.* 215:402-410. BLAST nucleotide searches are performed with the NBLAST program, score=100, wordlength=12. To obtain gapped alignments for comparison purposes, Gapped BLAST is used as described in Altschul et al. (1997), *Nucl. Acids Res.* 25:3389-3402. When utilizing BLAST and Gapped BLAST programs, the default parameters of the respective programs (NBLAST and XBLAST) are used. See NCBI/NIH website. The scores can also be calculated using the methods and algorithms of Crickmore et al. as described in the Background section, above.

The amino acid homology/similarity/identity will be highest in critical regions of the toxin which account for biological activity or are involved in the determination of three-dimensional configuration which is ultimately responsible for the biological activity. In this regard, certain amino acid substitutions are acceptable and can be expected to be tolerated. For example, these substitutions can be in regions of the protein that are not critical to activity. Analyzing the crystal structure of a protein, and software-based protein structure modeling, can be used to identify regions of a protein that can be modified (using site-directed mutagenesis, shuffling, etc.) to actually change the properties and/or increase the functionality of the protein.

Various properties and targeted 3D features of the protein can also be changed without adversely affecting the toxin activity/functionality of the protein. Conservative amino acid substitutions can be expected to be tolerated/to not adversely affect the three-dimensional configuration of the molecule. Amino acids can be placed in the following classes: nonpolar, uncharged polar, basic, and acidic. Conservative substitutions whereby an amino acid of one class is replaced with another amino acid of the same type fall within the scope of the subject invention so long as the substitution is not adverse to the biological activity of the compound. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the functional/biological activity of the toxin.

As used herein, reference to "isolated" polynucleotides and/or "purified" toxins refers to these molecules when they are not associated with the other molecules with which they would be found in nature. Thus, reference to "isolated" and/or "purified" signifies the involvement of the "hand of man" as described herein. For example, a bacterial toxin "gene" of the subject invention put into a plant for expression is an "isolated polynucleotide." Likewise, a *Paenibacillus* protein, exemplified herein, produced by a plant is an "isolated protein."

Because of the degeneracy/redundancy of the genetic code, a variety of different DNA sequences can encode the amino acid sequences disclosed herein. It is well within the skill of a person trained in the art to create alternative DNA sequences that encode the same, or essentially the same, toxins. These variant DNA sequences are within the scope of the subject invention.

Optimization of sequence for expression in plants. To obtain high expression of heterologous genes in plants it may be preferred to reengineer said genes so that they are more efficiently expressed in (the cytoplasm of) plant cells. Maize is one such plant where it may be preferred to re-design the heterologous gene(s) prior to transformation to increase the expression level thereof in said plant. Therefore, an additional step in the design of genes encoding a bacterial toxin is reengineering of a heterologous gene for optimal expression.

One reason for the reengineering of a bacterial toxin for expression in maize is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding a bacterial toxin for maize expression, more preferably referred to as plant optimized gene(s), is to generate a DNA sequence having a higher G+C content, and preferably one close to that of maize genes coding for metabolic enzymes. Another goal in the design of the plant optimized gene(s) encoding a bacterial toxin is to generate a DNA sequence in which the sequence modifications do not hinder translation.

The table below (Table 2) illustrates how high the G+C content is in maize. For the data in Table 2, coding regions of the genes were extracted from GenBank (Release 71) entries, and base compositions were calculated using the MacVector™ program (Accelerys, Burlington, Mass.). Intron sequences were ignored in the calculations.

Due to the plasticity afforded by the redundancy/degeneracy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within a mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

In reengineering genes encoding a bacterial toxin for maize (or other plant, such as cotton or soybean) expression, the codon bias of the plant has been determined. The codon bias for maize is the statistical codon distribution that the plant uses for coding its proteins and the preferred codon usage is shown in Table 3. After determining the bias, the percent frequency of the codons in the gene(s) of interest is determined. The primary codons preferred by the plant should be determined as well as the second and third choice of preferred codons. Afterwards, the amino acid sequence of the bacterial toxin of interest is reverse translated so that the resulting nucleic acid sequence codes for exactly the same protein as the native gene wanting to be heterologously expressed. The new DNA sequence is designed using codon bias information so that it corresponds to the most preferred codons of the desired plant. The new sequence is then analyzed for restriction enzyme sites that might have been created by the modification. The identified sites are further modified by replacing the codons with second or third choice preferred codons. Other sites in the sequence which could affect transcription or translation of the gene of interest are the exon:intron junctions (5' or 3'), poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

TABLE 2

Compilation of G + C contents of protein coding regions of maize genes

| Protein Class.sup.a | Range % G + C | Mean % G + C.sup.b |
|---|---|---|
| Metabolic Enzymes (76) | 44.4-75.3 | 59.0 (.+-. 8.0) |
| Structural Proteins (18) | 48.6-70.5 | 63.6 (.+-. 6.7) |
| Regulatory Proteins (5) | 57.2-68.8 | 62.0 (.+-. 4.9) |

TABLE 2-continued

Compilation of G + C contents of
protein coding regions of maize genes

| Protein Class.sup.a | Range % G + C | Mean % G + C.sup.b |
|---|---|---|
| Uncharacterized Proteins (9) | 41.5-70.3 | 64.3 (.+−. 7.2) |
| All Proteins (108) | 44.4-75.3 | 60.8 (.+−. 5.2) |

.sup.aNumber of genes in class given in parentheses.
.sup.bStandard deviations given in parentheses.
.sup.cCombined groups mean ignored in mean calculation It is preferred that the plant optimized gene(s) encoding a bacterial toxin contain about 63% of first choice codons, between about 22% to about 37% second choice codons, and between about 15% to about 0% third choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The preferred codon usage for engineering genes for maize expression are shown in Table 3. The method described above enables one skilled in the art to modify gene(s) that are foreign to a particular plant so that the genes are optimally expressed in plants. The method is further illustrated in PCT application WO 97/13402.

In order to design plant optimized genes encoding a bacterial toxin, the amino acid sequence of said protein is reverse translated into a DNA sequence utilizing a non-redundant genetic code established from a codon bias table compiled for the gene sequences for the particular plant, as shown in Table 2. The resulting DNA sequence, which is completely homogeneous in codon usage, is further modified to establish a DNA sequence that, besides having a higher degree of codon diversity, also contains strategically placed restriction enzyme recognition sites, desirable base composition, and a lack of sequences that might interfere with transcription of the gene, or translation of the product mRNA.

TABLE 3

Preferred amino acid codons for proteins
expressed in maize

| Amino Acid | Codon* |
|---|---|
| Alanine | GCC/GCG |
| Cysteine | TGC/TGT |
| Aspartic Acid | GAC/GAT |
| Glutamic Acid | GAG/GAA |
| Phenylalanine | TTC/TTT |
| Glycine | GGC/GGG |
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |
| Tryrosine | TAC/TAT |
| Stop | TGA/TAG |

*The first and second preferred codons for maize.

Thus, synthetic genes that are functionally equivalent to the toxins/genes of the subject invention can be used to transform hosts, including plants. Additional guidance regarding the production of synthetic genes can be found in, for example, U.S. Pat. No. 5,380,831.

In some cases, especially for expression in plants, it can be advantageous to use truncated genes that express truncated proteins. Höfte et al. 1989, for example, discussed in the Background Section above, discussed protoxin and core toxin segments of B.t. toxins. Preferred truncated genes will typically encode 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the full-length toxin.

Transgenic hosts. The toxin-encoding genes of the subject invention can be introduced into a wide variety of microbial or plant hosts. In preferred embodiments, transgenic plant cells and plants are used. Preferred plants (and plant cells) are corn, maize, and cotton.

In preferred embodiments, expression of the toxin gene results, directly or indirectly, in the intracellular production (and maintenance) of the pesticide proteins. Plants can be rendered insect-resistant in this manner. When transgenic/recombinant/transformed/transfected host cells (or contents thereof) are ingested by the pests, the pests will ingest the toxin. This is the preferred manner in which to cause contact of the pest with the toxin. The result is control (killing or making sick) of the pest. Sucking pests can also be controlled in a similar manner. Alternatively, suitable microbial hosts, e.g., *Pseudomonas* such as *P. fluorescens*, can be applied where target pests are present; the microbes can proliferate there, and are ingested by the target pests. The microbe hosting the toxin gene can be treated under conditions that prolong the activity of the toxin and stabilize the cell. The treated cell, which retains the toxic activity, can then be applied to the environment of the target pest.

Where the toxin gene is introduced via a suitable vector into a microbial host, and said host is applied to the environment in a living state, certain host microbes should be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilus, Agrobacterium, Acetobacter, Lactobacillus, Arthrobacter, Azotobacter, Leuconostoc,* and *Alcaligenes*; fungi, particularly yeast, e.g., genera *Saccharomyces, Cryptococcus, Kluyveromyces, Sporobolomyces, Rhodotorula,* and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinelandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Also of interest are pigmented microorganisms.

Insertion of genes to form transgenic hosts. One aspect of the subject invention is the transformation/transfection of plants, plant cells, and other host cells with polynucleotides of the subject invention that express proteins of the subject invention. Plants transformed in this manner can be rendered resistant to attack by the target pest(s).

A wide variety of methods are available for introducing a gene encoding a pesticidal protein into the target host under conditions that allow for stable maintenance and expression of the gene. These methods are well known to those skilled in the art and are described, for example, in U.S. Pat. No. 5,135,867.

For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1-46; and An et al. (1985) *EMBO J.* 4:277-287.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the right and left T-DNA border regions. They can be transformed directly into *Agrobacteria* (Holsters et al. [1978] *Mol. Gen. Genet.* 163: 181-187). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In some preferred embodiments of the invention, genes encoding the bacterial toxin are expressed from transcriptional units inserted into the plant genome. Preferably, said transcriptional units are recombinant vectors capable of stable integration into the plant genome and enable selection of transformed plant lines expressing mRNA encoding the proteins.

Once the inserted DNA has been integrated in the genome, it is relatively stable there (and does not come out again). It normally contains a selection marker that confers on the transformed plant cells resistance to a biocide or an antibiotic, such as kanamycin, G418, bleomycin, hygromycin, or chloramphenicol, inter alia. The individually employed marker should accordingly permit the selection of transformed cells rather than cells that do not contain the inserted DNA. The gene(s) of interest are preferably expressed either by constitutive or inducible promoters in the plant cell. Once expressed, the mRNA is translated into proteins, thereby incorporating amino acids of interest into protein. The genes encoding a toxin expressed in the plant cells can be under the control of a constitutive promoter, a tissue-specific promoter, or an inducible promoter.

Several techniques exist for introducing foreign recombinant vectors into plant cells, and for obtaining plants that stably maintain and express the introduced gene. Such techniques include the introduction of genetic material coated onto microparticles directly into cells (U.S. Pat. No. 4,945, 050 to Cornell and U.S. Pat. No. 5,141,131 to DowElanco, now Dow AgroSciences, LLC). In addition, plants may be transformed using *Agrobacterium* technology, see U.S. Pat. No. 5,177,010 to University of Toledo; U.S. Pat. No. 5,104, 310 to Texas A&M; European Patent Application 0131624B1; European Patent Applications 120516, 159418B1 and 176,112 to Schilperoot; U.S. Pat. Nos. 5,149, 645, 5,469,976, 5,464,763 and 4,940,838 and 4,693,976 to Schilperoot; European Patent Applications 116718, 290799, 320500 all to Max Planck; European Patent Applications 604662 and 627752, and U.S. Pat. No. 5,591,616, to Japan Tobacco; European Patent Applications 0267159 and 0292435, and U.S. Pat. No. 5,231,019, all to Ciba Geigy, now Novartis; U.S. Pat. Nos. 5,463,174 and 4,762,785, both to Calgene; and U.S. Pat. Nos. 5,004,863 and 5,159,135, both to Agracetus. Other transformation technology includes whiskers technology. See U.S. Pat. Nos. 5,302,523 and 5,464,765, both to Zeneca. Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems. Furthermore, viral vectors can also be used to produce transgenic plants expressing the protein of interest. For example, monocotyledonous plant can be transformed with a viral vector using the methods described in U.S. Pat. No. 5,569,597 to Mycogen Plant Science and Ciba-Giegy, now Novartis, as well as U.S. Pat. Nos. 5,589,367 and 5,316,931, both to Biosource.

As mentioned previously, the manner in which the DNA construct is introduced into the plant host is not critical to this invention. Any method which provides for efficient transformation may be employed. For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the *Agrobacterium* host is not critical to this invention. The Ti or Ri plasmid containing the T-DNA for recombination may be capable or incapable of causing gall formation, and is not critical to said invention so long as the vir genes are present in said host.

In some cases where *Agrobacterium* is used for transformation, the expression construct being within the T-DNA borders will be inserted into a broad spectrum vector such as pRK2 or derivatives thereof as described in Ditta et al., (PNAS USA (1980)77:7347-7351 and EPO 0 120 515, which are incorporated herein by reference. Included within the expression construct and the T-DNA will be one or more markers as described herein which allow for selection of transformed *Agrobacterium* and transformed plant cells. The particular marker employed is not essential to this invention, with the preferred marker depending on the host and construction used.

For transformation of plant cells using *Agrobacterium*, explants may be combined and incubated with the transformed *Agrobacterium* for sufficient time to allow transformation thereof. After transformation, the *Agrobacteria* are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a bacterial toxin is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue which is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein.

As mentioned above, a variety of selectable markers can be used, if desired. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialaphos); imidazolinones, sulfonylureas and triazolopyrimidine herbicides, such as chlorsulfuron; bromoxynil, dalapon and the like.

In addition to a selectable marker, it may be desirous to use a reporter gene. In some instances a reporter gene may be used with or without a selectable marker. Reporter genes are genes that are typically not present in the recipient organism or tissue and typically encode for proteins resulting in some phenotypic change or enzymatic property. Examples of such genes are provided in K. Wising et al. Ann. Rev. Genetics, 22, 421 (1988). Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (1987 Biochem. Soc. Trans. 15, 17-19) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see U.S.

Pat. No. 6,166,302, especially Example 7E) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, the maize streak virus coat protein leader sequence, as well as others available to a skilled artisan. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active during a certain stage of the plant's development as well as active in plant tissues and organs. Examples of such include but are not limited to pollen-specific, embryo-specific, corn-silk-specific, cotton-fiber-specific, root-specific, seed-endosperm-specific promoter regulatory elements and the like. Under certain circumstances it may be desirable to use an inducible promoter regulatory element, which is responsible for expression of genes in response to a specific signal, such as: physical stimulus (heat shock genes), light (RUBP carboxylase), hormone (Em), metabolites, chemical, and stress. Other desirable transcription and translation elements that function in plants may be used. Numerous plant-specific gene transfer vectors are known in the art.

Standard molecular biology techniques may be used to clone and sequence the toxins described herein. Additional information may be found in Sambrook, J., Fritsch, E. F., and Maniatis, T. (1989), Molecular Cloning, A Laboratory Manual, Cold Spring Harbor Press, which is incorporated herein by reference.

Resistance Management. With increasing commercial use of insecticidal proteins in transgenic plants, one consideration is resistance management. That is, there are numerous companies using *Bacillus thuringiensis* toxins in their products, and there is concern about insects developing resistance to B.t. toxins. One strategy for insect resistance management would be to combine the TC toxins produced by *Xenorhabdus, Photorhabdus*, and the like with toxins such as B.t., crystal toxins, soluble insecticidal proteins from *Bacillus* stains (see, e.g., WO 98/18932 and WO 99/57282), or other insect toxins. The combinations could be formulated for a sprayable application or could be molecular combinations. Plants could be transformed with bacterial genes that produce two or more different insect toxins (see, e.g., Gould, 38 *Bioscience* 26-33 (1988) and U.S. Pat. No. 5,500,365; likewise, European Patent Application 0 400 246 A1 and U.S. Pat. Nos. 5,866,784; 5,908,970; and 6,172,281 also describe transformation of a plant with two B.t. crystal toxins). Another method of producing a transgenic plant that contains more than one insect resistant gene would be to first produce two plants, with each plant containing an insect resistance gene. These plants could then be crossed using traditional plant breeding techniques to produce a plant containing more than one insect resistance gene. Thus, it should be apparent that the phrase "comprising a polynucleotide" as used herein means at least one polynucleotide (and possibly more, contiguous or not) unless specifically indicated otherwise.

Formulations and Other Delivery Systems. Formulated bait granules containing spores and/or crystals of the subject *Paenibacillus* isolate, or recombinant microbes comprising the genes obtainable from the isolate disclosed herein, can be applied to the soil. Formulated product can also be applied as a seed-coating or root treatment or total plant treatment at later stages of the crop cycle. Plant and soil treatments of cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Another delivery scheme is the incorporation of the genetic material of toxins into a baculovirus vector. Baculoviruses infect particular insect hosts, including those desirably targeted with the toxins. Infectious baculovirus harboring an expression construct for the toxins could be introduced into areas of insect infestation to thereby intoxicate or poison infected insects.

Insect viruses, or baculoviruses, are known to infect and adversely affect certain insects. The affect of the viruses on insects is slow, and viruses do not immediately stop the feeding of insects. Thus, viruses are not viewed as being optimal as insect pest control agents. However, combining the toxin genes into a baculovirus vector could provide an efficient way of transmitting the toxins. In addition, since different baculoviruses are specific to different insects, it may be possible to use a particular toxin to selectively target particularly damaging insect pests. A particularly useful vector for the toxins genes is the nuclear polyhedrosis virus. Transfer vectors using this virus have been described and are now the vectors of choice for transferring foreign genes into insects. The virus-toxin gene recombinant may be constructed in an orally transmissible form. Baculoviruses normally infect insect victims through the mid-gut intestinal mucosa. The toxin gene inserted behind a strong viral coat protein promoter would be expressed and should rapidly kill the infected insect.

In addition to an insect virus or baculovirus or transgenic plant delivery system for the protein toxins of the present invention, the proteins may be encapsulated using *Bacillus thuringiensis* encapsulation technology such as but not limited to U.S. Pat. Nos. 4,695,455; 4,695,462; 4,861,595 which are all incorporated herein by reference. Another delivery system for the protein toxins of the present invention is formulation of the protein into a bait matrix, which could then be used in above and below ground insect bait stations. Examples of such technology include but are not limited to PCT Patent Application WO 93/23998, which is incorporated herein by reference.

Plant RNA viral based systems can also be used to express bacterial toxin. In so doing, the gene encoding a toxin can be inserted into the coat promoter region of a suitable plant virus which will infect the host plant of interest. The toxin can then be expressed thus providing protection of the plant from insect damage. Plant RNA viral based systems are described in U.S. Pat. No. 5,500,360 to Mycogen Plant Sciences, Inc. and U.S. Pat. Nos. 5,316,931 and 5,589,367 to Biosource Genetics Corp.

In addition to producing a transformed plant, there are other delivery systems where it may be desirable to reengineer the bacterial gene(s). For example, a protein toxin can be constructed by fusing together a molecule attractive to insects as a food source with a toxin. After purification in the laboratory such a toxic agent with "built-in" bait could be packaged inside standard insect trap housings.

Mutants. Mutants of the DAS1529 and DB482 isolates of the invention can be made by procedures that are well known in the art. For example, an asporogenous mutant can be obtained through ethylmethane sulfonate (EMS) mutagenesis of an isolate. The mutants can be made using ultraviolet light and nitrosoguanidine by procedures well known in the art.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Isolation and Discovery of Insecticidal Activity of DAS1529 as a *Paenibacillus* Sp.

A bacterial strain, designated DAS1529, was found to produce factors that were growth inhibitory to neonates of lepidopteran insects, corn earworm (*Heliothis zea*; CEW), tobacco budworm (*Heliothis virescens*; TBW), and tobacco hornworm (*Manduca sexta*; THW).

DAS1529 was cultured in 2% Protease Peptone No. 3 (PP3) medium (Difco Laboratories, Detroit, Mich.) supplemented with 1.25% NaCl or in JB medium supplemented with 0.2% glucose. Bacterial culture was grown at 25° C. for 40 hours at 150 rpm.

The insecticidally active factors were initially found in the fermentation broth that was concentrated on 5 kDa molecular weight cutoff filters. Those factors were heat labile (inactivated by heating at 85° C. for 20 minutes). These data indicated that the factors were proteinaceous. See also end of Example 4.

To identify active factors in cell pellets, the bacterial culture was centrifuged at 8000 rpm at 4° C. for 15 minutes, washed once with sterile distilled water, and resuspended to 33× of the original culture volume in sterile distilled water, and subjected to insect bioassay as described below in Example 3. The bioassay data for DAS1529 strain is summarized in Table 4. The data showed that the culture broth and concentrated DAS1529 bacterial cells conferred good activity against CEW (30 to 50% mortality at 33×) and TBW (100% mortality at 33×). Those toxin factors in DAS1529 have significant relevance to the development of commercial transgenic products targeting lepidopteran insects (e.g. CEW and TBW) in corn and cotton.

TABLE 4

Bioassay of DAS 1529 Strain

| Insects | TBW | CEW | Grubs |
|---|---|---|---|
| Broth Activity | +++ | +++ | n.d. |
| Pellet Activity | +++ | ++ | – |

*n.d.—not determined; –, ++, +++, no, moderate and high activity, respectively

Example 2

Classification of DAS 1529

Molecular phylogeny was performed to determine the taxonomic affiliation of strain DAS1529. The nucleotide sequence of the 16S rDNA of DAS 1529 was determined and used for similarity and phylogenetic analyses (using the MicroSeq Kit from ABI). The sequence is provided as SEQ ID NO:16. BLAST search results are as follows:

| | | Core (bits) | E value |
|---|---|---|---|
| gi\|15395282\|emb\|AJ320490.1\|PTH320490 | *Paenibacillus thiamino* . . . | 2906 | 0.0 |
| gi\|3328014\|gb\|AF071859.1\|AF071859 | *Paenibacillus popilliae* s . . . | 2834 | 0.0 |
| gi\|3328015\|gb\|AF071860.1\|AF071860 | *Paenibacillus popilliae* s . . . | 2815 | 0.0 |
| gi\|2769591\|emb\|Y16129.1\|PS16SC168 | *Paenibacillus* sp. C-168 1 . . . | 2699 | 0.0 |
| gi\|2769590\|emb\|Y16128.1\|PS16ST168 | *Paenibacillus* sp. T-168 1 . . . | 2509 | 0.0 |
| gi\|2077917\|dbj\|D78475.1\|D78475 | *Paenibacillus thiaminolyticu* . . . | 2503 | 0.0 |
| gi\|3328016\|gb\|AF071861.1\|AF071861 | *Paenibacillus lentimorbus* . . . | 2493 | 0.0 |
| gi\|2895560\|gb\|AF039408.1\| | *Bacillus tipchiralis* 16S ribosoma . . . | 2493 | 0.0 |
| gi\|2077936\|dbj\|D88513.1\|D88513 | *Paenibacillus thiaminolyticu* . . . | 2493 | 0.0 |
| gi\|15395283\|emb\|AJ320491.1\|PAL320491 | *Paenibacillus alvei* pa . . . | 2404 | 0.0 |

These same top scoring sequences from the BLAST search were also compared using the Gap routine (Needleman and Wunsch, J. Mol. Biol. 48; 443-453 (1970)) from GCG version 10.2, with the following results:

| | | % Ident | % Sim |
|---|---|---|---|
| gi\|15395282\|emb\|AJ320490.1\|PTH320490 | *Paenibacillus thiamino* . . . | 99.2 | 99.6 |
| gi\|3328014\|gb\|AF071859.1\|AF071859 | *Paenibacillus popilliae* s . . . | 99.2 | 99.6 |
| gi\|3328015\|gb\|AF071860.1\|AF071860 | *Paenibacillus popilliae* s . . . | 99.2 | 99.3 |
| gi\|2769591\|emb\|Y16129.1\|PS16SC168 | *Paenibacillus* sp. C-168 1 . . . | 97.1 | 97.3 |
| gi\|2769590\|emb\|Y16128.1\|PS16ST168 | *Paenibacillus* sp. T-168 1 . . . | 97.4 | 97.4 |
| gi\|2077917\|dbj\|D78475.1\|D78475 | *Paenibacillus thiaminolyticu* . . . | 96.5 | 98.1 |
| gi\|3328016\|gb\|AF071861.1\|AF071861 | *Paenibacillus lentimorbus* . . . | 98.8 | 98.9 |
| gi\|2895560\|gb\|AF039408.1\| | *Bacillus tipchiralis* 16S ribosoma . . . | 96.0 | 96.9 |
| gi\|2077936\|dbj\|D88513.1\|D88513 | *Paenibacillus thiaminolyticu* . . . | 96.7 | 98.7 |
| gi\|15395283\|emb\|AJ320491.1\|PAL320491 | *Paenibacillus alvei* pa . . . | 95.2 | 95.3 |

[% Ident, matches of unambiguous bases; % Sim, % Ident plus potentially matching ambiguous bases]

A number of related sequences, including the top scoring sequences noted above, were also trimmed and aligned as described by Shida et al. (*Int. J. Syst. Bacteriol.* 47:289-298, 1997), using the sequence alignment program CLUSTAL W (Thompson, J. D., D. G. Higgins, and T. J. Gibson, *Nucleic Acids Res.* 22:4673-4680, 1994). The results clearly place DAS1529 in the *Paenibacillus popilliae/Paenibacillus lentimorbus* subcluster of the genus *Paenibacillus* identified by Pettersson et al. (*Int. J. Syst. Bacteriol.* 49:531-540, 1999), and are consistent with the analyses reported above. This subcluster includes the insect-associated species *P. popilliae* and *P. lentimorbus*, as well as *P. thiaminolyticus, Paenibacillus* sp. T-168 and C-168, and "*Bacillus tipchiralis*," which are not known to have an insect association (Pettersson et al., 1999). As noted by Wayne et al. (*Int. J. Syst. Bacteriol.* 37:463-464, 1987) and Vandamme et al. (*Microbiol. Rev.* 60:407-438), rDNA sequences that are greater than 97% identical cannot generally be used to assign a bacterial strain to a particular species in the absence of additional information. In the case of DAS1529, insecticidal activity on lepidoptera and evidence of a thiaminase are not consistent with known *P. popilliae* and *P. lentimorbus*, and the insect association is not consistent with known *P. thiaminolyticus* (as well as the other subcluster species).

As other *Paenibacillus* strains are known causative agents of milky disease in larvae of Japanese beetles (*Popillia jalonica*; Harrison et al., 2000), the DAS1529 was tested for activity on June beetles, a relative of Japanese beetles. No activity was found for cultures grown in JB and PP3 medium. Microscopic examination of those cultures revealed even-colored rods with no visible sporulation or parasporal crystals present. We are able to show DAS1529 can sporulate in defined medium and culture conditions and within the hemolymph of *Manduca sexta*. It is known that the Japanese beetle active *Paenibacillus* strains are typically associated with paraspore and parasporal bodies (Harrison et al., 2000).

Additional work will be needed to determine whether DAS1529 belongs to an existing species or should be assigned a new species designation.

Example 3

Insect Bioassay Methodology

Two insect bioassay methods were used to obtain results presented below. A 96-well format and a 128-well format were used for primary screening for activity against lepidopteran insects. A 24-well diet incorporation format was used to determine specific activity (LC50s) of the toxin.

For the 96-well format, artificial diet was dispensed into 96-well microtiter plates. Each well measured approximately 0.32 $cm^2$ and contained 150 µl artificial diet. Samples/toxins were applied at a rate of 50 µl/well for fermentation broth, cell pellets, and purified toxins. Positive control (Cry1Ac) at appropriate doses and negative controls (water, medium blank, bacterial host strains not expressing target toxin) at top dose were included. Samples were allowed to dry for approximately 1-3 hours so that the samples lost their moisture but the diet retained its moisture. Either insect eggs were dispersed onto the surface of the sample treated diet, or a single insect larva was seeded per well. The infested plate was sealed either with iron-on mylar covering or covered with sticky lidding with perforations. Tiny air holes were made in the mylar covering to ensure air supply to the insects. The plates were incubated at 28° C. for 5 days and scored for mortality and stunting. This was done on a per-well basis, ignoring the number of larvae per well, as multiple eggs are often deposited per well. Activity scores were then assigned to each treatment: 0=no activity, larvae healthy like water control wells, 1=larvae were stunted, or stunted with some mortality, 2=larvae were all dead.

The specific activities (LC50s) of samples/toxins were determined by diet incorporation bioassay in 24-well Nutrend trays (Nu-Trend™ Container Corp., Jacksonville, Fla.). Insect artificial diet was made just prior to use and held in liquid state at 55° C. in a water bath. Serial dilutions ($\geq 5$) were made by mixing 27 ml of artificial diet with no more than 3 ml of samples/toxins. A total of 30 ml sample and diet mixture was vortexed for 30 seconds and then evenly distributed into each tray, filling ~50% of the well volume. Trays were allowed to cool for at least 30 minutes prior to infesting. One test insect was infested into each well, and clear mylar was sealed over the top of each tray to contain the insects. Small holes were punched with an insect pin in the mylar over each well for air circulation. Assays were generally held at 25° C. for 6 days but some may have been held at 30° C. for 4 days if quicker results were needed. A set of positive and negative controls was run for each assay. Assays were graded on the basis of mortality but data on stunting was also recorded. Statistical methods were used to estimate LC50s for assayed samples and was expressed as ng or µg/ml diet.

Example 4

Biochemical Purification and Characterization of Insecticidal Toxins from DAS1529 Fermentation Broth—Thiaminase The fermentation broths of DAS1529 contained insecticidal activity against lepidopteran species, such as tobacco budworm, corn earworm, and tobacco hornworm. The nature of the insecticidal activity was investigated by biochemical purification and characterization. Corn earworm bioassay, as described in Example 3, was used during the purification process to follow insecticidal activities.

Fermentation broths of DAS1529 were produced using 2% PP3 supplemented with 1.25% NaCl and processed as described in Example 1. Four liters of broth was concentrated using an Amicon (Beverly, Mass.) spiral ultrafiltration cartridge Type S1Y10 (molecular weight cut off 10 kDa) attached to an Amicon M-12 filtration device according to the manufacturer's recommendations. The retentate was diafiltered with 20 mM sodium phosphate, pH 7.0 (Buffer A) and applied at 5 ml/min to a Q cepharose XL anion exchange column (1.6×10 cm). The column was washed with 5 bed volumes of Buffer A to remove unbound proteins. Toxin activity was eluted by 1.0 M NaCl in Buffer A.

The fraction containing the insecticidal activity was loaded in 20 ml aliquots onto a gel filtration column Macro-Prep SE1000/40 (2.6×100 cm) which was equilibrated with Buffer A. The protein was eluted in Buffer A at a flow rate of 3 ml/min. Fractions with activity against corn earworm were pooled and were applied to a MonoQ (1.0×10 cm) column equilibrated with 20 mM Tris-HCl, pH 7.0 (Buffer B) at a flow rate of 1 ml/min. The proteins bound to the column were eluted with a linear gradient of 0 to 1 M NaCl in Buffer B at 2 ml/min for 60 min. Two milliliter fractions were collected and activity was determined as described in Example 1.

Solid $(NH_4)_2SO_4$ was added to the above active protein fractions to a final concentration of 1.7 M. Proteins were then applied to a phenyl-Superose (1.0×10 cm) column equilibrated with 1.7 M $(NH_4)_2SO_4$ in 50 mM potassium phosphate buffer, pH 7 (Buffer C) at 1 ml/min. After washing the column with 10 milliliters of Buffer C, proteins bound to the column were eluted with a linear gradient Buffer C to 5 mM potassium phosphate, pH 7.0 at 1 ml/min for 120 min. The most active fractions determined by bioassay were pooled and dialyzed overnight against Buffer A.

The dialyzed sample was applied to a Mono Q (0.5×5 cm) column which was equilibrated with Buffer B at 1 ml/min. The proteins bound to the column were eluted at 1 ml/min by a linear gradient of 0 to 1 M NaCl in Buffer B. The active fractions were pooled and adjusted to a final $(NH_4)_2SO_4$ concentration of 1.7M. Proteins were then applied to a phenyl-Superose (0.5.0×5 cm) column equilibrated with Buffer C at 1 ml/min. Proteins bound to the column were eluted with a linear gradient of Buffer C to 5 mM potassium phosphate, pH 7.0 at 0.5 ml/min for 40 min. The purified fractions were pooled and dialyzed overnight against Buffer A.

The molecular weight of the final purified toxin was examined by a gel-filtration column Superdex S-200. The toxin exhibited a native molecular weight of approximately 40 kDa. SDS-PAGE of the purified toxins showed a predominant band of approximately 40 kDa. This suggested that the native DAS1529 toxin (in this fraction) was an approximately 40 kDa monomer.

The purified toxin was electrophoresed in 4-20% SDS-PAGE and transblotted to PVDF membrane. The blot underwent amino acid analysis and N-terminal amino acid sequencing (SEQ ID NO. 17). Searching protein database (NCBI-NR) using the sequence as a query revealed that it is 95% identical to the approximately 42 kDa thiaminase I from *Bacillus thiaminolyticus* (Campobasso et al., 1998; GENBANK Accession No. 2THIA; SEQ ID NO:18). Partial sequence alignments are illustrated in FIG. 3, which would be the same alignment with GENBANK Accession No. AAC44156 (thiaminase I precursor; U17168 is the corresponding entry in GENBANK for the DNA, which could be expressed to get a thiaminase produced and secreted from a bacterial cell). The purified thiaminase from DAS1529 was tested on corn earworm (CEW), the results were shown in FIG. 4. This toxin did not kill corn earworm (up to a concentration of 8 μg/$cm^2$) but exhibited 95% growth inhibition at a concentration as low as 5 ng/$cm^2$. It was also found that the purified thiaminase was not deactivated by proteinase K.

Example 5

Cloning of Genes Encoding Insecticidal Factors Produced by DAS 1529

In an attempt to clone the nucleotide sequencers) that encode the insecticidal factor(s) produced by DAS 1529, a cosmid library was constructed using total DNA isolated from DAS 1529 and was screened for insecticidal activity. Six recombinant cosmid clones were identified that produced insecticidal activity against corn earworm and tobacco budworm neonates. Three of the cosmid clones produced heat labile (when heated at 85° C. for 20 minutes) factors that resulted in insect mortality. The other three cosmid clones produced heat labile factors that were growth inhibitory to insects. One of the cosmids that produced insect mortality, designated as cosmid SB12, was chosen for nucleotide sequence analysis.

A. Construction of a Cosmid Library of DAS1529.

Total DNA was isolated from DAS1529 with a DNA purification kit (Qiagen Inc., Valencia, Calif.). Vector and insert DNA preparation, ligation, and packaging, followed instructions from the supplier (Stratagene, La Jolla, Calif.). The DAS1529 DNA inserts as Sau3A I DNA fragments were cloned into the BamHI site of SuperCos 1 cosmid vector. The ligated product was packaged with the Gigapack® III gold packaging extract and transfected into host cells XL1-Blue MRF'. Transformants were selected on LB-kanamycin agar plates. The cosmid library consisted of 960 randomly picked colonies that were grown in ten 96-well microtiter plates in 200 μl LB-kanamycin (50 μg/ml) for insect activity screening and long term storage.

B. Screening of DAS1529 Cosmid Library for Insecticidal Activity.

For the primary screening for clones active against lepdidopteran insects (CEW and TBW), a total of 960 cosmid clones as single colonies were grown in 2 ml cultures in 96 well plates. Cultures were spun and re-suspended in original culture media at approximately 10× concentration and submitted to bioassay. The SuperCos 1 vector (SB1) was included as a negative control. Sixteen positive clones (SB2 to SB17) were isolated from the first round of screening. Second and third rounds of screening were carried out to screen for activity against TBW and CEW; one cosmid clone (SB12) consistently showing the highest activity was chosen for further analysis. Table 5 summarizes the activity spectrum (as tested) of the SB12 cosmid. (BAW is beet armyworm, *Spodoptera exigua*; ECB is European cornborer, *Ostrinia nubilalis*; SCRW is Southern corn rootworm, *Diabrotica undecimpucata howardi*.) The broth of SB12 *E. coli* culture both contained no CEW activity; hence, the active factors in SB12 were different from the active factors in DAS1529 strain culture broth.

TABLE 5

Bioassay of SB12 $_{E.\ coli}$ Clone

| Insects | TBW | CEW | ECB | BAW | Grubs | SCR |
|---|---|---|---|---|---|---|
| Broth Activity | – | – | n.d.* | n.d. | n.d. | n.d. |
| Pellet Activity | +++ | ++ | + | ++ | – | – |

*n.d.—not determined; –, ++, +++, no, moderate and high activity, respectively

C. Sequencing of SB12 Cosmid Insert and Identification of tc- and cry-Like ORFs.

Nucleotide sequencing of cosmid SB12 showed that it contained a genomic insert of approximately 34 kb. Analysis of this sequence surprisingly revealed the presence of at least 10 putative open reading frames (ORFs) (see FIG. 2). Six of the identified ORFs were surprisingly found to have some degree of amino acid sequence identity (38-48%) to tcaA, tcaB, tcaC, and tccC previously identified from *Photorhabdus luminescens* (Waterfield et al., 2001), *Xenorhabdus nematophilus* (Morgan et al., 2001), *Serratia entomophila* (Hurst and Glare, 2002; Hurst et al., 2000), and *Yersinia pestis* (Cronin et al., 2001). Those TC protein genes from *Photorhabdus, Xenorhabdus*, and *Serratia* have been shown to encode insecticidal factors. Also very interesting was that one DAS 1529 ORF had ~40% amino acid sequence identity to Cry1Ac from *Bacillus thuringiensis*, another gene previously identified as an insecticidal factor (Schnepf et al., 1998; de Maagd et al., 2001). Those findings have significant implication in understanding toxin gene distribution in the bacterial kingdom and in developing further strategies for toxin gene mining and engineering.

The nucleotide sequence of the SB12 cosmid was determined. The assembled DNA of 41,456 bp long was further analyzed. Three gaps were located: two in the cosmid vector and one in the insert. Analysis of the nucleotide sequence of the longest contig of approximately 34,000 bp revealed the presence of at least 10 putative open reading frames (ORFs), identified as potential start codons followed by extended open reading frames. This method is known to mis-identify translational start sites by 19% (*Bacillus subtilis*) and 22% (*Bacillus halodurans*) in genomes related to *Paenibacillus* (Besemer, J., Lomsadze, A., Borodovsky, M., *Nucleic Acids Res.* 29:2607-2618, 2001). Therefore, the quality and position of bases complementary to the *B. subtilis* 16S rRNA 5' end (reviewed in Rocha, E. P. C., Danchin, A., Viari, A., *Nucleic Acids Res.* 27:3567-3576, 1999), N-terminal amino acid sequencing, and alignments to related genes were considered in identifying the native translation initiation sites. The putative ORFs and annotations are summarized in Table 6 and are discussed in more detail below.

TABLE 6

Sequence annotation for SB12 cosmid sequence

| SEQ ID NO: | Some ORF similarity to: | ORF Designation on SB12 | Comments | Sequence Location on SEQ ID NO: 1 |
|---|---|---|---|---|
| 1 | | | Entire insert of SB12 | (1-33521) |
| 2 | tcaA (truncated at 5') | ORF1 | | 1-3264 |
| 3 | | | Translation of ORF1 | (1-3261) |
| 4 | tcaB | ORF2 (with IS element removed) | | 3271-4740 (5' end); 6079-8226 (3' end) |
| 5 | | | Translation of ORF2 (without insertion) from 5'-most ATG | (amino acids 1-490/491-1205) |
| 6 | tcaA | ORF3 | | 9521-12820 |
| 7 | | | Translation of ORF3 | (9521-12817) |
| 8 | tcaB | ORF4 | | 12827-16453 |
| 9 | | | Translation of ORF4 from 5'-most ATG | (12827-16450) |
| 10 | tcaC | ORP5 | | 16516-20850 |
| 11 | | | Translation of ORF5 | (16516-20847) |
| 12 | tccC | ORF6 | | 20867-23659 |
| 13 | | | Translation of ORF6 (from better RBS) | (20867-23656) |
| 14 | | ORF7 (Cry1529) | | 24422-26213 |
| 15 | | | Translation of ORF7 | |
| 19 | tccC | | Translation from 5'-most ATG of ORF6 | 20798-23656 |

ORF1 begins with the first nucleotide of the cloning site for the DAS1529 DNA in cosmid SB12, and is therefore missing its native translation initiation site. ORF1 shares significant DNA sequence homology with ORF3, and sequence comparison analysis suggests the first 18 bp of ORF1 is truncated, and that the first six codons encode the amino acids Met-Val-Ser-Thr-Thr, as found in OFR3. The ORF1 translation start is presumably similar to that of ORF3, from approximately bases 9505 through 9523 of SEQ ID NO:1. Two predicted amino acid sequences are presented for ORF2, ORF4, and ORF6 (SEQ ID NOs:19 and 13), based on alternative translation initiation sites, as noted above. For ORF2, SEQ ID NO:5 is discussed above. The alternate, and preferred, start site is at residue 3295 of ORF1. Thus, the protein resulting from this start site would begin at amino acid residue 9 of SEQ ID NO:5 (translation from better RBS). Likewise, for ORF4, SEQ ID NO:9 is discussed above. The alternate, and preferred, start site is at residue 12,852 of SEQ ID NO:1. The resulting protein would also be missing the first eight amino acids of SEQ ID NO:9 (thus beginning with amino acid residue 9 of SEQ ID NO:8—translation from better RBS).

Example 6

Sequence Analysis of "Duplicated" TCs

The degree of sequence identity for the two ORF2 fragments (tcaB$_1$) compared to ORF4 (tcaB$_2$) was determined, as was that for ORF1 (tcaA$_1$) compared to ORF3 (tcaA$_2$). A similar sequence relationship was observed for both pairs of ORFs.

ORF2 was constructed by combining two fragments, because of an insertion sequence-like element which was inserted in nature (apparently spontaneously), and disrupted this ORF. See FIG. 2. The location of this insertion is determinable by analyzing/comparing the entire SB12 DNA sequence (SEQ ID NO:1) with the sequence of SEQ ID NO:4, the latter of which does not reflect the (non-coding) insertion. As indicated with brackets in FIG. 7, the sequence of the 5' translation product prior to residue 490 of SEQ ID NO:4 and the 3' translation product from residue 491 on, align well with ORF4 (SEQ ID NO:8). The DNA sequence at the apparent insertion point shows a 9 bp direct repeat commonly found flanking insertion elements (CACCGAGCA, bases 4734-4742 and 6071-6080 of SEQ ID NO:1).

Example 7

Further Sequence Analysis

Figure 8:
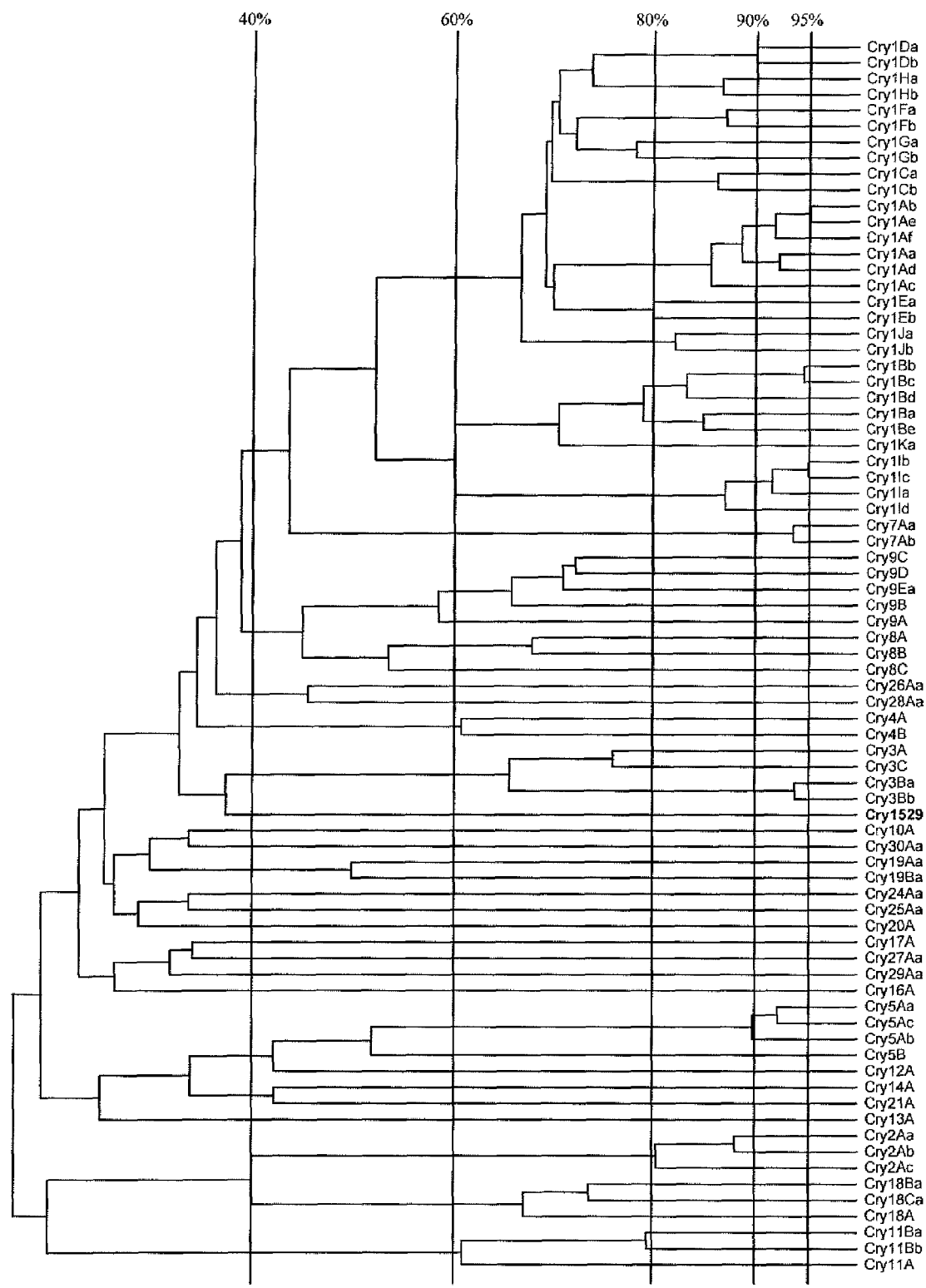
FIG. 8 shows a phylogenetic tree of DAS1529 ORF7 (Cry1529) compared to other Cry proteins.
Figure 9:
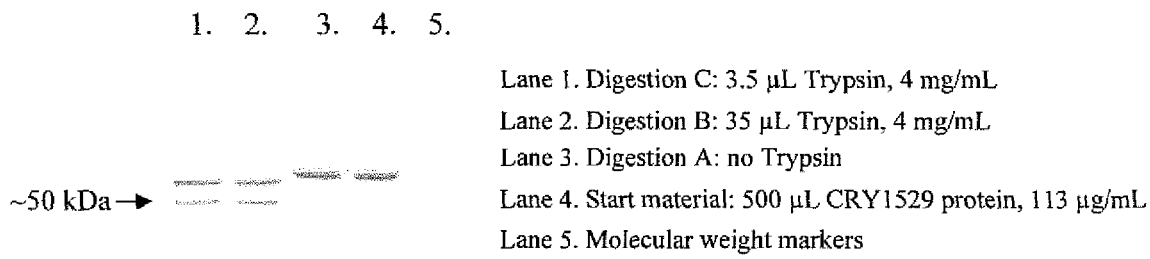
FIGS. 9 and 10 show results of trypsin digestion of wild-type and modified Cry1529 proteins.

In summary, according to Vector NTI clustalW, GCG, and/or Blastp analyses, six of the identified ORFs (ORF1 to ORF6) had 38-48% amino acids sequence identity to tcaA, tcaB, tcaC, and tccC (previously identified *Photorhabdus* tc genes). The ORF7 encoded a protein that shared ~40% amino acid sequence identity to Cry1Ac from *Bacillus thuringiensis*, another gene previously identified as an insecticidal factor. A phylogram was generated by incorporating ORF7 (Cry1529) sequence with a large number of other Cry proteins (FIG. 8). This phylogenetic tree suggests that Cry1529 is distantly related to other *P. popilliae* Cry sequences such as the Cry18s (Zhang et al., 1997, Zhang et al., 1998) that are closer to Cry2s; Cry1529 falls (remotely but most closely) into a group of Cry proteins containing commonly found lepidoptera(Cry1, Cry9), coleoptera (Cry3, Cry8, Cry7), and diptera (Cry4) toxins, which is a distinct group compared to those including nematode toxins Cry5, -12, -13, -14, and -21 and Cry2, -18.

It was a surprising and novel discovery to find Cry and TC protein genes (in the SB12 genomic insert) in *Paenibacillus*. The identification of new Cry and TC protein genes has relevance to the art's understanding of *Photorhabdus* and *Xenorhabdus*, and *Bacillus thuringiensis*, and broadens the scope of bacterial genera in which Cry and TC protein genes have been found. The size of the full-length Cry1529 identified herein corresponds to the core toxin of Cry1s; Cry1529 represents a new class of Cry proteins which also has implications for isolating further cry genes from *Bacillus thuringiensis* and *Paenibacillus*.

To verity that these surprising observations were not the result of strain contamination (i.e., to confirm that the 34 kb insert carrying TC and Cry ORFs was indeed from the total DNA of DAS1529), molecular analysis was carried out by Southern blot hybridization and PCR. For PCR validation, ORF6 (tccC-like) and ORF7 (Cry1529) specific primers (Example 8, Table 8) were used to amplify ORF6 and ORF7 from SB12 cosmid and DAS1529 total DNA. For ORF6, PCR amplifications were performed on a PE9600 thermal cycler (Perkin Elmer) with the following parameters: initial denaturation at 95° C. for 2 minutes; 30 cycles each with denaturing at 95° C. for 30 seconds, annealing at 60° C. for 45 seconds, extension at 72° C. for 2 minutes, and a final extension for 10 minutes at 72° C. For ORF7, amplification parameters were the same as ORF6, except the annealing temperature was 55° C. for 30 seconds and extension at 72° C. for 4 minutes. Specific PCR products with a single band of expected sizes were amplified for both ORF6 and ORF7.

Initial southern blot hybridization was based on partial SB12 DNA sequence and carried out according to standard protocol (Sambrock et al., 1990). DNA samples included total DNA of DAS1529 from two independent preparations, SB12 cosmid DNA, and one negative control DNA sample from NC1 (*Photorhabdus*). Both DAS1529 DNA samples were 16S rDNA sequence confirmed to be of *Paenibacillus* sp. origin, and one was originally used for cosmid library construction; the other was a new preparation. DNA samples were digested with EcoRI, blotted onto membrane, and hybridized with Roche DIG System (Roche) labeled 180 bp of PCR product amplified out of SB12. The PCR primers are 5' CCT CAC TAA AGG GAT CAC ACG G 3' annealing partially to the vector and truncated ORF1 (compared to full-length ORF3), and 5' GGC TAA TTG ATG AAT CTC CTT CGC 3' annealing to the truncated ORF1 (tcaA-like) and full length ORF3 (tcaA-like). A total of three DNA fragments (0.85, 2.7, and 8.0 kb) hybridizing to the PCR probe were detected, 0.85 and 8.0 in the SB12 and 2.7 and 8.0 in DAS1529 DNAs. No signals were detected in the negative control. The 0.85 kb (from first EcoRI ORF1 internal fragment to first EcoRI site in the vector) and 8.0 kb (from first 5' EcoRI site in ORF3 to the third EcoRI site in ORF1) matched the calculated sizes of the target DNA fragments from SB12. Detection of the 2.7 kb fragment suggests the presence of an EcoR1 site 2.7 kb immediately upstream of the first EcoRI site within ORF1 in DAS1529 DNA. Those results show that the SB12 insert was from DAS1529 total DNA and, based on hybridization and restriction analysis, all copies of the ORFs were accounted for.

Example 8

Characterization of Insecticidal Activities of Proteins Encoded by SB12 Cosmid ORFs Random transposon insertional mutagenesis (to disrupt an individual ORF or an entire operon) and heterologous expression (expressing individual ORFs or entire operons) were undertaken to isolate individual ORF(s) or operons conferring the insecticidal activities in the SB12 cosmid.

A. Random Transposon Mutagenesis of SB12 Cosmid

A Tn mutagenesis library was generated from DAS1529 cosmid SB12 using the GPS-1 Genome Priming System (New England BioLabs, Beverly, Mass.) following the kit instructions. Briefly, 2 µl 10× GPS buffer, 1 µl pGPS2.1 Donor DNA (0.02 µg), 1 µl SB12 cosmid (0.1 µg) and 18 µl sterile H$_2$O were added to a 0.5 ml tube. One µl of TnsABC Transposase was added; the mixture was vortexed and then spun briefly to collect the materials at the bottom of the tube. This reaction mixture was incubated for 10 minutes at 37° C. One µl of Start Solution was added and mixed by pipetting up and down several times. The reaction was incubated at 37° C. for 1 hour and was then heat inactivated at 75° C. for 10 minutes. One µl of the reaction mixture was diluted 10-fold with sterile H$_2$O; 1 µl of the diluted reaction was electroporated into 100 µl of Electro MAX DH5α-E *E. coli* (Gibco BRL, Rockville, Md.). After 1 hour of outgrowth in SOC medium at 37° C., 10 µl or 100 µl were plated on LB agar plates containing 20 µg/ml Kanamycin and 15 µg/ml chloramphenicol, followed by incubation overnight at 37° C.

Individual colonies from the SB12 Tn mutagenesis were streaked onto fresh LB agar plates containing 20 µg/ml Kanamycin and 15 µg/ml chloramphenicol. From the streaks, 50 ml cultures of LB containing 20 µg/ml Kanamycin and 15

μg/ml chloramphenicol were inoculated and grown at 28° C., 200 rpm for 48 hours. The cells were then collected by centrifugation at 3500 rpm for 20 minutes. The supernatant was removed and the pellet resuspended in 2.5 ml of the culture supernatant for a 20× concentration. The concentrated cell pellet was then assayed for activity against corn earworm. Forty μl of the 20× concentrate was surface applied to artificial diet using 8 wells per sample in 128 well plates. Newly hatched corn earworm larvae were added and allowed to feed for 5 days, at which time mortality and weights were recorded.

A total of 184 clones were tested for loss of activity against corn earworm. The results are summarized in Table 7. Bioassay of Tn clones revealed that a Tn insertion in the Cry1529 gene results in complete loss of activity. Initial bioassay showed that the activities of clones which carried Tn insertions in the tc genes were variable. Further analysis of those clones in which cultures were all normalized to the same cell density prior to bioassay showed no loss of activity as compared to SB12. Results from Tn analysis suggest that ORF7 (Cry1529) is the key insecticidally active component of SB12 cosmid.

TABLE 7

Bioassay of SB12, Cry1529 and tc tn insertion *E. coli* Clones

| Insects | TBW | CEW | THW | Grubs | SCRW |
|---|---|---|---|---|---|
| SB12 | +++ | ++ | +++ | − | n.d |
| Tn in Cry1529 | − | − | − | − | − |
| Tn in tcs | +++ | ++ | +++ | − | − |

* n.d.—not determined; −, ++, +++, no, moderate and high activity, respectively

B. Heterologous Expression SB12 ORFs/Operon.

Cry1529 (ORF7) and five tc ORFs (see Table 8 below) were expressed in pET101D® system. See FIG. 5. This expression vector has all the attributes of the basic T7-regulated pET expression system (Dubendorff and Studier, 1991; Studier and Moffatt, 1986) and allows directional cloning of a blunt-end PCR product into a vector for high-level, regulated expression, and simplified protein purification in *E. coli*. Optimal PCR amplification employed high-fidelity PfuTurbo™ DNA polymerase that is highly thermostable and possesses a 3' to 5' exonuclease proofreading activity to correct nucleotide-misincorportaion errors (Stratagene, La Jolla, Calif.). When ThermalAce™ polymerase (Invitrogen) is used, point mutations were introduced in the tc ORFs, which were corrected by the PfuTurbo™ based Quick-Change™ XL site-directed mutagenesis kit (Stratagene). The *E. coli* strain BL21 Star™ (DE3), was used as a host for expression since it contains the rne131 mutation (Lopez et al., 1999) that generally enhances mRNA stability and the yield of the recombinant proteins.

Individual ORFs were PCR amplified out of the SB12 cosmid with ORF specific primers (Table 8) under defined conditions. As a directional cloning requirement, the forward PCR primers were designed to contain the sequence, CACC, at the 5' end to ensure PCR product base pair with the overhang sequence, GTGG, in the pET101.D vector. The reverse primers when paired with forward primers will amplify each ORF, respectively. PCR reactions were carried out in 50 μl reaction mixture containing of 50 ng of SB12 cosmid DNA, 1× Pfu reaction buffer (Stratagene), 0.2 mM each of dNPT, 0.25 mM of each primer, and 2 U of PfuTurbo DNA polymerase (Stratagene). PCR amplifications were performed on a PE9600 thermal cycler (Perkin Elmer) with the following parameters: initial denaturation at 95° C. for 2 minutes, 35 cycles each with denaturing at 95° C. for 30 seconds, annealing at 55° C. for 30 seconds, extension at 72° C. for 2 minutes per kb ORF, and a final extension for 10 minutes at 72° C.

TABLE 8

Summary of PCR Primers for Cloning ORF1-7

| ORFs | Forward primers (5' to 3') | Reverse primers (5' to 3') |
|---|---|---|
| ORF1 ($tcaA_1$) | CACCATGCTTTATAAGGCCTGGC | TCAGGCCTGCACCGC |
| ORF3 ($tcaA_2$) | CACCATGGTGTCAACAACAGACAACAC | TCAGGCTTTCGCTGCAGC |
| ORF4 ($tcaB_2$) | CACCATGACCAAGGAAGGTGATAAGC | CTATTTCATAACATATCGAATTGG |
| ORF5 (tcaC) | CACCATGCCACAATCTAGCAATGC | TCACCGCGCAGGCGGTGAAG |
| ORF6 (tccC) | CACCATGAAAATGATACCATGGACTCATC | CTACTTTCTCTTCATTGAAAACCGGCGG |
| ORF7 (Cry 1529) | CACCATGAACTCAAATGAACCAAATTTATC | AACTGGAATTAACTTCGATTC |

PCR products for each ORF were cloned into pET101.D following instructions from the supplier (Invitrogen). The cloned ORF was purified as pET101.D plasmid DNA and sequenced verified. Since Tn analysis indicated ORF7 is the key component of SB12 for control of the tested pests, biochemical analysis and insect bioassay focused on heterologously expressed ORF7 proteins. For ORF7 expression clones, DNA sequence analysis showed 100% match with the original SB12 DNA sequence. Expression of ORF7 was induced by 0.5 mM IPTG for 4 hrs according to kit instructions (Invitrogen).

C. Bioassay for Insecticidal Activities of ORF7 and tc Operon.

Bioassay samples were prepared as whole *E. coli* cells, cell lysates, and purified toxins. The spectrum and specific activity of ORF7 (Cry1529) is summarized in Table 10. Cry1529 is most active against tobacco hornworm (*Manduca sexta*) and highly active (LC50 of 10 μg/ml diet) against tobacco budworm (*Heliothis virescens*); 100% mortality was observed for both insects. At higher doses, Cry1529 conferred some mortality (20 to 60%) and substantial growth inhibition on corn earworm (*Heliothis zea*), beet armyworm (*Spodoptera exigua*), and black cutworm (*Agrotis ipsilon*). For European cornborer (*Ostrinia nubilalis*), Cry1529 had some growth inhibition at higher doses. For some other insect species (fall armyworm, boll weevil, southern rootworm, mosquito), no activity was detected. The Cry1529 LC50s for Cry1A (Cry1Ac) resistant diamond back moth (DBMr) and sensitive diamond back moth (DBM) colonies are >50 μg/ml and <1.0 μg/ml, respectively, suggesting a potential cross resistance. Cry1529 did not confer detectable activity on grass grubs, a relative of Japanese beetles.

To test the activity of other non-Cry1529 factors in DAS1529, one Cry1529 tn knockout SB12 cosmid clone (tn67) was assayed against TBW, CEW, SCRW, ECB, BW, BAW, THW, and grass grubs; no activity was found against these pests. To address the issue of potential non- or low-expression of tc ORFs in SB12 background, individually expressed tc ORFs were tested independently and in combination with the other TCs from DAS 1529; no activity was found against TBW, CEW, and grass-grubs. Further, four ORFs were expressed as a single operon to very high levels in *E. coli* cells. When tested in vitro, the whole cells contained no detectable activity on TBW, CEW, and grass-grubs. While the lack of grub activity is somewhat interesting, these results are not surprising in that *Paenibacillus* typically infect a narrow range of grub hosts. In light of this, it could follow that the spectrum of activity of the insecticidal toxins might also be relatively narrow. Thus, screens (using known methods) involving a broader range of pests, and additional time, would be required to identify susceptible pests. The results presented herein should not lead one away from recognizing that the subject TC proteins have utility as do other TC proteins from *Xenorhabdus, Photorhabdus*, and the like.

Soluble proteins were extracted with 25 mM sodium phosphate pH 8.0, 100 mM sodium chloride and analyzed on 4-12% NuPAGE gradient gel with 1× MES buffer (Invitrogen). ORF7 protein was purified using standard procedures, and N-terminal sequencing revealed the expected sequence: MNSNEPNLSDV. A bioassay was performed with whole *E. coli* cells, with normalized cell density, expressing target proteins. See FIG. 6. Large scale purified ORF7 protein was used to obtain LC50s for ORF7 by in vitro bioassay. Thermal stability analysis of the purified ORF7 indicated that a 5 minute treatment at 75° C. is sufficient to abolish its activity against TBW. See Table 9.

TABLE 9

Thermal Stability of Purified Cry1529 (ORF7)

| Samples | Activity |
| --- | --- |
| Cry1529, room temperature | +++ |
| Cry1529, 50° C. for 5 min. | +++ |
| Cry1529, 50° C. for 10 min. | +++ |
| Cry1529, 75° C. for 5 min. | − |
| Cry1529, 75° C. for 10 min. | − |
| Cry1529, 100° C. for 5 min. | − |

−, +++, no and full activity, respectively

Figure 5:
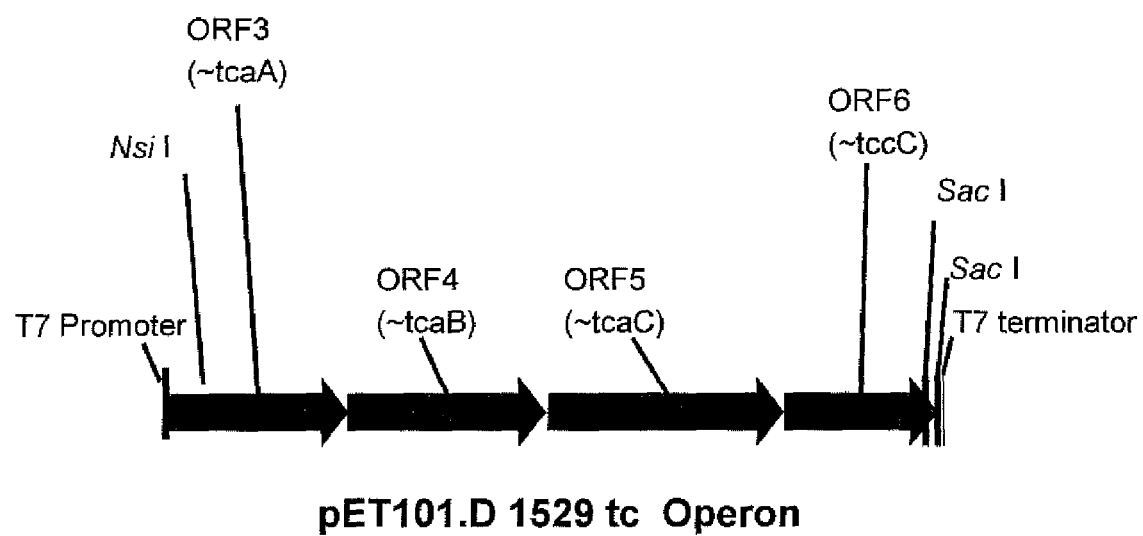
FIG. 5 shows ORF3-ORF6 in pEt101D.

For the tc genes, error-free clones of ORF3 and ORF6 were used as intermediate clones to generate a tc operon clone expressing ORF3 (tcaA), ORF4 (tcaB), ORF5 (tcaC), and ORF6 (tccC). To construct the tc operon in pET101.D, the NsiI/SacI fragment containing partial tcaA, entire tcaB and tcaC, and partial tccC was excised out of SB12 cosmid to replace the NsiI/SacI insert in pET101.D-tcaA; this was followed by the insertion of a 208 bp SacI fragment from pET101.D-tccC. See FIG. 5. All four ORFS were expressed to high levels by standard IPTG induction. For the ORF6 (tccC) expressed in the tc operon, the size of the expressed protein was slightly smaller than the ORF6 predicted by Vector NTI from the 5'-most ATG (SEQ ID NO:18) and expressed independently. Hence, the annotated ORF6 (SEQ ID NO:13) based on the presence of a ribosome binding site consensus is likely the native protein produced in SB12 and DAS1529.

D. Activity Spectrums of Toxins

The toxin activity spectrum of Cry1529 (ORF7) is summarized in Table 10.

TABLE 10

Spectrum activity for *E. coli* and *Pseudomonas* expressed Cry1529

| Species | Active (+++) | Format & Method | Material Production Method | LC$_{50}$ |
| --- | --- | --- | --- | --- |
| *H. virescens* (TBW) | +++ | 96 well top load and diet incorporation (scores, mortality, inhibition) | FCP, SE, purified, IC | 11 μg tox/ml diet with *E. coli* cell preps |
| *H. zea* (CEW) | + | 96 well top load and diet incorporation (scores, mortality, inhibition) | FCP, SE, purifed, IC | >100 μg tox/g diet |
| *S. exigua* (BAW) | + | 96 well top (score) | FCP, purifed | >78 μg/cm$^2$ |
| *S. frugiperda* (FAW) | − | 96 well top (score) | FCP, purifed | >>10 μg/cm$^2$ |
| *Plutella xylostella* (DBM) | +++ | 96 well top (score) | FCP, purifed | 0.02 μg tox/g diet |
| Cry1A resistant *Plutella xylostella* (rDBM) | + | 96 well top (score) | FCP, purifed | 59.7 μg tox/g diet |
| *A. ipsilon* (BCW) | + | 96 well top (score) | FCP, purifed | >10 μg/cm$^2$ |
| *O. nubilalis* (ECB) | + | 128 well top (weights) | FCP, purifed | >43 μg/cm$^2$ |
| *Culex* sp. (Mosquito) | − | 1 oz cups (mortality) | FCP, purifed | >20 μg/ml H$_2$0 |
| *Diabrotica undecimpunctata howardi* (SCRW) | − | 96 well top (score) | FCP, purifed | >>100 μg tox/cm$^2$ |
| *Anthonomous grandis grandis* (BW) | − | 128 well top (weights) | FCP, purifed | >>43 μg tox/cm$^2$ |
| *M. sexta* (THW) | +++ | | | (highly active) |
| *Continis mutabilis* (Beetles); surrogate for grass grub | − | | | >>100 μg tox/g soil |

Key: −, +, ++, +++ (no, low, moderate, high activity); FCP, frozen cell pellets; SE, soluble extract; purified = column purified Cry1529; IC, P.f. Cry1529 inclusion Only a limited range of pests was used in assays in an initial attempt to determine the activity spectrum of the subject TCs/tc ORFs. The following data, using the ORF3-OR6 operon, were obtained:

TABLE 11

Spectrum activity for Tc ORF's

| Species | Active (+++) | Format & Method | High Dose | Material Production Method | Comments |
|---|---|---|---|---|---|
| H. virescens (TBW) | – | 96 well top (score) | 10× | FCP | No effect |
| H. zea (CEW) | – | 96 well top (score) | 10× | FCP | No effect |
| S. exigua (BAW) | – | 96 well top (score) | 10× | FCP | No effect |
| Spodoptera frugiperda (FAW) | – | 96 well top (score) | 10× | FCP | No effect |
| A. ipsilon (BCW) | – | 96 well top (score) | 10× | FCP | No effect |

Again, while this initial round of screening did not reveal activity of these TCs against these pests, one skilled in the art would not doubt that the subject proteins are useful, as are the corresponding *Photorhabdus/Xenorhabdus* proteins. In addition, see Example 10, below.

Example 9

Use of PCR Primers for Identifying Cry1529 Homologues from Other Bacterial Genera, Species, and Strains For screening additional ORF7 cry1529 homologs from other (*Paenibacillus* or other) strains, gene specific and degenerate PCR primers were designed to amplify the target ORF7 DNA sequences of 1 kb. The PCR primers were deduced from two, well-conserved protein motifs (QAANLHL, domain I, block 1 core for forward primer; GPGFTGGD, domain III, block 3 for reverse primer) highly conserved in Cry proteins. Those primers are listed in Table 12 and were validated on DAS1529. PCR amplifications were performed on a PE9600 thermal cycler (Perkin Elmer) with the following parameters: initial denaturation at 95° C. for 2 minutes; 35 cycles each with denaturing at 95° C. for 30 seconds, annealing at 47° C. for 45 seconds, extension at 72° C. for 2 minutes, and a final extension for 10 minutes at 72° C. Those primer pairs were used to screen a bacterial (non-*B. thuringiensis*) culture collection by PCR. Five out of 192 strains (three *Paenibacillus*, one *Bacillus*, and one unidentified) produced PCR products of expected sizes. These strains were also found to have CEW activity according to primary bioassay screening. However, sequence analysis of amplicons obtained from one of these strains using different primers showed that the amplicons were not derived from a cry gene.

Notwithstanding this, and as these screens were not exhaustive, the subject invention includes methods of screening *Paenibacillus* spp., *Bacillus* spp. (including *Bacillus thuringiensis* and *sphaericus*), and the like for Cry1529-like proteins and genes. Given the significant nature of the discovery of lepidopteran-toxic Cry proteins in *Paenibacillus*, the subject invention also includes methods of screening *Paenibacillus* spp., generally, for lepidopteran-toxic Cry proteins and genes. Various screening methods are well-known in the art, including PCR techniques (as exemplified above), probes, and feeding assays (where whole cells are fed to target pests). As one skilled in the art would readily recognize, screening methods of the subject invention include the preparation and use of clone libraries (such as cosmid libraries) in these screens.

TABLE 12

PCR Primers for Screening ORF7 Homologs

| Gene-specific and degenerate Primers | DNA sequence (5' to 3') |
|---|---|
| Cry1529-F | CAAGCAGCCAACCTCCACCTA |
| Cry1529-R | ATCCCCTCCTGTAAAGCCTGG |
| CryPP-F | CAAGCNGCNAATYTWCATYT |
| CryPP-R | TCNCCNCCNGTAAANCCWGG |
| CryPT-F | CARGCSGCSAAYYTBCAYYT |
| CryPP-F2 | CAAGCWGCWAATYTWCATYT |
| CryPP-R2 | TCHCCWCCWGTAAAWCCWGG |
| CryPT-F2 | CAGGCSGCSAAYYTGCATYT |

1529 = gene specific; PP = *P. popilliae* codon bias; PT = *P. thiaminolyticus* codon bias Example 10

Complementation of *Xenorhabdus* XptA2 TC Protein Toxin with DAS1529 TC Proteins This example provides experimental evidence of the ability of DAS1529 TC proteins, expressed here with a single operon (ORFs 3-6; tcaA, tcaB, TcaC and tccC; see section C of Example 8), to complement the XptA2 toxin from *Xenorhabdus nematophilus* Xwi (see SEQ ID NO:49). Two independent experiments were carried out to express the DAS1529 TC operon and XptA2 independently, or to co-express the XptA2 gene and the TC operon in the same *E. coli* cells. Whole cells expressing different toxins/toxin combinations were tested for activity against the lepidopteran insects: corn earworm (*Heliothis zea*; CEW) and tobacco budworm (*Heliothis virescens*; TBW). The data from both experiments indicate that DAS1529 TC proteins are able to enhance *Xenorhabdus* TC protein XptA2 activity on both insect species tested.

A. Co-Expression of DAS1529 TCs and *Xenorhabdus* XptA2

Expression of the TC operon was regulated by the T7 promoter/lac operator in the pET101.D expression vector that carries a ColE1 replication origin and an ampicillin resistance selection marker (Invitrogen). Comprehensive description of cloning and expression of the tc operon can be found in section C of Example 8. The XptA2 gene was cloned in the pCot-3 expression vector, which carries a chloramphenicol resistance selection marker and a replication origin compatible with the ColE1. The pCot-3 vector expression system is also regulated by the T7 promoter/lac operator. Hence, compatible replication origins and different selection markers form the basis for co-expression of the TC operon and XptA2 in the same *E. coli* cells. Plasmid DNAs carrying the TC operon and XptA2 were transformed into *E. coli*, BL21 Star™ (DE3) either independently or in combination. Transformants were selected on LB agar plates containing 50 μg/ml carbenicillin for pET101.D-TC operon, 50 μg/ml chloramphenicol for pCot-3-XptA2, and both antibiotics for pET101.D-TC operon/pCot-3-XptA2. To suppress basal toxin expression, glucose at a final concentration of 50 mM were included in both agar and liquid LB medium.

For toxin production, 5 ml and 50 ml of LB medium containing antibiotics and 50 mM glucose were inoculated with overnight cultures growing on the LB agar plates. Cultures were grown at 30° C. on a shaker at 300 rpm. Once the culture density has reached an O.D. of ~0.4 at 600 nm, IPTG at a final concentration of 75 μM was added to the culture medium to induce gene expression. After 24 hours, *E. coli* cells were harvested for protein gel analysis by the NuPAGE system (Invitrogen). Cell pellets from 0.5 ml 1× culture broth was resuspended in 100 μl of 1× NuPAGE LDS sample buffer. Following brief sonication and boiling for 5 min, 5 μl of the sample was loaded onto 4 to 12% NuPAGE bis-tris gradient gel for total protein profile analysis. XptA2 expressed to detectable levels when expressed independently or in the presence of the TC operon. Based on gel scan analysis by a Personal Densitometer SI (Molecular Dynamics), XptA2 expressed nearly 8× as high by itself as when co-expressed with the TC operon. For the 5 ml induction experiment, there is a nearly equal expression of XptA2.

B. Bioassay for Insecticidal Activity

As described in Example 8, DAS1529 tc ORFs when expressed independently or as an operon, did not appear to be active against TBW and CEW. The following bioassay experiments focused on determining whether *Paenibacillus* (DAS1529) TC proteins (of ORFs 3-6; TcaA-, TcaB-, TcaC-, and TccC-like proteins) can complement *Xenorhabdus* TC protein toxin activity (XptA2 is exemplified). Bioassay samples were prepared as whole *E. coli* cells in 4× cell concentrate for the 5 ml induction experiment, both the XptA2 and XptA2/TC operon cells contained very low but nearly equal amount of the XptA2 toxin. Data in Table 13 showed that at the 4× cell concentration tested, TC proteins+*Xenorhabdus* XptA2 was active against CEW. This provided the first evidence of a complementation effect of *Paenibacillus* DAS1529 TC proteins on *Xenorhabdus* XptA2.

TABLE 13

Bioassay of DAS1529 TC complementation of Xeno. XptA2 on *H. zea*

| Insects: | CEW |
|---|---|
| Negative control | − |
| TCs (DAS1529) | − |
| Xeno. XptA2 | − |
| TC proteins + Xeno. XptA2 | ++ |

* −, ++, +++ = no, moderate and high activity, respectively

For the second bioassay experiment, the amount of XptA2 protein in the XptA2 cells and the XptA2+TC operon cells was normalized based on densitometer gel scan analysis. As shown in Table 14, XptA2 per se had moderate activity at 40× on TBW (*H. virescens*), but the activity dropped to a level undetectable at and below 20×. However, when co-expressed with TCs, high levels of activity were very apparent in the presence of 10× and 5× XptA2, and low activity was still noticeable at 1.25× XptA2. These observations indicate there is a significant potentiation effect of 1529 TC proteins on *Xenorhabdus* XptA2 against *H. virescens*. At the highest doses tested, neither the negative control nor the tc operon per se had any activity against this pest.

TABLE 14

Bioassay of IDAS1529 TC complementation of XptA2 on *H. virescens*

| Normalized XptA2 | 40× | 20× | 10× | 5× | 2.5× | 1.25× |
|---|---|---|---|---|---|---|
| XptA2 | + | − | − | − | n.d. | n.d. |
| TCs + XptA2 | n.d. | n.d. | ++ | ++ | + | − |

* n.d.—not determined; −, +, ++, +++ = no, low, moderate, and high activity, respectively

Example 11

Stabilization of Cry1529 Protein Against Trypsin Digestion

This example teaches modifications to the DNA sequence disclosed as SEQ ID NO:14, which encodes the Cry1529 protein (disclosed as SEQ ID NO:15) such that the new encoded proteins are more resistant to proteolytic digestion by trypsin than is the native protein. Digestion of proteins in the gut of insects limits the time of exposure of the insect to a protein toxin. Therefore, methods that decrease the susceptibility of a protein toxin to protease digestion can be used to increase potency of the protein.

For these tests, trypsin enzyme (e.g. Sigma Chemical #T1426) and trypsin inhibitors (e.g. Sigma Chemical #T9008) were prepared as stock solutions of 4 mg/mL or 10 mg/mL in 50 mM Tris HCl buffer, pH8.0. Test incubations with various concentrations of trypsin and Cry1529 protein were performed at 37° C. for 1 hour, and were terminated by addition of an equal volume of an equal concentration of trypsin inhibitors (e.g. a digestion that received 35 μL of 4 mg/mL trypsin solution was terminated by addition of 35 μl of 4 mg/mL trypsin inhibitors). For a typical experiment, Cry1529 protein was produced by appropriately engineered *E. coli* cells and purified by steps described previously, which included separation from other proteins by passage through a size-exclusion column. Following digestion, the protease products were analyzed by standard acrylamide gel electrophoresis followed by immunoblot analysis using antibody prepared against the Cry1529 protein. The results of such an experiment are shown in FIG. 9.

Trypsin digestion produces two major protein products, the smaller of which is approximately 50 kDa in molecular size. It is noted that this digestion pattern is the same as that produced from trypsin digestion of a Cry1529-$His_6$ protein, which is identical to the native Cry1529 protein amino acid sequence of SEQ ID NO:15 except for the addition of amino acids KGELNSKLEGKPIPNPLLGLDSTRTGHHHHHH to the carboxy-terminus. The coding region for Cry1529-$His_6$ was produced by ligating the coding region for the native Cry1529 protein into the pET101/D-TOPO® vector (Invitrogen™, Carlsbad, Calif.). This recombinant clone was made to facilitate purification of the recombinant Cry1529 protein by binding to a commercially available V5 antibody, whose epitope is represented by the amino acid sequence GKPIPNPLLGLDSTRTG (underlined above), or by purification schemes that expoit the six histidine residues (double underlined above). Procedures for these manipulations were performed according to the recommendations provided with the pET101/D-TOPO® vector.

Trypsin digestion of the Cry1529-$His_6$ protein was found to eliminate activity in insect bioassays against lepidopteran insects. MALDI-TOF analysis was used to determine the sequence of amino acids composing the N-terminus of the 50 kDa peptides, and two protease processing sites were determined, corresponding to amino acid residues 122 (R, Arginine) and 126 (K, Lysine) of SEQ ID NO:15.

Modifications to remove the first trypsin cleavage site in the encoded protein were made in the native DNA sequence (SEQ ID NO:14), using the QuickChange® mutagenesis methodology (Stratagene, La Jolla, Calif.). Three different types of mutations were made at amino acids in the region of 120 to 123 of SEQ ID NO:15: RARA to HANA, RARA to RARS, and RARA to QANA. The DNA oligonucleotide primers (listed in the 5' to 3' direction for each strand) for these mutations are listed in Table 15 below. The bases that differ from the native DNA sequence are underlined.

TABLE 15

| Mutation | Forward (Coding strand) Primer | Reverse (Complementary strand) Primer |
|---|---|---|
| RARA to HANA (pMYC2865) | AAAATGATTCTAATAATTT ACACGCGAACGCTGTAGTG AAAGAC | GTCTTTCACTACAGCGTT CGCGTGTAAATTATTAGA ATCATTTT |
| RARA to QANA (pMYC2866) | AAAATGATTCTAATAATTT ACAAGCGAACGCTGTAGTG AAAGAC | GTCTTTCACTACAGCGTT CGCTTGTAAATTATTAGA ATCATTTT |
| RARA to RARS (pMYC2867) | AAAATGATTCTAATAATTT AAGAGCGAGATCTGTAGTG AAAGAC | GTCTTTCACTACAGATCT CGCTCTTAAATTATTAGA ATCATTTT |

Comparison of the wild type and mutated coding regions induced by these primers are shown in this Table. The pertinent amino acid residues are shown in bold type.

TABLE 16

| Wild-type: | gAA | AAT | GAT | TCT | AAT | AAT | TTA | AGA | GCG | AGA | GCT | GTA | GTG | AAA | GAC |
|---|---|---|---|---|---|---|---|---|---|---|---|---|---|---|---|
| Amino Acids: | (E) | N | D | S | N | N | L | R | A | R | A | V | V | K | D |
| | | | 115 | | | | | 120 | | 122 | 123 | | 125 | 126 | |
| RABA to HANA: | gAA | AAT | GAT | TCT | AAT | AAT | TTA | CAC | GCG | AAC | GCT | GTA | GTG | AAA | GAC |
| Amino Acids: | (E) | N | D | S | N | N | L | H | A | N | A | V | V | K | D |
| RARA to QANA: | gAA | AAT | GAT | TCT | AAT | AAT | TTA | CAA | GCG | AAC | GCT | GTA | GTG | AAA | GAC |
| AMINO ACIDS: | (E) | N | D | S | N | N | L | Q | A | N | A | V | V | K | D |
| RAPA to RARS: | gAA | AAT | GAT | TCT | AAT | AAT | TTA | AGA | GCG | AGA | TCT | GTA | GTG | AAA | GAC |
| Amino Acids: | (E) | N | D | S | N | N | L | R | A | R | S | V | V | K | D |

Figure 10:
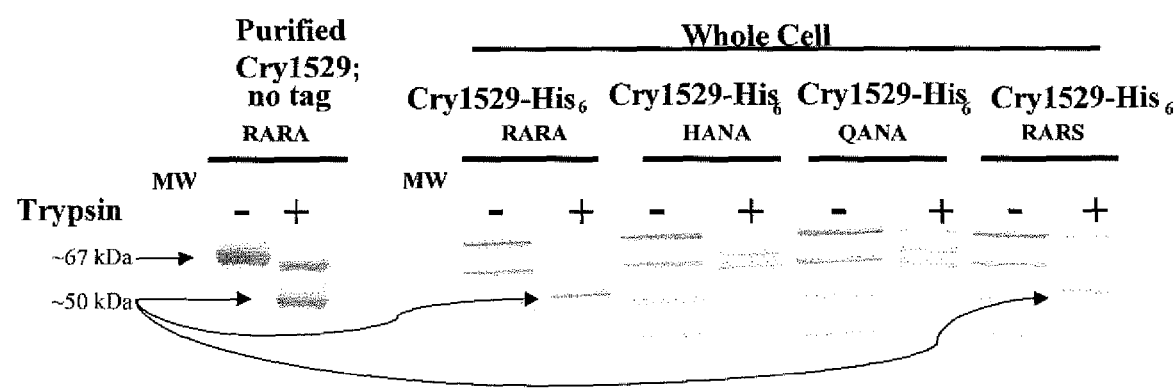

The separate, mutated coding regions were each cloned into the pET101/D-TOPO® vector, which allows inducible production of the Cry1529 variant proteins. E. coli cells containing the constructs were grown, and expression of the Cry1529 variant genes was induced by methods recommended by the supplier. Harvested whole cells were then tested in trypsin digestion assays, and analyzed as above. Typical results are shown in FIG. 10. For these experiments, 10 mg of whole cell pellet was suspended in 50 mM Tris HCl, pH8.0, and digested for 3 hours at 37° in a final volume of 1 mL, with 100 µL of 10 mg/mL trypsin. The reactions were mixed occasionally during incubation. Digestion was terminated by addition of 100 µL of 10 mg/mL trypsin inhibitors and the tubes were stored on ice.

These results demonstrate that both the native Cry1529 (RARA) and the Cry1529-His$_6$ (RARA) proteins are digested by trypsin to produce a major product of about 50 kDa. When the RARA sequence corresponding to the trypsin cleavage site was mutated to HANA or QANA, substantial resistance to trypsin digestion was obtained. No 50 kDa peptides were produced, and easily detectable amounts of the apparently full-length Cry1529-His$_6$ proteins were present. Mutation of the RARA site to RARS did not eliminate production of the 50 kDa peptides, but substantially reduced the rate of protease cleavage. Thus, it is apparent that mutation of protease processing sites in the Cry1529 protein substantially decreases its susceptibility to protease digestion. This allows the proteins to reside for longer periods of time in the insect gut following ingestion, resulting in increased potency to kill susceptible insects.

Example 12

Design of PCR Primers for Detection of Homologues of IDAS 1529 tcORFs in Other *Paenibacillus* Strains As shown above, *Paenibacillus* strain IDAS 1529 produces an extracellular protein that is toxic to various Lepidopteran insects. Molecular phylogeny of the 16S ribosomal gene of this strain indicates that it is most closely related to members of the *P. thiaminolyticus-P. lentimorbus-P. popilliae* cluster. It has also been shown that *Paenibacillus* strain IDAS 1529 contains both toxin complex genes hereafter designated as tc genes) and a novel insecticidal crystalline inclusion protein gene designated cry1529. In an attempt to determine if tc homologues are present in other members of the genus *Paenibacillus*, a collection of *Paenibacillus* strains was screened by polymerase chain reaction (PCR) and hybridization analyses. For the PCR analyses, total DNA isolated from *Paenibacillus* strains was used as template and screened using oligonucleotide primers specific to tc genes found in *Paenibacillus* strain IDAS 1529, *Photorhabdus* species, and *Xenorhabdus* species. Amplified products obtained with the tc primer sets were cloned and their nucleotide sequence was determined and compared to tc sequences obtained from *Paenibacillus* strain IDAS 1529. The following Examples illustrate how one can design tc-specific oligonucleotide primers and use PCR to search the total DNA of *Paenibacillus* isolates for DNA sequences that are homologous to tc genes identified in *Paenibacillus* strain IDAS 1529, *Photorhabdus* species, and *Xenorhabdus* species. By using PCR analysis (as described herein), it was (and is) possible to identify tc homologues in a species of *Paenibacillus* distinct from *Paenibacillus* strain IDAS 1529 and the *P. thiaminolyticus-P. lentimorbus-P. popilliae* cluster.

12.A.—Extraction of Total DNA from *Paenibacillus* Strains

*Paenibacillus* strains were grown on nutrient agar plates (8 g/l nutrient broth, 15 g/l Bacto agar; Difco Laboratories, Detroit, Mich.) for 3-5 days at 30° C. A single colony was picked and inoculated into a 500 ml tribaffled flask containing 100 ml of sterile nutrient broth (8 g/l nutrient broth; Difco Laboratories, Detroit, Mich.). Following 24-72 hrs of incubation at 30° C. on a rotary shaker at 150 rpm, the cultures were dispensed into sterile 500 ml polyethylene bottles and centrifuged at 6,500×g for 1 hr at 4° C. After centrifugation, the supernatant fluid was decanted and the bacterial cell pellet was retained. Total DNA was extracted from the cell pellet using the QIAGEN Genomic-tip System 100/G and associated Genomic DNA Buffer Set (QIAGEN Inc., Valencia, Calif., USA) by following The Sample Preparation and Lysis Protocol for Bacteria exactly as described by the manufacturer. The extracted total DNA was solubilized in 0.5 ml TE buffer (10 mM Tris-HCl, pH 8.0; 1 mM EDTA, pH 8.0).

12.B.—Selection of tc Specific Oligonucleotide Primers for PCR

To select oligonucleotide primers specific to the tc genes previously identified from *Paenibacillus* strain IDAS 1529, the tcaA, tcaB, tcdB and tccC nucleotide sequences obtained from *Paenibacillus* strain IDAS 1529, *Photorhabdus* strain W14, and *Xenorhabdus* strain Xwi were aligned using the Align program in the Vector NTI software package (Informax, Inc., Frederick, Md.). Nucleotide sequences used for this analysis are listed in Table 17.

TABLE 17

Nucleotide sequences used for tc specific primer selection

| Gene | Source organism | Source of nucleotide sequence | Gene Designation |
|---|---|---|---|
| tcaA1 | *Paenibacillus* strain IDAS 1529 | SEQ ID NO: 2 | tcaA1-1529 |
| tcaA2 | *Paenibacillus* strain IDAS 1529 | SEQ ID NO: 6 | tcaA2-1529 |
| tcaA | *Photorhabdus* strain W14 | GenBank: Accession No. AF346497 | tcaA-W14 |
| tcaB1 | *Paenibacillus* strain IDAS 1529 | SEQ ID NO: 4 | tcaB1-1529 |
| tcaB2 | *Paenibacillus* strain IDAS 1529 | SEQ ID NO: 8 | tcaB2-1529 |
| tcaB | *Photorhabdus* strain W14 | GenBank: Accession No. AF346497 | tcaB-W14 |
| tcdB1 | *Photorhabdus* strain W14 | SEQ ID NO: 42 | tcdB1-W14 |
| tcdB2 | *Photorhabdus* strain W14 | SEQ ID NO: 43 | tcdB2-W14 |
| xptC1 | *Xenorhabdus* strain Xwi | SEQ ID NO: 20 | xptC1-Xwi |
| tcaC | *Paenibacillus* strain IDAS 1529 | SEQ ID NO: 10 | tcaC-1529 |
| tccC1 | *Photorhabdus* strain W14 | SEQ ID NO: 44 | tccC1-W14 |
| tccC2 | *Photorhabdus* strain W14 | SEQ ID NO: 45 | tccC2-W14 |
| tccC3 | *Photorhabdus* strain W14 | SEQ ID NO: 46 | tccC3-W14 |
| tccC4 | *Photorhabdus* strain W14 | SEQ ID NO: 47 | tccC4-W14 |
| tccC5 | *Photorhabdus* strain W14 | SEQ ID NO: 48 | tccC5-W14 |
| xptB1 | *Xenorhabdus* strain Xwi | SEQ ID NO: 21 | xptB1-Xwi |
| tccC | *Paenibacillus* strain IDAS 1529 | SEQ ID NO: 19 | tccC-1529 |

12.B.i.—tcaA Specific Primer Selection

Nucleotide sequence alignment of tcaA1-1529, tcaA2-1529, and tcaA-W14 identified two regions of nucleotide sequence identity of sufficient length for the selection of PCR primers with minimal degeneracy (shown as boxed regions in FIG. 10.). These two regions were selected for the synthesis of tcaA specific primers, which were designated SB105 and SB106 (Tables 18 and 19).

12.B.ii.—tcaB Specific Primer Selection

Nucleotide sequence alignment of tcaB1-1529, tcaB2-1529, and tcaB-W14 identified four regions of nucleotide sequence identity of sufficient length for the selection of PCR primers with minimal degeneracy (FIG. 11.). These four regions were selected for the synthesis of tcaB specific primers, which were designated as SB101, SB102, SB103, and SB104 (Tables 18 and 19).

12.B.iii.—tcaC Specific Primer Selection

Nucleotide sequence alignment of tcdB1-W14, tcdB2-W14, xptC1-Xwi and tcaC-1529 identified two regions of nucleotide sequence identity of sufficient length for the selection of PCR primers with minimal degeneracy (FIG. 12.). These two regions were selected for the synthesis of tcaC specific primers, which were designated as SB215 and SB217 (Tables 18 and 19).

12.B.iv.—tccC Specific Primer Selection

Nucleotide sequence alignment of tccC1-W14, tccC2-W14, tccC3-W14, tccC4-W14, tccC5-W14, xptB1-Xwi and tccC-1529 identified two regions of nucleotide sequence identity of sufficient length for the selection of PCR primers with minimal degeneracy (FIG. 13.). These two regions were selected for the synthesis of tccC specific primers, which were designated as SB212 and SB213 (Tables 18 and 19).

TABLE 18 tc specific primers

| Primer designation | Primer length | Sequence of primer 5' to 3' | SEQ ID NO. |
|---|---|---|---|
| SB101 | 32 | GCKATGGCSGACCCGATGCAWTACAAGCTGGC* | 22 |
| SB102 | 32 | AGCGGYTGACCRTCCAGRCTCARATTGTGGCG | 23 |
| SB103 | 28 | TGTATAACTGGATGGCYGGWCGTCTSTC | 24 |
| SB104 | 26 | TCRAAAGGCAGRAAMCGGCTGTCGTT | 25 |
| SB105 | 28 | CTTCYCTKGATATCYTKYTGGATGTGCT | 26 |
| SB106 | 30 | ACGRCTGGYATTGGYAATCAGCCARTCCAA | 27 |
| SB212 | 27 | CGYTATIAATATGAYCCKGTVGGYAAT | 28 |
| SB213 | 25 | CATCBCGYTCTTTRCCIGARTARCG | 29 |
| SB215 | 33 | CGHAGCTCYICCCAGTWYTGGCTGGATGARAAA | 30 |
| SB217 | 32 | GTRTCATTTTCATCTTCRTTBACIRYAAACCA | 31 |

*K = C or T; S = G or C; W = A or T; Y = C or T; R = G or A; M = A or C; V = G or C or A; B = G or T or C; H = A or C or T, I = inosine

TABLE 19 tc primer combinations

| Target gene | Forward primer | Reverse primer | Approximate size of expected amplified product |
|---|---|---|---|
| tcaA | SB105 | SB106 | 1.4 kb |
| tcaB | SB101 | SB102 | 0.4 kb |
| tcaB | SB103 | SB104 | 0.65 kb |
| tcdB | SB215 | SB217 | 2.2 kb |
| tccC | SB212 | SB213 | 0.9 kb |

Example 13

PCR Amplification of *Paenibacillus* DNA

For PCR amplification using tcaA- and tcaB-specific primer sets, 3-5 ul of total DNA obtained from each of the *Paenibacillus* strains was mixed with 50 pmoles of each primer and 1× Eppendorf MasterMix (Eppendorf AG; Hamburg, Germany) in a 20 ul reaction volume. Amplification conditions were denaturation at 94° C. for 3 minutes followed by 30 cycles of denaturation at 94° C. for 1 minute, annealing at 52° C. for 1.5 minutes, and extension at 72° C. for 1.5 minutes, followed by a final extension at 72° C. for 5 minutes.

For PCR amplification using tcaC- and tccC-specific primer sets, approximately 375 ng of total DNA obtained from each of the Paenibacillus strains was mixed with 50 pmoles of each primer and 12.5 ul of Epicentre® FailSafe™ Buffer D and 2.5 U of Epicentre® FailSafe™ Polymerase (Epicentre; Madison, Wis.) in a 25 ul reaction volume. Amplification conditions were denaturation at 96° C. for 4 minutes followed by 40 cycles of denaturation at 94° C. for 30 seconds, annealing at 64° C. for 30 seconds, and extension at 70° C. for 30 seconds. Each cycle, the annealing temperature was lowered by 0.5° C. and the extension time was increased by 5 seconds.

13.A.—Gel Electrophoresis, Cloning, and Nucleotide Sequence Determination of PCR Amplified Products PCR amplification reactions were examined by gel electrophoresis using 0.8 to 1% Seakem LE agarose (BioWhittaker Molecular Applications, Rockland, Me.) in 1× TAE buffer. Amplified products were cloned in the vector pCR 2.1-TOPO® using the TOPO TA® Cloning Kit (Invitrogen™ Life Technologies, Carlsbad, Calif.) exactly as described by the manufacturer. The nucleotide sequences of the cloned amplified products were determined using M13 Forward, M13 Reverse, and tc sequence-specific sequencing primers as needed to obtain double stranded sequence of each cloned amplified product. Nucleotide sequencing was performed using the CEQ Dye Terminator Cycle Sequencing Quick Start Kit (Beckman Coulter, Fullerton, Calif., USA) and the CEQ 2000 XL DNA Analysis System (Beckman Coulter) exactly as directed by the manufacturer. The Sequencher (v. 4.1.4) software package (Gene Codes, Ann Arbor, Mich.) was used to construct contigs from the sequencing data and determine a consensus sequence for each amplified product.

13.B.—Nucleotide Sequence Analysis of PCR Amplified Products

13.B.i.—tcaA

When PCR using the tcaA-(primer combination SB105 and SB106) was performed using total DNA obtained from the collection of Paenibacillus strains, it was observed that total DNA from a Paenibacillus apairius strain (NRRL NRS 1438; hereafter designated as DB482) produced an amplified product of the expected sizes. The amplified product was cloned and sequenced.

The amplified product obtained using the SB105 and SB106 primer combination was designated as tcaA2-DB482. When the sequence of tcaA2-DB482 (SEQ ID NO:32) as compared to the tcaA sequences obtained from Paenibacillus strain IDAS 1529 and Photorhabdus strain W14, it was observed that tcaA2-DB482 have the greatest nucleotide sequence identity (90.5% over 1,239 nucleotides) to tcaA2-1529 (Table 20). The deduced amino acid sequence encoded by tcaA2-DB482 (designated as TcaA2-DB482; SEQ ID NO:33) was 89.1% identical to the corresponding deduced amino acid sequence of tcaA2-1529 (designated as TcaA2-1529; SEQ ID NO:7).

TABLE 20

Nucleotide and deduced amino acid sequence identity of tcaA2-DB482 with corresponding regions of tcaA1-1529, tcaA2-1529, and tcaA-W14

| Gene | % Nucleotide identity with tcaA2-DB482 | % deduced amino acid sequence identity with tcaA2-DB482 |
|---|---|---|
| tcaA1-1529 | 57 | 33 |
| tcaA2-1529 | 90 | 89 |
| tcaA-W14 | 50 | 32 |

13.B.ii.—tcaB

The amplified products obtained using the SB101 and SB102 primer combination and the SB103 and SB104 primer combination were designated as tcaB2a-DB482 and tcaB2b-DB482, respectively. When the sequences of tcaB2a-DB482 (SEQ ID NO:34) and tcaB2b-DB482 (SEQ ID NO:35) were compared to the tcaB sequences obtained from Paenibacillus strain IDAS 1529 and Photorhabdus strain W14, it was observed that both of these sequences have the greatest nucleotide sequence identity to tcaB1-1529 and tcaB2-1529 (Table 21). The nucleotide sequence identity of tcaB2a-DB482 and tcaB2b-DB482 to tcaB2-1529 was 92.6% and 89.8%, respectively. The deduced amino acid sequences encoded by tcaB2a-DB482 (designated as TcaB2a-DB482; SEQ ID NO:36) tcaB2b-DB482 (designated as TcaB2b-DB482; SEQ ID NO:37) were 91.2% and 91.1% identical, respectively, to the corresponding deduced amino acid sequence of tcaB2-1529 (designated as tcaB2-1529; SEQ ID NO:9).

TABLE 21

Nucleotide and deduced amino acid sequence identity of tcaB2a-DB482 and tcaB2b-DB482 with corresponding regions of tcaB1-1529, tcaB2-1529, and tcaB-W14

| Gene | % Nucleotide identity with tcaB2a-DB482 | % Nucleotide identity with tcaB2b-DB482 | % deduced amino acid sequence with TcaB2a-DB482 | % deduced amino acid sequence with TcaB2b-DB482 |
|---|---|---|---|---|
| tcaB1-1529 | 93 | 93 | 94 | 92 |
| tcaB2-1529 | 93 | 90 | 91 | 92 |
| tcaB-W14 | 63 | 57 | 59 | 57 |

13.B.iii.—tcdB

When PCR using the tcaC-specific primer combination (SB215 and SB217) was performed using total DNA obtained from DB482 produced an amplified product of the expected size. The amplified product was cloned and sequenced.

The amplified product obtained using the SB215 and SB217 primer combination was designated as tcaC-DB482. When the sequence of tcaC-DB482 (SEQ ID NO:38) was compared to the tcaC sequences obtained from Paenibacillus strain IDAS 1529, Xenorhabdus strain Xwi and Photorhabdus strain W14, it was observed that tcaC-DB482 has the greatest nucleotide sequence identity (93.5% over 2,091 nucleotides) to tcaC-1529 (Table 22). The deduced amino acid sequence encoded by tcaC-DB482 (designated as tcaC-DB482; SEQ ID NO:39) was 91.1% identical to the corresponding deduced amino acid sequence of tcaC-1529 (designated as TcaC-1529; SEQ ID NO:11).

TABLE 22

Nucleotide and deduced amino acid sequence identity
of tcaC-DB482 corresponding regions of xptC1-Xwi,
tcdB1-W14, and tcdB2-W14, and tcaC-1529

| Gene | % Nucleotide sequence identity with tcaC-DB482 | % deduced amino acid sequence identity with TcaC-DB482 |
|---|---|---|
| tcaC-1529 | 93 | 91 |
| xptC1-Xwi | 50 | 35 |
| tcdB1-W14 | 50 | 36 |
| tcdB2-W14 | 50 | 36 |

13.B.iv.—tccC

When PCR using the tccC-specific primer combination (SB212 and SB212) was performed using total DNA obtained from the collection of *Paenibacillus* strains, it was observed that total DNA from DB482 produced an amplified product of the expected size. The amplified product was cloned and sequenced.

The amplified product obtained using the SB212 and SB213 primer combination was designated as tccC-DB482. When the sequence of tccC-DB482 (SEQ ID NO:40) was compared to the tccC sequences obtained from *Paenibacillus* strain IDAS 1529, *Xenorhabdus* strain Xwi and *Photorhabdus* strain W14, it was observed that tccC-DB482 has the greatest nucleotide sequence identity (93.7% over 858 nucleotides) to tccC-1529 (Table 23). The deduced amino acid sequence encoded by tccC-DB482 (designated as TccC-DB482; SEQ ID NO:41) was 95.5% identical to the corresponding deduced amino acid sequence of tccC-1529 (designated as TccC-1529; SEQ ID NO:13).

TABLE 23

Nucleotide and deduced amino acid sequence identity of
tccC-DB482 corresponding regions of xptB1-Xwi, tc-W14,
tccC-1529, and tcc genes from *Photorhabdus* strain W14

| Gene | % Nucleotide sequence identity with tccC-DB482 | % deduced amino acid sequence identity with TccC-DB482 |
|---|---|---|
| tccC-1529 | 94 | 96 |
| xptB1-Xwi | 54 | 45 |
| tccC1-W14 | 54 | 48 |
| tccC2-W14 | 56 | 45 |
| tccC3-W14 | 56 | 46 |
| tccC4-W14 | 56 | 46 |
| tccC5-W14 | 54 | 44 |

13.C.—Summary of PCR Analyses

This example (and other examples herein) illustrate methods for designing oligonucleotide primers based on tc genes from three genera of bacteria, and that the use of these primers for PCR screening of *Paenibacillus* strains can identify tc homologues present in those strains. DB482, which is an isolate of *Paenibacillus apairius* (deposited as NRRL B-30670) that was isolated from honey bee larva, was shown to contain homologues of tcaA, tcaB, tcaC, and tccC. The finding of these tc homologues confirms that *Paenibacillus* strain IDAS 1529 is not unique within the genus *Paenibacillus* with regard to possessing tc genes. Therefore, one skilled in the art can now use these and other methods to identify other tc homologues in other species of *Paenibacillus* such as *P. chondroitinus, P. alginolyticus, P. larvae, P. validus, P. gordonae, P. alvei, P. lentimorbus, P. popilliae, P. thiaminolyticus, P. curdlanolyticus, P. kobensis, P. glucanolyticus, P. lautus, P. chibensis, P. macquariensis, P. azotofixans, P. peoriae, P. polymyxa, P. illinoisensis, P. amylolyticus, P. pabuli*, and *P. macerans*.

Example 14

**Detection of Homologues of IDAS 1529 tcORFS in Other *Paenibacillus* Strains by Southern Hybridization**

This example illustrates how one can use radioactively labeled DNA fragments as probes to search the genomic DNA of *Paenibacillus* isolates for DNA sequences (preferably having some homology to the known tcORFs first detected in IDAS 1529). The results demonstrate that sequences homologous to two of the tcORFs are detected in a *Paenibacillus apairius* isolate, DB482.

Genomic DNA from various *Paenibacillus* strains (or from *E. coli* to serve as a negative control) was prepared as described above in Example 12, and was digested with restriction enzyme to produce multiple fragments. A typical digestion contained 8 µg of DNA in a total volume of 400 µL of reaction buffer as supplied by the manufacturer of the EcoR I enzyme (New England Biolabs, Beverly, Mass.). The reaction, containing 200 units of enzyme, was incubated overnight at 37° C., then placed on ice. Digested DNA was further purified and concentrated by addition of 30 µL of 3M sodium acetate (pH5.2) and 750 µL of ice cold 100% ethanol, followed by centrifugation. The DNA pellet was washed twice with 70% ethanol, dried under vacuum, and resuspended in 50 µl of TE buffer [10 mM Tris HCl, pH8.0; 1 mM ethylenediaminetetraacetic acid (EDTA)]. An aliquot was then analyzed by agarose gel electrophoresis for visual assurance of limit digestion. In a similar manner, DNA of IDAS 1529 cosmid SB12 was digested with EcoR I, and was used as a positive control for the hybridization experiments.

EcoR I digested genomic DNA fragments to be blotted for Southern analysis were separated by electrophoresis through 0.7% or 1.2% agarose gels in TEA buffer (40 mM Tris-acetate, 2 mM EDTA, pH8.0) (1 µg DNA/well). On each gel, lanes containing a 1 kb DNA Molecular Weight Ladder (Invitrogen™, Carlsbad, Calif.) were used to provide molecular weight size standards. The 15 fragment sizes larger than 500 bp in this ladder (in kilobases) are: 12.2, 11.2, 10.1, 9.2, 8.1, 7.1, 6.1, 5.1, 4.1, 3.1, 2.0, 1.6, 1.0, 0.52, and 0.50. The DNA in the gel was stained with 50 µg/mL ethidium bromide, the gel was photographed, and then the DNA in the gel was depurinated (5 min in 0.2M HCl), denatured (15 min in 0.5M NaOH, 1.5M NaCl), neutralized (5 min in 0.2M HCl) and transferred to MAGNA 0.45 micron nylon transfer membrane (Osmonics, Westborough, Mass.) in 2×SSC (20×SSC contains 3M NaCl, 0.3M sodium citrate, pH 7.0). The DNA was crosslinked to the membrane by ultraviolet light (Stratalinker®; Stratagene, La Jolla, Calif.) and prepared for hybridization by incubating at 60° C. or 65° C. for 1 to 3 hours in "Minimal Hybridization" solution [contains 10% w/v polyethylene glycol (M.W. approx. 8000), 7% w/v sodium dodecylsulfate; 0.6×SSC, 5 mM EDTA, 100 µg/ml denatured salmon sperm DNA, and 10 mM sodium phosphate buffer (from a 1M stock containing 95 g/L $NaH_2PO_4.1H_2O$ and 84.5 g/L $Na_2HPO_4.7H_2O$)].

DNA fragments of the tcORFs for use as hybridization probes were first prepared by Polymerase Chain Reaction (PCR) using SB12 cosmid DNA as template (see previous examples). The forward and reverse primers for these amplifications are listed (5' to 3' directions of the respective DNA strands) in Table 24, below (bases in capital letters correspond to protein coding regions). Primer Set One is designed to amplify, from SB12 cosmid DNA, a DNA fragment that includes all of tcORF5, which is disclosed as SEQ ID NO:10, and which has some similarity to the *Photorhabdus* tcaC gene (Table 6). Primer Set Two is designed to amplify, from cosmid SB12, a DNA fragment that encodes the protein disclosed as SEQ ID NO:19. This DNA fragment and the encoded protein are somewhat longer than the DNA sequence of tcORF6 disclosed as SEQ ID NO:12, and the encoded protein disclosed as SEQ ID NO:13. The proteins disclosed as SEQ ID NO:13 and SEQ ID NO:19 both have some similarity to the protein encoded by the *Photorhabdus* tccC gene (Table 6). The amplified PCR products were cloned into the pCR®2.1-TOPO® cloning vector (Invitrogen™, Carlsbad, Calif.), and fragments containing the tcORFs were released from the resulting clones by restriction enzyme digestion (listed in the Table below), followed by purification from agarose gels using the GenElute™ Agarose Spin columns (Sigma Chemical Co, St Louis, Mo.). Recovered fragments were concentrated by precipitation using the Quick-Precip™ Plus Solution according to the supplier's instructions (Edge BioSystems, Gaithersburg, Md.).

TABLE 24

SB12 tcORF5 (SEQ ID No. 10)

PCR Primer Set One

Forward Primer SB126*
gtacgtcatctagaaaggagatataccATGCCACAATCTAGCAATGCCGA
TATCAAGCTATTGTC
Reverse Primer SB127*
tgacatcggtcgacattattaCCGCGCAGGCGGTGAAGCAAATAATGATG
AGTCCATGGTA
Cut from pCR ®2.1-TOPO ® clone with Sal I + Xba I + Pvu I and purify 4,368 bp fragment SB12 tcORF that encodes SEQ ID No. 19; encompassing tcORF6 (SEQ ID No. 12)

PCR Primer Set Two

Forward Primer SB128*, **
gtacgtcaactagtaaggagatataccATGAAAATGATACCgTGGACTCA
cCATTATTTGCTTCACC
Reverse Primer SB129*
tgacatcgctcgagattattaCTTTCTCTTCATTGAAAACCGGCGGAAAA
AGTTCCCA
Cut from pCR ®2.1-TOPO ® clone with EcoR I + Sph I /+ Pvu I and purify 2,925 bp fragment

*In this table, bases in lower case at the 5' ends of the primers are not complementary to the cosmid SB12 DNA sequence. They were used to provide restriction enzyme recognition sequences on the ends of the amplified products to facilitate subsequent cloning manipulations.
**Bases in lowercase bold were changed from those of the native sequence to eliminate a potential hairpin structure that might interfere with subsequent functional analysis of the clone.

Radioactively labeled DNA fragments were prepared using the High Prime Radioactive Labeling Kit (Roche Diagnostics, Mannheim, Germany) according to the supplier's instructions. Nonincorporated nucleotides were removed by passage through a QIAquick® PCR Purification column (Qiagen, Inc. Valencia, Calif.) according to the manufacturers instructions. Labeling of approximately 100 ng of DNA fragments by these methods resulted in specific activities of approximately 0.1 μCi/ng. The labeled DNA fragments were denatured by boiling for 5 minutes, then added to the hybridization blot in Minimal Hybridization solution and incubated overnight at 60° C. or 65° C. Loose radioactivity was removed from the blot by rinsing at room temperature in 2×SSC, then more tightly bound radioactivity was removed by washing the blot for at least one hour at 60° C. or 65° C. in 0.3×SSC+0.1% sodium dodecylsulfate. At least two such washes were performed. The blot was placed on X-ray film at −80° C. with two intensifying screens, and the exposed film was developed after 1 to 3 days exposure. Blots were stripped of hybridized DNA fragments by boiling for 10 minutes in 0.3×SSC+0.1% SDS, and reused once or twice for subsequent hybridizations.

Distinct fragments that hybridized to probes derived from Primer Sets One and Two were observed in genomic DNA obtained from *Paenibacillus apairius* strain DB482. The probe derived from Primer Set One (primers SB126 and SB127), which detects sequences homologous to the IDAS 1529 tcORF5, hybridized to fragments of estimated sizes (in kilobases) of 20, 10.2, and 8.4. Within this range of molecule sizes, mobilities of DNA fragments can provide only estimations of true molecular sizes. Signal intensity for the fragments estimated to be 20 kb and 8.4 kb were much more intense than the signal intensity for the fragment estimated to be 10.2 kb. Since each of these fragments is at least twice the size of the probe fragment (about 4.4 kb), one explanation for these results is that multiple copies of genes that are similar to the probe derived from IDAS1529 tc ORF5, and thus are similar to the *Photorhabdus* tcaC gene, are present in the genome of *Paenibacillus apairius* strain DB482. However, other explanations for this outcome are possible.

The probe derived from Primer Set Two (primers SB128 and SB129), which detects sequences homologous to the IDAS 1529 tcORF6 and its flanking 5' end sequences, hybridized to fragments of estimated sizes (in kilobases) of 7.8 and 4.5. Signal intensity for the fragment estimated to be 7.8 kb was very much more intense than the signal intensity seen for the fragment estimated to be 4.5 kb. One explanation for this result is that *Paenibacillus apairius* strain DB482 has a single gene similar to the IDAS 1529 tcORF6 and its 5' flanking sequences, and thus is similar to the *Photorhabdus* tccC gene, and that EcoR I cleaves the gene into two fragments that have unequal portions of the DNA sequences comprising the gene. However, other explanations for this outcome are possible, including the presence of multiple genes with different amounts of absolute homology to the probe.

These results (detection by PCR amplification followed by DNA sequence analyses) confirm the presence of relatives of the *Photorhabdus* tcaC and tccC genes in *Paenibacillus apairius* strain DB482.

Example 15

Insecticidal Activity of DB482

*Paenibacillus* strain DAS1529 has been shown to produce an extracellular protein that is toxic to Lepidopteran insects and has also been shown to contain a cry gene, designated as cry1529. As this strain produces an extracellular insecticidally active protein and intracellular insecticidally active proteins, the subject invention includes screening other strains of *Paenibacillus* for extracellular (released into culture supernatant fluid) and/or intracellular (cell-associated) insecticidally active agents. This example illustrates how one can produce fermentation broths of *Paenibacillus* strains, how to process these broths, and how to test samples derived from these broths for insecticidal activity.

15.A. Production and Processing of *Paenibacillus* Fermentation Broths

*Paenibacillus* strains were grown on nutrient agar plates (8 g/l nutrient broth, 15 g/l Bacto agar; Difco Laboratories, Detroit, Mich.) for 3-5 days at 30° C. A single colony was picked and inoculated into a 500 ml tribaffled flask containing 100 ml of sterile modified tryptic soy broth (tryptone 10-g/l, peptone 7 g/l, soytone 3 g/l, KCl 5 g/l, K$_2$PO$_4$ 2.5 g/l; Difco Laboratories, Detroit, Mich.). Following 72 hours of incubation at 28° C. on a rotary shaker at 150 rpm, the cultures were dispensed into sterile 500 ml polyethylene bottles and centrifuged at 4,000×g for 45 minutes at 4° C. After centrifugation, the supernatant fluid was decanted and filtered through a 0.22 um membrane filter (Millipore Corporation, Bedford, Mass.). The culture filtrate was then concentrated 20× using a Centricon Plus-20 centrifugal filter device with a 5,000 molecular weight cutoff membrane by centrifuging at 4,000×g. The bacterial cell pellet was resuspended in 10 mM potassium phosphate buffer (pH=8). These samples were then tested in insect bioassay for insecticidal activities contained in the processed supernatant and cell pellet samples.

15.B. Insect Bioassay of Processed Supernatant and Cell Pellets

The insect species included in these assays were *Diabrotica undecimpunctata howardi* (Southern corn rootworm, SCR), *Helicoverpa zea* (corn earworm, CEW), and *Heliothis virescens* (tobacco budworm, TBW) The artificial diet used to rear and bioassay SCR was described previously (Rose, R. L. and McCabe, J. M. 1973. J. Econ. Entomol. 66, 398-400). Standard artificial lepidopteran diet (Stoneville Yellow diet) was used to rear and bioassay ECB, CEW, and TBW. Forty ul aliquots of the concentrated supernatant or cell pellet samples were applied directly to the surface of wells (~1.5 cm$^2$) containing the artificial diet. Treated diet wells were allowed to air-dry in a sterile flow-hood, and each well was infested with a single, neonate insect hatched from surface-sterilized eggs. Assay trays were then sealed, placed in a humidified growth chamber, and maintained at 28° C. for 3-5 days. Mortality and larval weight determinations were then scored. Eight insects were used per treatment.

15.C. Insecticidal Activity of DB482

Concentrated supernatant and cell pellets from strain DB482 had insecticidal activity against SCR, TBW, and CEW relative to control treatments (Table 25.) It is possible that the insecticidal activity associated with concentrated supernatants and cell pellets from DB482 are the result of two different insecticidal factors, one that is cell-associated (i.e. Cry-like) and another that is released from the cells (i.e. TC-like). However, it is also possible that the insecticidal activities from both the concentrated supernatant and cell pellets from DB482 are the result of the same insecticidal factors being present in both cellular fractions.

TABLE 25

Insecticidal activity of DB482

| Insects Tested | Concentrated Supernatant activity | Cell pellet activity |
|---|---|---|
| SCR | +++* | +++ |
| TBW | ++ | ++ |
| CEW | +++ | ++ |
| Medium controls | − | − |

*−, ++, +++; no, moderate, and high activity, respectively

15.D. Summary of Insecticidal Activity Screening

This example illustrates a method for screening concentrated culture supernatants and cell pellets from *Paenibacillus* strains to identify strains possessing insecticidal activity against Coleopteran and Lepidopteran insects. DB482, which is an isolate of *Paenibacillus apairius* was shown herein to contain homologues of tcaA, tcaB, tcaC, and tccC. The finding of insecticidal activity in DB482 confirms that *Paenibacillus* strain DAS1529 is not unique within the genus *Paenibacillus* with regard to producing insecticidal activities against Lepidopteran insects. Therefore, the subject invention includes methods used to identify other strains of *Paenibacillus* with insecticidal activities against Lepidopteran insects in other species of *Paenibacillus* such as *P. chondroitinus, P. alginolyticus, P. larvae, P. validus, P. gordonae, P. alvei, P. lentimorbus, P. popilliae, P. thiaminolyticus, P. curdlanolyticus, P. kobensis, P. glucanolyticus, P. lautus, P. chibensis, P. macquariensis, P. azotofixans, P. peoriae, P. polymyxa, P. illinoisensis, P. amylolyticus, P. pabuli, P. macerans.*

The invention claimed is:

1. An isolated protein that has toxin activity against an insect wherein the amino acid sequence of said protein is at least 95% identical to SEQ ID NO:13.

2. The isolated protein of claim 1 wherein the amino acid sequence of said protein is at least 99% identical to SEQ ID NO:13.

3. The protein of claim 1 wherein said protein comprises the amino acid sequence shown in SEQ ID NO:13.

4. A method of controlling an insect wherein said method comprises the step of contacting said insect with a protein according to claim 1.

* * * * *